(12) United States Patent
Tomashek et al.

(10) Patent No.: US 9,885,028 B2
(45) Date of Patent: *Feb. 6, 2018

(54) CARBOHYDRATE BINDING MODULES WITH REDUCED BINDING TO LIGNIN

(71) Applicant: Iogen Energy Corporation, Ottawa (CA)

(72) Inventors: John J. Tomashek, Ottawa (CA); Brian R. Scott, Richmond (CA); Daniel Kolczynski, Ottawa (CA)

(73) Assignee: Iogen Energy Corporation, Ottawa (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/919,199

(22) Filed: Oct. 21, 2015

(65) Prior Publication Data

US 2016/0115464 A1    Apr. 28, 2016

Related U.S. Application Data

(63) Continuation of application No. 13/575,046, filed as application No. PCT/CA2011/000167 on Feb. 11, 2011, now Pat. No. 9,206,406.

(60) Provisional application No. 61/303,400, filed on Feb. 11, 2010.

(51) Int. Cl.
*C12N 9/42* (2006.01)
*C12P 19/14* (2006.01)
*C12P 7/06* (2006.01)
*C12P 19/02* (2006.01)
*C12N 9/24* (2006.01)

(52) U.S. Cl.
CPC .......... *C12N 9/2437* (2013.01); *C12N 9/2402* (2013.01); *C12N 9/2445* (2013.01); *C12P 7/06* (2013.01); *C12P 19/02* (2013.01); *C12P 19/14* (2013.01); *C12Y 302/01004* (2013.01); *C12Y 302/01021* (2013.01); *C07K 2319/20* (2013.01); *Y02E 50/16* (2013.01); *Y02E 50/17* (2013.01)

(58) Field of Classification Search
CPC ..... C12N 9/2434; C12N 9/2437; C12N 9/244
See application file for complete search history.

(56) References Cited

U.S. PATENT DOCUMENTS

| | | | |
|---|---|---|---|
| 6,114,296 A | 9/2000 | Schulein et al. | |
| 6,921,655 B1 | 7/2005 | Nakamura et al. | |
| 7,348,168 B2 | 3/2008 | Wu et al. | |
| 7,354,743 B2 | 4/2008 | Vlasenko et al. | |
| 7,375,197 B2 | 5/2008 | Adney et al. | |
| 7,604,967 B2 | 10/2009 | Yang et al. | |
| 7,875,444 B2 | 1/2011 | Yang et al. | |
| 7,932,073 B2 | 4/2011 | Teter et al. | |
| 8,008,056 B2 | 8/2011 | Aehle et al. | |
| 8,012,734 B2 | 9/2011 | Lavigne et al. | |
| 8,143,049 B2 | 3/2012 | Hill et al. | |
| 9,279,163 B2 * | 3/2016 | Montalibet | ............. C12P 19/14 |
| 2004/0185542 A1 | 9/2004 | Yang et al. | |
| 2006/0088922 A1 | 4/2006 | Yang et al. | |
| 2006/0205042 A1 | 9/2006 | Aehle et al. | |
| 2007/0173431 A1 | 7/2007 | Day et al. | |
| 2008/0167214 A1 | 7/2008 | Teter et al. | |
| 2009/0186381 A1 | 7/2009 | Lavigne et al. | |
| 2009/0209009 A1 | 8/2009 | Tolan et al. | |
| 2010/0041104 A1 | 2/2010 | Cascao-Pereira et al. | |
| 2010/0093040 A1 | 4/2010 | Hill et al. | |
| 2010/0221778 A1 | 9/2010 | Scott et al. | |
| 2010/0304438 A1 | 12/2010 | Scott et al. | |

FOREIGN PATENT DOCUMENTS

| | | |
|---|---|---|
| WO | 1994/07998 | 4/1994 |
| WO | 1994/29474 | 12/1994 |
| WO | 1999/01544 | 1/1999 |
| WO | 2005/024037 | 3/2005 |
| WO | 2005/028636 | 3/2005 |
| WO | 2005/093072 | 10/2005 |
| WO | 2006/074005 | 7/2006 |
| WO | 2006/128304 | 12/2006 |

(Continued)

OTHER PUBLICATIONS

T. Fukuda et al. "Enhancement of Cellulase Activity by Clones Selected from the Combinatorial Library of the Cellulose-Binding Domain by Cell Surface Engineering", Biotechnology Progress 22:933-938 (2006).*

(Continued)

*Primary Examiner* — Rebecca E Prouty
(74) *Attorney, Agent, or Firm* — Fitzpatrick, Cella, Harper & Scinto

(57) ABSTRACT

Provided is a modified Family 1 carbohydrate binding module (CBM) comprising amino acid substitutions at one or more of positions 10, 11, 12, 14, 17, 21, 24, 29, 31, 33, and 37, said position determined from alignment of a Family 1 CBM amino acid sequence with SEQ ID NO: 30, and exhibiting from about 50% to about 99.9% amino acid sequence identity to SEQ ID NO: 30. Also provided are modified glycosidase enzymes comprising the modified Family 1 CBM, genetic constructs and genetically modified microbes for expressing the modified Family 1 CBM or modified glycosidase enzyme. The modified Family 1 CBM confers reduced lignin binding and/or increased hydrolyzing activity in the presence of lignin to the modified glycosidase enzyme, which may be used in a process for hydrolyzing cellulose or hemicellulose in the presence of lignin.

23 Claims, 19 Drawing Sheets

(56) References Cited

FOREIGN PATENT DOCUMENTS

| WO | 2008/025164 | 3/2008 |
|---|---|---|
| WO | 2009/089630 | 7/2009 |
| WO | 2009/149202 | 12/2009 |
| WO | 2010/012102 | 2/2010 |
| WO | 2010/066411 | 6/2010 |
| WO | 2010/141779 | 12/2010 |

OTHER PUBLICATIONS

Bae, K., et al., "Prediction of Protein Interdomain Linker Regions by a Nonstationary Hidden Markov Model," Journal of the American Statistical Association, vol. 103, Issue 483 (2008) 1085-99.
Beckham, et al., "Identification of Amino Acids Responsible for Processivity in a Family 1 Carbodyhydrate-Binding Module from a Fungal Cellulase," J. Phys. Chem., vol. 114, No. 3 (2010) 1447-53.
Berlin, A., et al., "Weak Lignin-Binding Enzymes," Applied Biochemistry and Biotechnology, vol. 121-124 (2005) 163-70.
Boisset, C., et al., "Dynamic light scattering study of a two-domain structure of Humicola insolens endoglucanase V," FEBS Letters, vol. 376, Issue 1-2 (1995) 49-52.
Boraston, A.B., et al., "Carbohydrate-binding modules: fine tuning polysaccharide recognition," Biochemical Journal, vol. 382 (2004) 769-81.
Chernoglazov, V.M., et al., "Adsorption of high-purity endo-1,4-beta-glucanases from Trichoderma reesei on components of lignocellulosic materials: cellulose, lignin, and xylan," Enzyme and Microbial Technology, vol. 10, Issue 8 (1988) 503-07.
Davies, G et al., "Structures and mechanisms of glycosyl hydrolases," Structure, vol. 3, Issue 9 (1995) 853-9.
Excoffier, G., et al., "Saccharification of Steam-Exploded Poplar Wood," Biotechnology and Bioengineering, vol. 38, Issue 11 (1991) 1308-17.
Fagerstam, L.G., et al., "The primary structure of a 1,4-β-glucan cellobiohydrolase from the fungus *Trichoderma reesei* QM 9414," FEBS Letters, vol. 167, No. 2 (1984) 309-15.
Foreman, P.K., et al., "Transcriptional Regulation of Biomass-degrading Enzymes in the Filamentous Fungus *Trichoderma reesei*," Journal of Biological Chemistry, vol. 278, Issue 34 (2003) 31988-997.
Gilkes, N.R., et al., "Domains in Microbial beta-1,4-Glycanases: Sequence Conservation, Function, and Enzyme Families," Microbiology Reviews, vol. 55, Issue 2 (1991) 303-15.
Hashimoto, H., "Recent structural studies of carbohydrate-binding modules," Cell. Mol. Life Sci., vol. 63 (2006) 2954-67.
Herner, M.L., et al., "Enhancement of the Affinity of Cellobiohydrolases I and Its Catalytic Domain to Cellulose in the Presence of the Reaction Product—Cellobiose," Biochemistry (Moscow), vol. 64, Issue 9 (1999) 1012-20.
Ilmen, M., et al., "Regulation of cellulase gene expression in the filamentous fungus *Trichoderma reesei.*," Appl. Environ. Microbiol., vol. 63, Issue 4 (1997) 1298-06.
Kaya, F., et al., "Influence of lignin and its degradation products on enzymatic hydrolysis of xylan," Journal of Biotechnology, vol. 80, Issue 3 (2000) 241-47.
Kong, F., et al., "Effects of Cell-Wall Acetate, Xylan Backbone, and Lignin on Enzymatic Hydrolysis of Aspen Wood," Applied Biochemistry and Biotechnology, vol. 34/35 (1992) 23-5.
Kraulis, J., et al., "Determination of the Three-Dimensional Solution Structure of the C-Terminal Domain of Cellobiohydrolase I from Trichoderma reesei, A Study Using Nuclear Magnetic Resonance and Hybrid Distance Geometry-Dynamical Simulated Annealing, Biochemistry," vol. 28 (1998) 7241-57.
Linder, et al., "Identification of functionally important amino acids in the cellulose-binding domain of Trichoderma reesei cellobiohydrolase I," Protein Science, vol. 4, No. 6 (1995) 1056-64.
Linder, M., et al., "Design of a pH-dependent cellulose-binding domain," FEBS Letters, vol. 447 (1999) 13-16.
Mattinen, M.L., et al., "Interaction between cellohexaose and cellulose binding domains from Trichoderma reesei cellulases," FEBS Letters, vol. 407, Issue 3 (1997) 291-96.
Meunier-Goddik, L., et al., "Enzyme-Catalyzed Saccharification of Model Celluloses in the Presence of Lignacious Residues," Journal of Agricultural and Food Chemistry, vol. 47, Issue 1 (1999) 346-51.
Mooney, C.A., et al., "The effect of initial pore volume and lignin content on the enzymatic hydrolysis of softwoods," Bioresource Technology, vol. 64 (1998) 113-19.
Nidetzky, B., et al., "Cellulose hydrolysis by the cellulases from Trichoderma reesei: adsorption of two cellobiohydrolases, two endocellulases and their core proteins on filter paper and their relation to hydrolysis," Biochem. J., vol. 303 (1994) 817-23.
Palonen, H., et al., "Adsorption of Trichoderma reesei CBH I and EG II and their catalytic domains on steam pretreated softwood and isolated lignin," Journal of Biotechnology, vol. 107 (2004) 65-72.
Receveur, V., et al., "Dimension, Shape, and Conformational Flexibility of a Two Domain Fungal Cellulase in Solution Probed by Small Angle X-Ray Scattering, Journal of Biological Chemistry," vol. 277, Issue 43 (2002) 40887-892.
Reinikainen, et al., "Investigation of the Function of Mutated Cellulose-Binding Domains of Trichoderma reesei Cellobiohydrolase I," PROTEINS: Structure, Function and Genetics, vol. 14, No. 4 (1992) 475-82.
Saloheimo, M., et al., "Swollenin, a Trichoderma reesei protein with sequence similarity to the plant expansins, exhibits disruption activity on cellulosic materials," European Journal of Biochemistry, vol. 269 (2002) 4202-11.
Shen, H., et al., "Deletion of the Linker Connecting the Catalytic and Cellulose-binding Domains of Endoglucanase A (CenA) of Cellulomonas fimi Alters Its Conformation and Catalytic Activity," Journal of Biological Chemistry, vol. 266, Issue 17 (1991) 11335-340.
Suyama, M., et al., "DomCut: prediction of inter-domain linker regions in amino acid sequences," Bioinformatics, vol. 19, Issue 5 (2003) 673-74.
Tormo, J., et al., "Crystal structure of a bacterial family-III cellulose-binding domain: a general mechanism for attachment to cellulose," EMBO Journal, vol. 15, Issue 21 (1996) 5739-51.
Tu, M., et al., "Evaluating the Distribution of Cellulases and the Recycling of Free Cellulases during the Hydrolysis of Lignocellulosic Substrates," Biotechnology Progress, vol. 23, Issue 2 (2007) 398-06.
Yang, B., et al., "BSA Treatment to Enhance Enzymatic Hydrolysis of Cellulose in Lignin Containing Substrates," Biotechnology and Bioengineering, vol. 94, Issue 4 (2006) pp. 611-617.

* cited by examiner

A.
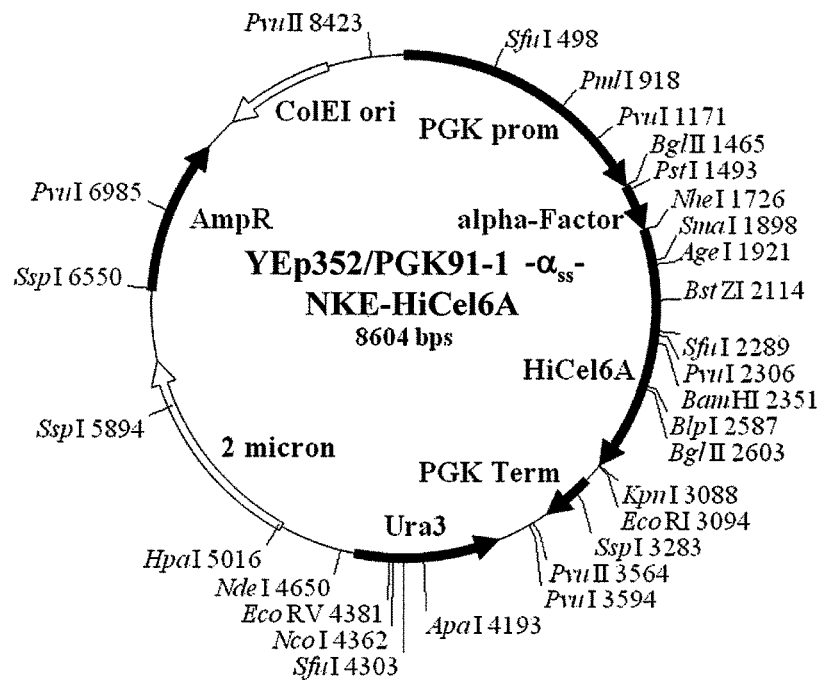
B.
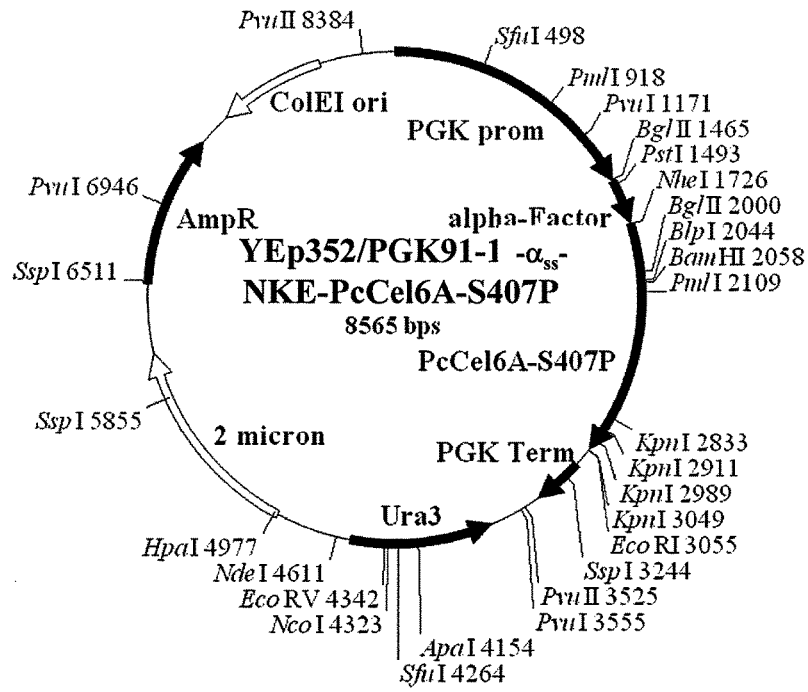
Figure 5

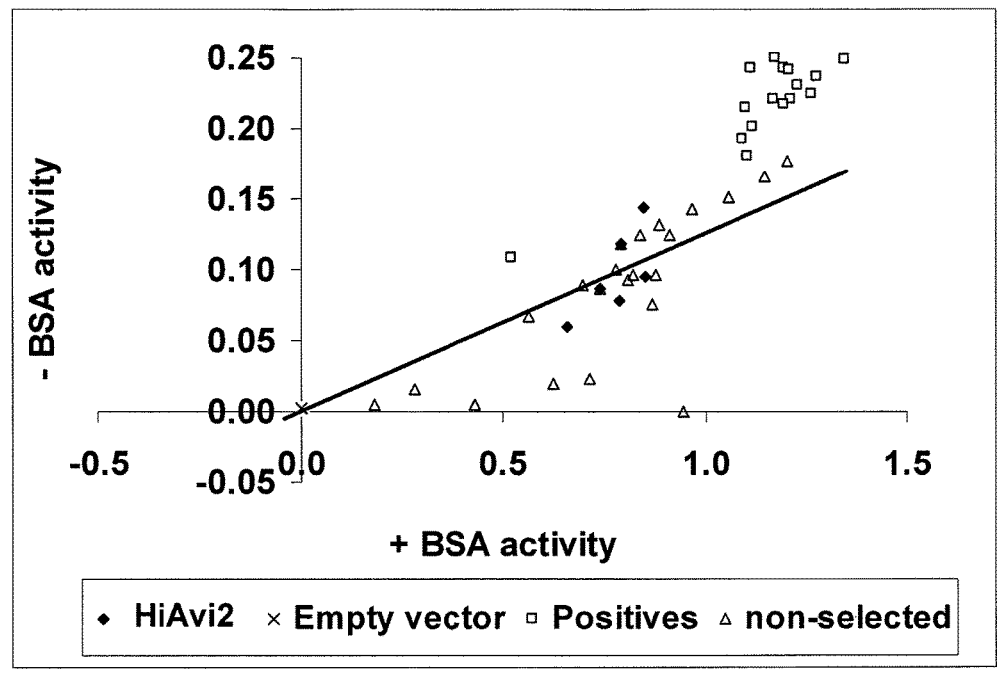
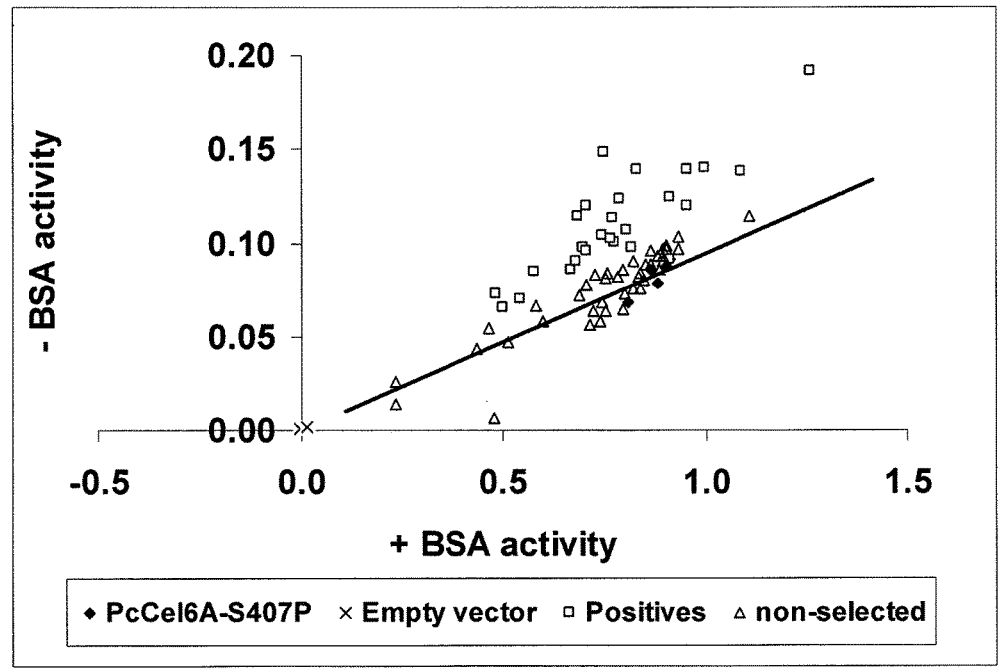
Figure 7

Value of $P$ = 0.0035 a. TrCel7A CBM
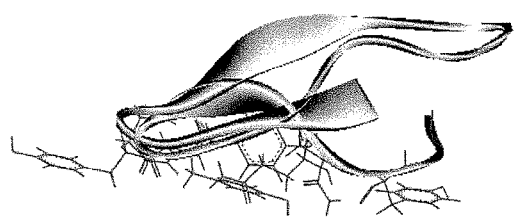
B. TrCel6A CBM
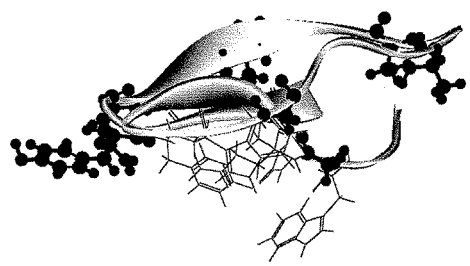
C. HiAvi2 CBM
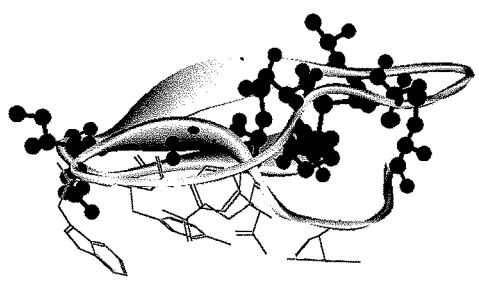
D. PcCel6A CBM
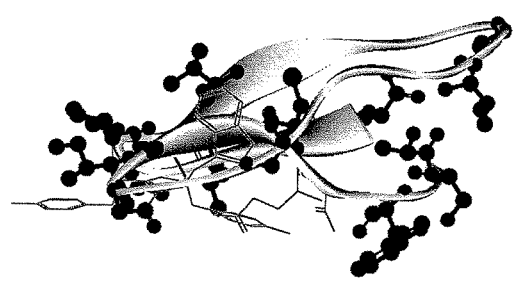
Figure 12

| SEQ ID NO: | | |
|---|---|---|
| 6 | AXE1_PENPU/346-382 | GVAAHWGQCGG..SGWTGPT.VCESGYTCTYSNA..WYSQCL |
| 7 | AXE1_TRIRE/266-302 | PTQTHWGQCGG..QGWTGPT.QCESGTTCQVISQ..WYSQCL |
| 8 | CEL1_AGABI/284-320 | GTIPQYGQCGG..IGWTGGT.GCVAPYQCKVIND..YYSQCL |
| 9 | FAEB_PENFN/317-353 | CTAAHWAQCGG..IGYSGCT.ACASPYTCQKAND..YYSQCL |
| 10 | GUN1_TRILO/427-463 | CTQTHWGQCGG..IGYTGCK.TCTSGTTCQYGND..YYSQCL |
| 11 | GUN1_TRIRE/423-459 | CTQTHWGQCGG..IGYSGCK.TCTSGTTCQYSND..YYSQCL |
| 12 | GUN2_TRIRE/21-57 | AQQTVWGQCGG..IGWSGPT.NCAPGSACSTLNP..YYAQCI |
| 13 | GUN3_HUMIN/16-52 | AQGGAWQQCGG..VGFSGST.SCVSGYTCVYLND..WYSQCQ |
| 14 | GUN4_TRIRE/307-343 | PTQTLYGQCGG..SGYSGPT.RCAPPATCSTLNP..YYAQCL |
| 15 | GUN5_TRIRE/205-241 | GQQTLYGQCGG..AGWTGPT.TCQAPGTCKVQNQ..WYSQCL |
| 16 | GUNB_FUSOX/25-61 | CSNGVWAQCGG..QNWSGTP.CCTSGNKCVKLND..FYSQCQ |
| 17 | GUNF_FUSOX/17-53 | AQAPIWGQCGG..NGWTGAT.TCASGLKCEKIND..WYYQCV |
| 18 | GUNK_FUSOX/335-374 | SVVPAYYQCGGskSAYPNGNlACATGSKCVKQNE..YYSQCV |
| 19 | GUX1A_NEUCR/485-521 | TGAAHWAQCGG..IGFSGPT.TCQSPYTCQKIND..YYSQCV |
| 20 | GUX1B_NEUCR/480-516 | TGAAHWAQCGG..IGFSGPT.TCPEPYTCAKDHD..IYSQCV |
| 21 | GUX1_ASPAC/505-540 | NVAQLYGQCGG..QGWTGPT.TCASG-TCTKQND..YYSQCL |
| 22 | GUX1_HUMGT/489-525 | PKAGRWQQCGG..IGFTGPT.QCEEPYICTKLND..WYSQCL |
| 23 | GUX1_PENJA/501-537 | TGARDWAQCGG..NGWTGPT.TCVSPYTCTKQND..WYSQCL |
| 24 | GUX1_PHACH/480-516 | VTVPQWGQCGG..IGYTGST.TCASPYTCHVLNP..YYSQCY |
| 25 | GUX1_TRIHA/469-505 | ATQTHYGQCGG..TGWTGPT.RCASGYTCQVLNP..FYSQCL |
| 26 | GUX1_TRIKO/477-513 | PTQSHYGQCGG..IGYSGPT.VCASGTTCQVLNP..YYSQCL |
| 27 | GUX1_TRIRE/477-513 | PTQSHYGQCGG..IGYSGPT.VCASGTTCQVLNP..YYSQCL |
| 28 | GUX1_TRIVI/478-514 | PTQTHYGQCGG..IGYSGPT.VCASGSTCQVLNP..YYSQCL |
| 29 | GUX2_AGABI/470-506 | PAQTMWGQCGG..QGWTGPT.ACQSPSTCHVIND..FYSQCF |
| 30 | GUX2_TRIRE/25-62 | QACSSVWGQCGG..QNWSGPT.CCASGSTCVYSND..YYSQCL |
| 31 | GUX3_AGABI/20-56 | AQSPVWGQCGG..NGWTGPT.TCASGSTCVKQND..FYSQCL |
| 32 | GUX6_HUMIN/25-61 | NCAPTWGQCGG..IGFNGPT.CCQSGSTCVKQND..WYSQCL |
| 33 | GUXC_FUSOX/478-514 | GSVDQWGQCGG..QNYSGPT.TCKSPFTCKKIND..FYSQCQ |
| 34 | PSBP_PORPU/22-58 | ACGVLYEQCGG..IGFDGVT.CCSEGLMCMKMGP..YYSQCR |
| 35 | PSBP_PORPU/65-101 | GQVKPYGQCGG..MNYSGKT.MCSPGFKCVELNE..FFSQCD |
| 36 | PSBP_PORPU/124-161 | VCGKEYAACGG..EMFMGAK.CCKFGLVCYETSGk.WQSQCR |
| 37 | PSBP_PORPU/168-206 | GEVGRYAQCGG..MGYMGST.MCVGGYKCMAISEgsMYKQCL |
| 38 | YKK5_SCHPO/25-61 | QCSPRYGTCGG..IYYDGPT.CCVVGSSCIYSNP..WYSQCI |
| 39 | YKK5_SCHPO/68-104 | PCAKLYQQCGG..INYNGPT.CCEPGSECIYNGP..YYSQCI |

```
                          1         10        20        30      38
TrCel6A-CBM (SEQ ID NO: 30)   QACSSVWGQCGGQNWSGPTCCASGSTCVYSNDYYSQCL
HiAvi2-CBM  (SEQ ID NO: 32)   ANCAPTWGQCGGIGFNGPTCCQSGSTCVKQNDWYSQCL
PcCel6A-CBM (SEQ ID NO: 99)   -A-SSEWGGCGGIGWTGPTTCVSGTTCTVLNPYYSQCL
TrCel7A-CBM (SEQ ID NO: 27)   PT-QSHYGQCGGIGYSGPTVCASGTTCGVLNPYYSQCL
```

Figure 15

SEQUENCE LISTING

```
<160> NUMBER OF SEQ ID NOS: 124

<210> SEQ ID NO 1
<211> LENGTH: 447
<212> TYPE: PRT
<213> ORGANISM: Trichoderma reesei

<400> SEQUENCE: 1

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95
```

```
Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
        115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Ser His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 2
<211> LENGTH: 453
<212> TYPE: PRT
<213> ORGANISM: Humicola insolens

<400> SEQUENCE: 2

Ala Ser Cys Ala Pro Thr Trp Gly Gln Cys Gly Gly Ile Gly Phe Asn
1               5                   10                  15

Gly Pro Thr Cys Cys Gln Ser Gly Ser Thr Cys Val Lys Gln Asn Asp
            20                  25                  30
```

```
Trp Tyr Ser Gln Cys Leu Pro Gly Ser Gln Val Thr Thr Ser Thr
        35                  40                  45
Thr Ser Thr Ser Ser Ser Thr Thr Ser Arg Ala Thr Ser Thr Thr
 50                  55                  60
Arg Thr Gly Gly Val Thr Ser Ile Thr Thr Ala Pro Thr Arg Thr Val
 65                  70                  75                  80
Thr Ile Pro Gly Gly Ala Thr Thr Thr Ala Ser Tyr Asn Gly Asn Pro
                 85                  90                  95
Phe Glu Gly Val Gln Leu Trp Ala Asn Asn Tyr Tyr Arg Ser Glu Val
                100                 105                 110
His Thr Leu Ala Ile Pro Gln Ile Thr Asp Pro Ala Leu Arg Ala Ala
                115                 120                 125
Ala Ser Ala Val Ala Glu Val Pro Ser Phe Gln Trp Leu Asp Arg Asn
130                 135                 140
Val Thr Val Asp Thr Leu Leu Val Glu Thr Leu Ser Glu Ile Arg Ala
145                 150                 155                 160
Ala Asn Gln Ala Gly Ala Asn Pro Pro Tyr Ala Ala Gln Ile Val Val
                165                 170                 175
Tyr Asp Leu Pro Asp Arg Asp Cys Ala Ala Ala Ser Asn Gly Glu
                180                 185                 190
Trp Ala Ile Ala Asn Asn Gly Ala Asn Asn Tyr Lys Gly Tyr Ile Asn
                195                 200                 205
Arg Ile Arg Glu Ile Leu Ile Ser Phe Ser Asp Val Arg Thr Ile Leu
210                 215                 220
Val Ile Glu Pro Asp Ser Leu Ala Asn Met Val Thr Asn Met Asn Val
225                 230                 235                 240
Ala Lys Cys Ser Gly Ala Ala Ser Thr Tyr Arg Glu Leu Thr Ile Tyr
                245                 250                 255
Ala Leu Lys Gln Leu Asp Leu Pro His Val Ala Met Tyr Met Asp Ala
                260                 265                 270
Gly His Ala Gly Trp Leu Gly Trp Pro Ala Asn Ile Gln Pro Ala Ala
                275                 280                 285
Glu Leu Phe Ala Lys Ile Tyr Glu Asp Ala Gly Lys Pro Arg Ala Val
                290                 295                 300
Arg Gly Leu Ala Thr Asn Val Ala Asn Tyr Asn Ala Trp Ser Ile Ser
305                 310                 315                 320
Ser Pro Pro Pro Tyr Thr Ser Pro Asn Pro Asn Tyr Asp Glu Lys His
                325                 330                 335
Tyr Ile Glu Ala Phe Arg Pro Leu Leu Glu Ala Arg Gly Phe Pro Ala
                340                 345                 350
Gln Phe Ile Val Asp Gln Gly Arg Ser Gly Lys Gln Pro Thr Gly Gln
                355                 360                 365
Lys Glu Trp Gly His Trp Cys Asn Ala Ile Gly Thr Gly Phe Gly Met
370                 375                 380
Arg Pro Thr Ala Asn Thr Gly His Gln Tyr Val Asp Ala Phe Val Trp
385                 390                 395                 400
Val Lys Pro Gly Gly Glu Cys Asp Gly Thr Ser Asp Thr Thr Ala Ala
                405                 410                 415
Arg Tyr Asp Tyr His Cys Gly Leu Glu Asp Ala Leu Lys Pro Ala Pro
                420                 425                 430
Glu Ala Gly Gln Trp Phe Gln Ala Tyr Phe Glu Gln Leu Leu Arg Asn
                435                 440                 445
```

-continued

```
Ala Asn Pro Pro Phe
    450

<210> SEQ ID NO 3
<211> LENGTH: 440
<212> TYPE: PRT
<213> ORGANISM: Phanerochaete chrysosporium

<400> SEQUENCE: 3

Ala Ser Ser Glu Trp Gly Gln Cys Gly Ile Gly Trp Thr Gly Pro
1               5                   10                  15

Thr Thr Cys Val Ser Gly Thr Thr Cys Thr Val Leu Asn Pro Tyr Tyr
            20                  25                  30

Ser Gln Cys Leu Pro Gly Ser Ala Val Thr Thr Ser Val Ile Thr
            35                  40                  45

Ser His Ser Ser Ser Val Ser Ser Val Ser Ser His Ser Gly Ser Ser
        50                  55                  60

Thr Ser Thr Ser Ser Pro Thr Gly Pro Thr Gly Thr Asn Pro Pro
65                  70                  75                  80

Pro Pro Ser Ala Asn Asn Pro Trp Thr Gly Phe Gln Ile Phe Leu Ser
                85                  90                  95

Pro Tyr Tyr Ala Asn Glu Val Ala Ala Ala Lys Gln Ile Thr Asp
                100                 105                 110

Pro Thr Leu Ser Ser Lys Ala Ala Ser Val Ala Asn Ile Pro Thr Phe
                115                 120                 125

Thr Trp Leu Asp Ser Val Ala Lys Ile Pro Asp Leu Gly Thr Tyr Leu
        130                 135                 140

Ala Ser Ala Ser Ala Leu Gly Lys Ser Thr Gly Thr Lys Gln Leu Val
145                 150                 155                 160

Gln Ile Val Ile Tyr Asp Leu Pro Asp Arg Asp Cys Ala Ala Lys Ala
                165                 170                 175

Ser Asn Gly Glu Phe Ser Ile Ala Asn Asn Gly Gln Ala Asn Tyr Glu
                180                 185                 190

Asn Tyr Ile Asp Gln Ile Val Ala Gln Ile Gln Gln Phe Pro Asp Val
            195                 200                 205

Arg Val Val Ala Val Ile Glu Pro Asp Ser Leu Ala Asn Leu Val Thr
    210                 215                 220

Asn Leu Asn Val Gln Lys Cys Ala Asn Ala Lys Thr Thr Tyr Leu Ala
225                 230                 235                 240

Cys Val Asn Tyr Ala Leu Thr Asn Leu Ala Lys Val Gly Val Tyr Met
                245                 250                 255

Tyr Met Asp Ala Gly His Ala Gly Trp Leu Gly Trp Pro Ala Asn Leu
                260                 265                 270

Ser Pro Ala Ala Gln Leu Phe Thr Gln Val Trp Gln Asn Ala Gly Lys
        275                 280                 285

Ser Pro Phe Ile Lys Gly Leu Ala Thr Asn Val Ala Asn Tyr Asn Ala
        290                 295                 300

Leu Gln Ala Ala Ser Pro Asp Pro Ile Thr Gln Gly Asn Pro Asn Tyr
305                 310                 315                 320

Asp Glu Ile His Tyr Ile Asn Ala Leu Ala Pro Leu Leu Gln Gln Ala
                325                 330                 335

Gly Trp Asp Ala Thr Phe Ile Val Asp Gln Gly Arg Ser Gly Val Gln
                340                 345                 350

Asn Ile Arg Gln Gln Trp Gly Asp Trp Cys Asn Ile Lys Gly Ala Gly
        355                 360                 365
```

```
Phe Gly Thr Arg Pro Thr Thr Asn Thr Gly Ser Gln Phe Ile Asp Ser
    370                 375                 380

Ile Val Trp Val Lys Pro Gly Gly Glu Cys Asp Gly Thr Ser Asn Ser
385                 390                 395                 400

Ser Ser Pro Arg Tyr Asp Ser Thr Cys Ser Leu Pro Asp Ala Ala Gln
            405                 410                 415

Pro Ala Pro Glu Ala Gly Thr Trp Phe Gln Ala Tyr Phe Gln Thr Leu
        420                 425                 430

Val Ser Ala Ala Asn Pro Pro Leu
    435                 440

<210> SEQ ID NO 4
<211> LENGTH: 447
<212> TYPE: PRT
<213> ORGANISM: Trichoderma reesei

<400> SEQUENCE: 4

Ala Ser Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
```

```
            290                 295                 300
Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 5
<211> LENGTH: 440
<212> TYPE: PRT
<213> ORGANISM: Phanerochaete chrysosporium

<400> SEQUENCE: 5

Ala Ser Ser Glu Trp Gly Gln Cys Gly Gly Ile Gly Trp Thr Gly Pro
1               5                  10                  15

Thr Thr Cys Val Ser Gly Thr Cys Thr Val Leu Asn Pro Tyr Tyr
                20                  25                  30

Ser Gln Cys Leu Pro Gly Ser Ala Val Thr Thr Thr Ser Val Ile Thr
            35                  40                  45

Ser His Ser Ser Ser Val Ser Ser Val Ser Ser His Ser Gly Ser Ser
        50                  55                  60

Thr Ser Thr Ser Ser Pro Thr Gly Pro Thr Gly Thr Asn Pro Pro Pro
65                  70                  75                  80

Pro Pro Ser Ala Asn Asn Pro Trp Thr Gly Phe Gln Ile Phe Leu Ser
                85                  90                  95

Pro Tyr Tyr Ala Asn Glu Val Ala Ala Ala Ala Lys Gln Ile Thr Asp
            100                 105                 110

Pro Thr Leu Ser Ser Lys Ala Ala Ser Val Ala Asn Ile Pro Thr Phe
        115                 120                 125

Thr Trp Leu Asp Ser Val Ala Lys Ile Pro Asp Leu Gly Thr Tyr Leu
    130                 135                 140

Ala Ser Ala Ser Ala Leu Gly Lys Ser Thr Gly Thr Lys Gln Leu Val
145                 150                 155                 160

Gln Ile Val Ile Tyr Asp Leu Pro Asp Arg Asp Cys Ala Ala Lys Ala
                165                 170                 175

Ser Asn Gly Glu Phe Ser Ile Ala Asn Asn Gly Gln Ala Asn Tyr Glu
            180                 185                 190

Asn Tyr Ile Asp Gln Ile Val Ala Gln Ile Gln Gln Phe Pro Asp Val
        195                 200                 205

Arg Val Val Ala Val Ile Glu Pro Asp Ser Leu Ala Asn Leu Val Thr
    210                 215                 220
```

-continued

```
Asn Leu Asn Val Gln Lys Cys Ala Asn Ala Lys Thr Thr Tyr Leu Ala
225                 230                 235                 240

Cys Val Asn Tyr Ala Leu Thr Asn Leu Ala Lys Val Gly Val Tyr Met
            245                 250                 255

Tyr Met Asp Ala Gly His Ala Gly Trp Leu Gly Trp Pro Ala Asn Leu
        260                 265                 270

Ser Pro Ala Ala Gln Leu Phe Thr Gln Val Trp Gln Asn Ala Gly Lys
    275                 280                 285

Ser Pro Phe Ile Lys Gly Leu Ala Thr Asn Val Ala Asn Tyr Asn Ala
290                 295                 300

Leu Gln Ala Ala Ser Pro Asp Pro Ile Thr Gln Gly Asn Pro Asn Tyr
305                 310                 315                 320

Asp Glu Ile His Tyr Ile Asn Ala Leu Ala Pro Leu Leu Gln Gln Ala
            325                 330                 335

Gly Trp Asp Ala Thr Phe Ile Val Asp Gln Gly Arg Ser Gly Val Gln
        340                 345                 350

Asn Ile Arg Gln Gln Trp Gly Asp Trp Cys Asn Ile Lys Gly Ala Gly
    355                 360                 365

Phe Gly Thr Arg Pro Thr Thr Asn Thr Gly Ser Gln Phe Ile Asp Ser
370                 375                 380

Ile Val Trp Val Lys Pro Gly Gly Glu Cys Asp Gly Thr Ser Asn Ser
385                 390                 395                 400

Ser Ser Pro Arg Tyr Asp Pro Thr Cys Ser Leu Pro Asp Ala Ala Gln
            405                 410                 415

Pro Ala Pro Glu Ala Gly Thr Trp Phe Gln Ala Tyr Phe Gln Thr Leu
        420                 425                 430

Val Ser Ala Ala Asn Pro Pro Leu
        435                 440

<210> SEQ ID NO 6
<211> LENGTH: 37
<212> TYPE: PRT
<213> ORGANISM: Penicillium purpurogenum

<400> SEQUENCE: 6

Gly Val Ala Ala His Trp Gly Gln Cys Gly Gly Ser Gly Trp Thr Gly
1               5                   10                  15

Pro Thr Val Cys Glu Ser Gly Tyr Thr Cys Thr Tyr Ser Asn Ala Trp
            20                  25                  30

Tyr Ser Gln Cys Leu
        35

<210> SEQ ID NO 7
<211> LENGTH: 37
<212> TYPE: PRT
<213> ORGANISM: Trichoderma reesei

<400> SEQUENCE: 7

Pro Thr Gln Thr His Trp Gly Gln Cys Gly Gly Gln Gly Trp Thr Gly
1               5                   10                  15

Pro Thr Gln Cys Glu Ser Gly Thr Thr Cys Gln Val Ile Ser Gln Trp
            20                  25                  30

Tyr Ser Gln Cys Leu
        35

<210> SEQ ID NO 8
<211> LENGTH: 37
```

```
<212> TYPE: PRT
<213> ORGANISM: Agaricus bisporus

<400> SEQUENCE: 8

Gly Thr Ile Pro Gln Tyr Gly Gln Cys Gly Gly Ile Gly Trp Thr Gly
1               5                   10                  15

Gly Thr Gly Cys Val Ala Pro Tyr Gln Cys Lys Val Ile Asn Asp Tyr
            20                  25                  30

Tyr Ser Gln Cys Leu
        35

<210> SEQ ID NO 9
<211> LENGTH: 37
<212> TYPE: PRT
<213> ORGANISM: Penicillium funiculosum

<400> SEQUENCE: 9

Cys Thr Ala Ala His Trp Ala Gln Cys Gly Gly Ile Gly Tyr Ser Gly
1               5                   10                  15

Cys Thr Ala Cys Ala Ser Pro Tyr Thr Cys Gln Lys Ala Asn Asp Tyr
            20                  25                  30

Tyr Ser Gln Cys Leu
        35

<210> SEQ ID NO 10
<211> LENGTH: 37
<212> TYPE: PRT
<213> ORGANISM: Trichoderma longibrachiatum

<400> SEQUENCE: 10

Cys Thr Gln Thr His Trp Gly Gln Cys Gly Gly Ile Gly Tyr Thr Gly
1               5                   10                  15

Cys Lys Thr Cys Thr Ser Gly Thr Thr Cys Gln Tyr Gly Asn Asp Tyr
            20                  25                  30

Tyr Ser Gln Cys Leu
        35

<210> SEQ ID NO 11
<211> LENGTH: 37
<212> TYPE: PRT
<213> ORGANISM: Trichoderma reesei

<400> SEQUENCE: 11

Cys Thr Gln Thr His Trp Gly Gln Cys Gly Gly Ile Gly Tyr Ser Gly
1               5                   10                  15

Cys Lys Thr Cys Thr Ser Gly Thr Thr Cys Gln Tyr Ser Asn Asp Tyr
            20                  25                  30

Tyr Ser Gln Cys Leu
        35

<210> SEQ ID NO 12
<211> LENGTH: 37
<212> TYPE: PRT
<213> ORGANISM: Trichoderma reesei

<400> SEQUENCE: 12

Ala Gln Gln Thr Val Trp Gly Gln Cys Gly Gly Ile Gly Trp Ser Gly
1               5                   10                  15

Pro Thr Asn Cys Ala Pro Gly Ser Ala Cys Ser Thr Leu Asn Pro Tyr
            20                  25                  30
```

Tyr Ala Gln Cys Ile
        35

<210> SEQ ID NO 13
<211> LENGTH: 37
<212> TYPE: PRT
<213> ORGANISM: Humicola insolens

<400> SEQUENCE: 13

Ala Gln Gly Gly Ala Trp Gln Gln Cys Gly Gly Val Gly Phe Ser Gly
1               5                   10                  15

Ser Thr Ser Cys Val Ser Gly Tyr Thr Cys Val Tyr Leu Asn Asp Trp
                20                  25                  30

Tyr Ser Gln Cys Gln
        35

<210> SEQ ID NO 14
<211> LENGTH: 37
<212> TYPE: PRT
<213> ORGANISM: Trichoderma reesei

<400> SEQUENCE: 14

Pro Thr Gln Thr Leu Tyr Gly Gln Cys Gly Gly Ser Gly Tyr Ser Gly
1               5                   10                  15

Pro Thr Arg Cys Ala Pro Pro Ala Thr Cys Ser Thr Leu Asn Pro Tyr
                20                  25                  30

Tyr Ala Gln Cys Leu
        35

<210> SEQ ID NO 15
<211> LENGTH: 37
<212> TYPE: PRT
<213> ORGANISM: Trichoderma reesei

<400> SEQUENCE: 15

Gly Gln Gln Thr Leu Tyr Gly Gln Cys Gly Gly Ala Gly Trp Thr Gly
1               5                   10                  15

Pro Thr Thr Cys Gln Ala Pro Gly Thr Cys Lys Val Gln Asn Gln Trp
                20                  25                  30

Tyr Ser Gln Cys Leu
        35

<210> SEQ ID NO 16
<211> LENGTH: 37
<212> TYPE: PRT
<213> ORGANISM: Fusarium oxysporum

<400> SEQUENCE: 16

Cys Ser Asn Gly Val Trp Ala Gln Cys Gly Gly Gln Asn Trp Ser Gly
1               5                   10                  15

Thr Pro Cys Cys Thr Ser Gly Asn Lys Cys Val Lys Leu Asn Asp Phe
                20                  25                  30

Tyr Ser Gln Cys Gln
        35

<210> SEQ ID NO 17
<211> LENGTH: 37
<212> TYPE: PRT
<213> ORGANISM: Fusarium oxysporum

<400> SEQUENCE: 17

```
Ala Gln Ala Pro Ile Trp Gly Gln Cys Gly Asn Gly Trp Thr Gly
1               5                   10                  15

Ala Thr Thr Cys Ala Ser Gly Leu Lys Cys Glu Lys Ile Asn Asp Trp
            20                  25                  30

Tyr Tyr Gln Cys Val
        35
```

```
<210> SEQ ID NO 18
<211> LENGTH: 40
<212> TYPE: PRT
<213> ORGANISM: Fusarium oxysporum

<400> SEQUENCE: 18

Ser Val Val Pro Ala Tyr Tyr Gln Cys Gly Gly Ser Lys Ser Ala Tyr
1               5                   10                  15

Pro Asn Gly Asn Leu Ala Cys Ala Thr Gly Ser Lys Cys Val Lys Gln
            20                  25                  30

Asn Glu Tyr Tyr Ser Gln Cys Val
        35                  40
```

```
<210> SEQ ID NO 19
<211> LENGTH: 37
<212> TYPE: PRT
<213> ORGANISM: Neurospora crassa

<400> SEQUENCE: 19

Thr Gly Ala Ala His Trp Ala Gln Cys Gly Gly Ile Gly Phe Ser Gly
1               5                   10                  15

Pro Thr Thr Cys Gln Ser Pro Tyr Thr Cys Gln Lys Ile Asn Asp Tyr
            20                  25                  30

Tyr Ser Gln Cys Val
        35
```

```
<210> SEQ ID NO 20
<211> LENGTH: 37
<212> TYPE: PRT
<213> ORGANISM: Neurospora crassa

<400> SEQUENCE: 20

Thr Gly Ala Ala His Trp Ala Gln Cys Gly Gly Ile Gly Phe Ser Gly
1               5                   10                  15

Pro Thr Thr Cys Pro Glu Pro Tyr Thr Cys Ala Lys Asp His Asp Ile
            20                  25                  30

Tyr Ser Gln Cys Val
        35
```

```
<210> SEQ ID NO 21
<211> LENGTH: 36
<212> TYPE: PRT
<213> ORGANISM: Aspergillus aculeatus

<400> SEQUENCE: 21

Asn Val Ala Gln Leu Tyr Gly Gln Cys Gly Gly Gln Gly Trp Thr Gly
1               5                   10                  15

Pro Thr Thr Cys Ala Ser Gly Thr Cys Thr Lys Gln Asn Asp Tyr Tyr
            20                  25                  30

Ser Gln Cys Leu
        35
```

```
<210> SEQ ID NO 22
```

```
<211> LENGTH: 37
<212> TYPE: PRT
<213> ORGANISM: Humicola grisea var. thermoidea

<400> SEQUENCE: 22

Pro Lys Ala Gly Arg Trp Gln Gln Cys Gly Gly Ile Gly Phe Thr Gly
1               5                   10                  15

Pro Thr Gln Cys Glu Glu Pro Tyr Ile Cys Thr Lys Leu Asn Asp Trp
            20                  25                  30

Tyr Ser Gln Cys Leu
        35

<210> SEQ ID NO 23
<211> LENGTH: 37
<212> TYPE: PRT
<213> ORGANISM: Penicillium janthinellum

<400> SEQUENCE: 23

Thr Gly Ala Arg Asp Trp Ala Gln Cys Gly Gly Asn Gly Trp Thr Gly
1               5                   10                  15

Pro Thr Thr Cys Val Ser Pro Tyr Thr Cys Thr Lys Gln Asn Asp Trp
            20                  25                  30

Tyr Ser Gln Cys Leu
        35

<210> SEQ ID NO 24
<211> LENGTH: 37
<212> TYPE: PRT
<213> ORGANISM: Phanerochaete chrysosporium

<400> SEQUENCE: 24

Val Thr Val Pro Gln Trp Gly Gln Cys Gly Gly Ile Gly Tyr Thr Gly
1               5                   10                  15

Ser Thr Thr Cys Ala Ser Pro Tyr Thr Cys His Val Leu Asn Pro Tyr
            20                  25                  30

Tyr Ser Gln Cys Tyr
        35

<210> SEQ ID NO 25
<211> LENGTH: 37
<212> TYPE: PRT
<213> ORGANISM: Trichoderma harzianum

<400> SEQUENCE: 25

Ala Thr Gln Thr His Tyr Gly Gln Cys Gly Gly Thr Gly Trp Thr Gly
1               5                   10                  15

Pro Thr Arg Cys Ala Ser Gly Tyr Thr Cys Gln Val Leu Asn Pro Phe
            20                  25                  30

Tyr Ser Gln Cys Leu
        35

<210> SEQ ID NO 26
<211> LENGTH: 37
<212> TYPE: PRT
<213> ORGANISM: Trichoderma koningii

<400> SEQUENCE: 26

Pro Thr Gln Ser His Tyr Gly Gln Cys Gly Gly Ile Gly Tyr Ser Gly
1               5                   10                  15

Pro Thr Val Cys Ala Ser Gly Thr Cys Gln Val Leu Asn Pro Tyr
            20                  25                  30
```

Tyr Ser Gln Cys Leu
        35

<210> SEQ ID NO 27
<211> LENGTH: 37
<212> TYPE: PRT
<213> ORGANISM: Trichoderma reesei

<400> SEQUENCE: 27

Pro Thr Gln Ser His Tyr Gly Gln Cys Gly Gly Ile Gly Tyr Ser Gly
1               5                   10                  15

Pro Thr Val Cys Ala Ser Gly Thr Thr Cys Gln Val Leu Asn Pro Tyr
            20                  25                  30

Tyr Ser Gln Cys Leu
        35

<210> SEQ ID NO 28
<211> LENGTH: 37
<212> TYPE: PRT
<213> ORGANISM: Trichoderma viride

<400> SEQUENCE: 28

Pro Thr Gln Thr His Tyr Gly Gln Cys Gly Gly Ile Gly Tyr Ser Gly
1               5                   10                  15

Pro Thr Val Cys Ala Ser Gly Ser Thr Cys Gln Val Leu Asn Pro Tyr
            20                  25                  30

Tyr Ser Gln Cys Leu
        35

<210> SEQ ID NO 29
<211> LENGTH: 37
<212> TYPE: PRT
<213> ORGANISM: Agaricus bisporus

<400> SEQUENCE: 29

Pro Ala Gln Thr Met Trp Gly Gln Cys Gly Gly Gln Gly Trp Thr Gly
1               5                   10                  15

Pro Thr Ala Cys Gln Ser Pro Ser Thr Cys His Val Ile Asn Asp Phe
            20                  25                  30

Tyr Ser Gln Cys Phe
        35

<210> SEQ ID NO 30
<211> LENGTH: 39
<212> TYPE: PRT
<213> ORGANISM: Trichoderma reesei

<400> SEQUENCE: 30

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Asn
        35

<210> SEQ ID NO 31
<211> LENGTH: 37
<212> TYPE: PRT
<213> ORGANISM: Agaricus bisporus

<400> SEQUENCE: 31

```
Ala Gln Ser Pro Val Trp Gly Gln Cys Gly Gly Asn Gly Trp Thr Gly
1               5                   10                  15

Pro Thr Thr Cys Ala Ser Gly Ser Thr Cys Val Lys Gln Asn Asp Phe
            20                  25                  30

Tyr Ser Gln Cys Leu
        35
```

<210> SEQ ID NO 32
<211> LENGTH: 38
<212> TYPE: PRT
<213> ORGANISM: Humicola insolens

<400> SEQUENCE: 32

```
Asn Cys Ala Pro Thr Trp Gly Gln Cys Gly Gly Ile Gly Phe Asn Gly
1               5                   10                  15

Pro Thr Cys Cys Gln Ser Gly Ser Thr Cys Val Lys Gln Asn Asp Trp
            20                  25                  30

Tyr Ser Gln Cys Leu Ala
        35
```

<210> SEQ ID NO 33
<211> LENGTH: 37
<212> TYPE: PRT
<213> ORGANISM: Fusarium oxysporum

<400> SEQUENCE: 33

```
Gly Ser Val Asp Gln Trp Gly Gln Cys Gly Gly Gln Asn Tyr Ser Gly
1               5                   10                  15

Pro Thr Thr Cys Lys Ser Pro Phe Thr Cys Lys Lys Ile Asn Asp Phe
            20                  25                  30

Tyr Ser Gln Cys Gln
        35
```

<210> SEQ ID NO 34
<211> LENGTH: 37
<212> TYPE: PRT
<213> ORGANISM: Porphyra purpurea

<400> SEQUENCE: 34

```
Ala Cys Gly Val Leu Tyr Glu Gln Cys Gly Gly Ile Gly Phe Asp Gly
1               5                   10                  15

Val Thr Cys Cys Ser Glu Gly Leu Met Cys Met Lys Met Gly Pro Tyr
            20                  25                  30

Tyr Ser Gln Cys Arg
        35
```

<210> SEQ ID NO 35
<211> LENGTH: 37
<212> TYPE: PRT
<213> ORGANISM: Porphyra purpurea

<400> SEQUENCE: 35

```
Gly Gln Val Lys Pro Tyr Gly Gln Cys Gly Gly Met Asn Tyr Ser Gly
1               5                   10                  15

Lys Thr Met Cys Ser Pro Gly Phe Lys Cys Val Glu Leu Asn Glu Phe
            20                  25                  30

Phe Ser Gln Cys Asp
        35
```

-continued

<210> SEQ ID NO 36
<211> LENGTH: 38
<212> TYPE: PRT
<213> ORGANISM: Porphyra purpurea

<400> SEQUENCE: 36

Val Cys Gly Lys Glu Tyr Ala Ala Cys Gly Gly Glu Met Phe Met Gly
1               5                   10                  15

Ala Lys Cys Cys Lys Phe Gly Leu Val Cys Tyr Glu Thr Ser Gly Lys
            20                  25                  30

Trp Gln Ser Gln Cys Arg
            35

<210> SEQ ID NO 37
<211> LENGTH: 39
<212> TYPE: PRT
<213> ORGANISM: Porphyra purpurea

<400> SEQUENCE: 37

Gly Glu Val Gly Arg Tyr Ala Gln Cys Gly Gly Met Gly Tyr Met Gly
1               5                   10                  15

Ser Thr Met Cys Val Gly Gly Tyr Lys Cys Met Ala Ile Ser Glu Gly
            20                  25                  30

Ser Met Tyr Lys Gln Cys Leu
            35

<210> SEQ ID NO 38
<211> LENGTH: 37
<212> TYPE: PRT
<213> ORGANISM: Schizosaccharomyces pombe

<400> SEQUENCE: 38

Gln Cys Ser Pro Arg Tyr Gly Thr Cys Gly Gly Ile Tyr Tyr Asp Gly
1               5                   10                  15

Pro Thr Cys Cys Val Val Gly Ser Ser Cys Ile Tyr Ser Asn Pro Trp
            20                  25                  30

Tyr Ser Gln Cys Ile
            35

<210> SEQ ID NO 39
<211> LENGTH: 37
<212> TYPE: PRT
<213> ORGANISM: Schizosaccharomyces pombe

<400> SEQUENCE: 39

Pro Cys Ala Lys Leu Tyr Gln Gln Cys Gly Gly Ile Asn Tyr Asn Gly
1               5                   10                  15

Pro Thr Cys Cys Glu Pro Gly Ser Glu Cys Ile Tyr Asn Gly Pro Tyr
            20                  25                  30

Tyr Ser Gln Cys Ile
            35

<210> SEQ ID NO 40
<211> LENGTH: 34
<212> TYPE: PRT
<213> ORGANISM: Trichoderma reesei

<400> SEQUENCE: 40

Gly His Tyr Ala Gln Cys Gly Gly Ile Gly Trp Thr Gly Pro Thr Gln
1               5                   10                  15

Cys Val Ala Pro Tyr Val Cys Gln Lys Gln Asn Asp Tyr Tyr Tyr Gln

```
                    20                  25                  30

Cys Val

<210> SEQ ID NO 41
<211> LENGTH: 32
<212> TYPE: PRT
<213> ORGANISM: Trichoderma reesei

<400> SEQUENCE: 41

Leu Tyr Gly Gln Cys Gly Gly Ser Gly Tyr Thr Gly Pro Thr Cys Cys
1               5                   10                  15

Ala Gln Gly Thr Cys Ile Tyr Ser Asn Tyr Trp Tyr Ser Gln Cys Leu
                20                  25                  30

<210> SEQ ID NO 42
<211> LENGTH: 33
<212> TYPE: PRT
<213> ORGANISM: Trichoderma reesei

<400> SEQUENCE: 42

His Tyr Gly Gln Cys Gly Gly Ile Gly Tyr Ser Gly Pro Thr Val Cys
1               5                   10                  15

Ala Ser Gly Thr Thr Cys Gln Val Leu Asn Pro Tyr Tyr Ser Gln Cys
                20                  25                  30

Leu

<210> SEQ ID NO 43
<211> LENGTH: 28
<212> TYPE: PRT
<213> ORGANISM: Trichoderma reesei

<400> SEQUENCE: 43

Trp Gly Gln Cys Gly Gly Ile Gly Trp Ser Gly Pro Thr Thr Cys Val
1               5                   10                  15

Gly Gly Ala Thr Cys Val Ser Tyr Asn Pro Tyr Tyr
                20                  25

<210> SEQ ID NO 44
<211> LENGTH: 34
<212> TYPE: PRT
<213> ORGANISM: Trichoderma reesei

<400> SEQUENCE: 44

Ala Leu Phe Gly Gln Cys Gly Gly Ile Gly Trp Ser Gly Thr Thr Cys
1               5                   10                  15

Cys Val Ala Gly Ala Gln Cys Ser Phe Val Asn Asp Trp Tyr Ser Gln
                20                  25                  30

Cys Leu

<210> SEQ ID NO 45
<211> LENGTH: 447
<212> TYPE: PRT
<213> ORGANISM: Trichoderma reesei

<400> SEQUENCE: 45

Ala Ser Cys Ser Ser Val Trp Gly Gln Cys Gly Gly Gln Asn Trp Ser
1               5                   10                  15

Gly Pro Thr Cys Cys Ala Ser Gly Ser Thr Cys Asp Tyr Ser Asn Asp
                20                  25                  30

Tyr Tyr Ser Gln Cys Leu Pro Gly Ala Ala Ser Ser Ser Ser Ser Thr
```

```
                35                  40                  45
Arg Ala Ala Ser Thr Thr Ser Arg Val Ser Pro Thr Thr Ser Arg Ser
 50                  55                  60

Ser Ser Ala Thr Pro Pro Gly Ser Thr Thr Thr Arg Val Pro Pro
 65                  70                  75                  80

Val Gly Ser Gly Thr Ala Thr Tyr Ser Gly Asn Pro Phe Val Gly Val
                     85                  90                  95

Thr Pro Trp Ala Asn Ala Tyr Tyr Ala Ser Glu Val Ser Ser Leu Thr
                100                 105                 110

Ile Pro Ser Leu Thr Gly Ala Met Ala Thr Ala Ala Val Ala
                115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Val
                180                 185                 190

Ala Lys Tyr Lys Asn Tyr Ile Asp Thr Ile Arg Gln Ile Val Val Glu
                195                 200                 205

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
                260                 265                 270

Pro Ala Asn Gln Asp Pro Ala Ala Gln Leu Phe Ala Asn Val Tyr Lys
                275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
                340                 345                 350

Arg Ser Gly Lys Glu Pro Thr Gly Gln Gln Gln Trp Gly Asp Trp Cys
                355                 360                 365

Asn Val Ile Gly Thr Gly Phe Gly Ile Arg Pro Ser Ala Asn Thr Gly
                370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                    405                 410                 415

Leu Pro Asp Ala Leu Gln Pro Ala Pro Gln Ala Gly Ala Trp Phe Gln
                420                 425                 430

Ala Tyr Phe Val Gln Leu Leu Thr Asn Ala Asn Pro Ser Phe Leu
                435                 440                 445

<210> SEQ ID NO 46
```

<211> LENGTH: 447
<212> TYPE: PRT
<213> ORGANISM: Trichoderma reesei

<400> SEQUENCE: 46

```
Ala Ser Cys Ser Ser Val Trp Asn Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Gly Ser Thr Thr Thr Arg Val Pro Pro
65                  70                  75                  80

Val Gly Ser Gly Thr Ala Met Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
```

```
            385                 390                 395                 400
Asp Gly Thr Ser Asp Ser Ser Ala Pro Arg Phe Asp Pro Tyr Cys Ala
                    405                 410                 415

Leu Pro Asp Ala Leu Gln Pro Ala Pro Gln Ala Gly Ala Trp Phe Gln
                    420                 425                 430

Ala Tyr Phe Val Gln Leu Leu Thr Asn Ala Asn Pro Ser Phe Leu
                    435                 440                 445

<210> SEQ ID NO 47
<211> LENGTH: 447
<212> TYPE: PRT
<213> ORGANISM: Trichoderma reesei

<400> SEQUENCE: 47

Ala Ser Cys Ser Ser Val Trp Gly Gln Cys Gly Gly Gln Asn Trp Ser
1               5                   10                  15

Asp Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
            35                  40                  45

Arg Ala Ala Ser Thr Thr Ser Arg Val Ser Pro Thr Thr Ser Arg Ser
50                  55                  60

Ser Ser Ala Thr Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
                100                 105                 110

Ile Pro Ser Leu Thr Gly Ala Met Ala Thr Ala Ala Ala Val Ala
            115                 120                 125

Lys Val Pro Ser Phe Met Trp Leu Asp Thr Leu Asp Lys Thr Pro Leu
            130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
            195                 200                 205

Tyr Ser Asp Ile Arg Thr Leu Leu Val Ile Glu Pro Asp Ser Leu Ala
            210                 215                 220

Asn Leu Val Thr Asn Leu Ser Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
            290                 295                 300

Asn Tyr Asn Gly Trp Asn Ile Thr Ser Pro Pro Ser Tyr Thr Gln Gly
305                 310                 315                 320
```

-continued

```
Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
            405                 410                 415

Leu Pro Asp Ala Leu Gln Pro Ala Pro Gln Ala Gly Ala Trp Phe Gln
        420                 425                 430

Ala Tyr Phe Val Gln Leu Leu Thr Asn Ala Asn Pro Ser Phe Leu
    435                 440                 445

<210> SEQ ID NO 48
<211> LENGTH: 447
<212> TYPE: PRT
<213> ORGANISM: Trichoderma reesei

<400> SEQUENCE: 48

Ala Ser Cys Ser Ser Val Trp Gly Gln Cys Gly Gly Gln Asn Trp Ser
1               5                   10                  15

Gly Pro Thr Cys Cys Thr Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255
```

-continued

```
Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 49
<211> LENGTH: 447
<212> TYPE: PRT
<213> ORGANISM: Trichoderma reesei

<400> SEQUENCE: 49

Ala Thr Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Asn Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
```

```
                180             185                 190
Ala Lys Tyr Lys Asn Tyr Ile Asp Thr Ile Arg Gln Ile Val Val Glu
            195                 200             205

Tyr Ser Asp Ile Arg Thr Leu Leu Val Ile Glu Pro Asp Ser Leu Ala
210             215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
            245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
            290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
            325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Trp Gly Asp Trp Cys
            355                 360                 365

Asn Val Ile Gly Thr Gly Phe Gly Ile Arg Pro Ser Ala Asn Thr Gly
            370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
            435                 440                 445

<210> SEQ ID NO 50
<211> LENGTH: 447
<212> TYPE: PRT
<213> ORGANISM: Trichoderma reesei

<400> SEQUENCE: 50

Ala Ser Cys Ser Ser Val Trp Asp Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110
```

```
Ile Pro Ser Leu Thr Gly Ala Met Ala Thr Ala Ala Ala Val Ala
            115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Ile Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 51
<211> LENGTH: 447
<212> TYPE: PRT
<213> ORGANISM: Trichoderma reesei

<400> SEQUENCE: 51

Ala Ser Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Ser Asp
            20                  25                  30

Tyr Tyr Ser Gln Cys Leu Pro Gly Ala Ala Ser Ser Ser Ser Ser Thr
        35                  40                  45
```

Arg Ala Ala Ser Thr Thr Ser Arg Val Ser Pro Thr Ser Arg Ser
50                  55                  60

Ser Ser Ala Thr Pro Pro Gly Ser Thr Thr Arg Val Pro Pro
65              70                  75                  80

Val Gly Ser Gly Thr Ala Thr Tyr Ser Gly Asn Pro Phe Val Gly Val
                    85                  90                  95

Thr Pro Trp Ala Asn Ala Tyr Tyr Ala Ser Glu Val Ser Ser Leu Ala
                100                 105                 110

Ile Pro Ser Leu Thr Gly Ala Met Ala Thr Ala Ala Ala Val Ala
            115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
                260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Asp
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 52
<211> LENGTH: 447

```
<212> TYPE: PRT
<213> ORGANISM: Trichoderma reesei

<400> SEQUENCE: 52

Ala Ser Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Ser Asp
            20                  25                  30

Tyr Tyr Ser Gln Cys Leu Pro Gly Ala Ser Ser Ser Ser Thr
        35                  40                  45

Arg Ala Ala Ser Thr Thr Ser Arg Val Ser Pro Thr Thr Ser Arg Ser
50                  55                  60

Ser Ser Ala Thr Pro Pro Gly Ser Thr Thr Thr Arg Val Pro Pro
65              70                  75                  80

Val Gly Ser Gly Thr Ala Thr Tyr Ser Gly Asn Pro Phe Val Gly Val
            85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
            115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
            165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
            195                 200                 205

Tyr Ser Asp Ile Arg Thr Leu Leu Val Ile Glu Pro Asp Ser Leu Ala
            210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
            245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
            325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Trp Gly Asp Trp Cys
            355                 360                 365

Asn Val Ile Gly Thr Gly Phe Gly Ile Arg Pro Ser Ala Asn Thr Gly
            370                 375                 380

Asp Ser Leu Leu Asp Ser Phe Val Trp Val Lys Pro Gly Gly Glu Cys
385                 390                 395                 400
```

-continued

Asp Gly Thr Ser Asp Ser Ser Ala Pro Arg Phe Asp Pro His Cys Ala
            405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
            435                 440                 445

<210> SEQ ID NO 53
<211> LENGTH: 447
<212> TYPE: PRT
<213> ORGANISM: Trichoderma reesei

<400> SEQUENCE: 53

Ala Ser Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Phe Pro Gly Ala Ala Ser Ser Ser Ser Ser Thr
            35                  40                  45

Arg Ala Ala Ser Thr Thr Ser Arg Glu Ser Pro Thr Thr Ser Arg Ser
50                  55                  60

Ser Ser Ala Thr Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
            85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
            115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Met Asn Gly Gly
145                 150                 155                 160

Asn Tyr Ala Gly Gln Phe Val Val Tyr Asp Leu Pro Asp Arg Asp Cys
            165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
            195                 200                 205

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
            245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
            290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu

```
                    325                 330                 335
Leu Ala Asn His Gly Trp Ser Asn Ala Phe Phe Ile Thr Asp Gln Gly
                340                 345                 350

Arg Ser Gly Lys Gln Pro Thr Gly Gln Gln Gln Trp Gly Asp Trp Cys
                355                 360                 365

Asn Val Ile Gly Thr Gly Phe Gly Ile Arg Pro Ser Ala Asn Thr Gly
                370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
                420                 425                 430

Ala Tyr Phe Val Gln Leu Leu Thr Asn Ala Asn Pro Ser Phe Leu
                435                 440                 445

<210> SEQ ID NO 54
<211> LENGTH: 447
<212> TYPE: PRT
<213> ORGANISM: Trichoderma reesei

<400> SEQUENCE: 54

Ala Ser Cys Ser Ser Val Trp Gly Gln Cys Gly Gly Gln Asn Trp Ser
1               5                   10                  15

Gly Pro Thr Cys Cys Ala Ser Gly Asn Thr Cys Val Tyr Ser Asn Asp
                20                  25                  30

Tyr Tyr Ser Gln Cys Leu Pro Gly Ala Ala Ser Ser Ser Ser Ser Thr
                35                  40                  45

Arg Ala Ala Ser Thr Thr Ser Arg Val Ser Pro Thr Thr Ser Arg Ser
            50                  55                  60

Ser Ser Ala Thr Pro Pro Pro Gly Ser Thr Thr Thr Arg Val Pro Pro
65              70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
                100                 105                 110

Ile Pro Ser Leu Thr Gly Ala Met Ala Thr Ala Ala Ala Ala Val Ala
                115                 120                 125

Lys Val Pro Ser Phe Met Trp Leu Asp Thr Leu Asp Lys Thr Pro Leu
            130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
                180                 185                 190

Ala Lys Tyr Lys Asn Tyr Ile Asp Thr Ile Arg Gln Ile Val Val Glu
                195                 200                 205

Tyr Ser Asp Ile Arg Thr Leu Leu Val Ile Glu Pro Asp Ser Leu Ala
                210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255
```

```
Asn Val Ala Met Tyr Leu Asp Ala Gly His Ala Gly Trp Leu Gly Trp
                260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
        290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 55
<211> LENGTH: 453
<212> TYPE: PRT
<213> ORGANISM: Humicola insolens

<400> SEQUENCE: 55

Ala Ser Cys Ala Pro Thr Trp Gly Gln Cys Gly Gly Ile Gly Phe Asn
1               5                   10                  15

Gly Pro Thr Cys Tyr Gln Ser Gly Ser Thr Cys Val Lys Gln Asn Asp
                20                  25                  30

Trp Tyr Ser Gln Cys Leu Pro Gly Ser Gln Val Thr Thr Ser Thr Thr
            35                  40                  45

Thr Ser Thr Ser Ser Ser Thr Thr Ser Arg Ala Thr Ser Thr Thr
        50                  55                  60

Arg Thr Gly Gly Val Thr Ser Ile Thr Ala Pro Thr Arg Thr Val
65                  70                  75                  80

Thr Ile Pro Gly Gly Ala Thr Thr Ala Ser Tyr Asn Gly Asn Pro
                85                  90                  95

Phe Glu Gly Val Gln Leu Trp Ala Asn Asn Tyr Tyr Arg Ser Glu Val
            100                 105                 110

His Thr Leu Ala Ile Pro Gln Ile Thr Asp Pro Ala Leu Arg Ala Ala
        115                 120                 125

Ala Ser Ala Val Ala Glu Val Pro Ser Phe Gln Trp Leu Asp Arg Asn
    130                 135                 140

Val Thr Val Asp Thr Leu Leu Val Glu Thr Leu Ser Glu Ile Arg Ala
145                 150                 155                 160

Ala Asn Gln Ala Gly Ala Asn Pro Pro Tyr Ala Ala Gln Ile Val Val
                165                 170                 175

Tyr Asp Leu Pro Asp Arg Asp Cys Ala Ala Ala Ala Ser Asn Gly Glu
            180                 185                 190
```

Trp Ala Ile Ala Asn Asn Gly Ala Asn Asn Tyr Lys Gly Tyr Ile Asn
            195                 200                 205

Arg Ile Arg Glu Ile Leu Ile Ser Phe Ser Asp Val Arg Thr Ile Leu
        210                 215                 220

Val Ile Glu Pro Asp Ser Leu Ala Asn Met Val Thr Asn Met Asn Val
225                 230                 235                 240

Ala Lys Cys Ser Gly Ala Ala Ser Thr Tyr Arg Glu Leu Thr Val Tyr
            245                 250                 255

Ala Leu Lys Gln Leu Asp Leu Pro His Val Ala Met Tyr Met Asp Ala
            260                 265                 270

Gly His Ala Gly Trp Leu Gly Trp Pro Ala Asn Ile Gln Pro Ala Ala
            275                 280                 285

Glu Leu Phe Ala Lys Ile Tyr Glu Asp Ala Gly Lys Pro Arg Ala Val
            290                 295                 300

Arg Gly Leu Ala Thr Asn Val Ala Asn Tyr Asn Ala Trp Ser Ile Ser
305                 310                 315                 320

Ser Pro Pro Pro Tyr Thr Ser Pro Asn Pro Asn Tyr Asp Glu Lys His
                325                 330                 335

Tyr Ile Glu Ala Phe His Pro Leu Leu Glu Ala Arg Gly Phe Pro Ala
            340                 345                 350

Gln Phe Ile Val Asp Gln Gly Arg Ser Gly Lys Gln Pro Thr Gly Gln
            355                 360                 365

Lys Glu Trp Gly His Trp Cys Asn Ala Ile Gly Thr Gly Phe Gly Met
            370                 375                 380

Arg Pro Thr Ala Asn Thr Gly His Gln Tyr Val Asp Ala Phe Val Trp
385                 390                 395                 400

Val Lys Pro Gly Gly Glu Cys Asp Gly Thr Ser Asp Thr Thr Ala Ala
            405                 410                 415

Arg Tyr Asp Tyr His Cys Ser Leu Glu Asp Ala Leu Lys Pro Ala Pro
            420                 425                 430

Glu Ala Gly Gln Trp Phe Gln Ala Tyr Phe Glu Gln Leu Leu Arg Asn
            435                 440                 445

Ala Asn Pro Pro Phe
      450

<210> SEQ ID NO 56
<211> LENGTH: 453
<212> TYPE: PRT
<213> ORGANISM: Humicola insolens

<400> SEQUENCE: 56

Ala Ser Cys Ala Pro Thr Trp Gly Gln Cys Gly Gly Ile Gly Phe Asn
1               5                   10                  15

Gly Pro Thr Cys Cys Gln Ser Gly Cys Thr Cys Val Lys Gln Ser Asp
            20                  25                  30

Trp Tyr Ser Gln Cys Leu Pro Gly Ser Gln Val Thr Thr Thr Ser Thr
        35                  40                  45

Thr Ser Thr Ser Ser Ser Thr Thr Ser Arg Ala Thr Ser Thr Ser Thr
    50                  55                  60

Arg Thr Gly Gly Val Thr Ser Ile Thr Thr Ala Pro Thr Arg Thr Val
65                  70                  75                  80

Thr Ile Pro Gly Gly Ala Thr Thr Thr Ala Ser Tyr Asn Gly Asn Pro
                85                  90                  95

Phe Glu Gly Val Gln Leu Trp Ala Asn Asn Tyr Tyr Arg Ser Glu Val

```
            100                 105                 110
His Thr Leu Ala Ile Pro Gln Ile Thr Asp Pro Ala Leu Arg Ala Ala
        115                 120                 125

Ala Ser Ala Val Ala Glu Val Pro Ser Phe Gln Trp Leu Asp Arg Asn
        130                 135                 140

Val Thr Val Asp Thr Leu Leu Val Glu Thr Leu Ser Glu Ile Arg Ala
145                 150                 155                 160

Ala Asn Gln Ala Gly Ala Asn Pro Pro Tyr Ala Ala Gln Ile Val Val
                165                 170                 175

Tyr Asp Leu Pro Asp Arg Asp Cys Ala Ala Ala Ser Asn Gly Glu
        180                 185                 190

Trp Ala Ile Ala Asn Asn Gly Ala Asn Asn Tyr Lys Gly Tyr Ile Asn
        195                 200                 205

Arg Ile Arg Glu Ile Leu Ile Ser Phe Ser Asp Val Arg Thr Ile Leu
210                 215                 220

Val Ile Glu Pro Asp Ser Leu Ala Asn Met Val Thr Asn Met Asn Val
225                 230                 235                 240

Ala Lys Cys Ser Gly Ala Ala Ser Thr Tyr Arg Glu Leu Thr Ile Tyr
                245                 250                 255

Ala Leu Lys Gln Leu Asp Leu Pro His Val Ala Met Tyr Met Asp Ala
            260                 265                 270

Gly His Ala Gly Trp Phe Gly Trp Pro Ala Asn Ile Gln Pro Ala Ala
                275                 280                 285

Glu Leu Phe Ala Lys Ile Tyr Glu Asp Ala Gly Lys Pro Arg Thr Val
        290                 295                 300

Arg Gly Leu Ala Thr Asn Val Ala Asn Tyr Asn Ala Trp Ser Ile Ser
305                 310                 315                 320

Ser Pro Pro Pro Tyr Thr Ser Pro Asn Pro Asn Tyr Asp Glu Lys His
                325                 330                 335

Tyr Ile Glu Ala Phe Arg Pro Leu Leu Glu Ala Arg Gly Phe Pro Ala
            340                 345                 350

Gln Phe Ile Val Asp Gln Gly Arg Ser Gly Lys Gln Pro Thr Gly Gln
        355                 360                 365

Lys Glu Trp Gly His Trp Cys Asn Ala Ile Gly Thr Gly Phe Gly Met
        370                 375                 380

Arg Pro Thr Ala Asn Thr Gly His Gln Tyr Val Asp Ala Phe Val Trp
385                 390                 395                 400

Val Lys Pro Gly Gly Glu Cys Asp Gly Thr Ser Asp Thr Thr Ala Ala
                405                 410                 415

Arg Tyr Asp Tyr His Cys Gly Leu Glu Asp Ala Leu Lys Pro Ala Pro
            420                 425                 430

Glu Ala Gly Gln Trp Phe Gln Ala Tyr Phe Glu Gln Leu Leu Arg Asn
        435                 440                 445

Ala Asn Pro Pro Phe
        450

<210> SEQ ID NO 57
<211> LENGTH: 453
<212> TYPE: PRT
<213> ORGANISM: Humicola insolens

<400> SEQUENCE: 57

Asp Ser Cys Ala Pro Thr Trp Gly Gln Cys Gly Gly Ile Gly Phe Asn
1               5                   10                  15
```

-continued

```
Gly Pro Thr Cys Cys Gln Ser Gly Ser Thr Cys Val Lys Gln Asn Asp
             20                  25                  30
Trp Tyr Ser Gln Cys Leu Pro Gly Ser Gln Val Thr Thr Thr Ser Thr
         35                  40                  45
Thr Ser Thr Ser Ser Ser Ser Thr Thr Ser Arg Ala Thr Ser Thr Thr
 50                  55                  60
Arg Thr Gly Gly Val Thr Ser Ile Thr Thr Ala Pro Thr Arg Thr Val
 65                  70                  75                  80
Thr Ile Pro Asp Gly Ala Thr Thr Thr Ala Ser Tyr Asn Gly Asn Pro
                 85                  90                  95
Phe Glu Gly Val Gln Leu Trp Ala Asn Asn Tyr Tyr Arg Ser Glu Val
             100                 105                 110
His Thr Leu Ala Ile Pro Gln Ile Thr Asp Pro Ala Leu Arg Ala Ala
         115                 120                 125
Ala Ser Ala Val Ala Glu Val Pro Ser Phe Gln Trp Leu Asp Arg Asn
130                 135                 140
Val Thr Val Asp Thr Leu Leu Val Glu Thr Leu Ser Glu Ile Arg Ala
145                 150                 155                 160
Ala Asn Gln Ala Gly Ala Asn Pro Pro Tyr Ala Ala Gln Ile Ala Val
                165                 170                 175
Tyr Asp Leu Pro Asp Arg Asp Cys Ala Ala Ala Ala Ser Asn Gly Glu
            180                 185                 190
Trp Ala Ile Ala Asn Asn Gly Ala Asn Asn Tyr Lys Gly Tyr Ile Asn
        195                 200                 205
Arg Ile Arg Glu Ile Leu Ile Ser Phe Ser Asp Val Arg Thr Ile Leu
210                 215                 220
Val Ile Glu Pro Asp Ser Leu Ala Asn Met Val Thr Asn Met Asn Val
225                 230                 235                 240
Ala Lys Cys Ser Gly Ala Ala Ser Thr Tyr Arg Glu Leu Thr Ile Tyr
                245                 250                 255
Ala Leu Arg Gln Leu Asp Leu Pro His Val Ala Met Tyr Met Asp Ala
            260                 265                 270
Gly His Thr Gly Trp Leu Gly Trp Pro Ala Asn Ile Gln Pro Ala Ala
        275                 280                 285
Glu Leu Phe Ala Lys Ile Tyr Glu Asp Ala Gly Lys Pro Arg Ala Val
290                 295                 300
Arg Gly Leu Ala Thr Asn Val Ala Asn Tyr Asn Ala Trp Ser Ile Ser
305                 310                 315                 320
Ser Pro Pro Pro Tyr Thr Ser Pro Asn Pro Asn Tyr Asp Glu Lys His
                325                 330                 335
Tyr Ile Glu Ala Phe Arg Pro Leu Leu Glu Ala Arg Gly Phe Pro Ala
            340                 345                 350
Gln Phe Ile Val Asp Gln Gly Arg Ser Gly Lys Gln Pro Thr Gly Gln
        355                 360                 365
Lys Glu Trp Gly His Trp Cys Asn Ala Ile Gly Thr Gly Phe Gly Met
370                 375                 380
Arg Pro Thr Ala Asn Thr Gly His Gln Tyr Val Asp Ala Phe Val Trp
385                 390                 395                 400
Val Lys Pro Gly Gly Glu Cys Asp Gly Thr Ser Asp Thr Thr Ala Ala
                405                 410                 415
Arg Tyr Asp Tyr His Cys Gly Leu Glu Asp Ala Leu Lys Pro Ala Pro
            420                 425                 430
Glu Ala Gly Gln Trp Phe Gln Ala Tyr Phe Glu Gln Leu Leu Arg Asn
```

Ala Asn Pro Pro Phe
    450

<210> SEQ ID NO 58
<211> LENGTH: 453
<212> TYPE: PRT
<213> ORGANISM: Humicola insolens

<400> SEQUENCE: 58

Ala Ser Cys Ala Pro Thr Trp Gly Gln Cys Gly Gly Thr Gly Phe Asn
1               5                   10                  15

Gly Pro Thr Cys Cys Gln Ser Gly Ser Thr Cys Val Lys Gln Asn Asp
            20                  25                  30

Trp Tyr Ser Gln Cys Leu Pro Gly Ser Gln Val Thr Thr Thr Ser Thr
        35                  40                  45

Thr Ser Thr Ser Ser Ser Ser Thr Thr Ser Arg Ala Ala Ser Thr Thr
    50                  55                  60

Arg Thr Gly Gly Val Thr Ser Ile Thr Thr Ala Pro Thr Arg Thr Val
65                  70                  75                  80

Thr Ile Pro Gly Gly Ala Thr Thr Thr Ala Ser Tyr Asn Gly Asn Pro
                85                  90                  95

Phe Glu Gly Val Gln Leu Trp Ala Asn Asn Tyr Tyr Arg Ser Glu Val
            100                 105                 110

His Thr Leu Ala Ile Pro Gln Ile Thr Asp Pro Ala Leu Arg Ala Ala
        115                 120                 125

Ala Ser Ala Val Ala Glu Val Pro Ser Phe Gln Trp Leu Asp Arg Asn
    130                 135                 140

Val Thr Val Asp Thr Leu Leu Val Glu Thr Leu Ser Glu Ile Arg Ala
145                 150                 155                 160

Ala Asn Gln Ala Gly Ala Asn Pro Pro Tyr Ala Ala Gln Ile Val Val
                165                 170                 175

Tyr Asp Leu Pro Asp Arg Asp Cys Ala Ala Ala Ser Asn Gly Glu
            180                 185                 190

Trp Ala Ile Ala Asn Asn Gly Ala Asn Asn Tyr Lys Gly Tyr Ile Asn
        195                 200                 205

Arg Ile Arg Glu Ile Leu Ile Ser Phe Ser Asp Val Arg Thr Ile Leu
    210                 215                 220

Val Ile Glu Pro Asp Ser Leu Ala Asn Met Val Thr Asn Met Asn Val
225                 230                 235                 240

Ala Lys Cys Ser Gly Ala Ala Ser Thr Tyr Arg Glu Leu Thr Ile Tyr
                245                 250                 255

Ala Leu Lys Gln Leu Asp Leu Pro His Val Ala Met Tyr Met Asp Ala
            260                 265                 270

Gly His Ala Gly Trp Leu Gly Trp Pro Ala Asn Ile Gln Pro Ala Ala
        275                 280                 285

Glu Leu Phe Ala Lys Ile Tyr Glu Asp Ala Gly Lys Pro Arg Ala Val
    290                 295                 300

Arg Gly Leu Ala Thr Asn Val Ala Asn Tyr Asn Ala Trp Ser Ile Ser
305                 310                 315                 320

Ser Pro Pro Pro Tyr Thr Ser Pro Asn Pro Asn Tyr Asp Glu Lys His
                325                 330                 335

Tyr Ile Glu Ala Phe Arg Pro Leu Leu Glu Ala Arg Gly Phe Pro Ala
            340                 345                 350

```
Gln Phe Ile Val Asp Gln Gly Arg Ser Gly Lys Gln Pro Thr Gly Gln
            355                 360                 365

Lys Glu Trp Gly His Trp Cys Asn Ala Ile Gly Thr Gly Phe Gly Met
370                 375                 380

Arg Pro Thr Ala Asn Thr Gly His Gln Tyr Val Asp Ala Phe Val Trp
385                 390                 395                 400

Val Lys Pro Gly Gly Glu Cys Asp Gly Thr Ser Asp Thr Thr Ala Ala
            405                 410                 415

Arg Tyr Asp Tyr His Cys Gly Leu Glu Asp Ala Leu Lys Pro Ala Pro
            420                 425                 430

Glu Ala Gly Gln Trp Phe Gln Ala Tyr Phe Glu Gln Leu Leu Arg Asn
            435                 440                 445

Ala Asn Pro Pro Phe
            450

<210> SEQ ID NO 59
<211> LENGTH: 453
<212> TYPE: PRT
<213> ORGANISM: Humicola insolens

<400> SEQUENCE: 59

Ala Ser Tyr Ala Pro Thr Trp Gly Gln Cys Gly Gly Ile Gly Phe Asn
1               5                   10                  15

Gly Pro Thr Cys Cys Gln Ser Gly Ser Ala Cys Val Lys Gln Asn Asp
            20                  25                  30

Trp Tyr Ser Gln Cys Leu Pro Gly Ser Gln Asp Thr Thr Thr Ser Thr
        35                  40                  45

Thr Ser Thr Ser Ser Ser Ser Thr Thr Ser Arg Ala Thr Ser Thr Thr
50                  55                  60

Arg Thr Gly Gly Val Thr Ser Ile Thr Thr Ala Pro Thr Arg Thr Val
65                  70                  75                  80

Thr Ile Pro Gly Gly Ala Thr Thr Thr Ala Ser Tyr Asn Gly Asn Pro
                85                  90                  95

Phe Glu Gly Val Gln Leu Trp Ala Asn Asn Tyr Tyr Arg Ser Glu Val
            100                 105                 110

His Thr Leu Ala Ile Pro Gln Ile Thr Asp Pro Ala Leu Arg Ala Ala
        115                 120                 125

Ala Ser Ala Val Ala Glu Val Pro Ser Phe Gln Trp Leu Asp Arg Asn
    130                 135                 140

Val Thr Val Asp Thr Leu Leu Val Glu Thr Leu Ser Glu Ile Arg Ala
145                 150                 155                 160

Ala Asn Gln Ala Gly Ala Asn Pro Pro Tyr Ala Ala Gln Ile Val Val
                165                 170                 175

Tyr Asp Leu Pro Asp Arg Asp Cys Ala Ala Ala Ser Asn Gly Glu
            180                 185                 190

Trp Ala Ile Ala Asn Asn Gly Ala Asn Asn Tyr Lys Gly Tyr Ile Asn
        195                 200                 205

Arg Ile Arg Glu Ile Leu Ile Ser Phe Ser Asp Val Arg Thr Ile Leu
210                 215                 220

Val Ile Glu Pro Asp Ser Leu Ala Asn Met Val Thr Asn Met Asn Val
225                 230                 235                 240

Ala Lys Cys Ser Gly Ala Ala Ser Thr Tyr Arg Glu Leu Thr Ile Tyr
                245                 250                 255

Ala Leu Lys Gln Leu Asp Leu Pro His Val Ala Met Tyr Met Asp Ala
            260                 265                 270
```

```
Gly His Ala Gly Trp Leu Gly Trp Pro Ala Asn Ile Gln Pro Ala Ala
        275                 280                 285

Glu Leu Phe Ala Lys Ile Tyr Glu Asp Ala Gly Lys Pro Arg Ala Val
    290                 295                 300

Arg Gly Leu Ala Thr Asn Val Ala Asn Tyr Asn Ala Trp Ser Ile Thr
305                 310                 315                 320

Ser Pro Pro Tyr Thr Ser Pro Asn Pro Asn Tyr Asp Glu Lys His
                325                 330                 335

Tyr Ile Glu Ala Phe Arg Pro Leu Leu Glu Ala Arg Gly Phe Pro Ala
                340                 345                 350

Gln Phe Ile Val Asp Gln Gly Arg Ser Gly Lys Gln Pro Thr Gly Gln
            355                 360                 365

Lys Glu Trp Gly His Trp Cys Asn Ala Ile Gly Thr Gly Phe Gly Met
        370                 375                 380

Arg Pro Thr Ala Asn Thr Gly His Gln Tyr Val Asp Ala Phe Val Trp
385                 390                 395                 400

Val Lys Pro Gly Gly Glu Cys Asp Gly Thr Ser Asp Thr Thr Ala Ala
                405                 410                 415

Arg Tyr Asp Tyr His Cys Gly Leu Glu Asp Ala Leu Lys Pro Ala Pro
                420                 425                 430

Glu Ala Gly Gln Trp Phe Gln Ala Tyr Phe Glu Gln Leu Leu Arg Asn
            435                 440                 445

Ala Asn Pro Pro Phe
        450

<210> SEQ ID NO 60
<211> LENGTH: 453
<212> TYPE: PRT
<213> ORGANISM: Humicola insolens

<400> SEQUENCE: 60

Ala Ser Cys Ala Pro Thr Trp Gly Gln Ser Gly Gly Ile Gly Phe Asn
1               5                   10                  15

Gly Pro Thr Cys Cys Gln Ser Gly Ser Thr Cys Val Lys Gln Asn Asp
            20                  25                  30

Trp Tyr Ser Gln Cys Leu Pro Gly Ser Gln Val Thr Thr Thr Ser Thr
        35                  40                  45

Thr Ser Thr Ser Ser Ser Ser Thr Thr Ser Arg Ala Thr Ser Thr Thr
    50                  55                  60

Arg Thr Gly Gly Val Thr Ser Ile Thr Thr Ala Pro Thr Arg Thr Val
65                  70                  75                  80

Thr Ile Pro Gly Gly Ala Thr Thr Thr Ala Ser Tyr Asn Gly Asn Pro
                85                  90                  95

Phe Glu Gly Val Gln Leu Trp Ala Asn Asn Tyr Tyr Arg Ser Glu Val
            100                 105                 110

His Thr Leu Ala Ile Pro Gln Ile Thr Asp Pro Ala Leu Arg Ala Ala
        115                 120                 125

Ala Ser Ala Val Ala Glu Val Pro Ser Phe Gln Trp Leu Asp Arg Asn
    130                 135                 140

Val Thr Val Asp Thr Leu Leu Val Glu Thr Leu Ser Gly Ile Arg Ala
145                 150                 155                 160

Ala Asn Gln Ala Gly Ala Asn Pro Pro Tyr Ala Ala Gln Ile Val Val
                165                 170                 175

Tyr Asp Leu Pro Asp Arg Asp Cys Ala Ala Ala Ala Ser Asn Gly Glu
```

-continued

```
                180                 185                 190
Trp Ala Ile Ala Asn Asn Gly Ala Asn Tyr Lys Gly Tyr Ile Asn
        195                 200                 205
Arg Ile Arg Glu Ile Leu Ile Ser Phe Ser Asp Val Arg Thr Ile Leu
        210                 215                 220
Val Ile Glu Pro Asp Ser Leu Ala Asn Met Val Thr Asn Met Asn Val
225                 230                 235                 240
Ala Lys Cys Ser Gly Ala Ala Ser Thr Tyr Arg Glu Leu Thr Ile Tyr
                245                 250                 255
Ala Leu Lys Gln Leu Asp Leu Pro His Val Ala Met Tyr Met Asp Ala
            260                 265                 270
Gly His Ala Gly Trp Leu Gly Trp Pro Ala Asn Ile Gln Pro Ala Ala
        275                 280                 285
Glu Leu Phe Ala Lys Ile Tyr Glu Asp Ala Gly Lys Pro Arg Ala Val
        290                 295                 300
Arg Gly Leu Ala Thr Asn Val Ala Asn Tyr Asn Ala Trp Ser Ile Ser
305                 310                 315                 320
Ser Pro Pro Pro Tyr Thr Ser Pro Asn Pro Asn Tyr Asp Glu Lys His
                325                 330                 335
Tyr Ile Glu Ala Phe Arg Pro Leu Leu Glu Ala Arg Gly Phe Pro Ala
            340                 345                 350
Gln Phe Ile Val Asp Gln Gly Arg Ser Gly Lys Gln Pro Thr Gly Gln
        355                 360                 365
Lys Glu Trp Gly His Trp Cys Asn Ala Ile Gly Thr Gly Phe Gly Met
370                 375                 380
Arg Pro Thr Ala Asn Thr Gly His Gln Tyr Val Asp Ala Phe Val Trp
385                 390                 395                 400
Val Lys Pro Gly Gly Glu Cys Asp Gly Thr Ser Asp Thr Thr Ala Ala
                405                 410                 415
Arg Tyr Asp Tyr His Cys Gly Leu Glu Asp Ala Leu Lys Pro Ala Pro
            420                 425                 430
Glu Ala Gly Gln Trp Phe Gln Ala Tyr Phe Glu Gln Leu Leu Arg Asn
        435                 440                 445
Ala Asn Pro Pro Phe
        450

<210> SEQ ID NO 61
<211> LENGTH: 453
<212> TYPE: PRT
<213> ORGANISM: Humicola insolens

<400> SEQUENCE: 61

Ala Ser Cys Ala Pro Thr Trp Gly Gln Cys Gly Gly Ile Gly Phe Asn
1               5                   10                  15
Gly Pro Thr Cys Cys Gln Ser Gly Ser Thr Cys Val Lys Gln Asp Asp
                20                  25                  30
Trp Tyr Ser Gln Cys Leu Pro Gly Ser Gln Val Thr Thr Ser Thr Thr
        35                  40                  45
Thr Ser Thr Ser Ser Ser Ser Thr Thr Ser Arg Ala Thr Ser Thr Thr
    50                  55                  60
Arg Thr Gly Gly Val Thr Ser Ile Thr Thr Ala Pro Thr Arg Thr Val
65                  70                  75                  80
Thr Ile Pro Gly Gly Ala Thr Thr Thr Ala Ser Tyr Asn Gly Asn Pro
                85                  90                  95
```

Phe Glu Gly Val Gln Leu Trp Ala Asn Asn Tyr Tyr Arg Ser Glu Val
            100                 105                 110

His Thr Leu Ala Ile Pro Gln Ile Thr Asp Pro Ala Leu Arg Ala Ala
        115                 120                 125

Ala Ser Ala Val Ala Glu Val Pro Ser Phe Gln Trp Leu Asp Arg Asn
    130                 135                 140

Val Thr Val Asp Thr Leu Leu Val Glu Thr Leu Ser Glu Ile Arg Ala
145                 150                 155                 160

Ala Asn Gln Ala Gly Ala Asn Pro Pro Tyr Ala Ala Gln Ile Val Val
                165                 170                 175

Tyr Asp Leu Pro Asp Arg Asp Cys Ala Ala Ala Ser Asn Gly Glu
            180                 185                 190

Trp Ala Ile Ala Asn Asn Gly Ala Asn Asn Tyr Lys Gly Tyr Ile Asn
        195                 200                 205

Arg Ile Arg Glu Ile Leu Ile Ser Phe Ser Asp Val Arg Thr Ile Leu
    210                 215                 220

Val Ile Glu Pro Asp Ser Leu Ala Asn Met Val Thr Asn Met Asn Val
225                 230                 235                 240

Ala Lys Cys Ser Gly Ala Ala Ser Thr Tyr Arg Glu Leu Thr Ile Tyr
                245                 250                 255

Ala Leu Lys Gln Leu Asp Leu Pro His Val Ala Met Tyr Met Asp Ala
            260                 265                 270

Gly His Ala Gly Trp Leu Gly Trp Pro Ala Asn Ile Gln Pro Ala Ala
        275                 280                 285

Glu Leu Phe Ala Lys Ile Tyr Glu Asp Ala Gly Lys Pro Arg Ala Val
    290                 295                 300

Arg Gly Leu Ala Thr Asn Val Ala Asn Tyr Asn Ala Trp Ser Ile Ser
305                 310                 315                 320

Ser Pro Pro Thr Tyr Thr Ser Pro Asn Pro Asn Tyr Asp Glu Lys His
                325                 330                 335

Tyr Ile Glu Ala Phe Arg Pro Leu Leu Glu Ala Arg Gly Phe Pro Ala
            340                 345                 350

Gln Phe Ile Val Asp Gln Gly Arg Ser Gly Lys Gln Pro Thr Gly Gln
        355                 360                 365

Lys Glu Trp Gly His Trp Cys Asn Ala Ile Gly Thr Gly Phe Gly Met
    370                 375                 380

Arg Pro Thr Ala Tyr Thr Gly His Gln Tyr Val Asp Ala Phe Val Trp
385                 390                 395                 400

Val Lys Pro Gly Gly Glu Cys Asp Gly Thr Ser Asp Thr Thr Ala Ala
                405                 410                 415

Arg Tyr Asp Tyr His Cys Gly Leu Glu Asp Ala Leu Lys Pro Ala Pro
            420                 425                 430

Glu Ala Gly Gln Trp Phe Gln Ala Tyr Phe Glu Gln Leu Leu Arg Asn
        435                 440                 445

Ala Asn Pro Pro Phe
    450

<210> SEQ ID NO 62
<211> LENGTH: 453
<212> TYPE: PRT
<213> ORGANISM: Humicola insolens

<400> SEQUENCE: 62

Ala Ser Cys Ala Pro Thr Trp Gly Gln Cys Gly Gly Ile Gly Phe Asn
1               5                   10                  15

-continued

Gly Pro Thr Cys Cys Gln Ser Gly Ser Thr Cys Val Lys Gln Asn Asp
          20                  25                  30

Trp Tyr Ser Gln Tyr Leu Pro Gly Ser Gln Val Thr Thr Ser Thr
         35                  40                  45

Thr Ser Thr Ser Ser Ser Ser Thr Thr Ser Arg Ala Thr Ser Thr Thr
50                  55                  60

Arg Thr Gly Gly Val Thr Ser Ile Thr Ala Pro Thr Arg Thr Val
65                  70                  75                  80

Thr Ile Pro Gly Gly Ala Thr Thr Thr Ala Ser Tyr Asn Gly Asn Pro
              85                  90                  95

Phe Glu Gly Val Gln Leu Trp Ala Asn Asn Tyr Arg Ser Glu Val
             100                 105                 110

His Thr Leu Ala Ile Pro Gln Ile Thr Asp Pro Ala Leu Arg Ala Ala
             115                 120                 125

Ala Ser Ala Val Ala Glu Val Pro Ser Phe Gln Trp Leu Asp Arg Asn
130                 135                 140

Val Thr Val Asp Thr Leu Leu Val Glu Thr Leu Ser Glu Ile Arg Ala
145                 150                 155                 160

Ala Asn Gln Ala Gly Ala Asn Pro Pro Tyr Ala Ala Gln Ile Val Val
             165                 170                 175

Tyr Asp Leu Pro Asp Arg Asp Cys Ala Ala Ala Ser Asn Gly Glu
             180                 185                 190

Trp Ala Ile Ala Asn Asn Gly Ala Asn Asn Tyr Lys Gly Tyr Ile Asn
             195                 200                 205

Arg Ile Arg Glu Ile Leu Ile Ser Phe Ser Asp Val Arg Thr Ile Leu
210                 215                 220

Val Ile Glu Pro Asp Ser Leu Ala Asn Met Val Thr Asn Met Asn Val
225                 230                 235                 240

Ala Lys Cys Ser Gly Ala Ala Ser Thr Tyr Arg Glu Leu Thr Ile Tyr
             245                 250                 255

Ala Leu Lys Gln Leu Asp Leu Pro His Val Ala Met Tyr Met Asp Ala
             260                 265                 270

Gly His Ala Gly Trp Leu Gly Trp Pro Ala Asn Ile Gln Pro Ala Ala
             275                 280                 285

Glu Leu Phe Ala Lys Ile Tyr Glu Asp Ala Gly Lys Pro Arg Ala Val
             290                 295                 300

Arg Gly Leu Ala Thr Asn Val Ala Asn Tyr Asn Ala Trp Ser Ile Ser
305                 310                 315                 320

Ser Pro Pro Pro Tyr Thr Ser Pro Asn Pro Asn Tyr Asp Glu Lys His
             325                 330                 335

Tyr Ile Glu Ala Phe Arg Pro Leu Leu Glu Ala Arg Gly Phe Pro Ala
             340                 345                 350

Gln Phe Ile Val Asp Gln Gly Arg Ser Gly Lys Gln Pro Thr Gly Gln
             355                 360                 365

Lys Glu Trp Gly His Trp Cys Asn Ala Ile Gly Thr Gly Phe Gly Met
             370                 375                 380

Arg Pro Thr Ala Asn Thr Gly His Gln Tyr Val Asp Ala Phe Val Trp
385                 390                 395                 400

Val Lys Pro Gly Gly Glu Cys Asp Gly Thr Ser Asp Thr Ala Ala
             405                 410                 415

Arg Tyr Asp Tyr His Cys Gly Leu Glu Asp Ala Leu Lys Pro Ala Pro
             420                 425                 430

-continued

Glu Ala Gly Gln Trp Phe Gln Ala Tyr Phe Glu Gln Leu Leu Arg Asn
            435                 440                 445

Ala Asn Pro Pro Phe
    450

<210> SEQ ID NO 63
<211> LENGTH: 453
<212> TYPE: PRT
<213> ORGANISM: Humicola insolens

<400> SEQUENCE: 63

Ala Ser Cys Ala Pro Thr Arg Gly Gln Cys Gly Gly Ile Gly Phe Asn
1               5                   10                  15

Gly Pro Thr Cys Cys Gln Ser Gly Ser Thr Cys Val Lys Gln Asn Asp
            20                  25                  30

Trp Tyr Ser Gln Cys Leu Pro Gly Ser Gln Val Thr Thr Thr Ser Thr
        35                  40                  45

Thr Ser Thr Ser Ser Ser Ser Thr Thr Ser Arg Ala Thr Ser Thr Thr
    50                  55                  60

Arg Thr Gly Gly Val Thr Ser Ile Thr Thr Pro Thr Arg Thr Val
65                  70                  75                  80

Thr Ile Pro Gly Gly Ala Thr Thr Thr Ala Ser Tyr Asn Gly Asn Pro
                85                  90                  95

Phe Glu Gly Val Gln Leu Trp Ala Asn Asn Tyr Tyr Arg Ser Glu Val
            100                 105                 110

His Thr Leu Ala Ile Pro Gln Ile Thr Asp Pro Ala Leu Arg Ala Ala
        115                 120                 125

Ala Ser Ala Val Ala Glu Val Pro Ser Phe Gln Trp Leu Asp Arg Asn
    130                 135                 140

Val Thr Val Asp Thr Leu Leu Val Glu Thr Leu Ser Glu Ile Arg Ala
145                 150                 155                 160

Ala Asn Gln Ala Gly Ala Asn Pro Pro Tyr Ala Ala Gln Ile Val Val
                165                 170                 175

Tyr Asp Leu Pro Asp Arg Asp Cys Ala Ala Ala Ala Ser Asn Gly Glu
            180                 185                 190

Trp Ala Ile Ala Asn Asn Gly Ala Asn Asn Tyr Lys Gly Tyr Ile Asn
        195                 200                 205

Arg Ile Arg Glu Ile Leu Ile Ser Phe Ser Asp Val Arg Thr Ile Leu
    210                 215                 220

Val Ile Glu Pro Asp Ser Leu Ala Asn Met Val Thr Asn Met Asn Val
225                 230                 235                 240

Ala Lys Cys Ser Gly Ala Ala Ser Thr Tyr Arg Glu Leu Thr Ile Tyr
                245                 250                 255

Ala Leu Lys Gln Leu Asp Leu Pro His Val Ala Met Tyr Thr Asp Ala
            260                 265                 270

Gly His Ala Gly Trp Leu Gly Trp Pro Ala Asn Ile Gln Pro Ala Ala
        275                 280                 285

Glu Leu Phe Ala Lys Ile Tyr Glu Asp Ala Gly Lys Pro Arg Ala Val
    290                 295                 300

Arg Gly Leu Ala Thr Asn Val Ala Asn Tyr Asn Ala Trp Ser Ile Ser
305                 310                 315                 320

Ser Pro Pro Pro Tyr Thr Ser Pro Asn Pro Asn Tyr Asp Glu Lys His
                325                 330                 335

Tyr Ile Glu Ala Phe Arg Pro Leu Leu Glu Ala Arg Gly Phe Pro Ala
            340                 345                 350

```
Gln Phe Ile Val Asp Gln Gly Arg Ser Gly Lys Gln Pro Thr Gly Gln
            355                 360                 365

Lys Glu Trp Gly His Trp Cys Asn Ala Ile Gly Thr Gly Phe Gly Met
    370                 375                 380

Arg Pro Thr Ala Asn Thr Gly His Gln Tyr Val Asp Ala Phe Val Trp
385                 390                 395                 400

Val Lys Pro Gly Gly Glu Cys Asp Gly Thr Ser Asp Thr Thr Ala Ala
                405                 410                 415

Arg Tyr Asp Tyr His Cys Gly Leu Glu Asp Ala Leu Lys Pro Ala Pro
                420                 425                 430

Glu Ala Gly Gln Trp Phe Gln Ala Tyr Phe Glu Gln Leu Leu Arg Asn
            435                 440                 445

Ala Asn Pro Pro Phe
        450

<210> SEQ ID NO 64
<211> LENGTH: 453
<212> TYPE: PRT
<213> ORGANISM: Humicola insolens

<400> SEQUENCE: 64

Ala Ser Cys Ala Pro Thr Trp Gly Gln Cys Gly Gly Phe Gly Phe Asn
1               5                   10                  15

Gly Pro Thr Cys Cys Gln Ser Gly Ser Thr Cys Val Lys Gln Asn Asp
            20                  25                  30

Trp Tyr Ser Gln Cys Leu Pro Gly Ser Gln Val Thr Thr Thr Leu Thr
        35                  40                  45

Thr Ser Thr Ser Ser Ser Thr Thr Ser Arg Ala Thr Ser Thr Thr
    50                  55                  60

Arg Thr Gly Gly Val Thr Ser Ile Thr Thr Ala Pro Thr Arg Thr Val
65                  70                  75                  80

Thr Ile Pro Gly Gly Ala Thr Thr Thr Ala Ser Tyr Asn Gly Asn Pro
                85                  90                  95

Phe Glu Gly Val Gln Leu Trp Ala Asn Asn Tyr Tyr Arg Ser Glu Val
            100                 105                 110

His Thr Leu Ala Ile Pro Gln Ile Thr Asp Pro Ala Leu Arg Ala Ala
        115                 120                 125

Ala Ser Ala Val Ala Glu Val Pro Ser Phe Gln Trp Leu Asp Arg Asn
    130                 135                 140

Val Thr Val Asp Thr Leu Leu Val Glu Thr Leu Ser Glu Ile Arg Ala
145                 150                 155                 160

Ala Asn Gln Ala Gly Ala Asn Pro Pro Tyr Ala Ala Gln Ile Val Val
                165                 170                 175

Tyr Asp Leu Pro Asp Arg Asp Cys Ala Ala Ala Ala Ser Asn Gly Glu
            180                 185                 190

Trp Ala Ile Ala Asn Asn Gly Ala Asn Asn Tyr Lys Gly Tyr Ile Asn
        195                 200                 205

Arg Ile Arg Glu Ile Leu Ile Ser Phe Ser Asp Val Arg Thr Ile Leu
    210                 215                 220

Val Ile Glu Pro Asp Ser Leu Ala Asn Met Val Thr Asp Met Asn Val
225                 230                 235                 240

Ala Lys Cys Ser Gly Ala Ala Ser Thr Tyr Arg Glu Leu Thr Ile Tyr
                245                 250                 255

Ala Leu Lys Gln Leu Asp Leu Pro His Val Ala Met Tyr Met Asp Ala
```

```
                260                 265                 270
Gly His Ala Gly Trp Leu Gly Trp Pro Ala Asn Ile Gln Pro Ala Ala
            275                 280                 285

Glu Leu Phe Ala Lys Ile Tyr Glu Asp Ala Gly Lys Pro Arg Ala Val
        290                 295                 300

Arg Gly Leu Ala Thr Asn Val Ala Asn Tyr Asn Ala Trp Ser Ile Ser
305                 310                 315                 320

Ser Pro Pro Tyr Thr Ser Pro Asn Pro Asn Tyr Asp Glu Lys His
                325                 330                 335

Tyr Ile Glu Ala Phe Arg Pro Leu Leu Glu Ala Arg Gly Phe Pro Ala
            340                 345                 350

Gln Phe Ile Val Asp Gln Gly Arg Ser Gly Lys Gln Pro Thr Gly Gln
        355                 360                 365

Lys Glu Trp Gly His Trp Cys Asn Ala Ile Gly Thr Gly Phe Gly Met
    370                 375                 380

Arg Pro Thr Ala Asn Thr Gly His Gln Tyr Val Asp Ala Phe Val Trp
385                 390                 395                 400

Val Lys Pro Gly Gly Glu Cys Asp Gly Thr Ser Asp Thr Thr Ala Ala
                405                 410                 415

Arg Tyr Asp Tyr His Cys Gly Leu Glu Asp Ala Leu Lys Pro Ala Pro
            420                 425                 430

Glu Ala Gly Gln Trp Phe Gln Ala Tyr Phe Glu Gln Leu Leu Arg Asn
        435                 440                 445

Ala Asn Pro Pro Phe
    450

<210> SEQ ID NO 65
<211> LENGTH: 453
<212> TYPE: PRT
<213> ORGANISM: Humicola insolens

<400> SEQUENCE: 65

Ala Ser Cys Ala Pro Thr Trp Gly Gln Cys Gly Gly Ile Gly Phe Asn
1               5                   10                  15

Gly Ser Thr Cys Cys Gln Ser Gly Ser Thr Cys Val Lys Gln Asn Asp
            20                  25                  30

Trp Tyr Ser Gln Cys Leu Pro Gly Ser Gln Val Thr Thr Thr Ser Thr
        35                  40                  45

Thr Ser Thr Ser Ser Ser Ser Thr Thr Ser Arg Ala Thr Ser Thr Thr
    50                  55                  60

Arg Thr Gly Gly Val Thr Ser Ile Thr Thr Ala Pro Thr Arg Thr Val
65                  70                  75                  80

Thr Ile Pro Gly Gly Ala Thr Thr Thr Ala Ser Tyr Asn Gly Asn Pro
                85                  90                  95

Phe Glu Gly Val Gln Leu Trp Ala Asn Asn Tyr Tyr Arg Ser Glu Val
            100                 105                 110

His Thr Leu Ala Ile Pro Gln Ile Thr Asp Pro Ala Leu Arg Ala Ala
        115                 120                 125

Ala Ser Ala Val Ala Glu Val Pro Ser Phe Gln Trp Leu Asp Arg Asn
    130                 135                 140

Val Thr Val Asp Thr Leu Leu Val Glu Thr Leu Ser Glu Ile Arg Ala
145                 150                 155                 160

Ala Asn Gln Ala Gly Ala Asn Pro Pro Tyr Ala Ala Gln Ile Val Val
                165                 170                 175
```

```
Tyr Asp Leu Pro Asp Arg Asp Cys Ala Ala Ala Ser Asn Gly Glu
            180                 185                 190

Trp Ala Ile Ala Asn Asn Gly Ala Asn Tyr Lys Gly Tyr Ile Asn
        195                 200                 205

Arg Ile Arg Glu Ile Leu Ile Ser Phe Ser Asp Val Arg Thr Ile Leu
    210                 215                 220

Val Ile Glu Pro Asp Ser Leu Ala Asn Met Val Thr Asn Met Asn Val
225                 230                 235                 240

Ala Lys Cys Ser Gly Ala Ala Ser Thr Tyr Arg Glu Leu Thr Ile Tyr
                245                 250                 255

Ala Leu Lys Gln Leu Asp Leu Pro His Val Ala Met Tyr Met Asp Ala
            260                 265                 270

Gly His Ala Gly Trp Leu Gly Trp Pro Ala Asn Ile Gln Pro Ala Ala
        275                 280                 285

Glu Leu Phe Ala Lys Ile Tyr Glu Asp Ala Gly Lys Pro Arg Ala Val
    290                 295                 300

Arg Gly Leu Ala Thr Asn Val Ala Asn Tyr Asn Ala Trp Ser Ile Ser
305                 310                 315                 320

Ser Pro Pro Pro Tyr Thr Ser Pro Asn Pro Asn Tyr Asp Glu Lys His
                325                 330                 335

Tyr Ile Glu Ala Phe Arg Pro Leu Leu Glu Ala Arg Gly Phe Pro Ala
            340                 345                 350

Gln Phe Ile Val Asp Gln Gly Arg Ser Gly Lys Gln Pro Thr Gly Gln
        355                 360                 365

Lys Glu Trp Gly His Trp Cys Asn Ala Ile Gly Thr Gly Phe Gly Met
    370                 375                 380

Arg Pro Thr Ala Asn Thr Gly His Gln Tyr Val Asp Ala Phe Val Trp
385                 390                 395                 400

Val Lys Pro Gly Gly Glu Cys Asp Gly Thr Ser Asp Thr Thr Ala Ala
                405                 410                 415

Arg Tyr Asp Tyr His Cys Gly Leu Glu Asp Ala Leu Lys Pro Ala Pro
            420                 425                 430

Glu Ala Gly Gln Trp Phe Gln Ala Tyr Phe Glu Gln Leu Leu Arg Asn
        435                 440                 445

Ala Asn Pro Pro Phe
    450

<210> SEQ ID NO 66
<211> LENGTH: 440
<212> TYPE: PRT
<213> ORGANISM: Phanerochaete chrysosporium

<400> SEQUENCE: 66

Ala Ser Ser Glu Trp Gly Gln Cys Gly Gly Ile Asp Trp Thr Gly Pro
1               5                   10                  15

Thr Thr Cys Val Ser Gly Thr Cys Thr Val Leu Asn Pro Tyr Tyr
            20                  25                  30

Ser Gln Cys Leu Pro Gly Ser Ala Val Thr Thr Ser Val Ile Thr
        35                  40                  45

Ser His Ser Ser Ser Val Ser Val Ser Ser His Ser Gly Ser Ser
    50                  55                  60

Thr Ser Thr Ser Ser Pro Thr Gly Pro Thr Gly Thr Asn Pro Pro
65                  70                  75                  80

Pro Pro Ser Ala Asn Asn Pro Trp Thr Gly Phe Gln Ile Phe Leu Ser
                85                  90                  95
```

```
Pro Tyr Tyr Ala Asn Glu Val Ala Ala Ala Lys Gln Ile Thr Asp
            100                 105                 110

Pro Thr Leu Ser Ser Lys Ala Ala Ser Val Ala Asn Ile Pro Thr Phe
            115                 120                 125

Thr Trp Leu Asp Ser Val Ala Lys Ile Pro Asp Leu Gly Thr Tyr Leu
        130                 135                 140

Ala Ser Ala Ser Ala Leu Gly Lys Ser Thr Gly Thr Lys Gln Leu Val
145                 150                 155                 160

Gln Ile Val Ile Tyr Asp Leu Pro Asp Arg Asp Cys Ala Ala Lys Ala
                165                 170                 175

Ser Asn Gly Glu Phe Ser Ile Ala Asn Asn Gly Gln Ala Asn Tyr Glu
            180                 185                 190

Asn Tyr Ile Asp Gln Ile Val Ala Gln Ile Gln Gln Phe Pro Asp Val
            195                 200                 205

Arg Val Val Ala Val Ile Glu Pro Asp Ser Leu Ala Asn Leu Val Thr
        210                 215                 220

Asn Leu Asn Val Gln Lys Cys Ala Asn Ala Lys Thr Thr Tyr Leu Ala
225                 230                 235                 240

Cys Val Asn Tyr Ala Leu Thr Asn Leu Ala Lys Val Gly Val Tyr Met
                245                 250                 255

Tyr Met Asp Ala Gly His Ala Gly Trp Leu Gly Trp Pro Ala Asn Leu
            260                 265                 270

Ser Pro Ala Ala Gln Leu Phe Thr Gln Val Trp Gln Asn Ala Gly Lys
            275                 280                 285

Ser Pro Phe Ile Lys Gly Leu Ala Thr Asn Val Ala Asn Tyr Asn Ala
            290                 295                 300

Leu Gln Ala Ala Ser Pro Asp Pro Ile Thr Gln Gly Asn Pro Asn Tyr
305                 310                 315                 320

Asp Glu Ile His Tyr Ile Asn Ala Leu Ala Pro Leu Leu Gln Gln Ala
                325                 330                 335

Gly Trp Asp Ala Thr Phe Ile Val Asp Gln Gly Arg Ser Gly Val Gln
            340                 345                 350

Asn Ile Arg Gln Gln Trp Gly Asp Trp Cys Asn Ile Lys Gly Ala Gly
            355                 360                 365

Phe Gly Thr Arg Pro Thr Thr Asn Thr Gly Ser Gln Phe Ile Asp Ser
        370                 375                 380

Ile Val Trp Val Lys Pro Gly Gly Glu Cys Asp Gly Thr Ser Asn Ser
385                 390                 395                 400

Ser Ser Pro Arg Tyr Asp Pro Thr Cys Ser Leu Pro Asp Ala Ala Gln
                405                 410                 415

Pro Ala Pro Glu Ala Gly Thr Trp Phe Gln Ala Tyr Phe Gln Thr Leu
            420                 425                 430

Val Ser Ala Ala Asn Pro Pro Leu
        435                 440

<210> SEQ ID NO 67
<211> LENGTH: 440
<212> TYPE: PRT
<213> ORGANISM: Phanerochaete chrysosporium

<400> SEQUENCE: 67

Ala Ser Ser Glu Arg Gly Gln Cys Gly Gly Ile Gly Trp Thr Gly Pro
1               5                   10                  15

Thr Thr Cys Val Ser Gly Thr Thr Cys Thr Val Leu Asn Pro Tyr Tyr
```

-continued

```
                20                  25                  30
    Ser Gln Cys Leu Pro Gly Ser Ala Val Thr Thr Ser Val Ile Thr
                35                  40                  45
    Ser His Ser Pro Ser Val Ser Val Ser Ser His Ser Gly Ser Ser
                50                  55                  60
    Thr Ser Thr Ser Ser Pro Thr Gly Pro Thr Gly Thr Asn Pro Pro
    65                  70                  75                  80
    Pro Pro Ser Ala Asn Asn Pro Trp Thr Gly Phe Gln Ile Phe Leu Ser
                    85                  90                  95
    Pro Tyr Tyr Ala Asn Glu Val Ala Ala Ala Lys Gln Ile Thr Asp
                100                 105                 110
    Pro Thr Leu Ser Ser Lys Ala Ala Ser Val Ala Asn Ile Pro Thr Phe
                115                 120                 125
    Thr Trp Leu Asp Ser Val Ala Lys Ile Pro Asp Leu Gly Thr Tyr Leu
                130                 135                 140
    Ala Ser Ala Ser Ala Leu Gly Lys Ser Thr Gly Thr Lys Gln Leu Val
    145                 150                 155                 160
    Gln Ile Val Ile Tyr Asp Leu Pro Asp Arg Asp Cys Ala Ala Lys Ala
                    165                 170                 175
    Ser Asn Gly Glu Phe Ser Ile Ala Asn Asn Gly Gln Ala Asn Tyr Glu
                180                 185                 190
    Asn Tyr Ile Asp Gln Ile Val Ala Gln Ile Gln Gln Phe Pro Asp Val
                195                 200                 205
    Arg Val Val Ala Val Ile Glu Pro Asp Ser Leu Ala Asn Leu Val Thr
                210                 215                 220
    Asn Leu Asn Val Gln Lys Cys Ala Asn Ala Lys Thr Thr Tyr Leu Ala
    225                 230                 235                 240
    Cys Val Asn Tyr Ala Leu Thr Asn Leu Ala Lys Val Gly Val Tyr Met
                    245                 250                 255
    Tyr Met Asp Ala Gly His Ala Gly Trp Leu Gly Trp Pro Ala Asn Leu
                260                 265                 270
    Ser Pro Ala Ala Gln Leu Phe Thr Gln Val Trp Gln Asn Ala Gly Lys
                275                 280                 285
    Ser Pro Phe Ile Lys Gly Leu Ala Thr Asn Val Ala Asn Tyr Asn Ala
    290                 295                 300
    Leu Gln Ala Ala Ser Pro Asp Pro Ile Thr Gln Gly Asn Pro Asn Tyr
    305                 310                 315                 320
    Asp Glu Ile His Tyr Ile Asn Ala Leu Ala Pro Leu Leu Gln Gln Ala
                    325                 330                 335
    Gly Trp Asp Ala Thr Phe Ile Val Asp Gln Gly Arg Ser Gly Val Gln
                340                 345                 350
    Asn Ile Arg Gln Gln Trp Gly Asp Trp Cys Asn Ile Lys Gly Ala Gly
                355                 360                 365
    Phe Gly Thr Arg Pro Thr Thr Asn Thr Gly Ser Gln Phe Ile Asp Ser
                370                 375                 380
    Ile Val Trp Val Lys Pro Gly Gly Glu Cys Asp Gly Thr Ser Asn Ser
    385                 390                 395                 400
    Ser Ser Pro Arg Tyr Asp Pro Thr Cys Ser Leu Pro Asp Ala Ala Gln
                    405                 410                 415
    Pro Ala Pro Glu Ala Gly Thr Trp Phe Gln Ala Tyr Phe Gln Thr Leu
                420                 425                 430
    Val Ser Ala Ala Asn Pro Pro Leu
                435                 440
```

<210> SEQ ID NO 68
<211> LENGTH: 440
<212> TYPE: PRT
<213> ORGANISM: Phanerochaete chrysosporium

<400> SEQUENCE: 68

```
Ala Ser Ser Glu Trp Gly Gln Cys Gly Gly Ile Gly Trp Thr Gly Pro
1               5                   10                  15
Thr Thr Cys Val Ser Asp Thr Thr Cys Thr Val Leu Asn Pro Tyr Tyr
                20                  25                  30
Ser Gln Cys Leu Pro Gly Ser Ala Val Thr Thr Thr Ser Val Ile Thr
            35                  40                  45
Ser His Ser Ser Ser Val Ser Ser Val Ser Ser His Ser Gly Ser Thr
        50                  55                  60
Thr Ser Thr Ser Ser Pro Thr Gly Pro Thr Gly Thr Asn Pro Pro Pro
65                  70                  75                  80
Pro Pro Ser Ala Asn Asn Pro Trp Thr Gly Phe Gln Ile Phe Leu Ser
                85                  90                  95
Pro Tyr Tyr Ala Asn Glu Val Ala Ala Ala Lys Gln Ile Thr Asp
                100                 105                 110
Pro Thr Leu Ser Ser Lys Ala Ala Ser Val Ala Asn Ile Pro Thr Phe
            115                 120                 125
Thr Trp Leu Asp Ser Val Ala Lys Ile Pro Asp Leu Gly Thr Tyr Leu
    130                 135                 140
Ala Ser Ala Ser Ala Leu Gly Lys Ser Thr Gly Thr Lys Gln Leu Val
145                 150                 155                 160
Gln Ile Val Ile Tyr Asp Leu Pro Asp Arg Asp Cys Ala Ala Lys Ala
                165                 170                 175
Ser Asn Gly Glu Phe Ser Ile Ala Asn Asn Gly Gln Ala Asn Tyr Glu
            180                 185                 190
Asn Tyr Ile Asp Gln Ile Val Ala Gln Ile Gln Phe Pro Asp Val
        195                 200                 205
Arg Val Val Ala Val Ile Glu Pro Asp Ser Leu Ala Asn Leu Val Thr
    210                 215                 220
Asn Leu Asn Val Gln Lys Cys Ala Asn Ala Lys Thr Thr Tyr Leu Ala
225                 230                 235                 240
Cys Val Asn Tyr Ala Leu Thr Asn Leu Ala Lys Val Gly Val Tyr Met
                245                 250                 255
Tyr Met Asp Ala Gly His Ala Gly Trp Leu Gly Trp Pro Ala Asn Leu
            260                 265                 270
Ser Pro Ala Ala Gln Leu Phe Thr Gln Val Trp Gln Asn Ala Gly Lys
        275                 280                 285
Ser Pro Phe Ile Lys Gly Leu Ala Thr Asn Val Ala Asn Tyr Asn Ala
    290                 295                 300
Leu Gln Ala Ala Ser Pro Asp Pro Ile Thr Gln Gly Asn Pro Asn Tyr
305                 310                 315                 320
Asp Glu Ile His Tyr Ile Asn Ala Leu Ala Pro Leu Leu Gln Glu Ala
                325                 330                 335
Gly Trp Asp Ala Thr Phe Ile Val Asp Gln Gly Arg Ser Gly Val Gln
            340                 345                 350
Asn Ile Arg Gln Gln Trp Gly Asp Trp Cys Asn Ile Lys Gly Ala Gly
        355                 360                 365
Phe Gly Thr Arg Pro Thr Thr Asn Thr Gly Ser Gln Phe Ile Asp Ser
```

```
                    370                 375                 380
Ile Val Trp Val Lys Pro Gly Glu Cys Asp Gly Thr Ser Asn Ser
385                 390                 395                 400

Ser Ser Pro Arg Tyr Asp Pro Thr Cys Ser Leu Pro Asp Ala Ala Gln
                405                 410                 415

Pro Ala Pro Glu Ala Gly Thr Trp Phe Gln Ala Tyr Phe Gln Thr Leu
                420                 425                 430

Val Ser Ala Ala Asn Pro Pro Leu
            435                 440

<210> SEQ ID NO 69
<211> LENGTH: 440
<212> TYPE: PRT
<213> ORGANISM: Phanerochaete chrysosporium

<400> SEQUENCE: 69

Ala Ser Ser Glu Trp Gly Gln Ser Gly Gly Ile Gly Trp Thr Gly Pro
1               5                   10                  15

Thr Thr Cys Val Ser Gly Thr Thr Cys Thr Val Leu Asn Pro Tyr Tyr
                20                  25                  30

Ser Gln Cys Leu Pro Gly Ser Ala Val Thr Thr Thr Ser Val Ile Thr
            35                  40                  45

Ser His Ser Ser Val Ser Ser Val Ser Ser His Ser Gly Ser Ser
        50                  55                  60

Thr Ser Thr Ser Ser Pro Thr Gly Pro Thr Gly Thr Asn Pro Pro Pro
65                  70                  75                  80

Pro Pro Ser Ala Asn Asn Pro Trp Thr Gly Phe Gln Ile Phe Leu Ser
                85                  90                  95

Pro Tyr Tyr Ala Asn Glu Val Ala Ala Ala Lys Gln Ile Thr Asp
            100                 105                 110

Pro Thr Leu Ser Ser Lys Ala Ala Ser Val Ala Asn Ile Pro Thr Phe
            115                 120                 125

Thr Trp Leu Asp Ser Val Ala Lys Ile Pro Asp Leu Gly Thr Tyr Leu
            130                 135                 140

Ala Ser Ala Ser Ala Leu Gly Lys Ser Thr Gly Thr Lys Gln Leu Val
145                 150                 155                 160

Gln Ile Val Ile Tyr Asp Leu Pro Asp Arg Asp Cys Ala Ala Lys Ala
                165                 170                 175

Ser Asn Gly Glu Phe Ser Ile Ala Asn Asn Gly Gln Ala Asn Tyr Glu
            180                 185                 190

Asn Tyr Ile Asp Gln Ile Val Ala Gln Ile Gln Phe Pro Asp Val
            195                 200                 205

Arg Val Val Ala Val Ile Glu Pro Asp Ser Leu Ala Asn Leu Val Thr
210                 215                 220

Asn Leu Asn Val Gln Lys Cys Ala Asn Ala Lys Thr Thr Tyr Leu Ala
225                 230                 235                 240

Cys Val Asn Tyr Ala Leu Thr Asn Leu Ala Lys Val Gly Val Tyr Met
                245                 250                 255

Tyr Met Asp Ala Gly His Ala Gly Trp Leu Gly Trp Pro Ala Asn Leu
            260                 265                 270

Ser Pro Ala Ala Gln Leu Phe Thr Gln Val Trp Gln Asn Ala Gly Lys
            275                 280                 285

Ser Pro Phe Ile Lys Gly Leu Ala Thr Asn Val Ala Asn Tyr Asn Ala
            290                 295                 300
```

```
Leu Gln Ala Ala Ser Pro Asp Pro Ile Thr Gln Gly Asn Pro Asn Tyr
305                 310                 315                 320

Asp Glu Ile His Tyr Ile Asn Ala Leu Ala Pro Leu Leu Gln Gln Ala
            325                 330                 335

Gly Trp Asp Ala Thr Phe Ile Val Asp Gln Gly Arg Ser Gly Val Gln
            340                 345                 350

Asn Ile Arg Gln Gln Trp Gly Asp Trp Cys Asn Ile Lys Gly Ala Gly
            355                 360                 365

Phe Gly Thr Arg Pro Thr Thr Asn Thr Gly Ser Gln Phe Ile Asp Ser
    370                 375                 380

Ile Val Trp Val Lys Pro Gly Gly Glu Cys Asp Gly Thr Ser Asn Ser
385                 390                 395                 400

Ser Ser Pro Arg Tyr Asp Pro Thr Cys Ser Leu Pro Asp Ala Ala Gln
            405                 410                 415

Pro Ala Pro Glu Ala Gly Thr Trp Phe Gln Ala Tyr Phe Gln Thr Leu
            420                 425                 430

Val Ser Ala Ala Asn Pro Pro Leu
            435                 440

<210> SEQ ID NO 70
<211> LENGTH: 440
<212> TYPE: PRT
<213> ORGANISM: Phanerochaete chrysosporium

<400> SEQUENCE: 70

Ala Ser Ser Glu Trp Gly Gln Cys Gly Gly Ile Gly Trp Thr Gly Pro
1               5                   10                  15

Thr Thr Cys Val Ser Asp Thr Cys Thr Val Leu Asn Pro Tyr Tyr
                20                  25                  30

Ser Gln Cys Leu Pro Gly Ser Ala Val Thr Thr Thr Ser Val Ile Thr
            35                  40                  45

Ser His Ser Ser Val Ser Ser Val Ser Ser His Ser Gly Ser Ser
        50                  55                  60

Thr Ser Thr Ser Ser Pro Thr Gly Pro Thr Gly Thr Asn Pro Pro Pro
65                  70                  75                  80

Pro Pro Ser Ala Asn Asn Pro Trp Thr Gly Phe Gln Ile Phe Leu Ser
                85                  90                  95

Pro Tyr Tyr Ala Asn Glu Val Ala Ala Ala Lys Gln Ile Thr Asp
            100                 105                 110

Pro Thr Leu Ser Ser Lys Ala Ala Ser Val Ala Asn Ile Pro Thr Phe
            115                 120                 125

Thr Trp Leu Asp Ser Val Ala Lys Ile Pro Asp Leu Gly Thr Tyr Leu
    130                 135                 140

Ala Ser Ala Ser Ala Leu Gly Lys Ser Thr Gly Thr Lys Gln Leu Val
145                 150                 155                 160

Gln Ile Val Ile Tyr Asp Leu Pro Asp Arg Asp Cys Ala Ala Lys Ala
            165                 170                 175

Ser Asn Gly Glu Phe Ser Ile Ala Asn Asn Gly Gln Ala Asn Tyr Glu
            180                 185                 190

Asn Tyr Ile Asp Leu Ile Val Ala Gln Ile Gln Gln Phe Pro Asp Val
            195                 200                 205

Arg Val Val Ala Val Ile Glu Pro Asp Ser Leu Ala Asn Leu Val Thr
    210                 215                 220

Asn Leu Asn Val Gln Lys Cys Ala Asn Ala Lys Thr Thr Tyr Leu Ala
225                 230                 235                 240
```

```
Cys Val Asn Tyr Ala Leu Thr Asn Leu Ala Lys Val Gly Val Tyr Met
                245                 250                 255

Tyr Met Asp Ala Gly His Ala Gly Trp Leu Gly Trp Pro Ala Asn Leu
            260                 265                 270

Ser Pro Ala Ala Gln Leu Phe Thr Gln Val Trp Gln Asn Ala Gly Lys
        275                 280                 285

Ser Pro Phe Ile Lys Gly Leu Ala Thr Asn Val Ala Asn Tyr Asn Ala
    290                 295                 300

Leu Gln Ala Ala Ser Pro Asp Pro Ile Thr Gln Gly Asn Pro Asn Tyr
305                 310                 315                 320

Asp Glu Ile His Tyr Ile Asn Ala Leu Ala Pro Leu Leu Gln Gln Ala
                325                 330                 335

Gly Trp Asp Ala Thr Phe Ile Val Asp Gln Gly Arg Ser Gly Val Gln
            340                 345                 350

Asn Ile Arg Gln Gln Trp Gly Asp Trp Cys Asn Ile Lys Gly Ala Gly
        355                 360                 365

Phe Gly Thr Arg Pro Thr Thr Asn Thr Gly Ser Gln Phe Ile Asp Ser
    370                 375                 380

Ile Val Trp Val Lys Pro Gly Glu Cys Asp Gly Thr Ser Asn Ser
385                 390                 395                 400

Ser Ser Pro Arg Tyr Asp Pro Thr Cys Ser Leu Pro Asp Ala Ala Gln
                405                 410                 415

Pro Ala Pro Glu Ala Gly Thr Trp Phe Gln Ala Tyr Phe Gln Thr Leu
            420                 425                 430

Val Ser Ala Ala Asn Pro Pro Leu
                435                 440

<210> SEQ ID NO 71
<211> LENGTH: 440
<212> TYPE: PRT
<213> ORGANISM: Phanerochaete chrysosporium

<400> SEQUENCE: 71

Ala Ser Ser Glu Trp Gly Gln Cys Gly Asp Ile Gly Trp Thr Gly Pro
1               5                   10                  15

Thr Thr Cys Val Ser Gly Thr Thr Cys Thr Val Leu Asn Pro Tyr Tyr
                20                  25                  30

Ser Gln Cys Leu Pro Gly Ser Ala Val Thr Thr Ser Val Ile Thr
            35                  40                  45

Ser His Ser Ser Val Ser Ser Val Ser Ser His Ser Gly Ser Ser
        50                  55                  60

Thr Ser Thr Ser Ser Pro Thr Gly Pro Thr Gly Thr Asn Pro Pro
65                  70                  75                  80

Pro Pro Ser Ala Asn Asn Pro Trp Thr Gly Phe Gln Ile Phe Leu Ser
                85                  90                  95

Pro Tyr Tyr Ala Asn Glu Val Ala Ala Ala Lys Gln Ile Thr Asp
            100                 105                 110

Pro Thr Leu Ser Ser Lys Ala Ala Ser Val Ala Asn Ile Pro Thr Phe
        115                 120                 125

Thr Trp Leu Asp Ser Val Ala Lys Ile Pro Asp Leu Gly Thr Tyr Leu
    130                 135                 140

Ala Ser Ala Ser Ala Leu Gly Lys Ser Thr Gly Thr Lys Gln Leu Val
145                 150                 155                 160

Gln Ile Val Ile Tyr Asp Leu Pro Asp Arg Asp Cys Ala Ala Lys Ala
```

```
               165                 170                 175
Ser Asn Gly Glu Phe Ser Ile Ala Asn Asn Gly Gln Ala Asn Tyr Glu
            180                 185                 190

Asn Tyr Ile Asp Gln Ile Val Ala Gln Ile Gln Gln Phe Pro Asp Val
        195                 200                 205

Arg Val Val Ala Val Ile Glu Pro Asp Ser Leu Ala Asn Leu Val Thr
    210                 215                 220

Asn Leu Asn Val Gln Lys Cys Ala Asn Ala Lys Thr Thr Tyr Leu Ala
225                 230                 235                 240

Cys Val Asn Tyr Ala Leu Thr Asn Leu Ala Lys Val Gly Val Tyr Met
                245                 250                 255

Tyr Met Asp Ala Gly His Ala Gly Trp Leu Gly Trp Pro Ala Asn Leu
            260                 265                 270

Ser Pro Ala Ala Gln Leu Phe Thr Gln Val Trp Gln Asn Ala Gly Lys
        275                 280                 285

Ser Pro Phe Ile Lys Gly Leu Ala Thr Asn Val Ala Asn Tyr Asn Ala
    290                 295                 300

Leu Gln Ala Ala Ser Pro Asp Pro Ile Thr Gln Gly Asn Pro Asn Tyr
305                 310                 315                 320

Asp Glu Ile His Tyr Ile Asn Ala Leu Ala Pro Leu Leu Gln Gln Ala
                325                 330                 335

Gly Trp Asp Ala Thr Phe Ile Val Asp Gln Gly Arg Ser Gly Val Gln
            340                 345                 350

Asn Ile Arg Gln Gln Trp Gly Asp Trp Cys Asn Ile Lys Gly Ala Gly
        355                 360                 365

Phe Gly Thr Arg Pro Thr Thr Asn Thr Gly Ser Gln Phe Ile Asp Ser
    370                 375                 380

Ile Val Trp Val Lys Pro Gly Gly Glu Cys Asp Gly Thr Ser Asn Ser
385                 390                 395                 400

Ser Ser Pro Arg Tyr Asp Pro Thr Cys Ser Leu Pro Asp Ala Ala Gln
                405                 410                 415

Pro Ala Pro Glu Ala Gly Thr Trp Phe Gln Ala Tyr Phe Gln Thr Leu
            420                 425                 430

Val Ser Ala Ala Asn Pro Pro Leu
        435                 440

<210> SEQ ID NO 72
<211> LENGTH: 440
<212> TYPE: PRT
<213> ORGANISM: Phanerochaete chrysosporium

<400> SEQUENCE: 72

Ala Ser Ser Glu Trp Gly Gln Cys Gly Gly Ile Gly Trp Thr Gly Pro
1               5                   10                  15

Thr Thr Cys Val Ser Gly Thr Thr Cys Thr Val Leu Asn Ser Tyr Tyr
            20                  25                  30

Ser Gln Cys Leu Pro Gly Ser Ala Val Thr Thr Thr Ser Val Ile Thr
        35                  40                  45

Ser His Ser Ser Val Ser Ser Val Ser Ser His Ser Gly Ser Ser
    50                  55                  60

Thr Ser Thr Ser Ser Pro Thr Gly Pro Thr Gly Thr Asn Pro Pro
65                  70                  75                  80

Pro Pro Ser Ala Asn Asn Pro Trp Thr Gly Phe Gln Ile Phe Leu Ser
                85                  90                  95
```

```
Pro Tyr Tyr Ala Asn Glu Val Ala Ala Ala Lys Gln Ile Thr Asp
            100                 105                 110

Pro Thr Leu Ser Ser Lys Ala Ala Ser Val Ala Asn Ile Pro Thr Phe
        115                 120                 125

Thr Trp Leu Asp Ser Val Ala Lys Ile Pro Asp Leu Gly Thr Tyr Leu
    130                 135                 140

Ala Ser Ala Ser Ala Leu Gly Lys Ser Thr Gly Thr Lys Gln Leu Val
145                 150                 155                 160

Gln Ile Val Ile Tyr Asp Leu Pro Asp Arg Asp Cys Ala Ala Lys Ala
                165                 170                 175

Ser Asn Gly Glu Phe Ser Ile Ala Asn Asn Gly Gln Ala Asn Tyr Glu
            180                 185                 190

Asn Tyr Ile Asp Gln Ile Val Ala Gln Ile Gln Gln Phe Pro Asp Val
        195                 200                 205

Arg Val Val Ala Val Ile Glu Pro Asp Ser Leu Ala Asn Leu Val Thr
    210                 215                 220

Asn Leu Asn Val Gln Lys Cys Ala Asn Ala Lys Thr Thr Tyr Leu Ala
225                 230                 235                 240

Cys Val Asn Tyr Ala Leu Thr Asn Leu Ala Lys Val Gly Val Tyr Met
                245                 250                 255

Tyr Met Asp Ala Gly His Ala Gly Trp Leu Gly Trp Pro Ala Asn Leu
            260                 265                 270

Ser Pro Ala Val Gln Leu Phe Thr Gln Val Trp Gln Asn Ala Gly Lys
        275                 280                 285

Ser Pro Phe Ile Lys Gly Leu Ala Thr Asn Val Ala Asn Tyr Asn Ala
    290                 295                 300

Leu Gln Ala Ala Ser Pro Asp Pro Ile Thr Gln Gly Asn Pro Asn Tyr
305                 310                 315                 320

Asp Glu Ile His Tyr Ile Asn Ala Leu Ala Pro Leu Leu Gln Gln Ala
                325                 330                 335

Gly Trp Asp Ala Thr Phe Ile Val Asp Gln Gly Arg Ser Gly Val Gln
            340                 345                 350

Asn Ile Arg Gln Gln Trp Gly Asp Trp Cys Asn Ile Lys Gly Ala Gly
        355                 360                 365

Phe Gly Thr Arg Pro Thr Thr Asn Thr Gly Ser Gln Phe Ile Asp Ser
    370                 375                 380

Ile Val Trp Val Lys Pro Gly Gly Glu Cys Asp Gly Thr Ser Asn Ser
385                 390                 395                 400

Ser Ser Pro Arg Tyr Asp Pro Thr Cys Ser Leu Pro Asp Ala Ala Gln
                405                 410                 415

Pro Ala Pro Glu Ala Gly Thr Trp Phe Gln Ala Tyr Phe Gln Thr Leu
            420                 425                 430

Val Ser Ala Ala Asn Pro Pro Leu
        435                 440

<210> SEQ ID NO 73
<211> LENGTH: 440
<212> TYPE: PRT
<213> ORGANISM: Phanerochaete chrysosporium

<400> SEQUENCE: 73

Ala Ser Ser Glu Trp Gly Gln Cys Gly Gly Ile Gly Trp Thr Gly Pro
1               5                   10                  15

Thr Thr Cys Val Ser Asp Thr Cys Thr Val Leu Asn Pro Tyr Tyr
            20                  25                  30
```

```
Ser Gln Cys Leu Pro Gly Ser Ala Val Thr Thr Ser Val Ile Thr
         35                  40                  45
Ser His Ser Ser Ser Val Ser Ser Val Ser Ser His Ser Gly Ser Ser
 50                      55                  60
Thr Ser Thr Ser Ser Pro Thr Gly Pro Thr Gly Thr Asn Pro Pro Pro
 65              70                  75                      80
Pro Pro Ser Ala Asn Asn Pro Trp Thr Gly Phe Gln Ile Phe Leu Ser
             85                  90                  95
Pro Tyr Tyr Ala Asn Glu Val Ala Ala Ala Lys Gln Ile Thr Asp
             100             105             110
Pro Thr Leu Ser Ser Lys Ala Ala Ser Val Ala Asn Ile Pro Thr Phe
             115             120             125
Thr Trp Leu Asp Ser Val Ala Lys Ile Pro Asp Leu Gly Thr Tyr Leu
         130             135             140
Ala Ser Ala Ser Ala Leu Gly Lys Ser Thr Gly Thr Lys Gln Leu Val
145             150             155             160
Gln Ile Val Ile Tyr Asp Leu Pro Asp Arg Asp Cys Ala Ala Lys Ala
                 165             170             175
Ser Asn Gly Glu Phe Ser Ile Ala Asn Asn Gly Gln Ala Asn Tyr Glu
             180             185             190
Asn Tyr Ile Asp Gln Ile Val Ala Gln Ile Gln Gln Phe Pro Asp Val
             195             200             205
Arg Val Val Ala Val Ile Glu Pro Asp Ser Leu Ala Asn Leu Val Thr
 210             215             220
Asn Leu Asn Val Gln Lys Cys Ala Asn Ala Lys Thr Thr Tyr Leu Ala
225             230             235             240
Cys Val Asn Tyr Ala Leu Thr Asn Leu Ala Lys Val Gly Val Tyr Met
                 245             250             255
Tyr Met Asp Ala Gly His Ala Gly Trp Leu Gly Trp Pro Ala Asn Leu
             260             265             270
Ser Pro Ala Ala Gln Leu Phe Thr Gln Val Trp Gln Asn Ala Gly Lys
         275             280             285
Ser Pro Phe Ile Lys Gly Leu Ala Thr Asn Val Ala Asn Tyr Asn Ala
         290             295             300
Leu Gln Ala Ala Ser Pro Asp Pro Ile Thr Gln Gly Asn Pro Asn Tyr
305             310             315             320
Asp Glu Ile His Tyr Ile Asn Ala Leu Ala Pro Leu Leu Gln Gln Ala
                 325             330             335
Gly Trp Asp Ala Thr Phe Ile Val Asp Gln Gly Arg Ser Gly Val Gln
             340             345             350
Asn Ile Arg Gln Gln Trp Gly Asp Trp Cys Asn Ile Lys Gly Ala Gly
         355             360             365
Phe Gly Thr Arg Pro Thr Thr Asn Thr Gly Ser Gln Phe Ile Asp Ser
 370             375             380
Ile Val Trp Val Lys Pro Gly Gly Glu Cys Asp Gly Thr Ser Asn Ser
385             390             395             400
Ser Ser Pro Arg Tyr Asp Pro Thr Cys Ser Leu Pro Asp Ala Ala Gln
             405             410             415
Pro Ala Pro Glu Ala Gly Thr Trp Phe Gln Ala Tyr Phe Gln Thr Leu
             420             425             430
Val Ser Ala Ala Asn Pro Pro Leu
             435             440
```

<210> SEQ ID NO 74
<211> LENGTH: 440
<212> TYPE: PRT
<213> ORGANISM: Phanerochaete chrysosporium

<400> SEQUENCE: 74

```
Ala Ser Ser Glu Trp Gly Gln Cys Gly Gly Ile Gly Trp Thr Gly Pro
1               5                   10                  15

Thr Thr Cys Leu Ser Gly Thr Thr Cys Thr Val Leu Asn Pro Tyr Tyr
            20                  25                  30

Ser Gln Cys Leu Pro Gly Ser Ala Val Thr Thr Ser Val Ile Thr
        35                  40                  45

Ser His Ser Ser Val Ser Ser Val Ser Ser His Ser Gly Ser Ser
    50                  55                  60

Thr Ser Thr Ser Ser Pro Thr Gly Pro Thr Gly Thr Asn Pro Pro Pro
65                  70                  75                  80

Pro Pro Ser Ala Asn Asn Pro Trp Thr Gly Phe Gln Ile Phe Leu Ser
                85                  90                  95

Pro Tyr Tyr Ala Asn Glu Val Ala Ala Ala Lys Gln Ile Thr Asp
            100                 105                 110

Pro Thr Leu Ser Ser Lys Ala Ala Ser Val Ala Asn Ile Pro Thr Phe
            115                 120                 125

Thr Trp Leu Asp Ser Val Ala Lys Ile Pro Asp Leu Gly Thr Tyr Leu
        130                 135                 140

Ala Ser Ala Ser Ala Leu Gly Lys Ser Thr Gly Thr Lys Gln Leu Val
145                 150                 155                 160

Gln Ile Val Ile Tyr Asp Leu Pro Asp Arg Asp Cys Ala Ala Lys Ala
                165                 170                 175

Ser Asn Gly Glu Phe Ser Ile Ala Asn Asn Gly Gln Ala Asn Tyr Glu
            180                 185                 190

Asn Tyr Ile Asp Gln Ile Val Ala Gln Ile Gln Gln Phe Pro Asp Val
        195                 200                 205

Arg Val Val Ala Val Ile Glu Pro Asp Ser Leu Ala Asn Leu Val Thr
210                 215                 220

Asn Leu Asn Val Gln Lys Cys Ala Asn Ala Lys Thr Thr Tyr Leu Ala
225                 230                 235                 240

Cys Val Asn Tyr Ala Leu Thr Asn Leu Ala Lys Val Gly Val Tyr Met
                245                 250                 255

Tyr Met Asp Ala Gly His Ala Gly Trp Leu Gly Trp Pro Ala Asn Leu
            260                 265                 270

Ser Pro Ala Ala Gln Leu Phe Thr Gln Val Trp Gln Asn Ala Gly Glu
        275                 280                 285

Ser Pro Phe Ile Lys Gly Leu Ala Thr Asn Val Ala Asn Tyr Asn Ala
    290                 295                 300

Leu Gln Ala Ala Ser Pro Asp Pro Ile Thr Gln Gly Asn Pro Asn Tyr
305                 310                 315                 320

Asp Glu Ile His Tyr Ile Asn Ala Leu Ala Pro Leu Leu Gln Gln Ala
                325                 330                 335

Gly Trp Asp Ala Thr Phe Ile Val Asp Gln Gly Arg Ser Gly Val Gln
            340                 345                 350

Asn Ile Arg Gln Gln Trp Gly Asp Trp Cys Asn Ile Lys Gly Ala Gly
        355                 360                 365

Phe Gly Thr Arg Pro Thr Thr Asn Thr Gly Ser Gln Phe Ile Asp Ser
    370                 375                 380
```

```
Ile Val Trp Val Lys Pro Gly Gly Glu Cys Asp Gly Thr Ser Asn Ser
385                 390                 395                 400

Ser Ser Pro Arg Tyr Asp Pro Thr Cys Ser Leu Pro Asp Ala Ala Gln
                405                 410                 415

Pro Ala Pro Glu Ala Gly Thr Trp Phe Gln Ala Tyr Phe Gln Thr Leu
            420                 425                 430

Val Ser Ala Ala Asn Pro Pro Leu
        435                 440

<210> SEQ ID NO 75
<211> LENGTH: 440
<212> TYPE: PRT
<213> ORGANISM: Phanerochaete chrysosporium

<400> SEQUENCE: 75

Ala Ser Ser Glu Trp Gly Gln Cys Gly Gly Ile Gly Trp Thr Gly Pro
1               5                   10                  15

Thr Thr Cys Val Ser Gly Thr Thr Cys Thr Val Leu Asn Ser Tyr Tyr
            20                  25                  30

Ser Gln Cys Leu Pro Gly Ser Ala Val Thr Thr Ser Val Ile Thr
        35                  40                  45

Ser His Ser Ser Val Ser Ser Val Ser Ser His Ser Gly Ser Ser
    50                  55                  60

Thr Ser Thr Ser Ser Pro Thr Gly Pro Thr Gly Thr Asn Pro Pro Pro
65                  70                  75                  80

Pro Pro Ser Ala Asn Asn Pro Trp Thr Gly Phe Gln Ile Phe Leu Ser
                85                  90                  95

Pro Tyr Tyr Ala Asn Glu Val Ala Ala Ala Ala Lys Gln Ile Thr Asp
            100                 105                 110

Pro Thr Leu Ser Ser Lys Ala Ala Ser Val Ala Asn Ile Pro Thr Phe
            115                 120                 125

Thr Trp Leu Asp Ser Val Ala Lys Ile Pro Asp Leu Gly Thr Tyr Leu
        130                 135                 140

Ala Ser Ala Ser Ala Leu Gly Lys Ser Thr Gly Thr Lys Gln Leu Val
145                 150                 155                 160

Gln Ile Val Ile Tyr Asp Leu Pro Asp Arg Asp Cys Ala Ala Lys Ala
                165                 170                 175

Ser Asn Gly Glu Phe Ser Ile Ala Asn Asn Gly Gln Ala Asn Tyr Glu
            180                 185                 190

Asn Tyr Ile Asp Gln Ile Val Ala Gln Ile Gln Gln Phe Pro Asp Val
        195                 200                 205

Arg Val Val Ala Val Ile Glu Pro Asp Ser Leu Ala Asn Leu Val Thr
210                 215                 220

Asn Leu Asn Val Gln Lys Cys Ala Asn Ala Lys Thr Thr Tyr Leu Ala
225                 230                 235                 240

Cys Val Asn Tyr Ala Leu Thr Asn Leu Ala Lys Val Gly Val Tyr Met
                245                 250                 255

Tyr Met Asp Ala Gly His Ala Gly Trp Leu Gly Trp Pro Ala Asn Leu
            260                 265                 270

Ser Pro Ala Ala Gln Leu Phe Thr Gln Val Trp Gln Asn Ala Gly Lys
        275                 280                 285

Ser Pro Phe Ile Lys Gly Leu Ala Thr Asn Val Ala Asn Tyr Asn Ala
    290                 295                 300

Leu Gln Ala Ala Ser Pro Asp Pro Ile Thr Gln Gly Asn Pro Asn Tyr
```

```
            305                 310                 315                 320
Asp Glu Thr His Tyr Ile Asn Ala Leu Ala Pro Leu Gln Gln Ala
                    325                 330                 335
Gly Trp Asp Ala Thr Phe Ile Val Asp Gln Gly Arg Ser Gly Val Gln
                340                 345                 350
Asn Ile Arg Gln Gln Trp Gly Asp Trp Cys Asn Ile Lys Gly Ala Gly
            355                 360                 365
Phe Gly Thr Arg Pro Thr Thr Asn Thr Gly Ser Gln Phe Ile Asp Ser
    370                 375                 380
Ile Val Trp Val Lys Pro Gly Gly Glu Cys Asp Gly Thr Ser Asn Ser
385                 390                 395                 400
Ser Ser Pro Arg Tyr Asp Pro Thr Cys Ser Leu Pro Asp Ala Ala Gln
                405                 410                 415
Pro Ala Pro Glu Ala Gly Thr Trp Phe Gln Ala Tyr Phe Gln Thr Leu
            420                 425                 430
Val Ser Ala Ala Asn Pro Pro Leu
                435                 440

<210> SEQ ID NO 76
<211> LENGTH: 440
<212> TYPE: PRT
<213> ORGANISM: Phanerochaete chrysosporium

<400> SEQUENCE: 76

Ala Ser Ser Glu Trp Gly Gln Cys Gly Gly Ile Gly Trp Thr Gly Pro
1               5                   10                  15
Thr Thr Cys Val Ser Gly Thr Thr Cys Thr Val Leu Asn Pro Tyr Tyr
                20                  25                  30
Ser Gln Cys Ser Pro Gly Ser Ala Val Thr Thr Thr Ser Val Ile Thr
            35                  40                  45
Ser His Ser Ser Val Ser Ser Val Ser Ser His Ser Gly Ser Ser
        50                  55                  60
Thr Ser Thr Ser Ser Pro Thr Gly Pro Thr Gly Thr Asn Pro Pro Pro
65              70                  75                  80
Pro Pro Ser Ala Asn Asn Pro Trp Thr Gly Phe Gln Ile Phe Leu Ser
                85                  90                  95
Pro Tyr Tyr Ala Asn Glu Val Ala Ala Ala Lys Gln Ile Thr Asp
                100                 105                 110
Pro Thr Leu Ser Ser Lys Ala Ala Ser Val Ala Asn Ile Pro Thr Phe
            115                 120                 125
Thr Trp Leu Asp Ser Val Ala Lys Ile Pro Asp Leu Gly Thr Tyr Leu
    130                 135                 140
Ala Ser Ala Ser Ala Leu Gly Lys Ser Thr Gly Thr Lys Gln Leu Val
145                 150                 155                 160
Gln Ile Val Ile Tyr Asp Leu Pro Asp Arg Asp Cys Ala Ala Lys Ala
                165                 170                 175
Ser Asn Gly Glu Phe Ser Ile Ala Asn Asn Gly Gln Ala Asn Tyr Glu
                180                 185                 190
Asn Tyr Ile Asp Gln Ile Val Ala Gln Ile Gln Gln Phe Pro Asp Val
            195                 200                 205
Arg Val Val Ala Val Ile Glu Pro Asp Ser Leu Ala Asn Leu Val Thr
    210                 215                 220
Asn Leu Asn Val Gln Lys Cys Ala Asn Ala Lys Thr Thr Tyr Leu Ala
225                 230                 235                 240
```

```
Cys Val Asn Tyr Ala Leu Thr Asn Leu Ala Lys Val Gly Val Tyr Met
                245                 250                 255

Tyr Met Asp Ala Gly His Ala Gly Trp Leu Gly Trp Pro Ala Asn Leu
            260                 265                 270

Ser Pro Ala Ala Gln Leu Phe Thr Gln Val Trp Gln Asn Ala Gly Lys
        275                 280                 285

Ser Pro Phe Ile Lys Gly Leu Ala Thr Asn Val Ala Asn Tyr Asn Ala
    290                 295                 300

Leu Gln Ala Ala Ser Pro Asp Pro Ile Thr Gln Gly Asn Pro Asn Tyr
305                 310                 315                 320

Asp Glu Ile His Tyr Ile Asn Ala Leu Ala Pro Leu Leu Gln Gln Ala
                325                 330                 335

Gly Trp Asp Ala Thr Phe Ile Val Asp Gln Gly Arg Ser Gly Val Gln
            340                 345                 350

Asn Ile Arg Gln Gln Trp Gly Asp Trp Cys Asn Ile Lys Gly Ala Gly
        355                 360                 365

Phe Gly Thr Arg Pro Thr Thr Asn Thr Gly Ser Gln Phe Ile Asp Ser
    370                 375                 380

Ile Val Trp Val Lys Pro Gly Gly Glu Cys Asp Gly Thr Ser Asn Ser
385                 390                 395                 400

Ser Ser Pro Arg Tyr Asp Pro Thr Cys Ser Leu Pro Asp Ala Ala Gln
                405                 410                 415

Pro Ala Pro Glu Ala Gly Thr Trp Phe Gln Ala Tyr Phe Gln Thr Leu
            420                 425                 430

Val Ser Ala Ala Asn Pro Pro Leu
        435                 440

<210> SEQ ID NO 77
<211> LENGTH: 440
<212> TYPE: PRT
<213> ORGANISM: Phanerochaete chrysosporium

<400> SEQUENCE: 77

Ala Ser Ser Glu Cys Gly Gln Cys Gly Gly Ile Gly Trp Thr Gly Pro
1               5                   10                  15

Thr Thr Cys Val Ser Gly Thr Thr Cys Thr Val Leu Asn Pro Tyr Tyr
                20                  25                  30

Ser Gln Cys Leu Pro Gly Ser Ala Val Thr Thr Thr Ser Val Ile Thr
            35                  40                  45

Ser His Ser Ser Val Ser Ser Val Ser Ser His Ser Gly Ser Ser
        50                  55                  60

Thr Ser Thr Ser Ser Pro Thr Gly Pro Thr Gly Thr Asn Pro Pro
65                  70                  75                  80

Pro Pro Leu Ala Asn Asn Pro Trp Thr Gly Phe Gln Ile Phe Leu Ser
                85                  90                  95

Pro Tyr Tyr Ala Asn Glu Val Ala Ala Ala Lys Gln Ile Thr Asp
            100                 105                 110

Pro Thr Leu Ser Ser Lys Ala Ala Ser Val Ala Asn Ile Pro Thr Phe
        115                 120                 125

Thr Trp Met Asp Ser Val Ala Lys Ile Pro Asp Leu Gly Thr Tyr Leu
    130                 135                 140

Ala Ser Ala Ser Ala Leu Gly Lys Ser Thr Gly Thr Lys Gln Leu Val
145                 150                 155                 160

Gln Ile Val Ile Tyr Asp Leu Pro Asp Arg Asp Cys Ala Ala Lys Ala
                165                 170                 175
```

```
Ser Asn Gly Glu Phe Ser Ile Ala Asn Asn Gly Gln Ala Asn Tyr Glu
                180                 185                 190

Asn Tyr Ile Asp Gln Ile Val Ala Gln Ile Gln Gln Phe Pro Asp Val
            195                 200                 205

Arg Val Val Ala Val Ile Glu Pro Asp Ser Leu Ala Asn Leu Val Thr
210                 215                 220

Asn Leu Asn Val Gln Lys Cys Ala Asn Ala Lys Thr Thr Tyr Leu Ala
225                 230                 235                 240

Cys Val Asn Tyr Ala Leu Thr Asn Leu Ala Lys Val Gly Val Tyr Met
                245                 250                 255

Tyr Met Asp Ala Gly His Ala Gly Trp Leu Gly Trp Pro Ala Asn Leu
                260                 265                 270

Ser Pro Ala Ala Gln Leu Phe Thr Gln Val Trp Gln Asn Ala Gly Lys
            275                 280                 285

Ser Pro Phe Ile Lys Gly Leu Ala Thr Asn Val Ala Asn Tyr Asn Ala
        290                 295                 300

Leu Gln Ala Ala Ser Pro Asp Pro Ile Thr Gln Gly Asn Pro Asn Tyr
305                 310                 315                 320

Asp Glu Ile His Tyr Ile Asn Ala Leu Ala Pro Leu Leu Gln Gln Ala
                325                 330                 335

Gly Trp Asp Ala Thr Phe Ile Val Asp Gln Gly Arg Ser Gly Val Gln
                340                 345                 350

Asn Ile Arg Gln Gln Trp Gly Asp Trp Cys Asn Ile Lys Gly Ala Gly
            355                 360                 365

Phe Gly Thr Arg Pro Thr Thr Asn Thr Gly Ser Gln Phe Ile Asp Ser
        370                 375                 380

Ile Val Trp Val Lys Pro Gly Gly Glu Cys Asp Gly Thr Ser Asn Ser
385                 390                 395                 400

Ser Ser Pro Arg Tyr Asp Pro Thr Cys Ser Leu Pro Asp Ala Ala Gln
                405                 410                 415

Pro Ala Pro Glu Ala Gly Thr Trp Phe Gln Ala Tyr Phe Gln Thr Leu
                420                 425                 430

Val Ser Ala Ala Asn Pro Leu
                435                 440

<210> SEQ ID NO 78
<211> LENGTH: 440
<212> TYPE: PRT
<213> ORGANISM: Phanerochaete chrysosporium

<400> SEQUENCE: 78

Ala Asn Ser Glu Trp Gly Gln Cys Gly Gly Ile Ser Trp Thr Gly Pro
1               5                   10                  15

Thr Thr Cys Val Ser Gly Thr Thr Cys Thr Val Leu Asn Pro Tyr Tyr
                20                  25                  30

Ser Gln Cys Leu Pro Gly Ser Ala Val Thr Thr Thr Val Ile Thr
            35                  40                  45

Ser His Ser Ser Val Ser Ser Val Ser Ser His Ser Gly Ser Ser
        50                  55                  60

Thr Ser Thr Ser Ser Pro Thr Gly Pro Thr Gly Thr Asn Pro Pro
65                  70                  75                  80

Pro Pro Ser Ala Asn Asn Pro Trp Thr Gly Phe Gln Ile Phe Leu Ser
                85                  90                  95

Pro Tyr Tyr Ala Asn Glu Val Ala Ala Ala Lys Gln Ile Thr Asp
```

```
                100             105              110
Pro Thr Leu Ser Ser Lys Ala Ala Ser Val Val Asn Ile Pro Thr Phe
            115                 120                 125

Thr Trp Leu Asp Ser Val Ala Lys Ile Pro Asp Leu Gly Thr Tyr Leu
            130                 135             140

Ala Ser Ala Ser Ala Leu Gly Lys Ser Thr Gly Thr Lys Gln Leu Val
145                 150                 155                 160

Gln Ile Val Ile Tyr Asp Leu Pro Asp Arg Asp Cys Ala Ala Lys Ala
            165                 170                 175

Ser Asn Gly Glu Phe Ser Ile Ala Asn Asn Gly Gln Ala Asn Tyr Glu
            180                 185                 190

Asn Tyr Ile Asp Gln Ile Val Ala Gln Ile Gln Gln Phe Pro Asp Val
            195                 200                 205

Arg Val Val Ala Val Ile Glu Pro Asp Ser Leu Ala Asn Leu Val Thr
            210                 215                 220

Asn Leu Asn Val Gln Lys Cys Ala Asn Ala Lys Thr Thr Tyr Leu Ala
225                 230                 235                 240

Cys Val Asn Tyr Ala Leu Thr Asn Leu Ala Lys Val Gly Val Tyr Met
                245                 250                 255

Tyr Met Asp Ala Gly His Ala Gly Trp Leu Gly Trp Pro Ala Asn Leu
            260                 265                 270

Ser Pro Ala Ala Gln Leu Phe Thr Gln Val Trp Gln Asn Ala Gly Lys
            275                 280                 285

Ser Pro Phe Ile Lys Gly Leu Ala Thr Asn Val Ala Asn Tyr Asn Ala
            290                 295                 300

Leu Gln Ala Ala Ser Pro Asp Pro Ile Thr Gln Gly Asn Pro Asn Tyr
305                 310                 315                 320

Asp Glu Ile His Tyr Ile Asn Ala Leu Ala Pro Leu Leu Gln Gln Ala
                325                 330                 335

Gly Trp Asp Ala Thr Phe Ile Val Asp Gln Gly Arg Ser Gly Val Gln
            340                 345                 350

Asn Ile Arg Gln Gln Trp Gly Asp Trp Cys Asn Ile Lys Gly Ala Gly
            355                 360                 365

Phe Gly Thr Arg Pro Thr Thr Asn Thr Gly Ser Gln Phe Ile Asp Ser
            370                 375                 380

Ile Val Trp Val Lys Pro Gly Gly Glu Cys Asp Gly Thr Ser Asn Ser
385                 390                 395                 400

Ser Ser Pro Arg Tyr Asp Pro Thr Cys Ser Leu Pro Asp Ala Ala Gln
                405                 410                 415

Pro Ala Pro Glu Ala Gly Thr Trp Phe Gln Ala Tyr Phe Gln Thr Leu
            420                 425                 430

Val Ser Ala Ala Asn Pro Pro Leu
            435                 440

<210> SEQ ID NO 79
<211> LENGTH: 440
<212> TYPE: PRT
<213> ORGANISM: Phanerochaete chrysosporium

<400> SEQUENCE: 79

Ala Ser Ser Glu Trp Gly Gln Cys Gly Gly Thr Gly Trp Thr Gly Pro
1               5                   10                  15

Thr Thr Cys Val Ser Gly Thr Cys Thr Val Leu Asn Pro Tyr Tyr
            20                  25                  30
```

```
Ser Gln Cys Leu Pro Gly Ser Ala Val Thr Thr Ser Val Ile Thr
        35                  40                  45
Ser His Ser Ser Ser Val Ser Ser Val Ser Ser His Ser Gly Ser Ser
 50                  55                  60
Thr Ser Thr Ser Ser Pro Thr Gly Pro Thr Gly Thr Asn Pro Pro Pro
 65                  70                  75                  80
Pro Pro Ser Ala Asn Asn Pro Trp Thr Gly Phe Gln Ile Phe Leu Ser
            85                  90                  95
Pro Tyr Tyr Ala Asn Glu Val Ala Ala Ala Lys Gln Ile Thr Asp
                100                 105                 110
Pro Thr Leu Ser Ser Lys Ala Ala Ser Val Ala Asn Ile Pro Thr Phe
            115                 120                 125
Thr Trp Leu Asp Ser Val Ala Lys Ile Pro Asp Leu Gly Thr Tyr Leu
    130                 135                 140
Ala Ser Ala Ser Ala Leu Gly Lys Ser Thr Gly Thr Lys Gln Leu Val
145                 150                 155                 160
Gln Ile Val Ile Tyr Asp Leu Pro Asp Arg Asp Cys Ala Ala Lys Ala
                165                 170                 175
Ser Asn Gly Glu Phe Ser Ile Ala Asn Asn Gly Gln Ala Asn Tyr Glu
            180                 185                 190
Asn Tyr Ile Asp Gln Ile Val Ala Gln Ile Gln Gln Phe Pro Asp Val
        195                 200                 205
Arg Val Val Ala Val Ile Glu Pro Asp Ser Leu Ala Asn Leu Val Thr
    210                 215                 220
Asn Leu Asn Val Gln Lys Cys Ala Asn Ala Lys Thr Thr Tyr Leu Ala
225                 230                 235                 240
Cys Val Asn Tyr Ala Leu Thr Asn Leu Ala Lys Val Gly Val Tyr Met
                245                 250                 255
Tyr Met Asp Ala Gly His Ala Gly Trp Leu Gly Trp Pro Ala Asn Leu
            260                 265                 270
Ser Pro Ala Ala Gln Leu Phe Thr Gln Val Trp Gln Asn Ala Gly Lys
        275                 280                 285
Ser Pro Phe Ile Lys Gly Leu Ala Thr Asn Val Ala Asn Tyr Asn Ala
    290                 295                 300
Leu Gln Ala Ala Ser Pro Asp Pro Ile Thr Gln Gly Asn Pro Asn Tyr
305                 310                 315                 320
Asp Glu Ile His Tyr Ile Asn Ala Leu Ala Pro Leu Leu Gln Gln Ala
                325                 330                 335
Gly Trp Asp Ala Thr Phe Ile Val Asp Gln Gly Arg Ser Gly Val Gln
            340                 345                 350
Asn Ile Arg Gln Gln Trp Gly Asp Trp Cys Asn Ile Lys Gly Ala Gly
        355                 360                 365
Phe Gly Thr Arg Pro Thr Thr Asn Thr Gly Ser Gln Phe Ile Asp Ser
    370                 375                 380
Ile Val Trp Val Lys Pro Gly Gly Glu Cys Asp Gly Thr Ser Asn Ser
385                 390                 395                 400
Ser Ser Pro Arg Tyr Asp Pro Thr Cys Ser Leu Pro Asp Ala Ala Gln
                405                 410                 415
Pro Ala Pro Glu Ala Gly Ile Trp Phe Gln Ala Tyr Phe Gln Thr Leu
            420                 425                 430
Val Ser Ala Ala Asn Pro Ser Leu
    435                 440
```

```
<210> SEQ ID NO 80
<211> LENGTH: 440
<212> TYPE: PRT
<213> ORGANISM: Phanerochaete chrysosporium

<400> SEQUENCE: 80

Ala Ser Ser Glu Trp Gly Gln Cys Gly Gly Ile Gly Trp Thr Gly Pro
  1               5                  10                  15

Thr Thr Cys Val Ser Gly Thr Thr Cys Thr Val Leu Asn Ser Tyr Tyr
             20                  25                  30

Ser Gln Cys Leu Pro Gly Ser Ala Val Thr Thr Ser Val Ile Thr
         35                  40                  45

Ser His Ser Ser Ser Val Ser Ser Val Ser Ser His Ser Gly Ser Ser
     50                  55                  60

Thr Ser Thr Ser Ser Pro Thr Gly Pro Thr Gly Thr Asn Pro Pro Pro
 65                  70                  75                  80

Pro Pro Ser Ala Asn Asn Pro Trp Thr Gly Phe Gln Ile Phe Leu Ser
                 85                  90                  95

Pro Tyr Tyr Ala Asn Glu Val Ala Ala Ala Lys Gln Ile Thr Asp
            100                 105                 110

Pro Thr Leu Ser Ser Lys Ala Ala Ser Val Ala Asn Ile Pro Thr Phe
            115                 120                 125

Thr Trp Leu Asp Ser Val Ala Lys Ile Pro Asp Leu Gly Thr Tyr Leu
        130                 135                 140

Ala Ser Ala Ser Ala Leu Gly Lys Ser Thr Gly Thr Lys Gln Leu Val
145                 150                 155                 160

Gln Ile Val Ile Tyr Asp Leu Pro Asp Arg Asp Cys Ala Ala Lys Ala
                165                 170                 175

Ser Asn Gly Glu Phe Ser Ile Ala Asn Asn Gly Gln Ala Asn Tyr Glu
            180                 185                 190

Asn Tyr Ile Asp Gln Ile Val Ala Gln Ile Gln Gln Phe Pro Asp Val
        195                 200                 205

Arg Val Val Ala Val Ile Glu Pro Asp Ser Leu Ala Asn Leu Val Thr
    210                 215                 220

Asn Leu Asn Val Gln Lys Cys Ala Asn Ala Lys Thr Thr Tyr Leu Ala
225                 230                 235                 240

Cys Val Asn Tyr Ala Leu Thr Asn Leu Ala Lys Val Gly Val Tyr Met
                245                 250                 255

Tyr Met Asp Ala Gly His Ala Gly Trp Leu Gly Trp Pro Ala Asn Leu
            260                 265                 270

Ser Pro Ala Ala Gln Leu Phe Thr Gln Val Trp Gln Asn Ala Gly Lys
        275                 280                 285

Ser Pro Phe Ile Lys Gly Leu Ala Thr Asn Val Ala Asn Tyr Asn Ala
    290                 295                 300

Leu Gln Ala Ala Ser Pro Asp Pro Ile Thr Gln Gly Asn Pro Asn Tyr
305                 310                 315                 320

Asp Glu Ile His Tyr Ile Asn Ala Leu Ala Pro Leu Leu Gln Gln Ala
                325                 330                 335

Gly Trp Asp Ala Thr Phe Ile Val Asp Gln Gly Arg Ser Gly Val Gln
            340                 345                 350

Asn Ile Arg Gln Gln Trp Gly Asp Trp Cys Asn Ile Lys Gly Ala Gly
        355                 360                 365

Phe Gly Thr Arg Pro Thr Thr Asn Thr Gly Ser Gln Phe Ile Asp Ser
    370                 375                 380
```

Ile Val Trp Val Lys Pro Gly Gly Glu Cys Asp Gly Thr Ser Asn Ser
385                 390                 395                 400

Ser Ser Pro Arg Tyr Asp Pro Thr Cys Ser Leu Pro Asp Ala Ala Gln
            405                 410                 415

Pro Ala Pro Glu Ala Gly Thr Trp Phe Gln Ala Tyr Phe Gln Thr Leu
        420                 425                 430

Val Ser Ala Ala Asn Pro Pro Leu
        435                 440

<210> SEQ ID NO 81
<211> LENGTH: 440
<212> TYPE: PRT
<213> ORGANISM: Phanerochaete chrysosporium

<400> SEQUENCE: 81

Ala Ser Ser Glu Trp Gly Gln Cys Gly Gly Ile Gly Trp Thr Gly Pro
1               5                   10                  15

Thr Thr Cys Val Ser Ser Thr Ser Cys Thr Val Leu Asn Pro Tyr Tyr
                20                  25                  30

Ser Gln Cys Leu Pro Gly Ser Ala Val Thr Thr Ser Val Ile Thr
            35                  40                  45

Ser His Ser Ser Ile Ser Ser Val Ser Ser His Ser Gly Ser Ser
        50                  55                  60

Thr Ser Thr Ser Ser Pro Thr Gly Pro Thr Gly Thr Asn Pro Pro
65                  70                  75                  80

Pro Pro Ser Ala Asn Asn Pro Trp Thr Gly Phe Gln Ile Phe Leu Ser
            85                  90                  95

Pro Tyr Tyr Ala Asn Glu Val Ala Ala Ala Lys Gln Ile Thr Asp
        100                 105                 110

Pro Thr Leu Ser Ser Lys Ala Ala Ser Val Ala Asn Ile Pro Thr Phe
        115                 120                 125

Thr Trp Leu Asp Ser Val Ala Lys Ile Pro Asp Leu Gly Thr Tyr Leu
    130                 135                 140

Ala Ser Ala Ser Ala Leu Gly Lys Ser Thr Gly Thr Lys Gln Leu Val
145                 150                 155                 160

Gln Ile Val Ile Tyr Asp Leu Pro Asp Arg Asp Cys Ala Ala Lys Ala
                165                 170                 175

Ser Asn Gly Glu Phe Ser Ile Ala Asn Asn Gly Gln Ala Asn Tyr Glu
            180                 185                 190

Asn Tyr Ile Asp Gln Ile Val Ala Gln Ile Gln Gln Phe Pro Asp Val
        195                 200                 205

Arg Val Val Ala Val Ile Glu Pro Asp Ser Leu Ala Asn Leu Val Thr
    210                 215                 220

Asn Leu Asn Val Gln Lys Cys Ala Asn Ala Lys Thr Thr Tyr Leu Ala
225                 230                 235                 240

Cys Val Asn Tyr Ala Leu Thr Asn Leu Ala Lys Val Gly Val Tyr Met
                245                 250                 255

Tyr Met Asp Ala Gly His Ala Gly Trp Leu Gly Trp Pro Ala Asn Leu
            260                 265                 270

Ser Pro Ala Ala Gln Leu Phe Thr Gln Val Trp Gln Asn Ala Gly Lys
        275                 280                 285

Ser Pro Phe Ile Lys Gly Leu Ala Thr Asn Val Ala Asn Tyr Asn Ala
    290                 295                 300

Leu Gln Ala Ala Ser Pro Asp Pro Ile Thr Gln Gly Asn Pro Asn Tyr
305                 310                 315                 320

```
Asp Glu Ile His Tyr Ile Asn Ala Leu Ala Pro Leu Leu Gln Gln Ala
            325                 330                 335

Gly Trp Asp Ala Thr Phe Ile Val Asp Gln Gly Arg Ser Gly Val Gln
        340                 345                 350

Asn Ile Arg Gln Gln Trp Gly Asp Trp Cys Asn Ile Lys Gly Ala Gly
    355                 360                 365

Phe Gly Thr Arg Pro Thr Thr Asn Thr Gly Ser Gln Phe Ile Asp Ser
370                 375                 380

Ile Val Trp Val Lys Pro Gly Gly Glu Cys Asp Gly Thr Ser Asn Ser
385                 390                 395                 400

Ser Ser Pro Arg Tyr Asp Pro Thr Cys Ser Leu Pro Asp Ala Ala Gln
            405                 410                 415

Pro Ala Pro Glu Ala Gly Thr Trp Phe Gln Ala Tyr Phe Gln Thr Leu
        420                 425                 430

Val Ser Ala Ala Asn Pro Pro Leu
            435                 440

<210> SEQ ID NO 82
<211> LENGTH: 440
<212> TYPE: PRT
<213> ORGANISM: Phanerochaete chrysosporium

<400> SEQUENCE: 82

Ala Ser Ser Glu Trp Gly Gln Cys Gly Gly Ile Gly Trp Thr Asp Pro
1               5                   10                  15

Thr Thr Cys Val Ser Gly Thr Thr Cys Thr Val Leu Asn Pro Tyr Tyr
            20                  25                  30

Ser Gln Cys Leu Pro Gly Ser Ala Val Thr Thr Ser Val Ile Thr
        35                  40                  45

Ser His Ser Ser Ser Val Ser Ser Val Ser Ser His Ser Gly Ser Ser
    50                  55                  60

Thr Ser Thr Ser Ser Pro Thr Gly Pro Thr Gly Thr Asn Pro Pro Leu
65                  70                  75                  80

Pro Pro Ser Ala Asn Asn Pro Trp Thr Gly Phe Gln Ile Phe Leu Ser
            85                  90                  95

Pro Tyr Tyr Ala Asn Glu Val Ala Ala Ala Lys Gln Ile Thr Asp
            100                 105                 110

Pro Thr Leu Ser Ser Lys Ala Ala Ser Val Ala Asn Ile Pro Thr Phe
            115                 120                 125

Thr Trp Leu Asp Ser Val Ala Lys Ile Pro Asp Leu Gly Thr Tyr Leu
    130                 135                 140

Ala Ser Ala Ser Ala Leu Gly Lys Ser Thr Gly Thr Lys Gln Leu Val
145                 150                 155                 160

Gln Ile Val Ile Tyr Asp Leu Pro Asp Arg Asp Cys Ala Ala Lys Ala
            165                 170                 175

Ser Asn Gly Glu Phe Ser Ile Thr Asn Asn Gly Gln Ala Asn Tyr Glu
            180                 185                 190

Asn Tyr Ile Asp Gln Ile Val Ala Gln Ile Gln Gln Phe Pro Asp Val
    195                 200                 205

Arg Val Val Ala Val Ile Glu Pro Asp Ser Leu Ala Asn Leu Val Thr
    210                 215                 220

Asn Leu Asn Val Gln Lys Cys Ala Asn Ala Lys Thr Thr Tyr Leu Ala
225                 230                 235                 240

Cys Val Asn Tyr Ala Leu Thr Asn Leu Ala Lys Val Gly Val Tyr Met
```

```
                    245                 250                 255
Tyr Met Asp Ala Gly His Ala Gly Trp Leu Gly Trp Pro Ala Asn Leu
            260                 265                 270

Ser Pro Ala Ala Gln Leu Phe Thr Gln Ile Trp Gln Asn Ala Gly Lys
        275                 280                 285

Ser Pro Phe Ile Lys Gly Leu Ala Thr Asn Val Ala Asn Tyr Asn Ala
        290                 295                 300

Leu Gln Ala Ala Ser Pro Asp Pro Ile Thr Gln Gly Asn Pro Asn Tyr
305                 310                 315                 320

Asp Glu Ile His Tyr Ile Asn Ala Leu Ala Pro Leu Leu Gln Gln Ala
                325                 330                 335

Gly Trp Asp Ala Thr Phe Ile Val Asp Gln Gly Arg Ser Gly Val Gln
                340                 345                 350

Asn Ile Arg Gln Gln Trp Gly Asp Trp Cys Asn Ile Lys Gly Ala Gly
            355                 360                 365

Phe Gly Thr Arg Pro Thr Thr Asn Thr Gly Ser Gln Phe Ile Asp Ser
        370                 375                 380

Ile Val Trp Val Lys Pro Gly Gly Glu Cys Asp Gly Thr Ser Asn Ser
385                 390                 395                 400

Ser Ser Pro Arg Tyr Asp Pro Thr Cys Ser Leu Pro Asp Ala Ala Gln
                405                 410                 415

Pro Ala Pro Glu Ala Gly Thr Trp Phe Gln Ala Tyr Phe Gln Thr Leu
                420                 425                 430

Val Ser Ala Ala Asn Pro Pro Leu
        435                 440

<210> SEQ ID NO 83
<211> LENGTH: 440
<212> TYPE: PRT
<213> ORGANISM: Phanerochaete chrysosporium

<400> SEQUENCE: 83

Ala Ser Ser Glu Trp Gly Gln Cys Gly Gly Ile Gly Trp Thr Gly Pro
1               5                   10                  15

Thr Thr Cys Val Ser Gly Thr Thr Cys Thr Val Leu Thr Pro Tyr Tyr
            20                  25                  30

Ser Gln Cys Leu Pro Gly Ser Ala Val Thr Thr Thr Ser Val Ile Thr
        35                  40                  45

Ser His Ser Ser Ser Val Ser Ser Val Ser Ser His Ser Gly Ser Ser
    50                  55                  60

Thr Ser Thr Ser Ser Pro Thr Gly Pro Thr Gly Thr Asn Pro Pro Pro
65                  70                  75                  80

Pro Pro Ser Ala Asn Asn Pro Trp Thr Gly Phe Gln Ile Phe Leu Ser
                85                  90                  95

Pro Tyr Tyr Ala Asn Glu Val Ala Ala Ala Lys Gln Ile Thr Asp
            100                 105                 110

Pro Thr Leu Ser Ser Lys Ala Ala Ser Val Ala Asn Ile Pro Thr Phe
        115                 120                 125

Thr Trp Leu Asp Ser Val Ala Lys Ile Pro Asp Leu Gly Thr Tyr Leu
    130                 135                 140

Ala Ser Ala Ser Ala Leu Gly Lys Ser Thr Gly Thr Lys Gln Leu Val
145                 150                 155                 160

Gln Ile Val Ile Tyr Asp Leu Pro Asp Arg Asp Cys Ala Ala Lys Ala
                165                 170                 175
```

```
Ser Asn Gly Glu Phe Ser Ile Ala Asn Asn Gly Gln Ala Asn Tyr Glu
            180                 185                 190

Asn Tyr Ile Asp Gln Ile Val Ala Gln Ile Gln Gln Phe Pro Asp Val
        195                 200                 205

Arg Val Val Ala Val Ile Glu Pro Asp Ser Leu Ala Asn Leu Val Thr
    210                 215                 220

Asn Leu Asn Val Gln Lys Cys Ala Asn Ala Lys Thr Thr Tyr Leu Ala
225                 230                 235                 240

Cys Val Asn Tyr Ala Leu Thr Asn Leu Ala Lys Val Gly Val Tyr Met
                245                 250                 255

Tyr Met Asp Ala Gly His Ala Gly Trp Leu Gly Trp Pro Ala Asn Leu
        260                 265                 270

Ser Pro Ala Ala Gln Leu Phe Thr Gln Val Trp Gln Asn Ala Gly Lys
    275                 280                 285

Ser Pro Phe Ile Lys Gly Leu Ala Thr Asn Val Ala Asn Tyr Asn Ala
    290                 295                 300

Leu Gln Ala Ala Ser Pro Asp Pro Ile Thr Gln Gly Asn Pro Asn Tyr
305                 310                 315                 320

Asp Glu Ile His Tyr Ile Asn Ala Leu Ala Pro Leu Leu Gln Gln Ala
                325                 330                 335

Gly Trp Asp Ala Thr Phe Ile Val Asp Gln Gly Arg Ser Gly Val Gln
        340                 345                 350

Asn Ile Arg Gln Gln Trp Gly Asp Trp Cys Asn Ile Lys Gly Ala Gly
    355                 360                 365

Phe Gly Thr Arg Pro Thr Thr Asn Thr Gly Ser Gln Phe Ile Asp Ser
    370                 375                 380

Ile Val Trp Val Lys Pro Gly Gly Glu Cys Asp Gly Thr Ser Asn Ser
385                 390                 395                 400

Ser Ser Pro Arg Tyr Asp Pro Thr Cys Ser Leu Pro Asp Ala Ala Gln
                405                 410                 415

Pro Ala Pro Glu Ala Gly Thr Trp Phe Gln Ala Tyr Phe Gln Thr Leu
        420                 425                 430

Val Ser Ala Ala Asn Pro Pro Leu
        435                 440

<210> SEQ ID NO 84
<211> LENGTH: 440
<212> TYPE: PRT
<213> ORGANISM: Phanerochaete chrysosporium

<400> SEQUENCE: 84

Ala Ser Ser Glu Trp Gly Gln Cys Gly Gly Ile Gly Trp Thr Gly Pro
1               5                   10                  15

Thr Thr Cys Val Ser Gly Thr Thr Cys Thr Val Leu Asn Pro Tyr Tyr
            20                  25                  30

Ser Gln Cys Ser Pro Gly Ser Ala Val Thr Thr Thr Ser Val Ile Thr
        35                  40                  45

Ser His Ser Ser Ser Val Ser Ser Val Ser Ser His Ser Gly Ser Ser
    50                  55                  60

Thr Ser Thr Ser Ser Pro Thr Gly Pro Thr Gly Thr Asn Pro Pro Pro
65                  70                  75                  80

Pro Pro Ser Ala Asn Asn Pro Trp Thr Gly Phe Gln Ile Phe Leu Ser
                85                  90                  95

Pro Tyr Tyr Ala Asn Glu Val Ala Ala Ala Lys Gln Ile Thr Asp
            100                 105                 110
```

```
Pro Thr Leu Ser Ser Lys Ala Ala Ser Val Ala Asn Ile Pro Thr Phe
        115                 120                 125

Thr Trp Leu Asp Ser Val Ala Lys Ile Pro Asp Leu Gly Thr Tyr Leu
130                 135                 140

Ala Ser Ala Ser Ala Leu Gly Lys Ser Thr Gly Thr Lys Gln Leu Val
145                 150                 155                 160

Gln Ile Val Ile Tyr Asp Leu Pro Asp Arg Asp Cys Ala Ala Lys Ala
                165                 170                 175

Ser Asn Gly Glu Phe Ser Ile Ala Asn Asn Gly Gln Ala Asn Tyr Glu
            180                 185                 190

Asn Tyr Ile Asp Gln Ile Val Ala His Ile Gln Gln Phe Pro Asp Val
        195                 200                 205

Arg Val Val Ala Val Ile Glu Pro Asp Ser Leu Ala Asn Leu Val Thr
    210                 215                 220

Asn Leu Asn Val Gln Lys Cys Ala Asn Ala Lys Thr Thr Tyr Leu Ala
225                 230                 235                 240

Cys Val Asn Tyr Ala Leu Thr Asn Leu Ala Lys Val Gly Val Tyr Met
                245                 250                 255

Tyr Met Asp Ala Gly His Ala Gly Trp Leu Gly Trp Pro Ala Asn Leu
            260                 265                 270

Ser Pro Ala Ala Gln Leu Phe Thr Gln Val Trp Gln Asn Ala Gly Lys
        275                 280                 285

Ser Pro Phe Ile Lys Gly Leu Ala Thr Asn Val Ala Asn Tyr Asn Gly
    290                 295                 300

Leu Gln Ala Ala Ser Pro Asp Pro Ile Thr Gln Gly Asn Pro Asn Tyr
305                 310                 315                 320

Asp Glu Ile His Tyr Ile Asn Ala Leu Ala Pro Leu Leu Gln Gln Ala
                325                 330                 335

Gly Trp Asp Ala Thr Phe Ile Val Asp Gln Gly Arg Ser Gly Val Gln
            340                 345                 350

Asn Ile Arg Gln Gln Trp Gly Asp Trp Cys Asn Ile Lys Gly Ala Gly
        355                 360                 365

Phe Gly Thr Arg Pro Thr Thr Asn Thr Gly Ser Gln Phe Ile Asp Ser
    370                 375                 380

Ile Val Trp Val Lys Pro Gly Gly Glu Cys Asp Gly Thr Ser Asn Ser
385                 390                 395                 400

Ser Ser Pro Arg Tyr Asp Pro Thr Cys Ser Leu Pro Asp Ala Ala Gln
                405                 410                 415

Pro Ala Pro Glu Ala Gly Thr Trp Phe Gln Ala Tyr Phe Gln Thr Leu
            420                 425                 430

Val Ser Ala Ala Asn Pro Pro Leu
        435                 440

<210> SEQ ID NO 85
<211> LENGTH: 440
<212> TYPE: PRT
<213> ORGANISM: Phanerochaete chrysosporium

<400> SEQUENCE: 85

Ala Ser Ser Glu Trp Gly Gln Cys Gly Gly Ile Asp Trp Thr Gly Pro
1               5                   10                  15

Thr Thr Cys Val Ser Gly Thr Thr Cys Thr Val Leu Asn Pro Tyr Tyr
            20                  25                  30

Ser Gln Cys Leu Pro Gly Ser Ala Val Thr Thr Thr Ser Val Ile Thr
```

35                  40                  45
Ser His Ser Ser Ser Val Ser Val Ser Ser His Ser Gly Ser Ser
 50                  55                  60

Thr Ser Thr Ser Ser Pro Thr Gly Pro Thr Gly Thr Asn Pro Pro Pro
 65                  70                  75                  80

Pro Pro Ser Ala Asn Asn Pro Trp Thr Gly Phe Gln Ile Phe Leu Ser
                 85                  90                  95

Pro Tyr Tyr Ala Asn Glu Val Ala Ala Ala Lys Gln Ile Thr Asp
            100                 105                 110

Pro Thr Leu Ser Ser Lys Ala Ala Ser Val Ala Asn Ile Pro Thr Phe
            115                 120                 125

Thr Trp Leu Asp Ser Val Ala Lys Ile Pro Asp Leu Gly Thr Tyr Leu
130                 135                 140

Ala Ser Ala Ser Ala Leu Gly Lys Ser Thr Gly Thr Lys Gln Leu Val
145                 150                 155                 160

Gln Ile Val Ile Tyr Asp Leu Pro Asp Arg Asp Cys Ala Ala Lys Ala
                165                 170                 175

Ser Asn Gly Glu Phe Ser Ile Ala Asn Asn Gly Gln Ala Asn Tyr Glu
            180                 185                 190

Asn Tyr Ile Asp Gln Ile Val Ala Gln Ile Gln Phe Pro Asp Val
            195                 200                 205

Arg Val Val Ala Val Ile Glu Pro Asp Ser Leu Ala Asn Leu Val Thr
210                 215                 220

Asn Leu Asn Val Gln Lys Cys Ala Asn Ala Lys Thr Thr Tyr Leu Ala
225                 230                 235                 240

Cys Val Asn Tyr Ala Leu Thr Asn Leu Ala Lys Val Gly Val Tyr Met
                245                 250                 255

Tyr Met Asp Ala Gly His Ala Gly Trp Leu Gly Trp Pro Ala Asn Leu
            260                 265                 270

Ser Pro Ala Ala Gln Leu Phe Thr Gln Val Trp Gln Asn Ala Gly Lys
            275                 280                 285

Ser Pro Phe Ile Lys Gly Leu Ser Thr Asn Val Ala Asn Tyr Asn Ala
            290                 295                 300

Leu Gln Ala Ala Ser Pro Asp Pro Ile Thr Gln Gly Asn Pro Asn Tyr
305                 310                 315                 320

Asp Glu Ile His Tyr Ile Asn Ala Leu Ala Pro Leu Leu Gln Gln Ala
                325                 330                 335

Gly Trp Asp Ala Thr Phe Ile Val Asp Gln Gly Arg Ser Gly Val Gln
            340                 345                 350

Asn Ile Arg Gln Gln Trp Gly Asp Trp Cys Asn Ile Lys Gly Ala Gly
            355                 360                 365

Phe Gly Thr Arg Pro Thr Thr Asn Thr Gly Ser Gln Phe Ile Asp Ser
            370                 375                 380

Ile Val Trp Val Lys Pro Gly Gly Glu Cys Asp Gly Thr Ser Asn Ser
385                 390                 395                 400

Ser Ser Pro Arg Tyr Asp Pro Thr Cys Ser Leu Pro Asp Ala Ala Gln
                405                 410                 415

Pro Ala Pro Glu Ala Gly Thr Trp Phe Gln Ala Tyr Phe Gln Thr Leu
            420                 425                 430

Val Ser Ala Ala Asn Pro Pro Leu
            435                 440

<210> SEQ ID NO 86

```
<211> LENGTH: 440
<212> TYPE: PRT
<213> ORGANISM: Phanerochaete chrysosporium

<400> SEQUENCE: 86

Ala Ser Ser Glu Trp Gly Gln Cys Gly Gly Ile Gly Trp Thr Gly Pro
1               5                   10                  15

Thr Thr Cys Val Ser Gly Thr Thr Cys Thr Asp Leu Asn Pro Tyr Tyr
            20                  25                  30

Ser Gln Cys Leu Pro Gly Ser Ala Val Thr Thr Thr Ser Val Ile Thr
        35                  40                  45

Ser His Ser Ser Ser Val Ser Ser Val Ser Ser Tyr Ser Gly Ser Ser
    50                  55                  60

Thr Ser Thr Ser Ser Pro Thr Gly Pro Thr Gly Thr Asn Pro Pro Thr
65                  70                  75                  80

Pro Pro Ser Ala Asn Asn Pro Trp Thr Gly Phe Gln Ile Phe Leu Ser
                85                  90                  95

Pro Tyr Tyr Ala Asn Glu Val Ala Ala Ala Lys Gln Ile Thr Asp
            100                 105                 110

Pro Thr Leu Ser Ser Lys Ala Ala Ser Val Ala Asn Ile Pro Thr Phe
        115                 120                 125

Thr Trp Leu Asp Ser Val Ala Lys Ile Pro Asp Leu Gly Thr Tyr Leu
    130                 135                 140

Ala Ser Ala Ser Ala Leu Gly Lys Ser Thr Gly Thr Lys Gln Leu Val
145                 150                 155                 160

Gln Ile Val Ile Tyr Asp Leu Pro Asp Arg Asp Cys Ala Ala Lys Ala
                165                 170                 175

Ser Asn Gly Glu Phe Ser Ile Ala Asn Asn Gly Gln Ala Asn Tyr Glu
            180                 185                 190

Asn Tyr Ile Asp Gln Ile Val Ala Gln Ile Gln Gln Phe Pro Asp Val
        195                 200                 205

Arg Val Val Ala Val Ile Glu Pro Asp Ser Leu Ala Asn Leu Val Thr
    210                 215                 220

Asn Leu Asn Val Gln Lys Cys Ala Asn Ala Lys Thr Thr Tyr Leu Ala
225                 230                 235                 240

Cys Val Asn Tyr Ala Leu Thr Asn Leu Ala Lys Val Gly Val Tyr Met
                245                 250                 255

Tyr Met Asp Ala Gly His Ala Gly Trp Leu Gly Trp Pro Ala Asn Leu
            260                 265                 270

Ser Pro Ala Ala Gln Leu Phe Thr Gln Val Trp Gln Asn Ala Gly Lys
        275                 280                 285

Ser Pro Phe Ile Lys Gly Leu Ala Thr Asn Val Ala Asn Tyr Asn Ala
    290                 295                 300

Leu Gln Ala Ala Ser Pro Asp Pro Ile Thr Gln Gly Asn Pro Asn Tyr
305                 310                 315                 320

Asp Glu Ile His Tyr Ile Asn Ala Leu Ala Pro Leu Leu Gln Gln Ala
                325                 330                 335

Gly Trp Asp Ala Thr Phe Ile Val Asp Gln Gly Arg Ser Gly Val Gln
            340                 345                 350

Asn Ile Arg Gln Gln Trp Gly Asp Trp Cys Asn Ile Lys Gly Ala Gly
        355                 360                 365

Phe Gly Thr Arg Pro Thr Thr Asn Thr Gly Ser Gln Phe Ile Asp Ser
    370                 375                 380

Ile Val Trp Val Lys Pro Gly Gly Glu Cys Asp Gly Thr Ser Asn Ser
```

```
                385                 390                 395                 400
Ser Ser Pro Arg Tyr Asp Pro Thr Cys Ser Leu Pro Asp Ala Ala Gln
                405                 410                 415

Pro Ala Pro Glu Ala Gly Thr Trp Phe Gln Ala Tyr Phe Gln Thr Leu
                420                 425                 430

Val Ser Ala Ala Asn Pro Pro Leu
                435                 440

<210> SEQ ID NO 87
<211> LENGTH: 440
<212> TYPE: PRT
<213> ORGANISM: Phanerochaete chrysosporium

<400> SEQUENCE: 87

Asp Ser Ser Glu Trp Gly Gln Cys Gly Gly Ile Gly Trp Thr Gly Pro
1               5                   10                  15

Thr Thr Cys Val Ser Gly Thr Thr Cys Thr Val Pro Asn Pro Tyr Tyr
                20                  25                  30

Ser Gln Cys Leu Pro Gly Ser Ala Val Thr Thr Thr Ser Val Ile Thr
            35                  40                  45

Ser His Ser Ser Val Ser Ser Val Ser Ser His Ser Gly Ser Ser
        50                  55                  60

Thr Ser Thr Ser Ser Pro Thr Gly Pro Thr Gly Thr Asn Pro Pro
65                  70                  75                  80

Pro Pro Ser Ala Asn Asn Pro Trp Thr Gly Phe Gln Ile Phe Leu Ser
                85                  90                  95

Pro Tyr Tyr Ala Asn Glu Val Ala Ala Ala Lys Gln Ile Thr Asp
                100                 105                 110

Pro Thr Leu Ser Ser Lys Ala Ala Ser Val Ala Asn Ile Pro Thr Phe
            115                 120                 125

Thr Trp Leu Asp Ser Val Ala Lys Ile Pro Asp Leu Gly Thr Tyr Leu
        130                 135                 140

Ala Ser Ala Ser Ala Leu Gly Lys Ser Thr Gly Thr Lys Gln Leu Val
145                 150                 155                 160

Gln Ile Val Ile Tyr Asp Leu Pro Asp Arg Asp Cys Ala Ala Lys Ala
                165                 170                 175

Ser Asn Gly Glu Phe Ser Ile Ala Asn Asn Gly Gln Ala Asn Tyr Glu
                180                 185                 190

Asn Tyr Ile Asp Gln Ile Val Ala Gln Ile Gln Gln Phe Pro Asp Val
                195                 200                 205

Arg Val Val Ala Val Ile Glu Pro Asp Ser Leu Ala Asn Leu Val Thr
210                 215                 220

Asn Leu Asn Val Gln Lys Cys Ala Asn Ala Lys Thr Thr Tyr Leu Ala
225                 230                 235                 240

Cys Val Asn Tyr Ala Leu Thr Asn Leu Ala Lys Val Gly Val Tyr Met
                245                 250                 255

Tyr Met Asp Ala Gly His Ala Gly Trp Leu Gly Trp Pro Ala Asn Leu
                260                 265                 270

Ser Pro Ala Ala Gln Leu Phe Thr Gln Val Trp Gln Asn Ala Gly Lys
            275                 280                 285

Ser Pro Phe Ile Lys Gly Leu Ala Thr Asn Val Ala Asn Tyr Asn Ala
            290                 295                 300

Leu Gln Ala Ala Ser Pro Asp Pro Ile Thr Gln Gly Asn Pro Asn Tyr
305                 310                 315                 320
```

-continued

```
Asp Glu Ile His Tyr Ile Asn Ala Leu Ala Pro Leu Leu Gln Gln Ala
                325                 330                 335

Gly Trp Asp Ala Thr Phe Ile Val Asp Gln Gly Arg Ser Gly Val Gln
            340                 345                 350

Asn Ile Arg Gln Gln Trp Gly Asp Trp Cys Asn Ile Lys Gly Ala Gly
        355                 360                 365

Phe Gly Thr Arg Pro Thr Thr Asn Thr Gly Ser Gln Phe Ile Asp Ser
    370                 375                 380

Ile Val Trp Val Lys Pro Gly Glu Cys Asp Gly Thr Ser Asn Ser
385                 390                 395                 400

Ser Ser Pro Arg Tyr Asp Pro Thr Cys Ser Leu Pro Asp Ala Ala Gln
                405                 410                 415

Pro Ala Pro Glu Ala Gly Thr Trp Phe Gln Ala Tyr Phe Gln Thr Leu
            420                 425                 430

Val Ser Ala Ala Lys Pro Pro Leu
        435                 440
```

<210> SEQ ID NO 88
<211> LENGTH: 22
<212> TYPE: DNA
<213> ORGANISM: Artificial Sequence
<220> FEATURE:
<223> OTHER INFORMATION: Primer sequence

<400> SEQUENCE: 88
ctagctgatc actgaggtac cg                                            22

<210> SEQ ID NO 89
<211> LENGTH: 22
<212> TYPE: DNA
<213> ORGANISM: Artificial Sequence
<220> FEATURE:
<223> OTHER INFORMATION: Primer sequence

<400> SEQUENCE: 89
aattcggtac ctcagtgatc ag                                            22

<210> SEQ ID NO 90
<211> LENGTH: 35
<212> TYPE: DNA
<213> ORGANISM: Artificial Sequence
<220> FEATURE:
<223> OTHER INFORMATION: Primer sequence

<400> SEQUENCE: 90
ctattgctag ctgtgccccg acttggggcc agtgc                              35

<210> SEQ ID NO 91
<211> LENGTH: 44
<212> TYPE: DNA
<213> ORGANISM: Artificial Sequence
<220> FEATURE:
<223> OTHER INFORMATION: Primer sequence

<400> SEQUENCE: 91
ctattgaatt cggtacctca gaacggcgga ttggcattac gaag                    44

<210> SEQ ID NO 92
<211> LENGTH: 35
<212> TYPE: DNA
<213> ORGANISM: Artificial Sequence
<220> FEATURE:
<223> OTHER INFORMATION: Primer sequence

<400> SEQUENCE: 92
ctattgctag ctcggagtgg ggacagtgcg gtggc                                35

<210> SEQ ID NO 93
<211> LENGTH: 44
<212> TYPE: DNA
<213> ORGANISM: Artificial Sequence
<220> FEATURE:
<223> OTHER INFORMATION: Primer sequence

<400> SEQUENCE: 93
ctattgaatt cggtaccta cagcggcggg ttggcagcag aaac                       44

<210> SEQ ID NO 94
<211> LENGTH: 40
<212> TYPE: DNA
<213> ORGANISM: Artificial Sequence
<220> FEATURE:
<223> OTHER INFORMATION: Primer sequence

<400> SEQUENCE: 94
ggtatctttg gataaaaggg ctagctcgga gtggggacag                           40

<210> SEQ ID NO 95
<211> LENGTH: 35
<212> TYPE: DNA
<213> ORGANISM: Artificial Sequence
<220> FEATURE:
<223> OTHER INFORMATION: Primer sequence

<400> SEQUENCE: 95
ggagatcgaa ttcggtacct acagcggcgg gttgg                                35

<210> SEQ ID NO 96
<211> LENGTH: 27
<212> TYPE: DNA
<213> ORGANISM: Artificial Sequence
<220> FEATURE:
<223> OTHER INFORMATION: Primer sequence

<400> SEQUENCE: 96
ccccgctacg accctacttg ttctctg                                         27

<210> SEQ ID NO 97
<211> LENGTH: 21
<212> TYPE: DNA
<213> ORGANISM: Artificial Sequence
<220> FEATURE:
<223> OTHER INFORMATION: Primer sequence

<400> SEQUENCE: 97
agcacaaata acgggttatt g                                               21

<210> SEQ ID NO 98
<211> LENGTH: 23
<212> TYPE: DNA
<213> ORGANISM: Artificial Sequence
<220> FEATURE:
<223> OTHER INFORMATION: Primer sequence

<400> SEQUENCE: 98
gcaacacctg gcaattcctt acc                                             23

<210> SEQ ID NO 99

```
<211> LENGTH: 36
<212> TYPE: PRT
<213> ORGANISM: Phanerochaete chrysosporium

<400> SEQUENCE: 99

Ala Ser Ser Glu Trp Gly Gln Cys Gly Gly Ile Gly Trp Thr Gly Pro
1               5                   10                  15

Thr Thr Cys Val Ser Gly Thr Thr Cys Thr Val Leu Asn Pro Tyr Tyr
            20                  25                  30

Ser Gln Cys Leu
        35

<210> SEQ ID NO 100
<211> LENGTH: 713
<212> TYPE: PRT
<213> ORGANISM: Trichoderma reesei

<400> SEQUENCE: 100

Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
            20                  25                  30

Ser Gly Val Gly Trp Asn Gly Gly Pro Cys Val Gly Asn Thr Ser Pro
        35                  40                  45

Ala Ser Lys Ile Ser Tyr Pro Ser Leu Cys Leu Gln Asp Gly Pro Leu
    50                  55                  60

Gly Val Arg Tyr Ser Thr Gly Ser Thr Ala Phe Thr Pro Gly Val Gln
65                  70                  75                  80

Ala Ala Ser Thr Trp Asp Val Asn Leu Ile Arg Glu Arg Gly Gln Phe
                85                  90                  95

Ile Gly Glu Glu Val Lys Ala Ser Gly Ile His Val Ile Leu Gly Pro
            100                 105                 110

Val Ala Gly Pro Leu Gly Lys Thr Pro Gln Gly Gly Arg Asn Trp Glu
        115                 120                 125

Gly Phe Gly Val Asp Pro Tyr Leu Thr Gly Ile Ala Met Gly Gln Thr
    130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                165                 170                 175

Asp Asp Arg Thr Leu His Glu Leu Tyr Thr Trp Pro Phe Ala Asp Ala
            180                 185                 190

Val Gln Ala Asn Val Ala Ser Val Met Cys Ser Tyr Asn Lys Val Asn
        195                 200                 205

Thr Thr Trp Ala Cys Glu Asp Gln Tyr Thr Leu Gln Thr Val Leu Lys
    210                 215                 220

Asp Gln Leu Gly Phe Pro Gly Tyr Val Met Thr Asp Trp Asn Ala Gln
225                 230                 235                 240

His Thr Thr Val Gln Ser Ala Asn Ser Gly Leu Asp Met Ser Met Pro
                245                 250                 255

Gly Thr Asp Phe Asn Gly Asn Asn Arg Leu Trp Gly Pro Ala Leu Thr
            260                 265                 270

Asn Ala Val Asn Ser Asn Gln Val Pro Thr Ser Arg Val Asp Asp Met
        275                 280                 285

Val Thr Arg Ile Leu Ala Ala Trp Tyr Leu Thr Gly Gln Asp Gln Ala
    290                 295                 300
```

```
Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
            325                 330                 335

Asp Ala Asn Ile Leu Pro Leu Lys Lys Pro Ala Ser Ile Ala Val Val
                340                 345                 350

Gly Ser Ala Ala Ile Ile Gly Asn His Ala Arg Asn Ser Pro Ser Cys
            355                 360                 365

Asn Asp Lys Gly Cys Asp Asp Gly Ala Leu Gly Met Gly Trp Gly Ser
370                 375                 380

Gly Ala Val Asn Tyr Pro Tyr Phe Val Ala Pro Tyr Asp Ala Ile Asn
385                 390                 395                 400

Thr Arg Ala Ser Ser Gln Gly Thr Gln Val Thr Leu Ser Asn Thr Asp
            405                 410                 415

Asn Thr Ser Ser Gly Ala Ser Ala Ala Arg Gly Lys Asp Val Ala Ile
            420                 425                 430

Val Phe Ile Thr Ala Asp Ser Gly Glu Gly Tyr Ile Thr Val Glu Gly
            435                 440                 445

Asn Ala Gly Asp Arg Asn Asn Leu Asp Pro Trp His Asn Gly Asn Ala
450                 455                 460

Leu Val Gln Ala Val Ala Gly Ala Asn Ser Asn Val Ile Val Val Val
465                 470                 475                 480

His Ser Val Gly Ala Ile Ile Leu Glu Gln Ile Leu Ala Leu Pro Gln
                485                 490                 495

Val Lys Ala Val Val Trp Ala Gly Leu Pro Ser Gln Glu Ser Gly Asn
            500                 505                 510

Ala Leu Val Asp Val Leu Trp Gly Asp Val Ser Pro Ser Gly Lys Leu
            515                 520                 525

Val Tyr Thr Ile Ala Lys Ser Pro Asn Asp Tyr Asn Thr Arg Ile Val
530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
                565                 570                 575

Leu Ser Tyr Thr Lys Phe Asn Tyr Ser Arg Leu Ser Val Leu Ser Thr
            580                 585                 590

Ala Lys Ser Gly Pro Ala Thr Gly Ala Val Val Pro Gly Gly Pro Ser
            595                 600                 605

Asp Leu Phe Gln Asn Val Ala Thr Val Thr Val Asp Ile Ala Asn Ser
            610                 615                 620

Gly Gln Val Thr Gly Ala Glu Val Ala Gln Leu Tyr Ile Thr Tyr Pro
625                 630                 635                 640

Ser Ser Ala Pro Arg Thr Pro Pro Lys Gln Leu Arg Gly Phe Ala Lys
                645                 650                 655

Leu Asn Leu Thr Pro Gly Gln Ser Gly Thr Ala Thr Phe Asn Ile Arg
            660                 665                 670

Arg Arg Asp Leu Ser Tyr Trp Asp Thr Ala Ser Gln Lys Trp Val Val
            675                 680                 685

Pro Ser Gly Ser Phe Gly Ile Ser Val Gly Ala Ser Ser Arg Asp Ile
            690                 695                 700

Arg Leu Thr Ser Thr Leu Ser Val Ala
705                 710
```

<210> SEQ ID NO 101
<211> LENGTH: 788
<212> TYPE: PRT
<213> ORGANISM: Trichoderma reesei

<400> SEQUENCE: 101

```
Val Val Pro Pro Ala Gly Thr Pro Trp Gly Thr Ala Tyr Asp Lys Ala
 1               5                  10                  15

Lys Ala Ala Leu Ala Lys Leu Asn Leu Gln Asp Lys Val Gly Ile Val
                20                  25                  30

Ser Gly Val Gly Trp Asn Gly Gly Pro Cys Val Gly Asn Thr Ser Pro
            35                  40                  45

Ala Ser Lys Ile Ser Tyr Pro Ser Leu Cys Leu Gln Asp Gly Pro Leu
        50                  55                  60

Gly Val Arg Tyr Ser Thr Gly Ser Thr Ala Phe Thr Pro Gly Val Gln
 65                  70                  75                  80

Ala Ala Ser Thr Trp Asp Val Asn Leu Ile Arg Glu Arg Gly Gln Phe
                85                  90                  95

Ile Gly Glu Glu Val Lys Ala Ser Gly Ile His Val Ile Leu Gly Pro
            100                 105                 110

Val Ala Gly Pro Leu Gly Lys Thr Pro Gln Gly Gly Arg Asn Trp Glu
        115                 120                 125

Gly Phe Gly Val Asp Pro Tyr Leu Thr Gly Ile Ala Met Gly Gln Thr
130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                165                 170                 175

Asp Asp Arg Thr Leu His Glu Leu Tyr Thr Trp Pro Phe Ala Asp Ala
            180                 185                 190

Val Gln Ala Asn Val Ala Ser Val Met Cys Ser Tyr Asn Lys Val Asn
        195                 200                 205

Thr Thr Trp Ala Cys Glu Asp Gln Tyr Thr Leu Gln Thr Val Leu Lys
210                 215                 220

Asp Gln Leu Gly Phe Pro Gly Tyr Val Met Thr Asp Trp Asn Ala Gln
225                 230                 235                 240

His Thr Thr Val Gln Ser Ala Asn Ser Gly Leu Asp Met Ser Met Pro
                245                 250                 255

Gly Thr Asp Phe Asn Gly Asn Asn Arg Leu Trp Gly Pro Ala Leu Thr
            260                 265                 270

Asn Ala Val Asn Ser Asn Gln Val Pro Thr Ser Arg Val Asp Asp Met
        275                 280                 285

Val Thr Arg Ile Leu Ala Ala Trp Tyr Leu Thr Gly Gln Asp Gln Ala
290                 295                 300

Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
                325                 330                 335

Asp Ala Asn Ile Leu Pro Leu Lys Lys Pro Ala Ser Ile Ala Val Val
            340                 345                 350

Gly Ser Ala Ala Ile Ile Gly Asn His Ala Arg Asn Ser Pro Ser Cys
        355                 360                 365

Asn Asp Lys Gly Cys Asp Asp Gly Ala Leu Gly Met Gly Trp Gly Ser
370                 375                 380
```

```
Gly Ala Val Asn Tyr Pro Tyr Phe Val Ala Pro Tyr Asp Ala Ile Asn
385                 390                 395                 400

Thr Arg Ala Ser Ser Gln Gly Thr Gln Val Thr Leu Ser Asn Thr Asp
            405                 410                 415

Asn Thr Ser Ser Gly Ala Ser Ala Ala Arg Gly Lys Asp Val Ala Ile
            420                 425                 430

Val Phe Ile Thr Ala Asp Ser Gly Glu Gly Tyr Ile Thr Val Glu Gly
            435                 440                 445

Asn Ala Gly Asp Arg Asn Asn Leu Asp Pro Trp His Asn Gly Asn Ala
            450                 455                 460

Leu Val Gln Ala Val Ala Gly Ala Asn Ser Asn Val Ile Val Val Val
465                 470                 475                 480

His Ser Val Gly Ala Ile Ile Leu Glu Gln Ile Leu Ala Leu Pro Gln
            485                 490                 495

Val Lys Ala Val Val Trp Ala Gly Leu Pro Ser Gln Glu Ser Gly Asn
            500                 505                 510

Ala Leu Val Asp Val Leu Trp Gly Asp Val Ser Pro Ser Gly Lys Leu
            515                 520                 525

Val Tyr Thr Ile Ala Lys Ser Pro Asn Asp Tyr Asn Thr Arg Ile Val
530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
            565                 570                 575

Leu Ser Tyr Thr Lys Phe Asn Tyr Ser Arg Leu Ser Val Leu Ser Thr
            580                 585                 590

Ala Lys Ser Gly Pro Ala Thr Gly Ala Val Val Pro Gly Gly Pro Ser
            595                 600                 605

Asp Leu Phe Gln Asn Val Ala Thr Val Thr Val Asp Ile Ala Asn Ser
            610                 615                 620

Gly Gln Val Thr Gly Ala Glu Val Ala Gln Leu Tyr Ile Thr Tyr Pro
625                 630                 635                 640

Ser Ser Ala Pro Arg Thr Pro Lys Gln Leu Arg Gly Phe Ala Lys
                645                 650                 655

Leu Asn Leu Thr Pro Gly Gln Ser Gly Thr Ala Thr Phe Asn Ile Arg
            660                 665                 670

Arg Arg Asp Leu Ser Tyr Trp Asp Thr Ala Ser Gln Lys Trp Val Val
            675                 680                 685

Pro Ser Gly Ser Phe Gly Ile Ser Val Gly Ala Ser Ser Arg Asp Ile
            690                 695                 700

Arg Leu Thr Ser Thr Leu Ser Val Ala Pro Thr Ser Ile Gly Ser Thr
705                 710                 715                 720

Gly Asn Pro Ser Gly Gly Asn Pro Gly Gly Asn Pro Gly Thr
            725                 730                 735

Thr Thr Thr Arg Arg Pro Ala Thr Thr Thr Gly Ser Ser Pro Gly Pro
            740                 745                 750

Thr Gln Ser His Tyr Gly Gln Cys Gly Gly Ile Gly Tyr Ser Gly Pro
            755                 760                 765

Thr Val Cys Ala Ser Gly Thr Thr Cys Gln Val Leu Asn Pro Tyr Tyr
            770                 775                 780

Ser Gln Cys Leu
785
```

<210> SEQ ID NO 102
<211> LENGTH: 30
<212> TYPE: DNA
<213> ORGANISM: Artificial Sequence
<220> FEATURE:
<223> OTHER INFORMATION: Primer sequence

<400> SEQUENCE: 102
accaaaagat ctatgagatt tccttcaatt                           30

<210> SEQ ID NO 103
<211> LENGTH: 30
<212> TYPE: DNA
<213> ORGANISM: Artificial Sequence
<220> FEATURE:
<223> OTHER INFORMATION: Primer sequence

<400> SEQUENCE: 103
tgagcagcta gcccttttat ccaaagatac                           30

<210> SEQ ID NO 104
<211> LENGTH: 30
<212> TYPE: DNA
<213> ORGANISM: Artificial Sequence
<220> FEATURE:
<223> OTHER INFORMATION: Primer sequence

<400> SEQUENCE: 104
aaaagggcta gctgctcaag cgtctggggc                           30

<210> SEQ ID NO 105
<211> LENGTH: 36
<212> TYPE: DNA
<213> ORGANISM: Artificial Sequence
<220> FEATURE:
<223> OTHER INFORMATION: Primer sequence

<400> SEQUENCE: 105
gagctcagat ctggtacctt acaggaacga tgggtt                    36

<210> SEQ ID NO 106
<211> LENGTH: 30
<212> TYPE: DNA
<213> ORGANISM: Artificial Sequence
<220> FEATURE:
<223> OTHER INFORMATION: Primer sequence

<400> SEQUENCE: 106
gaattggtcg gatccgactt gctgtgcttc                           30

<210> SEQ ID NO 107
<211> LENGTH: 28
<212> TYPE: DNA
<213> ORGANISM: Artificial Sequence
<220> FEATURE:
<223> OTHER INFORMATION: Primer sequence

<400> SEQUENCE: 107
agcaagtcgg atccgaccaa ttctggcc                             28

<210> SEQ ID NO 108
<211> LENGTH: 23
<212> TYPE: DNA
<213> ORGANISM: Artificial Sequence
<220> FEATURE:
<223> OTHER INFORMATION: Primer sequence

```
<400> SEQUENCE: 108
gcacatgcgt cgactccaac gac                                              23

<210> SEQ ID NO 109
<211> LENGTH: 23
<212> TYPE: DNA
<213> ORGANISM: Artificial Sequence
<220> FEATURE:
<223> OTHER INFORMATION: Primer sequence

<400> SEQUENCE: 109
gtcgttggag tcgacgcatg tgc                                              23

<210> SEQ ID NO 110
<211> LENGTH: 23
<212> TYPE: DNA
<213> ORGANISM: Artificial Sequence
<220> FEATURE:
<223> OTHER INFORMATION: Primer sequence

<400> SEQUENCE: 110
cgtctactcc accgactatt act                                              23

<210> SEQ ID NO 111
<211> LENGTH: 23
<212> TYPE: DNA
<213> ORGANISM: Artificial Sequence
<220> FEATURE:
<223> OTHER INFORMATION: Primer sequence

<400> SEQUENCE: 111
agtaatagtc ggtggagtag acg                                              23

<210> SEQ ID NO 112
<211> LENGTH: 18
<212> TYPE: DNA
<213> ORGANISM: Artificial Sequence
<220> FEATURE:
<223> OTHER INFORMATION: Primer sequence

<400> SEQUENCE: 112
gcctgcactc tccaatcg                                                    18

<210> SEQ ID NO 113
<211> LENGTH: 20
<212> TYPE: DNA
<213> ORGANISM: Artificial Sequence
<220> FEATURE:
<223> OTHER INFORMATION: Primer sequence

<400> SEQUENCE: 113
gttgctcatt tgcggtctac                                                  20

<210> SEQ ID NO 114
<211> LENGTH: 29
<212> TYPE: DNA
<213> ORGANISM: Artificial Sequence
<220> FEATURE:
<223> OTHER INFORMATION: Primer sequence

<400> SEQUENCE: 114
tacggccagt ctggcggtat tggctacag                                        29

<210> SEQ ID NO 115
```

```
<211> LENGTH: 28
<212> TYPE: DNA
<213> ORGANISM: Artificial Sequence
<220> FEATURE:
<223> OTHER INFORMATION: Primer sequence

<400> SEQUENCE: 115
aataccgcca gactggccgt agtgagac                                            28

<210> SEQ ID NO 116
<211> LENGTH: 21
<212> TYPE: DNA
<213> ORGANISM: Artificial Sequence
<220> FEATURE:
<223> OTHER INFORMATION: Primer sequence

<400> SEQUENCE: 116
ggccagtgct gcggtattgg c                                                   21

<210> SEQ ID NO 117
<211> LENGTH: 21
<212> TYPE: DNA
<213> ORGANISM: Artificial Sequence
<220> FEATURE:
<223> OTHER INFORMATION: Primer sequence

<400> SEQUENCE: 117
caataccgca gcactggccg t                                                   21

<210> SEQ ID NO 118
<211> LENGTH: 27
<212> TYPE: DNA
<213> ORGANISM: Artificial Sequence
<220> FEATURE:
<223> OTHER INFORMATION: Primer sequence

<400> SEQUENCE: 118
agtgcggcga cattggctac agcggcc                                             27

<210> SEQ ID NO 119
<211> LENGTH: 26
<212> TYPE: DNA
<213> ORGANISM: Artificial Sequence
<220> FEATURE:
<223> OTHER INFORMATION: Primer sequence

<400> SEQUENCE: 119
gtagccaatg tcgccgcact ggccgt                                              26

<210> SEQ ID NO 120
<211> LENGTH: 26
<212> TYPE: DNA
<213> ORGANISM: Artificial Sequence
<220> FEATURE:
<223> OTHER INFORMATION: Primer sequence

<400> SEQUENCE: 120
cacggtctat gccagcggca caactt                                              26

<210> SEQ ID NO 121
<211> LENGTH: 25
<212> TYPE: DNA
<213> ORGANISM: Artificial Sequence
<220> FEATURE:
<223> OTHER INFORMATION: Primer sequence

<400> SEQUENCE: 121
```

```
gccgctggca tagaccgtgg ggccg                                              25
```

<210> SEQ ID NO 122
<211> LENGTH: 27
<212> TYPE: DNA
<213> ORGANISM: Artificial Sequence
<220> FEATURE:
<223> OTHER INFORMATION: Primer sequence

<400> SEQUENCE: 122

```
tactactctc agtacctgta aggtacc                                            27
```

<210> SEQ ID NO 123
<211> LENGTH: 27
<212> TYPE: DNA
<213> ORGANISM: Artificial Sequence
<220> FEATURE:
<223> OTHER INFORMATION: Primer sequence

<400> SEQUENCE: 123

```
ggtaccttac aggtactgag agtagta                                            27
```

<210> SEQ ID NO 124
<211> LENGTH: 497
<212> TYPE: PRT
<213> ORGANISM: Trichoderma reesei

<400> SEQUENCE: 124

```
Gln Ser Ala Cys Thr Leu Gln Ser Glu Thr His Pro Pro Leu Thr Trp
1               5                   10                  15

Gln Lys Cys Ser Ser Gly Gly Thr Cys Thr Gln Gln Thr Gly Ser Val
                20                  25                  30

Val Ile Asp Ala Asn Trp Arg Trp Thr His Ala Thr Asn Ser Ser Thr
            35                  40                  45

Asn Cys Tyr Asp Gly Asn Thr Trp Ser Ser Thr Leu Cys Pro Asp Asn
        50                  55                  60

Glu Thr Cys Ala Lys Asn Cys Cys Leu Asp Gly Ala Ala Tyr Ala Ser
65                  70                  75                  80

Thr Tyr Gly Val Thr Thr Ser Gly Asn Ser Leu Ser Ile Gly Phe Val
                85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
        115                 120                 125

Phe Asp Val Asp Val Ser Gln Leu Pro Cys Gly Leu Asn Gly Ala Leu
    130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Glu Pro Ser Ser Asn Asn Ala Asn Thr Gly Ile Gly Gly His Gly Ser
        195                 200                 205

Cys Cys Ser Glu Met Asp Ile Trp Glu Ala Asn Ser Ile Ser Glu Ala
    210                 215                 220

Leu Thr Pro His Pro Cys Thr Thr Val Gly Gln Glu Ile Cys Glu Gly
225                 230                 235                 240
```

-continued

```
Asp Gly Cys Gly Gly Thr Tyr Ser Asp Asn Arg Tyr Gly Gly Thr Cys
            245                 250                 255

Asp Pro Asp Gly Cys Asp Trp Asn Pro Tyr Arg Leu Gly Asn Thr Ser
            260                 265                 270

Phe Tyr Gly Pro Gly Ser Ser Phe Thr Leu Asp Thr Thr Lys Lys Leu
            275                 280                 285

Thr Val Val Thr Gln Phe Glu Thr Ser Gly Ala Ile Asn Arg Tyr Tyr
            290                 295                 300

Val Gln Asn Gly Val Thr Phe Gln Gln Pro Asn Ala Glu Leu Gly Ser
305                 310                 315                 320

Tyr Ser Gly Asn Glu Leu Asn Asp Asp Tyr Cys Thr Ala Glu Glu Ala
                325                 330                 335

Glu Phe Gly Gly Ser Ser Phe Ser Asp Lys Gly Gly Leu Thr Gln Phe
            340                 345                 350

Lys Lys Ala Thr Ser Gly Gly Met Val Leu Val Met Ser Leu Trp Asp
            355                 360                 365

Asp Tyr Tyr Ala Asn Met Leu Trp Leu Asp Ser Thr Tyr Pro Thr Asn
            370                 375                 380

Glu Thr Ser Ser Thr Pro Gly Ala Val Arg Gly Ser Cys Ser Thr Ser
385                 390                 395                 400

Ser Gly Val Pro Ala Gln Val Glu Ser Gln Ser Pro Asn Ala Lys Val
                405                 410                 415

Thr Phe Ser Asn Ile Lys Phe Gly Pro Ile Gly Ser Thr Gly Asn Pro
            420                 425                 430

Ser Gly Gly Asn Pro Pro Gly Gly Asn Pro Pro Gly Thr Thr Thr
            435                 440                 445

Arg Arg Pro Ala Thr Thr Thr Gly Ser Ser Pro Gly Pro Thr Gln Ser
450                 455                 460

His Tyr Gly Gln Cys Gly Gly Ile Gly Tyr Ser Gly Pro Thr Val Cys
465                 470                 475                 480

Ala Ser Gly Thr Thr Cys Gln Val Leu Asn Pro Tyr Tyr Ser Gln Cys
            485                 490                 495

Leu
```

CARBOHYDRATE BINDING MODULES WITH REDUCED BINDING TO LIGNIN

This application is a continuation application of U.S. patent application Ser. No. 13/575,046, filed on Jul. 25, 2012, now U.S. Pat. No. 9,206,406, which is a national stage entry of International Application No. PCT/CA2011/000167, filed Feb. 11, 2011, which claims the benefit of U.S. Provisional Patent Application No. 61/303,400 filed Feb. 11, 2010. The contents of the aforementioned applications are incorporated herein by reference in their entireties.

FIELD OF THE INVENTION

The present invention relates to modified carbohydrate binding modules. More specifically, the invention relates to a modified Family 1 carbohydrate binding module exhibiting reduced binding to lignin. The present invention also relates to modified glycosidase enzymes comprising the modified Family 1 carbohydrate binding module, genetic constructs comprising nucleotide sequences encoding the modified Family 1 carbohydrate binding modules or the modified glycosidase enzyme, and the use of the modified glycosidase enzyme comprising the modified Family 1 carbohydrate binding module in the hydrolysis of cellulose or hemicellulose substrates in the presence of lignin.

BACKGROUND OF THE INVENTION

More than 50% of organic carbon on earth is found in the cell walls of plants. Plant cell walls consist mainly of the compounds: cellulose, hemicellulose, and lignin. Collectively these compounds are called "lignocellulose," and they represent a potential source of sugars and other organic molecules for fermentation to ethanol or to other high-value products.

The conversion of lignocellulose (or lignocellulosic biomass) to ethanol has become a key feature of emerging energy policies due to the environmentally favorable and sustainable nature of cellulosic ethanol. There are several technologies being developed for cellulose conversion. Of interest here is a method by which lignocellulosic biomass is subjected to a pretreatment that increases its susceptibility to hydrolytic enzymes, followed by enzymatic hydrolysis of the pretreated lignocellulose to sugars and the fermentation of those sugars to ethanol or other high-value organic molecules (e.g. butanol). Common pretreatment methods include dilute acid steam explosion (U.S. Pat. No. 4,461,648), ammonia freeze explosion (AFEX; Holtzapple et al., 1991), and organosolv extraction (U.S. Pat. No. 4,409,032). Hydrolysis and fermentation systems may be either separate (sequential hydrolysis and fermentation; SHF) or coincident (simultaneous saccharification and fermentation; SSF). In all instances, the hemicellulose and cellulose are broken down to sugars that may be fermented, while the lignin becomes separated and may be used either as a solid fuel or as a source for other organic molecules.

The enzymatic hydrolysis of the pretreated lignocellulose is carried out by cellulase enzymes. The term cellulase (or cellulase enzymes) broadly refers to a class of glycoside hydrolase enzymes (or glycosidases) that catalyze the hydrolysis of the beta-1,4-glucosidic bonds joining individual glucose units in the cellulose polymer. The catalytic mechanism involves the synergistic actions of endoglucanases (Enzyme Commission number E.C. 3.2.1.4), cellobiohydrolases (E.C. 3.2.1.91) and beta-glucosidase (E.C. 3.2.1.21). Endoglucanases hydrolyze accessible glucosidic bonds in the middle of the cellulose chain, while cellobiohydrolases release cellobiose from these chain ends processively. Beta-glucosidases hydrolyze cellobiose to glucose and, in so doing, minimize product inhibition of the cellobiohydrolases. Collectively, the enzymes operate as a system that can hydrolyze a cellulose substrate.

Cellulase enzymes, as well as other glycoside hydrolases or glycosidases that hydrolyze poly- or oligo-saccharides, typically have a similar modular structure, consisting of one or more catalytic domain(s) and one or more carbohydrate-binding modules (CBM) joined together by flexible linker peptide(s). Many hemicellulases, e.g., xylanases (E.C. 3.2.1.8), mannanases (E.C. 3.2.1.78) and arabinofuranosidases (E.C. 3.2.1.55), are known to have a similar modular structure of a catalytic domain joined to a CBM via a flexible linker. Hemicellulases are enzymes that catalyze hydrolysis of the glycosidic linkages in the xylan backbone polysaccharide of hemicellulose or glycosidic linkages between xylose units in the xylan backbone and other sugars attached to the backbone.

The catalytic domain is a distinct structural domain that catalyzes the hydrolysis of the glycosidic linkages in the substrate. Many glycoside hydrolase catalytic domains have been isolated and characterized. The catalytic domain is typically, though not necessarily, the larger of the two domains. Glycoside hydrolases sharing a common three-dimensional structure and catalytic mechanism, though not necessarily substrate specificity, have been grouped into Families (Davies and Henrissat, 1995). To date, there are over 150 Glycoside Hydrolase (GH) families. Cellulase enzymes are found in many GH families including, but not limited to, Family 5, 6, 7, 8, 9, 12, 44, 45, 48, 51, 61 and 74; xylanase enzymes are found in Family 5, 8, 10, 11 and 43; mannanase enzyme are found in Family 5, 26 and 113; arabinofuranosidase enzymes are found in Family 3, 43, 51, 54 and 62; and beta-glucosidase enzymes are found in Family 1 and 3.

Linker peptides are extended yet flexible structures that maintain the spatial orientation of the catalytic domain relative to the CBM (Shen et al., 1991; Receveur et al., 2002; Boisset et al., 1995). Naturally-occurring linker peptides in cellulase and hemicellulase enzymes, whether from bacterial or fungal sources, vary from 6-60 amino acids in length. These peptides are similar in their chemical properties and amino acid composition, if not their specific sequences, with the amino acids serine, threonine, and proline accounting for more than 50% of the amino acids in the linker peptide (reviewed in Gilkes et al. (1991). Linkers also contain several charged residues of a common type, either all negative (such as Glu or Asp) or all positive (such as Lys, Arg or His). The serine and threonine residues may be modified with O-linked glycans, which, in fungi, are predominantly mannose (Fagerstam et al., 1984). Results from small-angle x-ray or dynamic light scattering suggest that glycosylation of the linker peptide favours a more extended conformation, altering the relative positioning of the catalytic domain and CBM.

The carbohydrate binding module (CBM) is typically, though not always, smaller than the catalytic domain. The role of the CBM is to bring the enzyme into close and prolonged contact with the carbohydrate substrate and to increase the rate of substrate degradation. CBMs are found in a variety of enzymes involved in the degradation of carbohydrate substrates, including cellulases, hemicellulases, glucanases, amylases, glucoamylases, chitinases and the like. Thus, CBMs can recognize and bind to crystalline cellulose, non-crystalline cellulose, chitin, beta-1,3 glucans, mixed beta-1,3-1,4 glucans, xylan, mannan, galactan, and starch.

As is the case for catalytic domains, CBMs assume a variety of structures that govern their substrate binding affinities and can therefore also be classified into Families based on their structural and functional relationships. To date there are 59 known CBM Families (see URL cazy.org/fam/acc_CDM.html). Much research has been conducted over the past two decades to elucidate the function and structure of CBMs (as reviewed by Boraston et al., 2004; Hashimoto 2006 and Shoseyov et al., 2006).

The present application relates to Family 1 CBMs. These CBMs are found almost exclusively in fungal enzymes, including cellulase and hemicellulase enzymes produced by *Trichoderma* ssp., *Aspergillus* ssp., *Hypocrea* ssp., *Humicola* ssp., *Neurospora* ssp., *Orpinomyces* ssp., *Gibberella* ssp., *Emericella* ssp., *Chaetomium* ssp., *Chrysosporium* ssp., *Fusarium* ssp., *Penicillium* ssp., *Magnaporthe* ssp., *Phanerochaete* ssp., *Trametes* ssp., *Lentinula edodes*, *Gleophyllum trabeiu*, *Ophiostoma piliferum*, *Corpinus cinereus*, *Geomyces pannorum*, *Cryptococcus laurentii*, *Aureobasidium pullulans*, *Amorphotheca resinae*, *Leucosporidium scotti*, *Cunninghamella elegans*, *Thermomyces lanuginosa*, *Sporotrichum thermophile*, and *Myceliophthora thermophilum*.

Family 1 CBMs were initially identified as cellulose binding domains (or CBDs) of fungal cellulases. Family 1 CBMs comprise approximately 40 amino acids and may be found at either the N- or C-terminus of the enzyme. Family 1 CBMs assume a small, wedge-shaped beta-sandwich structure with a flat binding surface containing three aromatic amino acids (usually tryptophan) spaced about 10 angstroms apart (Kraulis et al., 1989; Mattinen et al., 1997). These aromatic residues facilitate binding to the surfaces of crystalline substrates such as cellulose and chitin via van der Waal's contacts with the substrate surface (Mattinen et al., 1997; Reinikainen et al., 1992, Tormo et al., 1996).

The enzymatic hydrolysis of pretreated lignocellulosic feedstocks is an inefficient step in the production of cellulosic ethanol and its cost constitutes one of the major barriers to commercial viability. Improving the enzymatic activity of cellulases or increasing cellulase production efficiency has been widely regarded as an opportunity for significant cost savings.

The negative effects of lignin on cellulase enzyme systems are well documented. Removal of lignin from hardwood (aspen) was shown to increase sugar yield by enzymatic hydrolysis (Kong et al., 1992). Similarly, removal of lignin from softwood (Douglas fir) was shown to improve enzymatic hydrolysis of the cellulose, an effect attributed to improved accessibility of the enzymes to the cellulose (Mooney et al., 1998). Other groups have demonstrated that cellulases purified from *Trichoderma reesei* bind to isolated lignin (Chernoglazov et al., 1988) and have speculated on the role of the different binding domains in the enzyme-lignin interaction (Palonen et al., 2004). Binding to lignin and inactivation of *Trichoderma reesei* cellulases has been observed when lignin is added back to a pure cellulose system (Escoffier et al., 1991). Another study showed that lignin did not have any significant effect on cellulases (Meunier-Goddik and Penner, 1999). While other reports suggest that some hemicellulases may be resistant to, and even activated by, lignin and lignin breakdown products (Kaya et al., 2000). Nonetheless, it is generally recognized that lignin is a serious limitation to enzymatic hydrolysis of cellulose.

Cellulases purified from *Trichoderma reesei* have been shown to bind to isolated lignin (Chernoglazov et al., 1988). Further work has shown that all three domains, catalytic core, linker and CBM, will bind to lignin (Palonen et al., 2004). For example, Cel7B from *Humicola* sp., which exists naturally as just a catalytic domain without a CBM, is bound extensively by lignin (Berlin et al., 2005). Similarly *Trichoderma* Cel5A core, devoid of a CBM, does not bind enzymic lignin and binds alkali extracted lignin to a lesser extent than does the full-length protein (Palonen et al., 2004). CBMs are reportedly involved in lignin binding. For example, removal of the CBM from *Trichoderma* Cel7A essentially eliminates binding to alkali extracted lignin and to residual lignin prepared by enzyme hydrolysis (Palonen et al., 2004).

The absence of lignin resistant cellulases represents a large hurdle in the commercialization of cellulose conversion to soluble sugars including glucose for the production of ethanol and other products. The development of lignin resistant enzymes must preserve their cellulolytic activity. A variety of methods have been suggested to reduce the negative impact of lignin on the cellulase system. Non-specific binding proteins (e.g. bovine serum albumin; BSA) have been shown to block interactions between cellulases and lignin surfaces (Yang and Wyman, 2006; U.S. Publication No. 2004/0185542A1, U.S. Publication No. 2006/0088922A1; WO05024037 A2, A3; WO09429474 A1). Other chemical blocking agents and surfactants have been shown to have a similar effect (Tu et al., 2007; U.S. Pat. No. 7,354,743).

Modified glycosidase enzymes and methods for modification have been extensively described. In most instances, mutations are specifically directed to the catalytic domain of the enzyme. For example, variants of *Trichoderma reesei* Cel7A and Cel6A catalytic domains to improve thermostability have been reported (U.S. Pat. No. 7,375,197; WO 2005/028636; U. S. Publication No. 2007/0173431; Publication No. 2008/167214; WO 2006/074005; Publication No. 2006/0205042; U.S. Pat. No. 7,348,168; WO 2008/025164). In particular, substitution of the amino acid at the equivalent of position 413 in *T. reesei* Cel6A with a proline in Family 6 cellulases, e.g., a S407P mutation in the *Phanerochaete chrysosporium* Cel6A, confers increased thermostability (WO 2008/025164). Mutations at the equivalent of positions 103, 136, 186, 365 and 410 within the catalytic domain of *T. reesei* Cel6A and other Family 6 cellulases have been shown to lead to reduce inhibition by glucose (U.S. Publication No. 2009/0186381A1). Variants with resistance to proteases and to surfactants for detergent formulations have been created for textile applications (WO 99/01544; WO 94/07998; and U.S. Pat. No. 6,114,296).

Recently, modified cellulases exhibiting reduced interactions with, or reduced inactivation by, lignin have been reported. For example, WO2010/012102 reports that mutations at the equivalent of positions 129, 322, 363, 365 and 410 within the catalytic domain of *T. reesei* Cel6A (TrCel6A) and other Family 6 cellulases results in increased hydrolytic activity in the presence of lignin. Similarly, WO2009/149202 discloses cellulase variants with mutations that remove positive charges or introduce negative charges at the equivalents of positions 63, 77, 129, 147, 153, 161, 194, 197, 203, 237, 247, 254, 281, 285, 289, 294, 327, 339, 344, 356, 378 and 382 in the linker peptide and catalytic domain of Cel6A from *Hypocrea jecorina*. Such cellulase variants show reduced affinity to lignin, ethanol or heat treatment.

Only in a few instances has the linker peptide been identified as playing a critical role or as a target for modification. The linker peptide of the *Humicola* Family 45 endoglucanase was modified to reduce proteolysis (WO 94/07998; U.S. Pat. No. 6,114,296) and the linker peptide of the *Trichoderma* Cel7A was modified to promote thermostability (U.S. Pat. No. 7,375,197). U.S. Publication No. 2010/0221778A1 reports that mutations that reduce the isoelectric point and/or increase the Ser/Thr ratio of the linker peptide can also lead to increased hydrolytic activity in the presence of lignin.

There are relatively few reports of modifying CBMs. In one instance, Linder et al. (1995) showed that mutations of the tyrosine residues on the binding face of the Family 1 CBM from *T. reesei* Cel7A significant reduce its binding to cellulose while mutations at other highly conserved, but non-aromatic, amino acids on the binding surface result in less of a reduction of cellulose binding. In another instance, it was reported that substitution of the tyrosine residue at the "tip" of the wedge-shape structure, equivalent to Tyr33 in the TrCel6A-CBM to a histidine resulted in pH-dependent binding to cellulose (Linder et al., 1999). However, while it has been observed that Family 1 CBMs interact with lignin, there are no reports on the development of modified Family 1 CBMs with reduced binding to lignin.

SUMMARY OF THE INVENTION

The present invention relates to modified carbohydrate binding modules. More specifically, the invention relates to a modified Family 1 carbohydrate binding module exhibiting reduced binding to lignin. The present invention also relates to modified glycosidase enzymes comprising the modified Family 1 carbohydrate binding module, genetic constructs comprising nucleotide sequences encoding the modified Family 1 carbohydrate binding modules or the modified glycosidase enzyme, and the use of the modified glycosidase enzyme comprising the modified Family 1 carbohydrate binding module in the hydrolysis of cellulose or hemicellulose substrates in the presence of lignin.

The present invention provides a modified Family 1 carbohydrate binding module with reduced binding to lignin and the ability to confer not only reduced lignin binding but also increased substrate hydrolyzing activity, in the presence of lignin, to a modified glycosidase enzyme comprising the modified Family 1 carbohydrate binding module. Such modified glycosidase enzymes may also be more easily recovered and reused from any residual lignin present at the end of the hydrolysis reaction.

The present invention also relates to a modified Family 1 carbohydrate binding module comprising amino acid substitutions at one or more one positions selected from the group consisting of 10, 11, 12, 14, 17, 21, 24, 29, 31, 33, and 37. The one or more positions containing amino acid substitutions is determined from alignment of a Family 1 carbohydrate binding module amino acid sequence with a *Trichoderma reesei* Cel6A carbohydrate binding module (TrCel6A-CBM) amino acid sequence as defined in SEQ ID NO: 30. The modified Family 1 carbohydrate binding module of the present invention comprises an amino acid sequence that is from about 50% to about 99.9% identical to SEQ ID NO: 30 and has the ability to bind to crystalline cellulose. For example, the modified Family 1 carbohydrate binding module of the present invention comprises an amino acid sequence that is from about 60% to about 99.9% identical to SEQ ID NO: 30 or is from about 75% to about 99.9% identical to SEQ ID NO: 30.

In an alternate embodiment, the modified Family 1 carbohydrate binding module of the present invention comprises substitution of a basic or charge-neutral amino acid at one or more positions selected from the group consisting of 11, 12, 14, 17, 24, 29, and 31 to an acidic amino acid and exhibits from about 50% to about 99.9% identity to SEQ ID NO: 30 as well as the ability to bind to crystalline cellulose. For example, the amino acid at one or more of positions 11, 12, 14, 17, 24, 29, and 31 is substituted by an aspartic acid.

And furthermore, the modified Family 1 carbohydrate binding module of the present invention comprises amino acid substitutions at one or more positions selected from the group consisting of 10, 21, 33 and 37 and exhibits from about 50% to about 99.9% identity to SEQ ID NO: 30 as well as the ability to bind to crystalline cellulose. For example, the amino acid substitution at position 10 is to serine, the amino acid substitution at position 21 is to an aromatic amino acid such as tyrosine, the amino acid substitution at position 33 is to asparagine, and the amino acid substitution at position 37 is to an aromatic amino acid such as tyrosine.

The present invention also relates to a modified glycosidase enzyme comprising one or more catalytic domain and one or more carbohydrate binding module, at least one of the one or more carbohydrate binding module(s) being a modified Family 1 carbohydrate binding module as defined above, functionally joined by one or more linker peptides. The modified glycosidase enzyme exhibits an increase in hydrolyzing activity in the presence of lignin and/or a reduction in lignin binding relative to a parental glycosidase comprising a parental Family 1 carbohydrate binding module from which the modified carbohydrate binding module is derived, the same one or more one or more catalytic domain and the same one or more carbohydrate binding module joined by the same one or more linker peptide.

The one or more catalytic domain in the modified glycosidase of the present invention may be a cellulase catalytic domain, a hemicellulase catalytic domain, a beta-glucosidase catalytic domain and an accessory component catalytic domain. The one or more catalytic domain in the modified glycosidase of the present invention may be a wild-type catalytic domain or a modified catalytic domain comprising amino acid substitutions, insertions or deletions relative to a wild-type catalytic domain.

The one or more catalytic domain in the modified glycosidase of the present invention may be a cellulase catalytic domain of Glycoside Hydrolase Family 5, 6, 7, 8, 9, 12, 44, 45, 48, 51, 61 and 74. For example, the cellulase catalytic domain may comprise amino acids 1-436 of *Trichoderma reesei* Cel7A (SEQ ID NO: 124), amino acids 83-447 of *Trichoderma reesei* Cel6A (SEQ ID NO: 1), amino acids 97-460 of *Humicola insolens* Avi2 (SEQ ID NO: 2), or amino acids 81-440 of *Phanerochaete chrysosporium* Cel6A (SEQ ID NO: 3). For example, the cellulase catalytic domain may comprise amino acids 83-447 of *Trichoderma reesei* Cel6A (TrCel6A as in SEQ ID NO: 1) with one or more amino acid substitutions selected from the group consisting of Y103H, Y103K, Y103R, Y103A, Y103V, Y103L, Y103P, K129E L136V, L136I, S186K, S186T, S186Y, Q204K, G213D, A322D, Q363E, G365D, G365E, G365Q, G365S, R410A, R410F, R410L, R410Q, R410S and S413P.

The one or more catalytic domain in the modified glycosidase of the present invention may also be a hemicellulase catalytic domain from Glycoside Hydrolase Family 5, 8, 10, 11, 26, 43, 51, 54, 62 or 113, a beta-glucosidase catalytic domain from Glycoside Hydrolase Family 1 or 3, or an accessory component catalytic domain such as a swollenin, CIP or expansin catalytic domain. For example, a beta-glucosidase catalytic domain may be *Trichoderma reesei* Cel3A of SEQ ID No: 100 with one or more amino acid substitutions selected from the group consisting of V43X, V66X, S72X, V101X, T235X, N248X, F260X, N369X, A386X, and I543X.

The one or more carbohydrate binding module, other than the modified Family 1 carbohydrate binding module, in the modified glycosidase of the present invention may be a wild-type carbohydrate binding module or a modified carbohydrate binding module comprising amino acid substitutions, insertions or deletions relative to a wild-type catalytic domain. Similarly, the one or more linker peptide in the modified glycosidase of the present invention may be a wild-type linker peptide or a modified linker peptide comprising amino acid substitutions, insertions or deletions relative to a wild-type linker peptide. For example, the one or more linker peptide may be a modified linker peptide being about 6 to about 60 amino acids in length, with least about 50% of the amino acids being either proline, serine or threonine and comprising one or more amino acid substitutions, insertions, or deletions that result in a decrease in the calculated isoelectric point of the linker peptide and/or an increase in the ratio of threonine:serine in the linker peptide relative to a parental linker peptide from which the modified linker peptide is derived. Such a modified linker peptide confers to the modified glycosidase an increase in hydrolyzing activity in the presence of lignin and/or a reduction in lignin binding relative to a parental glycosidase comprising the parental linker peptide.

Any one or all of the modified Family 1 carbohydrate binding module, catalytic domain, other carbohydrate binding module or linker peptide may be derived from one or more fungal glycosidase enzymes produced by such organisms including, but not limited to, *Trichoderma* ssp., *Aspergillus* ssp., *Hypocrea* ssp., *Humicola* ssp., *Neurospora* ssp., *Orpinomyces* ssp., *Gibberella* ssp., *Emericella* ssp., *Chaetomium* ssp., *Chrysosporium* ssp., *Fusarium* ssp., *Penicillium* ssp., *Magnaporthe* ssp., *Phanerochaete* ssp., *Trametes* ssp., *Lentinula elodes, Gleophyllum trabeiu, Ophiostoma piliferum, Corpinus cinereus, Geomyces pannorum, Cryptococcus laurentii, Aureobasidium pullulans, Amorphotheca resinae, Leucosporidium scotti, Cunninghamella elegans, Thermomyces lanuginosus, Myceliophthora thermophila* and *Sporotrichum thermophile.*

The present invention further relates to genetic constructs comprising nucleic acid sequences encoding the modified Family 1 carbohydrate binding module or modified glycosidase enzyme as described above and to genetically modified microbes comprising such genetic constructs for the expression and secretion of the Family 1 carbohydrate binding module or modified glycosidase enzyme. The genetically modified microbe may be a bacterium, yeast or filamentous fungus, such as a species of *Streptomyces, Saccharomyces, Pichia, Hansenula, Hypocrea, Trichoderma, Aspergillus, Fusarium, Neurospora, Chrysoporium* or *Myceliophthora*.

The present invention also relates to a process for producing the modified Family 1 carbohydrate binding module or modified glycosidase enzyme as described above comprising the steps of growing the genetically modified microbe comprising a genetic construct encoding the modified Family 1 carbohydrate binding module or modified glycosidase enzyme under conditions that induce the expression and secretion of the modified Family 1 carbohydrate binding module or modified glycosidase enzyme and recovering the modified Family 1 carbohydrate binding module or modified glycosidase enzyme from the culture medium. Such process for producing the modified Family 1 carbohydrate binding module or modified glycosidase enzyme as described above may include a step of transforming a host cell with a genetic construct encoding the modified cellulase enzyme.

The present invention also relates to a process for hydrolyzing a cellulose or hemicellulose substrate to sugars comprising contacting the substrate with the modified glycosidase as described above. In one embodiment of such a process, the cellulose or hemicellulose substrate may be a pretreated lignocellulosic substrate. In another embodiment of such a process, the modified glycosidase enzyme exhibits improved recovery from the process relative to a parental glycosidase enzyme comprising the same one or more catalytic domain, one or more linker peptide and one or more carbohydrate binding module in which at least one of the one or more carbohydrate binding module is a parental Family 1 carbohydrate binding module from which the modified Family 1 carbohydrate binding module in the modified glycosidase is derived.

The process for hydrolyzing a cellulose or hemicellulose substrate to sugars may be conducted as a continuous, semi-continuous or fed-batch process. In addition, the process for hydrolyzing a cellulose or hemicellulose substrate to sugars may be followed by microbial fermentation of the sugars to alcohol or sugar alcohol.

BRIEF DESCRIPTION OF THE DRAWINGS

FIG. 5 depicts plasmid vectors YEp352/PGK91-1-$\alpha_{ss}$-NKE-HiAvi2 (Panel A) and YEp352/PGK91-1-$\alpha_{ss}$-NKE-PcCel6A-S407P (Panel B) directing the expression and secretion of native and modified HiAvi2 and PcCel6A from recombinant *Saccharomyces cerevisiae*, respectively.

FIG. 7 contains two scatter plots. Panel A is a scatter plot of enzyme activity in the presence of BSA-treated lignin (+BSA activity) versus enzyme activity in the presence of untreated lignin (−BSA activity) for the high-throughput assay described in Example 10b. The data relate to the screening of filtrates from micro plate cultures (Example 9) containing parental and modified HiAvi2 cellulases or filtrates from empty vector transformants. Panel B is a scatter plot of enzyme activity in the presence of BSA-treated lignin (+BSA) activity versus enzyme activity in the presence of untreated lignin (−BSA activity for the high-throughput assay described in Example 10c. The data relate to the screening of filtrates from microplate cultures (Example 9) containing parental (PcCel6A-S407P) and modified PcCel6A cellulases or filtrates from empty vector transformants.

FIG. 12 shows the structure of the Family 1 CBM from TrCel7A (PCB entry 1az6) and the calculated structures of CBMs from TrCel6A, HiAvi2 and PcCel6A, based from the structure of the Family 1 CBM from TrCel7A (PDB entry 1az6). The beta-sheet structures are shown as ribbons. Amino acids equivalent to those observed to participate in cellulose binding in the CBM of TrCel7A are depicted by gray stick structures while those amino acids that interact with lignin are shown as black ball and stick structures. Residues that interact with lignin and cellulose are also shown as black ball and stick structures.

FIG. 13 shows a Clustal W alignment of 34 Family 1 CBMs as obtained from the ProSite URL expasy.ch/cgi-bin/aligner?psa=PS00562&color-1&maxinsert=10&linelen=0.

FIG. 14 shows the amino acid sequence identity between pairs of CBM sequences from FIG. 13.

FIG. 15 shows an alignment of the Family 1 CBMs from TrCel6A, HiAvi2, PcCel6A and TrCel7A. Amino acids that were found to be substituted in modified Family 1 CBMs with reduced lignin binding using the method of Examples 4 are shown in bold font.

DETAILED DESCRIPTION OF THE INVENTION

Figure 1:
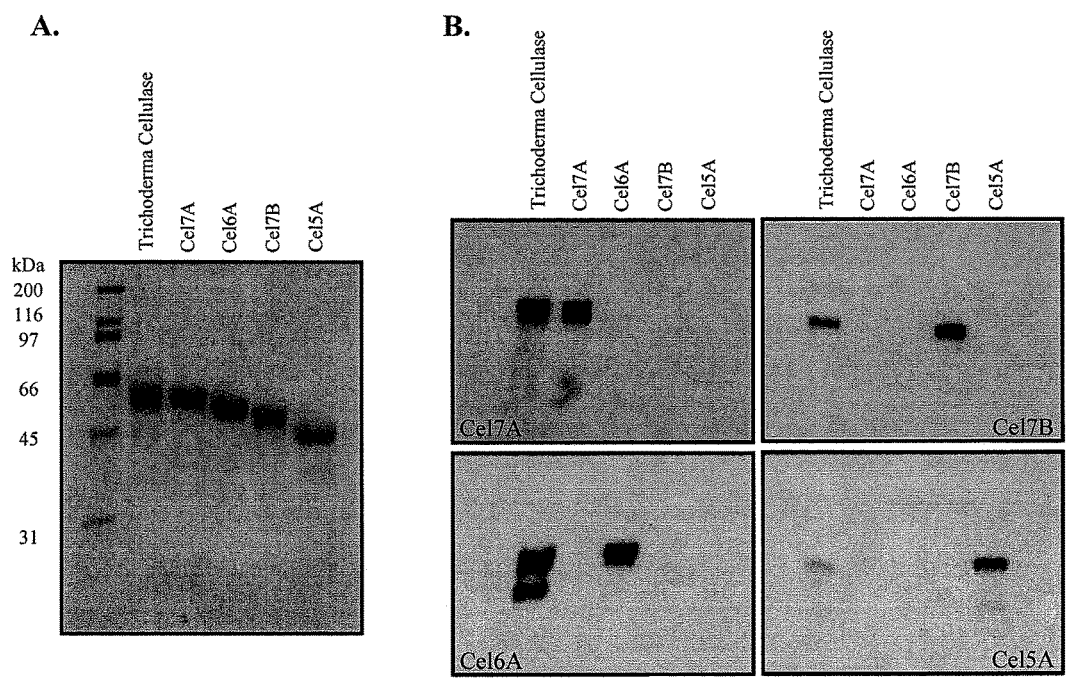
FIG. 1 contains the SDS-PAGE and Western blot analysis of the purified cellulase components from *Trichoderma reesei*. Panel A shows Coomassie Blue stain of purified Cel7A, Cel6A, Cel7B and Cel5A after SDS-PAGE. A *Trichoderma* cellulase mixture was analyzed in parallel for comparison. Panel B shows component-specific Western blots (as indicated in the lower left or lower right corner of each blot) of these samples performed following SDS-PAGE separation and electro-transfer to a PVDF membrane.

The present invention relates to modified carbohydrate binding modules. More specifically, the invention relates to a modified Family 1 carbohydrate binding module exhibiting reduced binding to lignin. The present invention also relates to modified glycosidase enzymes comprising the modified Family 1 carbohydrate binding module, genetic constructs comprising nucleotide sequences encoding the modified Family 1 carbohydrate binding modules or the modified glycosidase enzyme, and the use of the modified glycosidase enzyme comprising the modified Family 1 carbohydrate binding module in the hydrolysis cellulose or hemicellulose substrates in the presence of lignin.

The present invention provides a modified Family 1 carbohydrate binding module with reduced binding to lignin, and the ability to confer not only reduced lignin binding but also increased substrate hydrolyzing activity, in the presence of lignin, to a modified glycosidase enzyme comprising the modified Family 1 carbohydrate binding module.

The following description is of a preferred embodiment by way of example only and without limitation to the combination of features necessary for carrying the invention into effect. The headings provided are not meant to be limiting of the various embodiments of the invention. Terms such as "comprises", "comprising", "comprise", "includes", "including" and "include" are not meant to be limiting. In addition, the use of the singular includes the plural, and "or" means "and/or" unless otherwise stated. Unless otherwise defined herein, all technical and scientific terms used herein have the same meaning as commonly understood by one of ordinary skill in the art.

Family 1 Carbohydrate Binding Modules

Carbohydrate binding modules or CBMs are non-catalytic domains in glycoside hydrolases and other proteins that recognize and bind to polysaccharides. CBMs are often found in fungal and bacterial proteins that contain a glycoside hydrolase domain that degrade insoluble polysaccharides. However, CBMs have also been identified in proteins that do not contain a glycoside hydrolase domain but are involved in the degradation of insoluble polysaccharides such as cellulose. These include but are not limited to Cip1 (Foreman et al., 2003) and swollenin (Saloheimo et al., 2002). CBMs are divided into families based on amino acid sequence similarity; there are currently 59 families of CBMs (http://www.cazy.org/Carbohydrate-Binding-Modules.html). Amongst these CBMs, different members have been shown to recognize crystalline cellulose, non-crystalline cellulose, chitin, beta-glucans, xylan, mannan, galactan and starch. CBMs that bind to cellulose are sometimes referred to by the term "cellulose-binding domain" or "CBD". Family 1 CBMs have a high binding affinity for crystalline cellulose while CBMs from other families have a high binding affinity for amorphous cellulose or single-chain polysaccharides (Boraston, et al., 1004).

As summarized by Shoseyov et al. (2006), the carbohydrate-binding activity of CBMs has been exploited for a number of uses. For example, isolated CBMs have been shown to play a role in the non-hydrolytic disruption of cellulose fibres as well as in the alteration of fibre properties. In addition, CBMs have been used in biotechnological applications as affinity tags for bio-specific affinity purification of recombinant fusion proteins or for targeting enzymes that normally do not contain a CBM to natural fibres (such as targeting oxidative enzymes to textiles surfaces). CBMs have also found utility as analytical tools for characterization of fibre surfaces or detection of polysaccharides in plant cell walls. CBM dimers have been developed as novel cellulose cross-linking proteins that have shown to be effective in enhancing mechanical properties or altering surface properties of paper. Finally, CBMs, when expressed in transgenic plants, have been shown to increase the rate of cellulose biosynthesis and/or growth.

In fungi, CBMs are homologous and members of CBM Family 1 (CBM1). Sequences of CBMs from *T. reesei* cellulases, hemicellulases and related proteins are shown in Table 1. Four cysteines are highly conserved and form two disulfide bridges. Three aromatic amino acids (tryptophan, tyrosine or phenylalanine) are also conserved, form a planar surface and interact directly with the glucose units of the cellulose polymer via van der Waals' interactions. Family 1 CBMs have a high binding affinity for crystalline cellulose.

A Family 1 CBM is defined herein as any protein sequence that is classified as such according to the CAZy system (see http://www.cazy.org/Carbohydrate-Binding-Modules.html for reference). A Family 1 CBM may exhibit from about 50% amino acid sequence identity with amino acids sequence of the CBM of *Trichoderma reesei* Cel6A (also known as cellobiohydolase II or CBH2) as defined in SEQ ID NO: 30. For example, the Family 1 CBM may show from about 50%, 60%, 70%, 80%, 90%, or 95% amino acid identity with the *Trichoderma reesei* TrCel6A CBM as provided in SEQ ID NO: 30. One of skill in the art recognizes that the amino acid sequence of a given CBM may be modified by the addition, deletion or substitution of one or more amino acids and still be considered a CBM.

When the CBM is located at the N-terminus of the secreted glycosidase, one of skill in the art recognizes that amino acids which compose a secretion signal peptide are discounted when numbering the amino acids the CBM. Herein, numbering of the amino acids in the Family 1 CBMs begins at the equivalent of the first glutamine (Q) in TrCel6A (SEQ ID NO: 1).

TABLE 1

Sequences of Family 1 CBMs from *Trichoderma reesei* proteins

| Enzyme | CBM Sequence (delete SEQ ID No's) | % Identity with T. reesei Cel6A CBM (aa 3-39) |
|---|---|---|
| CBH1 (TrCel7A) | PTQSHYGQCGGIGYSGPTVCASGTTCQVLNPY YSQCL (SEQ ID NO: 27) | 63.9 |
| CBH2 (TrCel6A) | QACSSVVVGQCGGQNWSGPTCCASGSTCVYSN DYYSQCL (SEQ ID NO: 30) | 100.0 |
| EG1 (TrCel7B) | CTQTHWGQCGGIGYSGCKTCTSGTTCQYSND YYSQCL (SEQ ID NO: 11) | 63.9 |
| EG2 (TrCel5A) | AQQTVWGQCGGIGWSGPTNCAPGSACSTLNP YYAQCI (SEQ ID NO: 12) | 61.1 |
| EG4 (TrCel61A) | PTQTLYGQCGGSGYSGPTRCAPPATCSTLNPY YAQCL (SEQ ID NO: 14) | 52.8 |
| EG5 (TrCel145A) | GQQTLYGQCGGAGWTGPTTCQAPGTCKVQN QWYSQCL (SEQ ID NO: 15) | 50.0 |
| TrCel74A | GHYAQCGGIGWTGPTQCVAPYVCQKQNDYY YQ (SEQ ID NO: 40) | 56.0 |
| Cip1 | HYGQCGGIGYSGPTVCASGTTCQVLNPYYSQC L (SEQ ID NO: 42) | 61.1 |
| Cip2 | WGQCGGIGWSGPTTCVGGAYCVSYNPYY (SEQ ID NO: 43) | 64.0 |
| Swollenin | ALFGQCGGIGWSGTTCCVAGAQCSFVNDWYS QCL (SEQ ID NO: 44) | 58.3 |

TABLE 1-continued

Sequences of Family 1 CBMs from *Trichoderma reesei* proteins

| Enzyme | CBM Sequence (delete SEQ ID No's) | % Identity with T. reesei Cel6A CBM (aa 3-39) |
|---|---|---|
| Man5A | LYGQCGGSGYTGPTCCAQGTCIYSNTWTSQCL (SEQ ID No: 41) | 65.0 |
| Axe1 | PTQTHWGQCGGQGWTGPTQCESGTTCQVISQ WYSQCL (SEQ ID NO: 7) | 70.0 |

Figure 14:
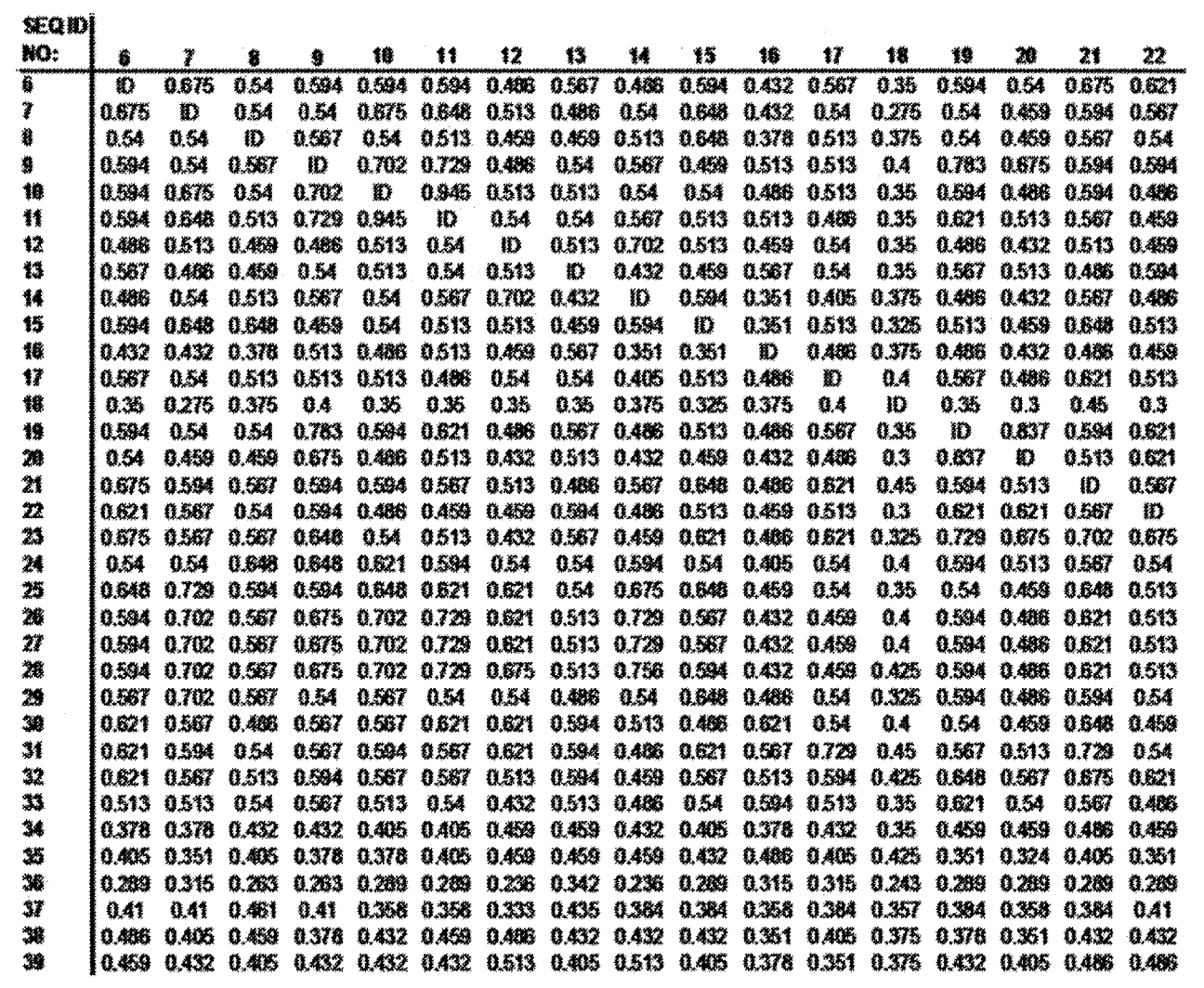
Figure 14:
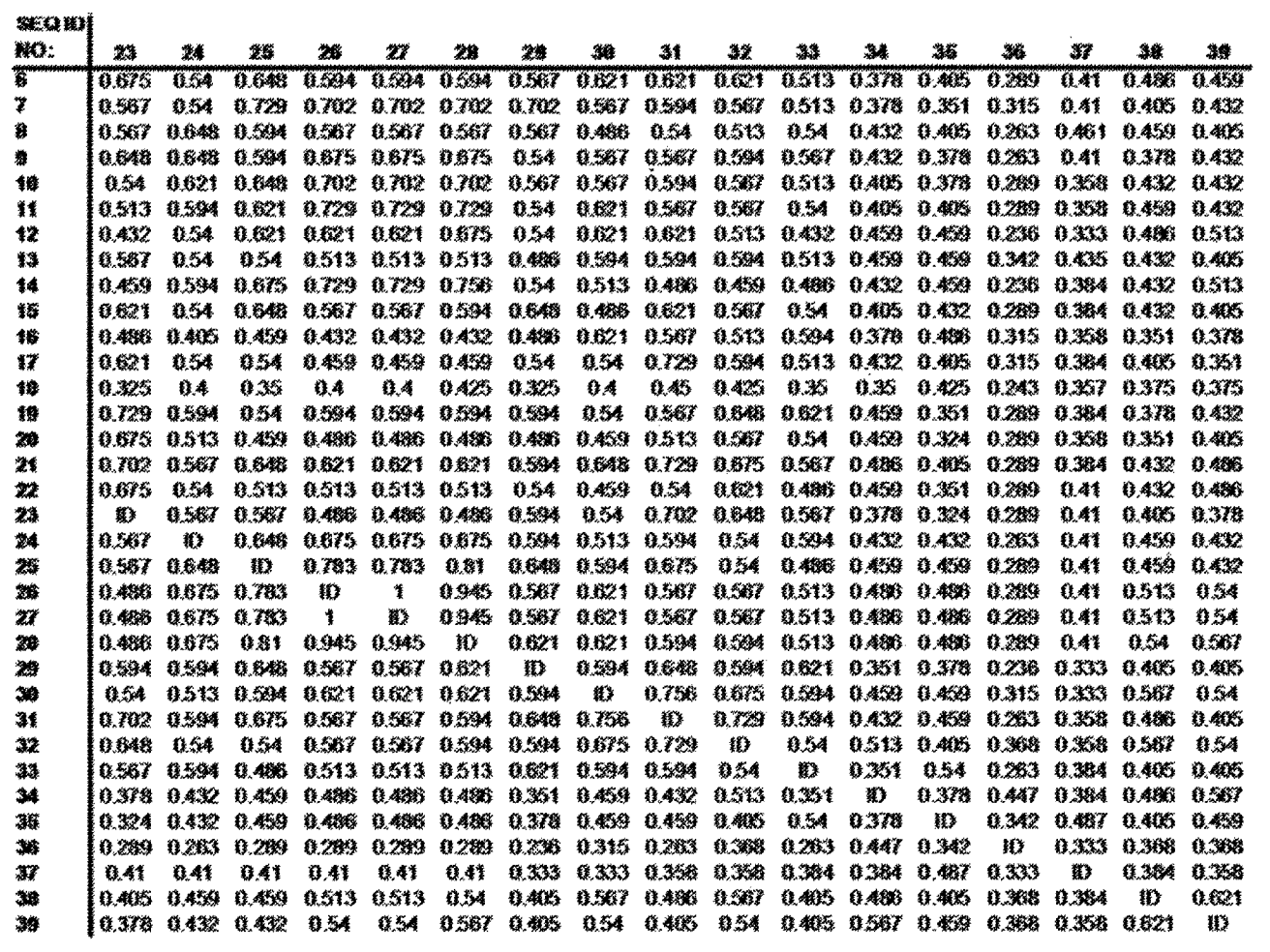

As shown in FIG. 13, there is a high degree of conservation of primary amino acid sequence among Family 1 cellulose binding domains. Multiple alignment across 34 currently known Family 1 CBM amino acid sequences of fungal origin shows that most naturally occurring Family 1 CBMs exhibit from about 45% to about 100% amino acid sequence identity to amino acids 3-39 comprising the Family 1 CBM of TrCel6A and from about 40% to about 95% amino acid sequence identity to at least one other Family 1 CBM (FIG. 14).

Sequence identity can be readily determined by alignment of the amino acids of the two sequences, either using manual alignment, or any sequence alignment algorithm as known to one of skill in the art. The alignments and identity calculations present in FIGS. 13 and 14, respectively, were determined using ClustalW Multiple Alignment tool with default settings, found in the BioEdit software version 7.0.9.0 (Jun. 27, 2007). Other alignment algorithms known by one of skill in the art include, but not limited to, BLAST algorithm (BLAST and BLAST 2.0; Altschul et al., 1997 and 1990), the algorithm disclosed by Smith & Waterman (1981), by the homology alignment algorithm of Needleman & Wunsch (1970), \search for similarity method of Pearson & Lipman (1988), computerized implementations of these algorithms (GAP, BESTFIT, FASTA, and TFASTA in the Wisconsin Genetics Software Package, Genetics Computer Group, 575 Science Dr., Madison, Wis.), or manual alignment and visual inspection.

By "modified Family 1 carbohydrate binding module" or "modified Family 1 CBM", it is meant a Family 1 CBM which exhibits binding to crystalline cellulose and comprises amino acid substitution at one or more positions selected from the group consisting of 10, 11, 12, 14, 17, 21, 24, 29, 31, 33, and 37, said position determined from alignment of a Family 1 carbohydrate binding module amino acid sequence with a *Trichoderma reesei* Cel6A carbohydrate binding module amino acid sequence as defined in SEQ ID NO: 30. As used herein, a modified Family 1 CBM does not include naturally-occurring CBMs.

As known to one of skill in the art, binding of a protein, such as a CBM, to its ligand or substrate, such as cellulose, can be quantified by establishing a binding isotherm. In such experiments, the fractional absorption of the protein added to a solution or suspension containing constant amount of substrate or ligand will increase with increasing amount of added protein until the substrate is saturated with protein. Methods to assess and quantify the binding of Family 1 CBMs to cellulose using binding isotherms are described in Linder et al. (1995 and 1999), Mattinen et al. (1997) and Reinikainen et al. (1992). Binding of a glycosidases comprising parental or modified Family 1 CBMs to a cellulose substrate may be assessed and quantified using the methods of Nidetzky et al. (1994) or using the methods provided in Examples 4 and 14.

For example, the modified Family 1 CBM may comprise substitution of a basic or charge-neutral amino acid at one or more positions selected from the group consisting of 11, 12, 14, 17, 24, 29, and 31 to an acidic amino acid. As defined herein, "basic amino acid" refers to any one of histidine, lysine or arginine, "acid amino acid" refers to any one of aspartic acid or glutamic acid and "charge-neutral amino acid" is any amino acid that is not a basic or acidic amino acid.

The modified Family 1 CBM may also comprise amino acid substitution at one or more positions selected from the group consisting of 10, 21, 33, and 37. For example, the amino acid substitution at position 10 is to serine, the amino acid substitution at position 21 is to an aromatic amino acid such as tyrosine, the amino acid substitution at position 33 is to asparagine, and the amino acid substitution at position 37 is to an aromatic amino acid such as tyrosine.

The modified Family 1 carbohydrate binding module amino acid sequence exhibits from about 50% to about 99.9% amino acid sequence identity to SEQ ID NO: 30, or any amount therebetween. For example, a modified Family 1 CBM may have an amino acid sequence that exhibits about 50%, 55%, 60%, 65%, 70%, 75%, 80%, 85%, 90%, 95% or 99.9% amino acid sequence identity to SEQ ID NO: 30. By "wild type" or "native" Family 1 CBM, it is meant a Family 1 CBM as it is found in nature, without any amino acid substitutions, insertions or deletions.

It will be understood that modified Family 1 CBM may be derived from a wild-type Family 1 CBM or from a Family 1 CBM that already contains other amino acid substitutions.

The modified Family 1 CBM of the present invention is encoded by a nucleic acid sequence that can be generated using genetic material or nucleic acid or amino acid sequence information specific to the desired modified Family 1 CBM or to a corresponding parental Family 1 CBM. As is known by one of skill in the art, such genetic material or sequence information can be used to generate a nucleic acid sequence encoding a desired modified Family 1 CBM using one or more molecular biology techniques for altering amino acid sequences including, but not limited to, site-directed mutagenesis, cassette mutagenesis, random mutagenesis, synthetic oligonucleotide construction, cloning, sub-cloning, amplification by PCR, in vitro synthesis and other genetic engineering techniques known to one of skill in the art. It will be understood that the modified Family 1 may be derived from any parental Family 1 CBM—i.e., it may be derived from a naturally-occurring or "wild-type" Family 1 CBM or from a Family 1 CBM that already contains other amino acid substitutions.

For example, the modified Family 1 CBM may exhibit reduced binding to lignin. In another embodiment, the modified Family 1 carbohydrate binding module may confer reduced binding to lignin, or increased substrate hydrolyzing activity in the presence of lignin, to a glycosidase enzyme comprising the modified Family 1 carbohydrate binding module, one or more catalytic domain and one or more carbohydrate binding module joined by one or more linker peptide.

For the purposes of the present invention, a "parental Family 1 CBM" or "parental Family 1 carbohydrate binding module" is a Family 1 CBM that does not contain the amino acid substitution(s) present in the modified Family 1 CBM. As such, the parental Family 1 CBM may be a Family 1 CBM that contains amino acid substitutions at other positions that have been introduced by genetic engineering or other techniques and that is capable of binding to cellulose. The parental Family 1 CBM could also be a wild-type Family 1 CBM. Alternatively, after production of a modified Family 1 CBM, the modified Family 1 CBM may be subsequently further modified to contain additional amino acid substitutions.

Modified Glycosidase Enzymes

A glycosidase enzyme, as used herein, comprises a one or more catalytic domain and one or more carbohydrate binding module (CBM) joined by one or more linker peptide positioned between the domains. The one or more catalytic domain, one or more CBM and one or more linker peptide may be homologous with respect to each other—i.e., belonging to the same glycosidase as isolated in nature or heterologous with respect to at least one other domain—i.e., being isolated from two or more different naturally occurring glycosidase from the same, or different, source organism(s). The amino acid sequences of the one or more catalytic domain, one or more CBM and one or more linker peptide may be "native" or "wild type"—i.e., as found in unmodified glycosidase enzymes produced in nature—or they may be "derived" from native or wild-type glycosidase enzymes by modification of their amino acid sequences. The term "glycosidase enzyme" may be used interchangeably with the term "glycoside hydrolase" or "glycoside hydrolase enzyme".

A glycosidase enzyme may comprise additional functional domains, e.g., cohesins, dockerins, or fibronectin-like (Fn3) domains and still be considered a glycosidase enzyme.

Examples of glycosidase enzymes from which the one or more catalytic domain, one or more CBM and one or more linker peptide may be isolated or derived include glycosidase enzymes from various microorganism such as *Trichoderma* ssp., *Aspergillus* ssp., *Hypocrea* ssp., *Humicola* ssp., *Neurospora* ssp., *Orpinomyces* ssp., *Gibberella* ssp., *Emericella* ssp., *Chaetomium* ssp., *Chrysosporium* ssp., *Fusarium* ssp., *Penicillium* ssp., *Magnaporthe* ssp., *Phanerochaete* ssp., *Trametes* ssp., *Lentinula edodes*, *Gleophyllum trabeiu*, *Ophiostoma piliferum*, *Corpinus cinereus*, *Geomyces pannorum*, *Cryptococcus laurentii*, *Aureobasidium pullulans*, *Amorphotheca resinae*, *Leucosporidium scotti*, *Cunninghamella elegans*, *Thermomyces lanuginosa*, *Sporotrichum thermophile*, or *Myceliophthora thermophila*. The practice of the invention is not limited by the glycosidase(s) from which the one or more catalytic domain, one or more CBM and one or more linker peptide may be derived.

A "modified glycosidase enzyme" as used herein, is a glycosidase enzyme comprising the one or more catalytic domain, one or more CBM, and one or more linker peptide with at least one of the one or more CBM being the modified Family 1 CBM comprising amino acid substitution at one or more positions selected from the group consisting of 10, 11, 12, 14, 17, 21, 24, 29, 31, 33, and 37, and exhibiting binding to crystalline cellulose and being from about 50% to about 99.9% identical to SEQ ID NO: 30. The one or more catalytic domain may be a wild-type or modified catalytic domain and the one or more linker peptide may be a wild-type or modified linker peptide. As used herein, the term "modified glycosidase enzyme" does not include naturally-occurring glycosidase enzymes.

As used herein, a "parental glycosidase enzyme" is a glycosidase enzyme comprising the same one or more catalytic domain, one or more CBM and one or more linker peptide as the modified glycosidase enzyme except that at least one or more CBM is a parental Family 1 CBM from which the modified Family 1 CBM in the modified glycosidase is derived. Furthermore, the parental Family 1 CBM in the parental glycosidase is identical to the modified Family 1 CBM of the modified glycosidase enzyme except that it has does not contain amino acid substitution at one or more positions selected from the group consisting of 10, 11, 12, 14, 17, 21, 24, 29, 31, 33, and 37. One of skill in the art recognizes that the one or more catalytic domain, one or more CBM, the parental Family 1 CBM, and one or more linker peptide may contain amino acid substitutions, insertions or deletions relative to naturally-occurring catalytic domains, CBMs, or linker peptides provided that these amino acid substitutions are also present in the modified glycosidase enzyme.

In the modified glycosidase of the present invention, the one or more catalytic domain may be a cellulase catalytic domain, a hemicellulase catalytic domain, a beta-glucosidase catalytic domain or an accessory protein catalytic domain.

A "cellulase catalytic domain" is defined as any domain that is capable of cleaving the beta-1,4 glycosidic linkages in a cellulose polymer. A cellulase catalytic domain can be an endoglucanase (EC 3.2.1.4), which cleaves internal beta-1,4 glycosidic linkages in the cellulose polymer to decrease the degree of polymerization of the polymer and/or release oligosaccharides. A cellulase catalytic domain can also be an exoglucanase or cellobiohydrolase (EC 3.2.1.91), which releases small oligosaccharides, primarily cellobiose, from the ends of the cellulose polymer. A cellulose polymer can be natural cellulose, such as that produced by plants or algae or other organisms, and may be pure or be one of several constituents in plant biomass, which also comprises lignin and hemicellulose. The cellulose polymer may also be a cellulose derivative, such as carboxymethyl cellulose or hydroxyethyl cellulose. A cellulase catalytic domain may be a member of GH Family 5, 6, 7, 8, 9, 12, 44, 45, 48, 51, 61 and 74. For example, the cellulase catalytic domain may comprise amino acids 1-436 of *Trichoderma reesei* Cel7A SEQ ID NO: 124), amino acids 83-447 of *Trichoderma reesei* Cel6A (SEQ ID NO: 1), amino acids 97-460 of *Humicola insolens* Avi2 (SEQ ID NO: 2), or amino acids 81-440 of *Phanerochaete chrysosporium* Cel6A (SEQ ID NO: 3). For example, the cellulase catalytic domain may comprise amino acids 83-447 of *Trichoderma reesei* Cel6A (SEQ ID NO: 1) with one or more amino acid substitutions selected from the group consisting of Y103H, Y103K, Y103R, Y103A, Y103V, Y103L, Y103P, K129E L136V, L136I, S186K, S186T, S186Y, Q204K, G231D, A322D, Q363E, G365D, G365E, G365Q, G365S, R410A, R410F, R410L, R410Q, and R410S.

A "hemicellulase catalytic domain" is defined as any domain that is capable of cleaving the beta-1,4 glycosidic linkages in a hemicellulose polymer. For example, a hemicellulase catalytic domain may be a xylanase (E. C. 3.2.1.8), a beta-mannanase (E.C. 3.2.1.78), or an arabinofuranosidase (E.C. 3.2.1.55). Alternatively, a hemicellulase catalytic domain may be a member of Glycoside Hydrolase Family 5, 8, 10, 11, 26, 43, 51, 54, 62 or 113.

A "beta-glucosidase" catalytic domain is defined as any domain that is capable of producing glucose from small beta-1,4 linked oligosaccharides, such as cellobiose. Beta-glucosidases (E.C. 3.2.1.21) may be a member of Glycoside Hydrolase Family 1 or 3. For example, a beta-glucosidase catalytic domain may be a *Trichoderma reesei* Cel3A (SEQ ID NO: 100) with one or more amino acid substitutions selected from the group consisting of V43X, V66X, S72X, V101X, T235X, N248X, F260X, N369X, A386X, and I543X, which confer improved stability and/or catalytic efficiency to the TrCel3A beta-glucosidase (U.S. Publication No. 2010/0093040A1 and U.S. Publication No. 2010/0304438A1).

Finally, an "accessory protein catalytic domain" includes proteins that interact with cellulose to facilitate its hydrolysis including, but not limited to, Cip1, Cip2, swollenins and expansins. Accessory protein catalytic domain also includes other proteins that assist in the hydrolysis of lignocellulose, such as acetyl xylan esterases (E.C. 3.1.1.72), ferulic acid esterases (E.C. 3.1.1.73), and cellobiose dehydrogenase (E.C. 1.1.99.18).

One of skill in the art recognizes that the amino acid sequence of a given catalytic domain may be modified by the addition, deletion or substitution of one or more amino acids and still be considered a cellulase catalytic domain.

CBMs and catalytic domains are often separated by linker peptides. The term "linker peptide" is intended to be understood as a stretch of amino acids located between two functional domains and comprising from about 6 to about 60 amino acids. Linker peptides can be identified from amino acid sequence information using models such as described by Bae et al. (2008) and Suyama et al. (2003). Gilkes et al., (1991) presents the sequences of linkers from a variety of cellulases and other bacterial and fungal proteins encompassed by this definition. Linker peptides are typically basic peptides, particularly enriched in serine, threonine and proline, relative to non-linker sequences. As presented in Table I of Gilkes et al (1991), proline, serine and threonine account for 50% or more of the amino acids in all linker peptide sequences from bacterial and fungal glycoside hydrolases (xylanases, endoglucanases, exoglucanases). For the purposes defined herein, a linker peptide maybe be defined as a stretch of about 6 to about 60 amino acids, at least 50% of which are proline, serine or threonine, that is naturally found between a catalytic domain and a CBM, two catalytic domains, two CBMs, or between another functional domain and either a catalytic domain or a CBM. Proline, serine and threonine may account for 50%, 60%, 70%, 80% 90% or 100% of the amino acids in the linker peptide ((# proline+threonine+serine)/# amino acids in linker×100%). One of skill in the art recognizes that the amino acid sequence of a given linker may be modified by the addition, deletion or substitution of one or more amino acids and still be considered a linker peptide.

The modified glycosidase may comprise additional CBMs, in addition to the modified Family 1 CBM as defined above. These additional CBMs may be derived from any of the 59 CBM Families defined using the CAZy system (see http://www.cazy.org/Carbohydrate-Binding-Modules.html for reference).

Finally, the modified glycosidase may comprises other domains including, but not limited to fibronectin-like (Fn3) domains, cohesions, dockerins or other carbohydrate-active domains such amylases, glucoamylases, chitinases and the like.

Measuring Lignin Binding

Figure 16:
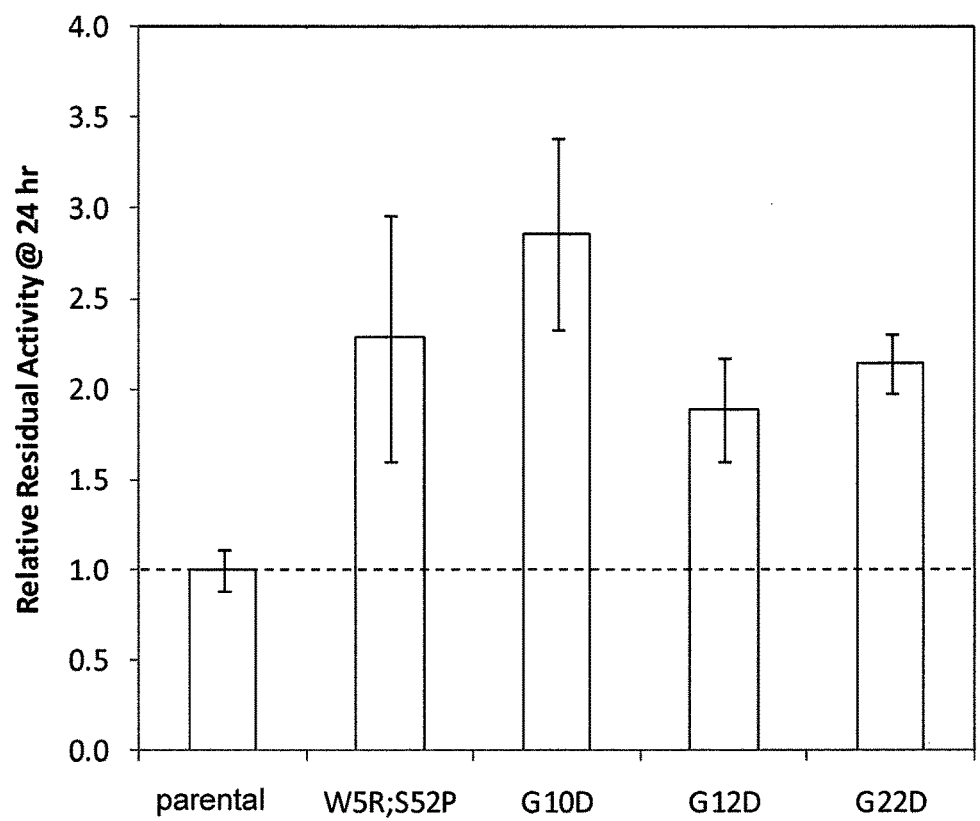
FIG. 16 shows the relative residual activity of parental (WT) and modified PcCel6A glycosidases after a 24 h incubation with lignin as described in Example 4.

The extent to which parental or modified Family 1 CBMs, or parental and modified glycosidase enzymes, as defined above, bind to lignin can be determined by pre-incubating the CBM or glycosidase enzyme with purified lignin for a set period of time and then measuring the residual protein concentration and/or enzyme activity in solution, and/or in the lignin-protein slurry, using assay methods known to one of skill in the art. The relative residual activities of parental and modified glycosidases comprising a Family 6 cellulase catalytic domain and a parental or modified Family 1 CBM after a 24 h incubation with lignin are shown in FIG. 16.

If the purified lignin is insoluble, the protein-lignin complexes can be readily separated from the bulk solution containing unbound protein by centrifugation or filtration. The lignin may be purified from a lignocellulosic feedstock (described below) by acid-extraction, alkali extraction, extraction with organic solvents, or enzymatic digestion of the lignocellulose with hydrolytic enzymes. The determination of the relative binding of parental and modified Family 1 CBMs or glycosidases is not dependent on the method used to purify the lignin, the source of the lignin or the assay methods used to detect the protein in solution. Methods for measuring the relative binding of parental and modified Family 1 CBMs, and parental and modified glycosidase enzymes, are provided in Example 4.

Figure 17:
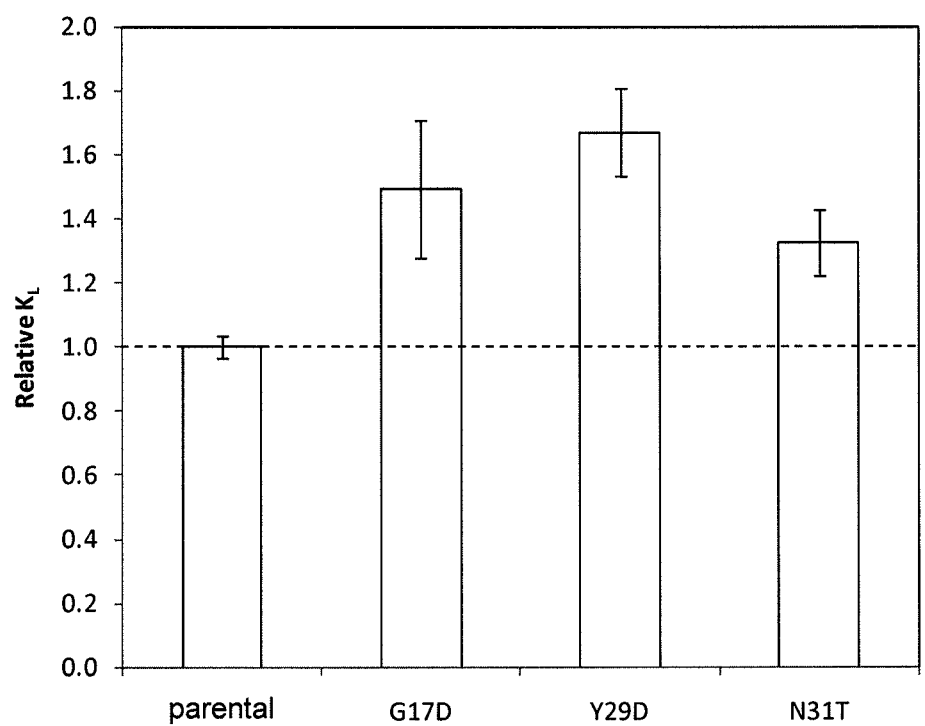
FIG. 17 shows the relative lignin dissociation constants ($K_L$) of parental (WT) and modified TrCel6A glycosidases determined as described in Example 4.
Figure 18:
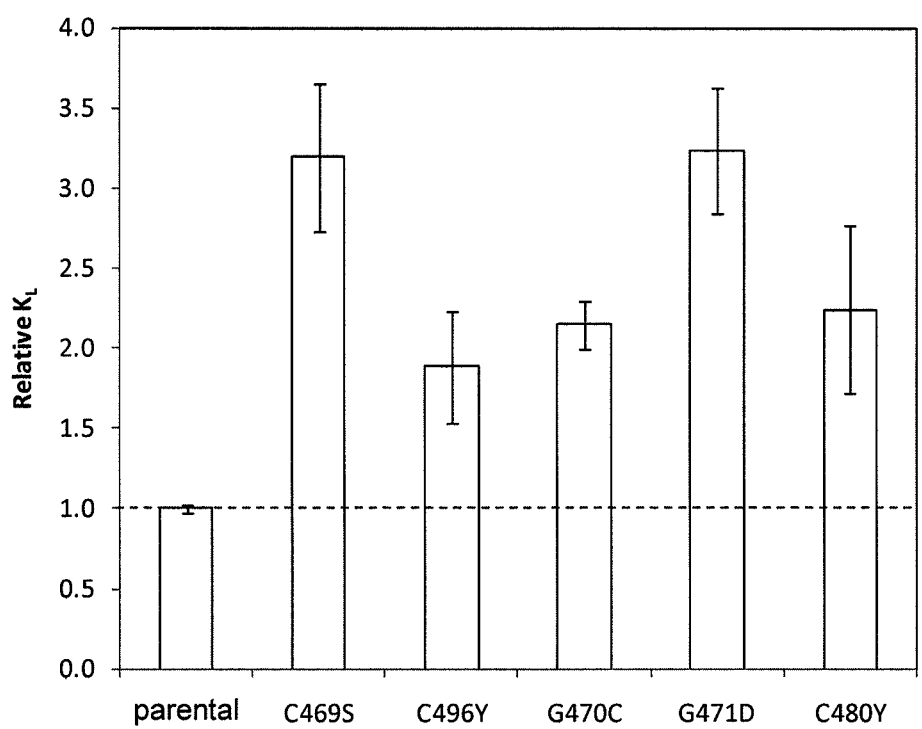
FIG. 18 shows the relative lignin dissociation constants ($K_L$) of parental (WT) and modified TrCel7A glycosidases determined as described in Example 4.

The relative lignin binding of parental and modified Family 1 CBMs or parental and modified glycosidases may be determined by calculating the lignin dissociation constant ($K_L$) for the modified Family 1 CBM or glycosidase and dividing by the lignin dissociation constant (KO calculated for the parental CBM or glycosidase as described in Example 4. The relative $K_L$ values for modified glycosidases comprising Family 6 or 7 cellulase catalytic domains are shown in FIGS. 17 and 18.

The decrease in the inactivation of the modified glycosidase enzymes by lignin can be determined by measuring the degradation of a substrate (such as azo-glucan or cellulose) in the presence and absence of lignin and then taking the ratio of activity in the presence of lignin to the activity in the absence of lignin. The lignin present in such a hydrolysis reaction can be part of the insoluble substrate, such as in pre-treated lignocellulose, or be isolated in a soluble or insoluble form. If the lignin is isolated or purified, the inactivation of the modified or parental glycosidase enzyme by lignin is determined by measuring the activity in equivalent hydrolysis reactions, wherein one of the reactions contains a sufficient amount of lignin to reduce the glycosidase activity. Alternatively, isolated lignin that has been treated to be less deactivating by coating with a non-specific protein such as bovine serum albumin (BSA), a surfactant or other chemical can be added to the control reaction in the same amounts as the untreated lignin. If the lignin is part of the insoluble substrate, the inactivation of the modified or parental glycosidase enzyme by lignin is determined by taking the ratio of glycosidase activity on a bleached substrate (from which the lignin has been removed, for example, by an oxidant such as chlorine dioxide) and the glycosidase activity on an unbleached, lignin-containing substrate. A modified glycosidase enzyme with decreased inactivation by lignin will show a higher activity ratio (untreated, isolated lignin:no lignin or treated lignin) than the parental glycosidase enzyme. Methods for measuring the relative activity of parental and modified glycosidases comprising, respectively, parental and modified Family 1 CBMs, in the presence of lignin enzymes, are provided in Example 10.

There are several assays for measuring substrate hydrolyzing activity of the modified and parental glycosidase enzymes known to one of skill in the art. For example, hydrolysis of cellulose or hemicellulose can be monitored by measuring the enzyme-dependent release of reducing sugars, which are quantified in subsequent chemical or chemoenzymatic assays known to one of skill in the art, including reaction with dinitrosalisylic acid (DNS). Hydrolysis of polysaccharides can also be monitored by chromatographic methods that separate and quantify soluble mono-, di- and oligosaccharides released by the enzyme activity. In addition, soluble colorimetric substrates may be incorporated into agar-medium on which a host microbe expressing and secreting a parental or modified cellulase enzyme is grown. In such an agar plate assay, activity of the cellulase is detected as a colored or colorless halo around the individual microbial colony expressing and secreting an active cellulase. It will be appreciated, however, that the practice of the present invention is not limited by the method used to assess the activity of the modified glycosidase enzyme.

Figure 2:
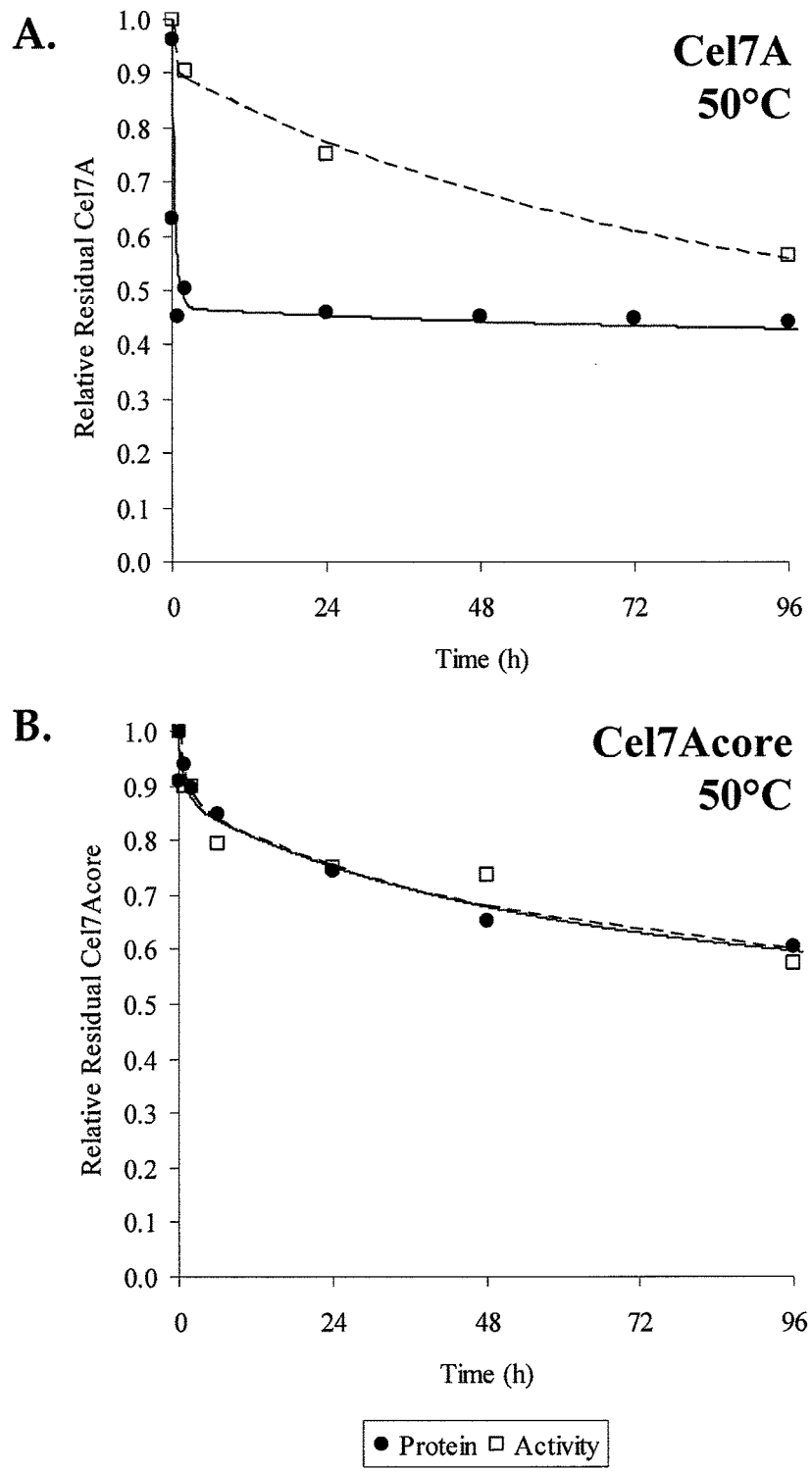
FIG. 2 shows the effects of lignin on *T. reesei* Cel7A with and without a CBM (Cel7A and Cel7Acore). Panel A shows the loss of *T. reesei* Cel7A protein and Cel7A activity and Panel B shows the loss of Cel7Acore protein and Cel7Acore activity in the presence of lignin at 50° C. Cel7A and papain-treated Cel7A (Cel7Acore) were incubated with acid extracted lignin for up to 96 h. The concentrations Cel7A and Cel7Acore protein in the supernatant, free from lignin, were measured in samples taken at different times throughout the experiment. Residual Cel7A and Cel7Acore activities on pretreated wheat straw were measured in the lignin slurry over time.
Figure 3:
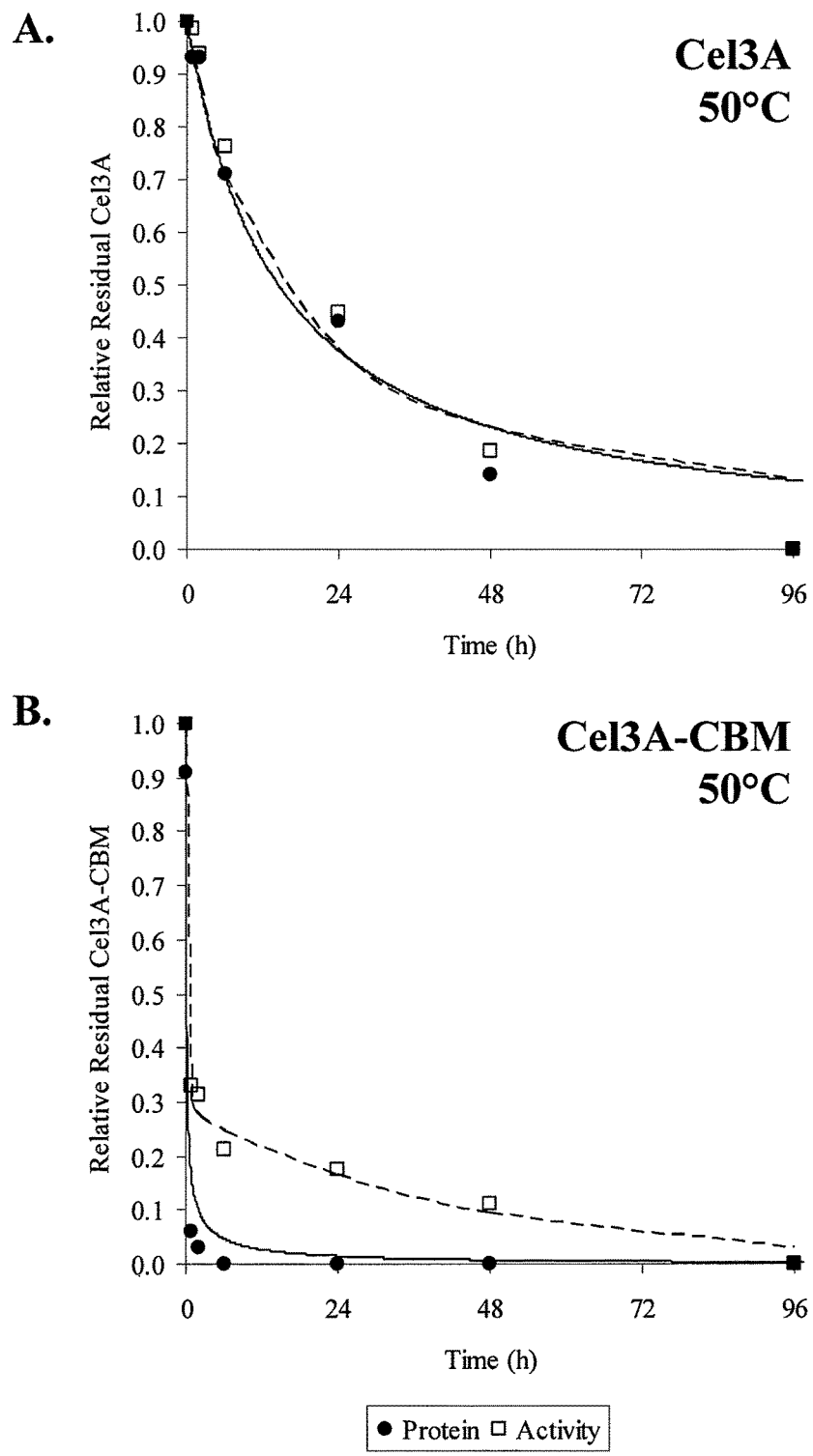
FIG. 3 shows that adding the CBM from *T. reesei* Cel7A to *T. reesei* Cel3A increased lignin-binding and lignin-associated inactivation of Cel3A. Cel3A (Panel A) and Cel3A-CBM (Panel B) were incubated with acid extracted lignin for up to 96 h at 50° C. The concentrations of these proteins in their respective supernatants, free from lignin, were measured in samples taken at different times throughout the experiment. Their residual activities were also measured in their respective lignin slurries over time.
Figure 4:
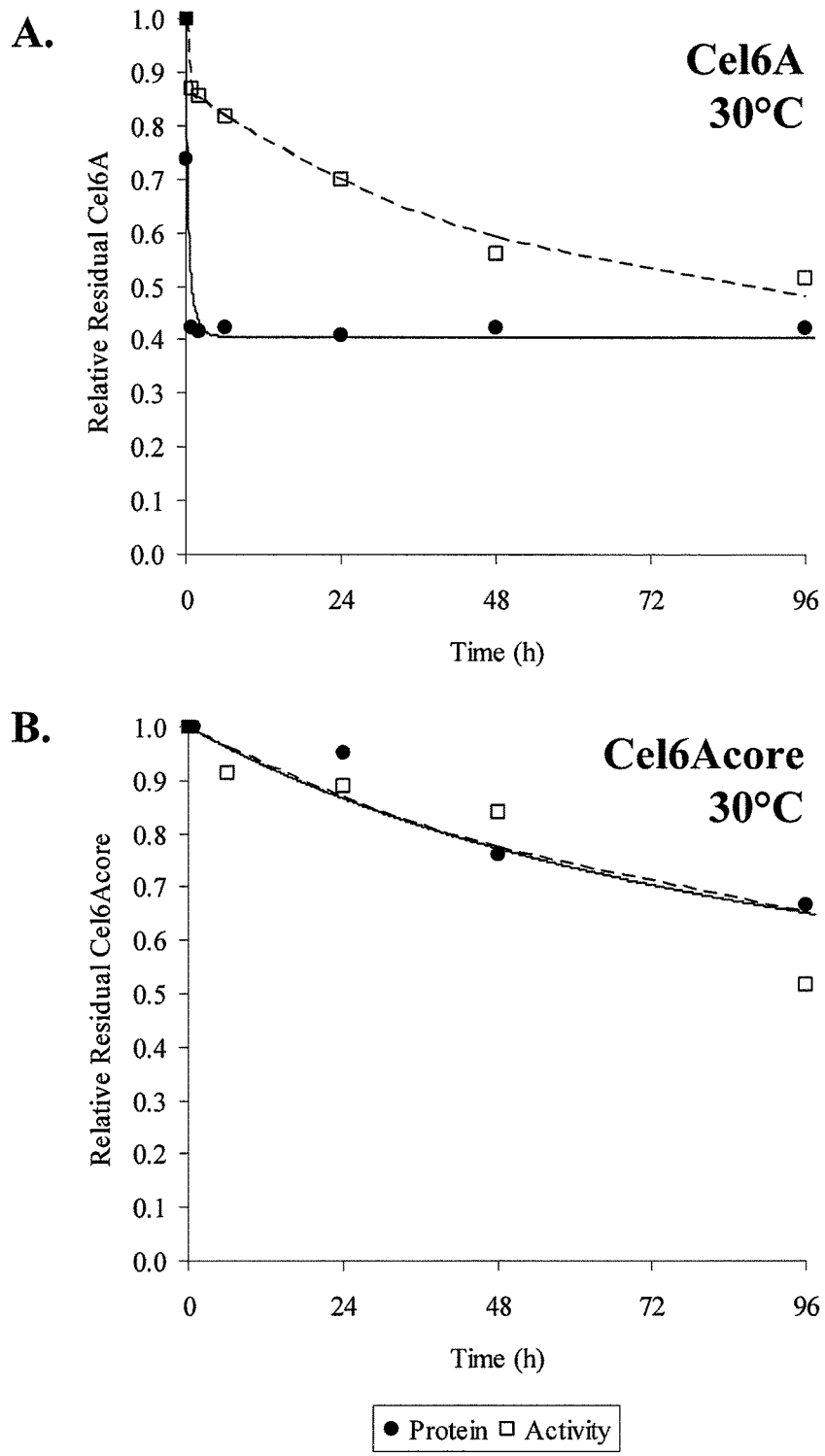
FIG. 4 shows the effects of lignin on *T. reesei* Cel6A with and without a CBM (Cel6A and Cel6Acore). Panel A shows compares the loss of Cel6A protein and Ce6A activity and Panel B shows loss of Cel6Acore protein and Cel6Acore activity in the presence of lignin at 30° C. Cel6A (Panel A) and Cel6Acore produced by papain treatment (Panel B) were incubated with acid extracted lignin for up to 96 h at 30° C. The concentrations of these proteins in their respective supernatants and their residual activities on pretreated wheat straw were measured over time.
Figure 11:
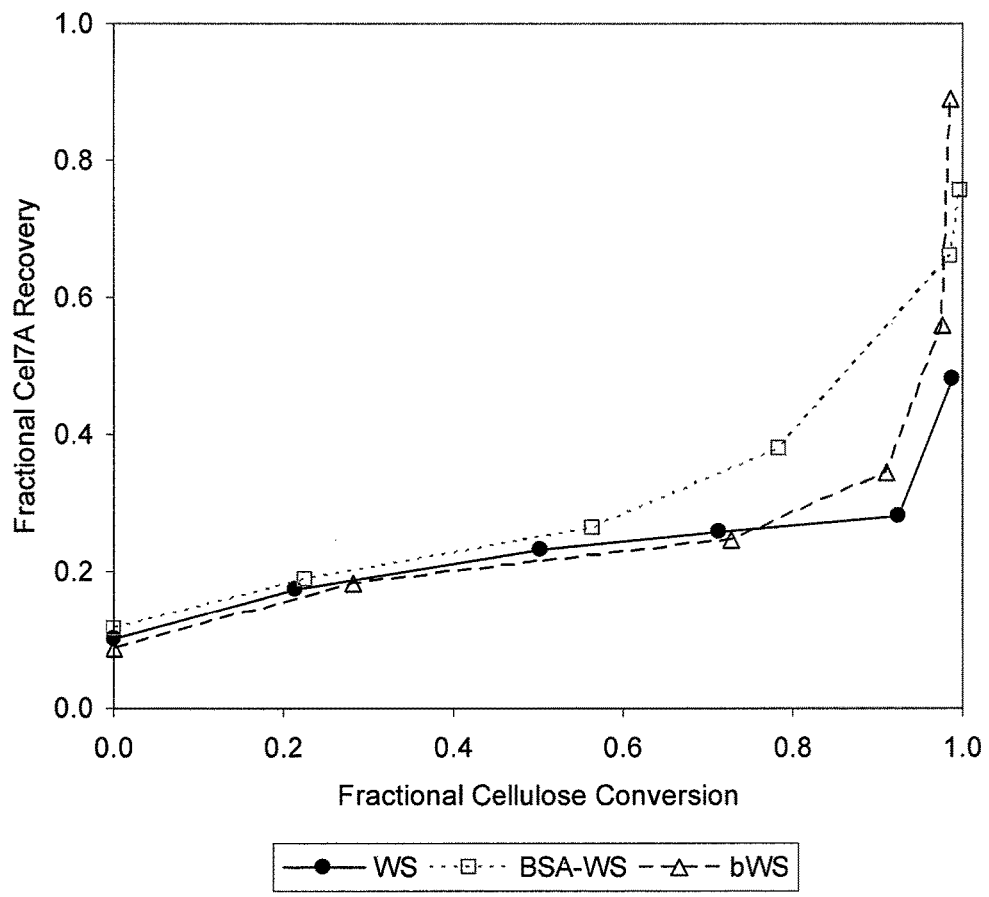
FIG. 11 demonstrates that recovery of wild-type TrCel7A glycosidase from pre-treated lignocellulose increases upon removal or blocking of in situ lignin. A *Trichoderma reesei* cellulase mixture with enhance levels of TrCel3A beta-glucosidase was incubated with pretreated wheat straw (WS), hypochlorite-bleached pretreated wheat straw (bWS) and pretreated wheat straw that was pre-incubated with bovine serum albumin to block lignin (BSA-WS). Sample supernatants were collected throughout the hydrolysis time-course and assayed for glucose and TrCel7A concentrations. At a fractional conversion of 0.98, more TrCel7A was present in the supernatant from the reactions involving bWS and BSA-WS, compared to the WS control.

The effect of the presence or absence of a Family 1 CBM on protein stability and substrate hydrolyzing activity of cellulase catalytic domains, for example, Family 7 and Family 6 catalytic domains, or of a Family 3 beta-glucosidase catalytic domain may be determined after pre-incubation in a lignin slurry. The data FIGS. 2, 3 and 4 show that the presence of a Family 1 CBM dramatically increases the sequestration of protein from solution by the lignin in the hydrolysis reaction, but has little effect on the hydrolyzing activity of the catalytic domain to which it is attached. Furthermore, FIG. 11 shows that Cel7A with a wild-type Family 1 CBM is more recoverable from hydrolysis reactions from which the substrate was made to be lignin-free or in which the lignin was "blocked" by non-specific protein.

The cellulose-hydrolyzing activity of the parental and modified glycosidase enzymes, comprising parental or modified Family 1 CBMs, in the presence of untreated lignin (–BSA) and treated lignin (+BSA), was determined via a comparative study of the parental and modified glycosidase enzymes as described in Example 10. The results are shown in Table 2, below. All of the modified glycosidase enzymes comprising Family 1 CBMs show at least a 20% decrease in lignin binding (20% higher KO and/or 11% higher ratio of activity in the presence of untreated lignin:activity in the presence of BSA-treated lignin (10% increase in ±BSA activity ratio).

TABLE 2

Modified Glycosidases Comprising Modified Family 1 CBMs and Exhibiting Enhanced Hydrolytic Activity in the Presence of Lignin (relative to a parental glycosidase)

| SEQ ID NO. | Normalized –/+ BSA ratio | |
|---|---|---|
| | | Mutations in PcCel6A-S407P (positions as listed in SEQ ID NO: 5) |
| 5 | 1.00 | None |
| 66 | 1.69 ± 0.01 | G12D |
| 67 | 1.76 ± 0.04 | W5R, S52P |
| 68 | 1.75 ± 0.25 | G22D, S64T, Q335E |
| 69 | 1.86 ± 0.42 | C8S |
| 70 | 1.49 ± 0.01 | G22D, Q197L |
| 71 | 1.89 ± 0.33 | G10D |
| 72 | 1.64 ± 0.23 | P30S, A276V |
| 73 | 1.65 ± 0.13 | G22D |
| 74 | 1.73 ± 0.26 | V20L, K288E |
| 75 | 1.77 ± 0.05 | P30S, I323T |
| 77 | 1.70 ± 0.29 | W5C, S83L, L131M |
| 78 | 2.29 ± 0.53 | S2N, G12S, A123V |
| 79 | 2.05 ± 0.53 | I11T, T423I, P439S |
| 80 | 1.70 ± 0.40 | P30S |
| 81 | 1.71 ± 0.23 | C8S, V54I |
| 82 | 2.15 ± 0.71 | G15D, P80L, A184T, V282I |
| 83 | 1.93 ± 0.22 | N29T |
| 85 | 1.89 ± 0.60 | G12D, A296S |
| 86 | 1.87 ± 0.20 | V27D, H60Y, P80T |
| 87 | 1.61 ± 0.22 | A1D, L28P, N437K |
| 102 | 2.36 ± 0.08 | G12D |
| 76 | 1.57 ± 0.30 | L36S |
| 84 | 2.00 ± 0.72 | L36S, Q201H, A304G |
| | | Mutations in HiAvi2 (positions as listed in SEQ ID NO: 2) |
| 2 | 1.00 | None |
| 55 | 1.26 | C21Y, I255V, R342H, G423S |
| 56 | 1.36 | S25C, N31S, L278F, A303T |
| 57 | 1.35 | A1D, G84D, V175A, K259R, A275T |
| 58 | 1.63 | I13T, T61A |
| 59 | 1.22 | C3Y, T26A, V43D, S320T |
| 60 | 1.20 | C10S, E157G |
| 61 | 1.84 | N31D, P324T, N389Y |
| 62 | 1.25 | C37Y |
| 63 | 1.35 | W7R, A75T, M270T |
| 64 | 1.24 | G11C, I13F, S47L, N237D |
| 65 | 1.37 | P18S |
| | | Mutations in TrCel6A-S413P (positions as listed in SEQ ID NO: 4) |
| 4 | 1.00 | None |
| 45 | 1.29 | V28D, A112T, Q357E |
| 46 | 1.25 | G8N, T87M, H414Y |
| 47 | 1.74 | G17D, G231S |
| 48 | 1.17 | A22T |
| 49 | 1.55 | Y33N |
| 50 | 1.15 | G8D, V217I |
| 51 | 1.13 | N31S, G320D |
| 52 | 1.13 | N31S |
| 53 | 1.50 | L38F, V57E, K157M |
| 54 | 1.14 | S25N |

Genetic Constructs Encoding the Modified Family 1 Carbohydrate Binding Module or Modified Glycosidase Enzyme The present invention also relates to genetic constructs comprising a polynucleotide sequence encoding the modified Family 1 carbohydrate binding module or modified glycosidase enzyme operably linked to regulatory polynucleotide sequences directing the expression and secretion of the modified Family 1 carbohydrate binding module or modified glycosidase enzyme from a host microbe. By "regulatory polynucleotide sequences" it is meant a promoter and a polynucleotide sequence encoding a secretion signal peptide. The regulatory polynucleotide sequences may be derived from genes that are highly expressed and secreted in the host microbe under industrial fermentation conditions. For example, the regulatory sequences are derived from any one or more of the *Trichoderma reesei* cellulase or hemicellulase genes.

The genetic construct may further comprise a selectable marker gene to enable isolation of a genetically modified microbe transformed with the construct as is commonly known to those of skill in the art. The selectable marker gene may confer resistance to an antibiotic or the ability to grow on medium lacking a specific nutrient to the host organism that otherwise could not grow under these conditions. The present invention is not limited by the choice of selectable marker gene, and one of skill in the art may readily determine an appropriate gene. For example, the selectable marker gene may confer resistance to hygromycin, phleomycin, kanamycin, geneticin, or G418, complement a deficiency of the host microbe in one of the trp, arg, leu, pyr4, pyr, ura3, ura5, his, or ade genes or confers the ability to grow on acetamide as a sole nitrogen source.

The genetic construct may further comprise other polynucleotide sequences, for example, transcriptional terminators, polynucleotide encoding peptide tags, synthetic sequences to link the various polynucleotide sequences together, origins of replication, and the like. The practice of the present invention is not limited by the presence of any one or more of these other polynucleotide sequences.

Genetically Modified Microbes Producing the Modified Family 1 Carbohydrate Binding Module or Modified Glycosidase Enzyme The modified Family 1 carbohydrate binding module or modified glycosidase enzyme may be expressed and secreted from a genetically modified microbe produced by transformation of a host microbe with a genetic construct encoding the modified Family 1 carbohydrate binding module or modified glycosidase enzyme. The host microbe may be a bacterium, such as *Escherichia coli* or *Streptomyces lividans*, a yeast such *Saccharomyces*, *Pichia*, or *Hansenula*, or a filamentous fungus such as *Trichoderma*, *Hypocrea*, *Aspergillus*, *Fusarium*, *Humicola*, *Chrysosporium*, *Myceliophthora*, *Sporotrichum*, *Thielavia*, or *Neurospora*. In a most preferred embodiment, the host microbe is an industrial strain of *Trichoderma reesei*.

The genetic construct may be introduced into the host microbe by any number of methods known by one skilled in the art of microbial transformation, including but not limited to, treatment of cells with $CaCl_2$, electroporation, biolistic bombardment, PEG-mediated fusion of protoplasts (e.g. White et al., WO 2005/093072). After selecting the recombinant fungal strains expressing the modified cellulase enzyme, the selected recombinant strains may be cultured in submerged liquid fermentations under conditions that induce the expression of the modified cellulase enzyme.

Production of the Modified Family 1 Carbohydrate Binding Module or the Modified Glycosidase Enzyme A modified Family 1 carbohydrate binding module or modified glycosidase enzyme of the present invention may be produced in a fermentation process using a genetically modified microbe comprising a genetic construct encoding the modified Family 1 carbohydrate binding module or modified glycosidase enzyme, e.g., in submerged liquid culture fermentation.

Submerged liquid fermentations of microorganisms, including *Trichoderma* and related filamentous fungi, are typically conducted as a batch, fed-batch or continuous process. In a batch process, all the necessary materials, with the exception of oxygen for aerobic processes, are placed in a reactor at the start of the operation and the fermentation is allowed to proceed until completion, at which point the product is harvested. A batch process for producing the modified Family 1 carbohydrate binding module or modified glycosidase enzyme of the present invention may be carried out in a shake-flask or a bioreactor.

In a fed-batch process, the culture is fed continuously or sequentially with one or more media components without the removal of the culture fluid. In a continuous process, fresh medium is supplied and culture fluid is removed continuously at volumetrically equal rates to maintain the culture at a steady growth rate.

One of skill in the art is aware that fermentation medium comprises a carbon source, a nitrogen source and other nutrients, vitamins and minerals which can be added to the fermentation media to improve growth and enzyme production of the host cell. These other media components may be added prior to, simultaneously with or after inoculation of the culture with the host cell.

For the process for producing the modified Family 1 carbohydrate binding module or modified glycosidase enzyme of the present invention, the carbon source may comprise a carbohydrate that will induce the expression of the modified Family 1 carbohydrate binding module or modified glycosidase enzyme from a genetic construct in the genetically modified microbe. For example, if the genetically modified microbe is a strain of *Trichoderma*, the carbon source may comprise one or more of cellulose, cellobiose, sophorose, and related oligo- or poly-saccharides known to induce expression of cellulases and beta-glucosidase in *Trichoderma*.

In the case of batch fermentation, the carbon source may be added to the fermentation medium prior to or simultaneously with inoculation. In the cases of fed-batch or continuous operations, the carbon source may also be supplied continuously or intermittently during the fermentation process. For example, when the genetically modified microbe is a strain of *Trichoderma*, the carbon feed rate is between 0.2 and 2.5 g carbon/L of culture/h, or any amount therebetween.

The process for producing the modified Family 1 carbohydrate binding module or modified glycosidase enzyme of the present invention may be conducted at a temperature from about 20° C. to about 50° C., or any temperature therebetween, for example from about 25° C. to about 37° C., or any temperature therebetween, or from 20, 22, 25, 26, 27, 28, 29, 30, 32, 35, 37, 40, 45 or 50° C. or any temperature therebetween.

The process for producing the modified Family 1 carbohydrate binding module or modified glycosidase enzyme of the present invention may be carried out at a pH from about 3.0 to 6.5, or any pH therebetween, for example from about pH 3.5 to pH 5.5, or any pH therebetween, for example from about pH 3.0, 3.2, 3.4, 3.5, 3.7, 3.8, 4.0, 4.1, 4.2, 4.3, 4.4, 4.5, 4.6, 4.7, 4.8, 4.9, 5.0, 5.2, 5.4, 5.5, 5.7, 5.8, 6.0, 6.2, 6.5 or any pH therebetween.

Following fermentation, the fermentation broth containing the modified Family 1 carbohydrate binding module or modified glycosidase enzyme may be used directly, or the modified Family 1 carbohydrate binding module or modified glycosidase enzyme may be separated from the fungal cells, for example by filtration or centrifugation. Low molecular weight solutes such as unconsumed components of the fermentation medium may be removed by ultra-filtration. The modified Family 1 carbohydrate binding module or modified glycosidase enzyme may be concentrated, for example, by evaporation, precipitation, sedimentation or filtration. Chemicals such as glycerol, sucrose, sorbitol and the like may be added to stabilize the cellulase enzyme. Other chemicals, such as sodium benzoate or potassium sorbate, may be added to the cellulase enzyme to prevent growth of microbial contamination.

Hydrolysis of Cellulose or Hemicellulose Using the Modified Glycosidase Enzymes

The modified glycosidase enzymes of the present invention are used for the enzymatic hydrolysis of cellulose or hemicellulose in a hydrolysis reaction further comprising lignin. For example, the modified glycosidase enzyme of the present invention is used for the enzymatic hydrolysis of a pretreated lignocellulosic substrate, such as in industrial processes producing fermentable sugars, sugar alcohols or fuel alcohols from lignocellulose, or in the enzymatic hydrolysis of pulp. The modified glycosidase enzymes of the present invention may be part of an enzyme mixture comprising other cellulase enzymes, hemicellulases, glucosidases, and non-hydrolytic proteins known to alter cellulose structure, such as swollenins and expansins.

By the term "enzymatic hydrolysis", it is meant a process by which glycosidase enzymes or mixtures, including those comprising the modified glycosidase enzyme of the present invention, act on polysaccharides to convert all or a portion thereof to soluble sugars.

The modified glycosidase enzyme of the invention is used for the enzymatic hydrolysis of a "pretreated lignocellulosic substrate." A pretreated lignocellulosic substrate is a material of plant origin that, prior to pretreatment, contains 20-90% cellulose (dry wt), more preferably about 30-90% cellulose, even more preferably 40-90% cellulose, for example 20, 22, 24, 26, 28, 30, 32, 34, 36, 38, 40, 42, 44, 46, 48, 50, 55, 60, 65, 70, 75, 80, 85, 90% or any % therebetween, and at least 10% lignin (dry wt), more typically at least 12% (dry wt) and that has been subjected to physical and/or chemical processes to make the fiber more accessible and/or receptive to the actions of cellulolytic enzymes.

After pretreatment, the lignocellulosic feedstock may contain higher levels of cellulose. For example, if acid pretreatment is employed, the hemicellulose component is hydrolyzed, which increases the relative level of cellulose. In this case, the pretreated feedstock may contain greater than about 20% cellulose and greater than about 12% lignin. In one embodiment, the pretreated lignocellulosic feedstock contains greater than about 20% cellulose and greater than about 10% lignin.

Lignocellulosic feedstocks that may be used in the invention include, but are not limited to, agricultural residues such as corn stover, wheat straw, barley straw, rice straw, oat straw, canola stover, and soybean stover; fiber process residues such as corn fiber, sugar beet pulp, pulp mill fines and rejects or sugar cane bagasse; forestry residues such as aspen wood, other hardwoods, softwood, and sawdust; grasses such as switch grass, *miscanthus*, cord grass, and reed canary grass; or post-consumer waste paper products.

The lignocellulosic feedstock may be first subjected to size reduction by methods including, but not limited to, milling, grinding, agitation, shedding, compression/expansion, or other types of mechanical action. Size reduction by mechanical action can be performed by any type of equipment adapted for the purpose, for example, but not limited to, a hammer mill.

Non-limiting examples of pretreatment processes include chemical treatment of a lignocellulosic feedstock with sulfuric or sulfurous acid, or other acids; ammonia, lime, ammonium hydroxide, or other alkali; ethanol, butanol, or other organic solvents; or pressurized water (See U.S. Pat. Nos. 4,461,648; 5,916,780; 6,090,595; 6,043,392; 4,600,590).

The pretreatment may be carried out to hydrolyze the hemicellulose, or a portion thereof, that is present in the lignocellulosic feedstock to monomeric sugars, for example xylose, arabinose, mannose, galactose, or a combination thereof. Preferably, the pretreatment is carried out so that nearly complete hydrolysis of the hemicellulose and a small amount of conversion of cellulose to glucose occurs. During the pretreatment, typically an acid concentration in the aqueous slurry from about 0.02% (w/w) to about 2% (w/w), or any amount therebetween, is used for the treatment of the lignocellulosic feedstock. The acid may be, but is not limited to, hydrochloric acid, nitric acid, or sulfuric acid. For example, the acid used during pretreatment is sulfuric acid.

One method of performing acid pretreatment of the feedstock is steam explosion using the process conditions set out in U.S. Pat. No. 4,461,648. Another method of pretreating the feedstock slurry involves continuous pretreatment, meaning that the lignocellulosic feedstock is pumped though a reactor continuously. Continuous acid pretreatment is familiar to those skilled in the art; see, for example, U.S. Pat. No. 5,536,325; WO 2006/128304; and U.S. Pat. No. 4,237,226. Additional techniques known in the art may be used as required such as the process disclosed in U.S. Pat. No. 4,556,430.

As noted above, the pretreatment may be conducted with alkali. In contrast to acid pretreatment, pretreatment with alkali does not hydrolyze the hemicellulose component of the feedstock, but rather the alkali reacts with acidic groups present on the hemicellulose to open up the surface of the substrate. The addition of alkali may also alter the crystal structure of the cellulose so that it is more amenable to hydrolysis. Examples of alkali that may be used in the pretreatment include ammonia, ammonium hydroxide, potassium hydroxide, and sodium hydroxide. The pretreatment is preferably not conducted with alkali that is insoluble in water, such as lime and magnesium hydroxide.

An example of a suitable alkali pretreatment is Ammonia Freeze Explosion, Ammonia Fiber Explosion or Ammonia Fiber Expansion ("AFEX" process). According to this process, the lignocellulosic feedstock is contacted with ammonia or ammonium hydroxide in a pressure vessel for a sufficient time to enable the ammonia or ammonium hydroxide to alter the crystal structure of the cellulose fibers. The pressure is then rapidly reduced, which allows the ammonia to flash or boil and explode the cellulose fiber structure. (See U.S. Pat. Nos. 5,171,592; 5,037,663; 4,600,590; 6,106,888; 4,356,196; 5,939,544; 6,176,176; 5,037,663 and 5,171,592). The flashed ammonia may then be recovered according to known processes.

The pretreated lignocellulosic feedstock may be processed after pretreatment but prior to the enzymatic hydrolysis by any of several steps, such as dilution with water, washing with water, buffering, filtration, or centrifugation, or a combination of these processes, prior to enzymatic hydrolysis, as is familiar to those skilled in the art.

The pretreated lignocellulosic feedstock is next subjected to enzymatic hydrolysis. By the term "enzymatic hydrolysis", it is meant a process by which cellulase enzymes act on cellulose to convert all or a portion thereof to soluble sugars. Soluble sugars are meant to include water-soluble hexose monomers and oligomers of up to six monomer units that are derived from the cellulose portion of the pretreated lignocellulosic feedstock. Examples of soluble sugars include, but are not limited to, glucose, cellobiose, cellodextrins, or mixtures thereof. The soluble sugars may be predominantly cellobiose and glucose. The soluble sugars may predominantly be glucose.

The enzymatic hydrolysis using the cellulase mixture may be batch hydrolysis, continuous hydrolysis, or a combination thereof. The hydrolysis may be agitated, unmixed, or a combination thereof.

The enzymatic hydrolysis is preferably carried out at a temperature of about 30° C. to about 75° C., or any temperature therebetween, for example a temperature of 30, 35, 40, 45, 50, 55, 60, 65, 70, 75° C., or any temperature therebetween, and a pH of about 3.5 to about 7.5, or any pH therebetween, for example a temperature of 3.5, 4.0, 4.5, 5.0, 5.5, 6.0, 6.5, 7.0, 7.5, or pH therebetween. The initial concentration of cellulose in the hydrolysis reactor, prior to the start of hydrolysis, is preferably about 0.5% (w/w) to about 15% (w/w), or any amount therebetween, for example 0.5, 1, 2, 4, 6, 8, 10, 12, 14, 15% or any amount therebetween. The combined dosage of all primary cellulase enzymes may be about 0.001 to about 100 mg protein per gram cellulose, or any amount therebetween, for example 0.001, 0.01, 0.1, 1, 5, 10, 15, 20, 25, 30, 40, 50, 60, 70, 80, 90, 100 mg protein per gram cellulose or any amount therebetween. The hydrolysis may be carried out for a time period of about 0.5 hours to about 200 hours, or any time therebetween, for example, the hydrolysis may be carried out for a period of 2 hours to 100 hours, or any time therebetween, or it may be carried out for 0.5, 1, 2, 5, 7, 10, 12, 14, 15, 20, 25, 30, 35, 40, 45, 50, 55, 60, 65, 70, 75, 80, 85, 90, 95, 100, 120, 140, 160, 180, 200 or any time therebetween. It should be appreciated that the reaction conditions are not meant to limit the invention in any manner and may be adjusted as desired by those of skill in the art.

The enzymatic hydrolysis is typically carried out in a hydrolysis reactor. The enzyme mixture is added to the pretreated lignocellulosic feedstock (also referred to as the "substrate") prior to, during, or after the addition of the substrate to the hydrolysis reactor.

Preferably, the modified glycosidase enzyme is produced in one or more submerged liquid culture fermentations and may be separated from the cells at the end of the fermentation by filtration, centrifugation, or other processes familiar to those skilled in the art. The cell-free cellulase-containing fraction may then be concentrated (for example, via ultrafiltration), preserved, and/or stabilized prior to use. Alternatively, the modified glycosidase enzyme(s) are not separated from the cells, but are added to the enzymatic hydrolysis with the cells.

EXAMPLES

Example 1: Preparation of *Trichoderma reesei* Cel7A, Cel7A Catalytic Domain, Cel6A and Cel6A Catalytic Domains A strain of *Trichoderma reesei* was grown in submerged liquid fermentation under conditions that induce cellulase production as known to those skilled in the art. The crude mixture of *Trichoderma* proteins was secreted by the cells into the fermentation broth. The fungal cells were removed from the fermentation broth by filtration across a glass microfiber filter containing a Harborlite filter bed. Cel7A and Cel6A were separated from the crude filtrate by anion exchange chromatography using a DEAE-Sepharose column as described by Bhikhabhai et al. (1984). Cel7A and Cel6A were then further purified by p-aminophenyl-1-thio-β-D-cellobioside affinity chromatography as reported by Piyachomkwan et al. (1997, 1998). These components were concentrated and buffer exchanged into 50 mM sodium citrate, pH 5.0 using a stirred ultrafiltration cell (Amicon) and a 10 kDa NMWL polyethersulfone membrane.

To demonstrate that each component preparation was devoid of contaminating primary cellulases, purified Cel7A and Cel6A were analyzed by Western blotting using component-specific polyclonal antisera from rabbit (FIG. 1, panel B). Proteins were separated by 10% SDS-PAGE and transferred to a polyvinylidene fluoride (PVDF) membrane at 100 V for 1 h using a Mini Trans-Blot® Cell from BioRad. Western blotting was performed using the method of Birkett et al. (1985). The component-specific polyclonal antisera were generated using synthetic peptides, the sequences of which were based on the primary amino acid sequence of Cel7A, Cel6A, Cel7B and Cel5A from *Trichoderma reesei*, as known to those skilled in the art.

These examples demonstrated that the purification methods used yielded substantially pure Cel7A, Cel6A, Cel7B and Cel5A. This also demonstrated the specificity of these antisera for each of these primary cellulase components.

The catalytic domains of *T. reesei* TrCel7A and Cel6A were prepared by incubating the purified full-length proteins with the protease papain. Papain cleaves cellulase enzymes within the linker peptide, separating the CBM from the catalytic (core) domain. This method is known to one of skill in the art and has been used to study the contribution of the CBM and catalytic domain in, for example, substrate binding and catalysis (Nidetsky et al., 2004; Herner et al., 1999). Papain treatment of a cellulase enzyme decreases its molecular mass. Therefore, the papain treatments of Cel7A and Cel6A were monitored by SDS-PAGE in order to ensure complete digestion of the full-length protein. The products of papain-treatment of Cel7A and Cel6A, referred to as Cel7Acore and Cel6Acore, respectively, were purified, concentrated and buffer exchanged as described above.

Protein concentrations were determined chemically using the method of Bradford et al. (1976).

Example 2: Preparation of Cel3A and Cel3A-CBM

Strains of *Trichoderma reesei* that over-express Cel3A (SEQ ID NO: 100) or Cel3A-CBM (SEQ ID NO: 101), as described in U.S. Publication No. 2009/0209009A1 were grown in submerged liquid fermentations under conditions that induce cellulase production as known to those skilled in the art. The crude mixtures of *Trichoderma* proteins were secreted by the cells into the fermentation broth. The fungal cells were removed from the fermentation broth by filtration across a glass microfiber filter containing a Harborlite filter bed. Cel3A and Cel3A-CBM were separated from their respective culture filtrates by anion exchange and cation exchange chromatography.

A column of DEAE-Sepharose was equilibrated in 5 mM sodium phosphate, pH 7.2. *Trichoderma* culture filtrate containing Cel3A or Cel3A-CBM was adjusted to pH 7.2 and applied to the column at 10 mL/min. The column was washed with 4 column volumes of the equilibration buffer and then bound protein was eluted with 4 column volumes of 5 mM sodium phosphate, pH 7.2 containing 0.5 M NaCl. Column fractions were assayed for activity on cellobiose. The flow-though peak contained greater than 95% of the total activity on cellobiose in the sample initially loaded on the DEAE column. These fractions were pooled and separated by cation exchange chromatography. A column of SP-Sepharose was equilibrated in 5 mM sodium acetate, pH 5.5. The flow-though pool from anion exchange chromatography was adjusted to pH 5.5 and diluted to a conductivity ≤0.6 mS. After loading, Cel3A or Cel3A-CBM was eluted using a linear gradient of 5-50 mM sodium acetate at pH 5.5. Purified Cel3A and Cel3A-CBM were concentrated and buffer exchanged into 50 mM sodium citrate, pH 5.0 using a stirred ultrafiltration cell (Amicon) and a 10 kDa NMWL polyethersulfone membrane. Protein concentrations were determined chemically using the method of Bradford et al. (1976).

Example 3: Preparation of Lignin

Wheat straw was pretreated using the methods described in U.S. Pat. No. 4,461,648. Following pretreatment, sodium benzoate was added at a concentration of 0.5% as a preservative. The pretreated material was then washed with six volumes of lukewarm (~35° C.) tap water using a Buchner funnel and filter paper.

A sample of pretreated wheat straw (167 g wet wt; 30% solids; 60% cellulose) was added to 625 mL of 82% $H_2SO_4$ with stirring in a 1 L flask, then stoppered and incubated at 50° C. with shaking for 4 hours. The remaining solids were filtered to dampness using a Buchner funnel and a glass fiber filter, resuspended in 1 L of water and adjusted to pH 4.5 with NaOH. The solids were filtered and washed with ~8 L water. The solids, which were determined to contain less than 1% (dry wt) cellulose, are referred to herein as "lignin".

Bovine serum albumin (BSA) treatment of lignin was performed by incubating equal amounts (w/w) of lignin and BSA, at a concentration of 30 g/L in 50 mM citrate buffer (pH 5) containing 0.1% sodium benzoate, for 5 days at 50° C. with shaking. The solids were filtered and washed with approximately 8 L of water.

Example 4: Characterizing the Inactivation of Purified Cellulase Components in the Presence of Lignin Purified catalytic domains or intact glycosidase enzymes (comprising a catalytic domain and CBM joined by a linker peptide) prepared as in Examples 1, 2, and 12 (0.06 mg) were incubated with untreated lignin (29 mg) in stoppered, glass flasks in a total volume of 1.2 mL of 50 mM citrate buffer, pH 5.0. Incubations were done at 30 or 50° C. with orbital shaking. Under the conditions tested, the proteins were essentially stable in solution in the absence of lignin for up to 96 h. 0.2 mL samples were collected from each flask at times ranging from 0 up to a maximum of 96 h. Each sample was centrifuged to separate the lignin and stored at 4° C.

Upon completion of the time course, the protein concentration in the supernatant of each time course sample was measured using the method of Bradford. Samples were then mixed briefly to resuspend the pellet and 0.05 mL of slurry containing both soluble and insoluble material added to a microtitre plate containing 3 glass beads/well. To microtitre wells containing Cel7A, Cel7Acore, Cel6A and Cel6Acore and lignin, 0.02 mL of a dilute preparation of *Trichoderma* cellulase devoid of Cel7A and Cel6A cellobiohydrolases (1 µg total protein) was added to each well in the microtitre plate to complement the cellobiohydrolase activity. Purified *Trichoderma* Cel3A (1.4 µg) was also added to the microtitre plate wells to complement cellulose hydrolysis activity. Finally, 0.2 mL slurry of delignified cellulose (0.25% cellulose) was added to each well. For microtitre plate wells containing TrCel3A or TrCel3A-CBM and lignin, 0.02 mL of a dilute preparation of *Trichoderma* cellulase (1 µs total protein) was added to each well in the microtitre plate to complement Cel3A activity. Finally, 0.2 mL slurry of delignified cellulose (0.25% cellulose) was added to each well. The assay plates were incubated at 50° C. for 2 h with orbital shaking. The plate was then centrifuged at 710×g for 2 min and the glucose concentrations measured as described by Trinder et al. (1969).

Glucose concentrations were converted to enzyme activity, expressed as mg glucose produced/h/mg of protein. Activities measured throughout the time course were divided by the activity measured at t=0 h (prior to the addition of lignin) in order to calculate a relative residual activity for each enzyme throughout the time course. For the purposes of analyzing the results, measurements of relative residual activity were considered representative of the relative residual active enzyme concentration in the lignin slurry. Similarly, the protein concentrations measured throughout the time course were divided by the protein concentration at t=0 h for each reaction in order to calculate a relative residual protein concentration.

For the purpose of characterizing lignin binding and inactivation of cellulase components from *Trichoderma reesei* with and without a CBM, the relative residual protein and/or relative residual activity versus time data were modeled using Equation 1. In this equation, E represents the free enzyme, L represents lignin, EL represents a reversible enzyme-lignin complex and EL* represents an irreversible enzyme-lignin complex. $K_L$ represents [E][L]/[EL] at steady state while $k_L$ is a rate constant describing the rate of conversion of the reversible to the irreversible enzyme-lignin complex. The relative residual protein in the supernatant at each time was fit to the E parameter in Equation 1 while the relative residual activity in the slurry was fit to a sum of the E+EL parameters.

Modeling was done using a $4^{th}$ order Runge-Kutta spreadsheet in Microsoft Excel. The data for each experiment involving one component were fit by varying $K_L$ and $k_L$. Error minimization was done by the method of least squares as known to those of skill in the art.

Equation 1

The lignin inactivation profiles of Cel7A and Cel7Acore at 50° C. are shown in FIG. 2. Approximately 55% of Cel7A was lost from the supernatant within 0.5 h (panel A, solid circles). In this time period only about 10% of the total Cel7A activity was lost from the lignin slurry (Panel A, open squares). Throughout the rest of the time course, the Cel7A concentration in the supernatant remained essentially constant while Cel7A activity in the slurry decreased slowly. This indicates that Cel7A is rapidly bound by lignin in a manner that preserves its activity in this experiment, since incubating these samples with crystalline cellulose resulted in much higher relative residual Cel7A activity than Cel7A protein. No such rapid loss of Cel7Acore protein was observed (Panel B, solid circles), suggesting that *T. reesei* Cel7A rapidly associates with lignin via its CBM.

The lignin inactivation profiles of *T. reesei* Cel3A, which does not have a CBM, and Cel3A-CBM, *T. reesei* Cel3A linked to the Family 1 CBM from *T. reesei* Cel7A at its C-terminus, are shown in FIG. 3. The loss of Cel3A protein from the supernatant (Panel A, solid circles) and activity from the slurry (Panel A, open squares) occur at similar rates. Cel3A-CBM protein (FIG. 3, Panel B, solid circles) and activity (Panel B, closed squares) decreased much more rapidly, compared to Cel3A. Approximately 70% of Cel3A-CBM activity was lost from the supernatant within 0.5 h, while about 95% of Cel3A-CBM activity was lost from the slurry. These results demonstrate that Cel3A-CBM binds lignin much more rapidly than does Cel3A and further implicates the Family 1 CBM, from Cel7A in this case, in lignin binding.

Similar results were obtained for *T. reesei* Cel6A and Cel6A catalytic domain (Cel6Acore) in lignin inactivation experiments at 30° C. The Cel6A concentration in the supernatant decreased by about 60% within 0.5 h (FIG. 4, Panel A, solid circles) while Cel6A activity (open squares) decreased by about 14%. Any further changes in the concentration of Cel6A in the supernatant were negligible during the remainder of the experiment while Cel6A activity decreased slowly. As was observed for Cel7Acore, Cel6Acore protein concentrations (Panel B, solid circles) decreased slowly throughout the time course in parallel with Cel6Acore activity (open squares) in the slurry, suggesting *T. reesei* Cel6A rapidly associates with lignin via its CBM.

Further, the presence of the CBM significantly increased the binding affinity of the *T. reesei* Cel7A, Cel6A and Cel3A enzymes, as evidenced by a much lower value of $K_L$ for the glycosidase enzymes comprising CBMs as compared to those that do not (Cel7Acore and Cel6Acore) (Table 3).

TABLE 3

Effects of the CBM on Binding of Isolated Cellulase Components to Lignin

| Enzyme | Relative $K_L$ |
| --- | --- |
| Cel7A | 1.0 |
| Cel7Acore | 62.5 |
| Cel3A | 1.0 |
| Cel3A-CBM | 0.2 |
| Cel6A | 1.0 |
| Cel6Acore | 40.5 |

Example 5: Construction of a Vector Expressing TrCel7A (SEQ ID NO: 124)

Figure 9:
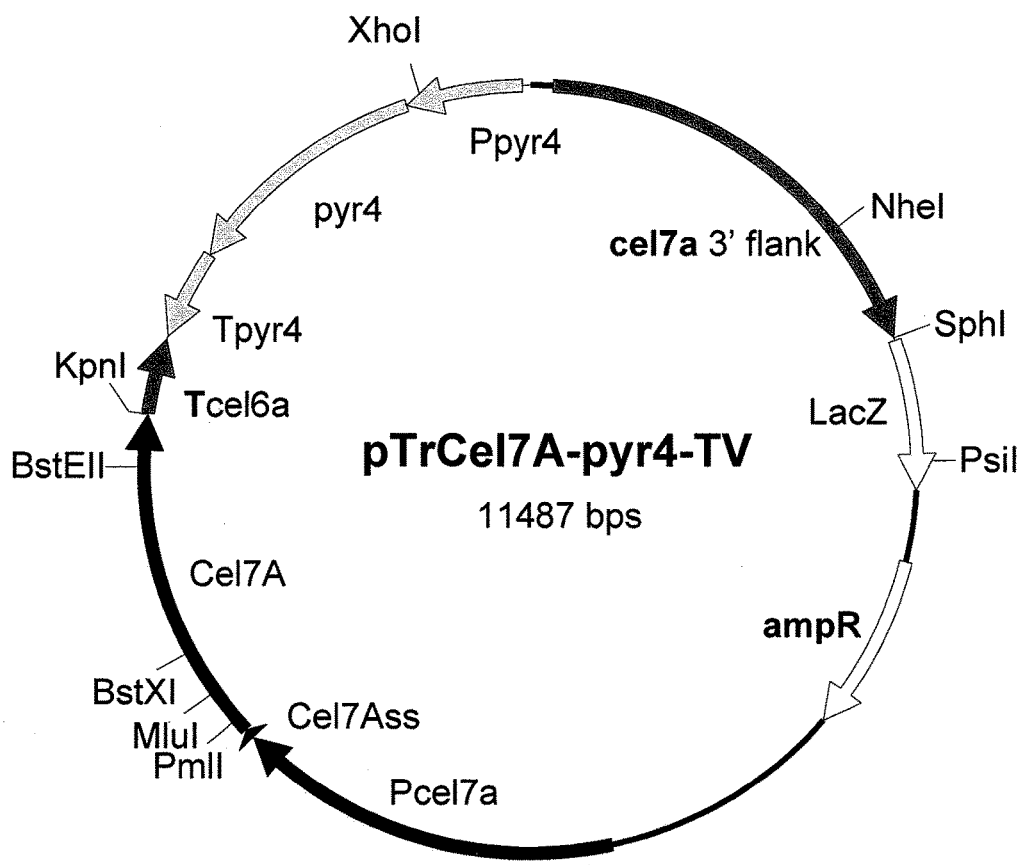
FIG. 9 depicts vector pTrCel7A-pyr4-TV directing the expression and secretion of native and modified TrCel7A glycosidases from recombinant *Trichoderma reesei*.

A vector was constructed to express and secrete parental and modified TrCel7A glycosidases and target the native cel7a locus in the genome of a host *T. reesei* strain. The vector was constructed using pUC19 vector (Fermentas, #SD0061) as a backbone. To facilitate targeting, sequences adjacent to the 5' and 3' ends of the native Trcel7a gene amplified from *T. reesei* genomic DNA were inserted into the transformation vectors so as to flank the expression and selection cassettes. The entire *N. crassa* pyr4 (orotidine-5'-monophosphate decarboxylase) gene (GenBank #AL669988.1, position 65346-66992) was used as a selection cassette. The expression cassette contains the following sequences from the native *T. reesei* cel7a gene: promoter (PCel7A), secretion signal (Cel7A ss) and mature protein coding sequences (Cel7A). These sequences are operatively linked to each other and to the transcriptional terminator of the native *T. reesei* cel6a gene (TCel6a). All *Trichoderma* sequences present in the final transformation vector are available from the complete *Trichoderma reesei* genome sequence (version 2) via the DOE Joint Genomics Institute, as described in Table 4. A map of the complete pTRCel7A-pyr4-TV vector is shown in FIG. 9.

TABLE 4

Origins of *Trichoderma* sequences present in transformations vectors.

| Fragment name | JGI scaffold | position |
| --- | --- | --- |
| Cel7a 3' flank | 29 | 334132-336251 |
| Pcel7a | 29 | 330605-332455 |
| Cel7A | 29 | 332456-334131 |
| Tcel6a | 3 | 14184-14547 |

Sequence information can be found at URL: genome.jgi-psf.org/Trire2/Trere2.home.html Example 6: Construction of Vectors Expressing HiAvi2 (SEQ ID NO: 2) and PcCel6A-S407P (SEQ ID NO: 5)

Construction of Vector YEp352/PGK91-1-$\alpha_{ss}$-NKE

*Saccharomyces cerevisiae* strain YDR483W BY4742 [14317] (MATα his3Δ1 leu2Δ0 lys2Δ0 ura3Δ0 Δkre2) was obtained from ATCC (cat#4014317). *Humicola insolens* and *Phanerochaete chrysosporium* strains were obtained from ATCC® (#22082™ and #201542™ respectively). *Escherichia coli* strain DH5α (F⁻ φ80lacZΔM15 Δ(lacZYA-argF) U169 recA1 endA1 hdR17($r_k^-$, $m_k^+$)phoA supE44 thi-1 gyrA96 relA1λ⁻) was obtained from Invitrogen (cat#18265-017).

A DNA adapter containing NheI, KpnI, and EcoRI restriction sites was prepared by annealing primers AT046 and AT047 together. The adapter was inserted into a YEp based-plasmid (YEp352/PGK91-1$\alpha_{ss}$) containing the pgk1 promoter, alpha mating factor secretion signal, and pgk1 terminator sequences to make plasmid YEp352/PGK91-1/$\alpha_{ss}$ NKE. Specifically, the linker was inserted as a NheI/EcoRI fragment into the NheI and EcoRI sites located downstream of the alpha mating factor secretion signal and upstream of the pgk1 terminator. Primer sequences are shown below:

```
AT046
                              (SEQ ID NO: 88)
5' CTA GCT GAT CAC TGA GGT ACC G

AT047
                              (SEQ ID NO: 89)
5' AAT TCG GTA CCT CAG TGA TCA G
```

Construction of the YEp352/PGK91-1-$\alpha_{ss}$-NKE-HiAvi2 Vector

Lyophilized *H. insolens* was resuspended in 300 μL sterile H₂O and 50 μL was spread onto Emerson YPSS pH 7 agar plate (0.4% Yeast extract, 0.1% K₂HPO₄, 0.05% MgSO₄.7H₂O, 1.5% Glucose, 1.5% Agar). The agar plate was incubated for 6 days at 45° C., then spores were inoculated in Novo media (as per Barbesgaard U.S. Pat. No. 4,435,307): Incubation for 48 hours at 37° C. in 100 mL growth phase media (2.4% CSL, 2.4% Glucose, 0.5% Soy oil, pH adjusted to 5.5, 0.5% CaCO₃), then 6 mL of pre-culture was transferred into 100 mL production phase media (0.25% NH₄NO₃, 0.56% KH₂PO₄, 0.44% K₂HPO₄, 0.075% MgSO₄.7H₂O, 2% Sigmacell, pH adjusted to 7, 0.25% CaCO₃) and culture was incubated for up to 4 days prior to biomass harvest. Then, 50 mg of biomass was used to isolate total RNA with the Absolutely RNA Miniprep Kit (Stratagene) according to the manufacturer's procedure. Total cDNA was generated from the total RNA using the SuperScript® II Reverse Transcriptase (Invitrogen) according to the manufacturer's procedure. A polynucleotide encoding for HiAvi2 was amplified from the cDNA using the following primers (which introduced a NheI site upstream the gene and KpnI and EcoRI sites downstream the HiAvi2 coding region):

```
5'HiAvi2-cDNA
                              (SEQ ID NO: 90)
5' CTA TTG CTA GCT GTG CCC CGA CTT GGG GCC AGT
GC

3'HiAvi2-cDNA
                              (SEQ ID NO: 91)
5' CTA TTG AAT TCG GTA CCT CAG AAC GGC GGA TTG
GCA TTA CGA AG
```

The PCR amplicon was cloned into the pGEM®-T Easy vector by TA-cloning according to the manufacturer's recommendations. This vector was digested with NheI and KpnI and the released HiAvi2 gene was ligated to the NheI and KpnI digested YEp352/PGK91-1/$\alpha_{ss}$-NKE vector. The ligation mix was transformed into DH5α chemically-competent *E. coli* cells, plasmid isolated, and sequenced to confirm sequence and cloning site integrity. Resulting vector is called YEp352/PGK91-1-αss-NKE-HiAvi2 (FIG. 5A). Introduction of the NheI site upstream the gene changed the first two amino acids of the mature protein for an alanine and a serine respectively. Thus the parental HiAvi2 glycosidase defined in SEQ ID NO: 2 is HiAvi2-Q1A-N2S.

Construction of Vector YEp352/PGK91-1-α$_{ss}$-NKE-PcCel6A-S407P

Lyophilized *P. chrysosporium* was resuspended in 300 μL sterile H$_2$O and 50 μL were spread onto PDA plates. Plates were incubated at 24° C. for 4 days. Spores for *P. chrysosporium* were inoculated on a cellophane circle on top of a PDA plate and biomass was harvested after 4-6 days at 24° C. Then, 50 mg of biomass was used to isolate total RNA with the Absolutely RNA® Miniprep Kit (Stratagene) according to the manufacturer's procedure. Total cDNA was generated from the total RNA using the SuperScript® II Reverse Transcriptase (Invitrogen) according to the manufacturer procedure. A polynucleotide encoding for PcCel6A was amplified from the cDNA using the following primers (which introduced a NheI site upstream the gene and KpnI and EcoRI sites downstream the PcCel6A coding region):

```
5'PcCel6A-cDNA
                                (SEQ ID NO: 92)
5' CTA TTG CTA GCT CGG AGT GGG GAC AGT GCG GTG
GC

3'PcCel6A-cDNA
                                (SEQ ID NO: 93)
5' CTA TTG AAT TCG GTA CCC TAC AGC GGC GGG TTG
GCA GCA GAA AC
```

The PCR amplicon was cloned into the pGEM®-T Easy vector by TA-cloning according to the manufacturer's recommendations which yield to plasmid pGEM-PcCel6A. The coding sequence for PcCel6A was then amplified from that source to introduce mutation S407P. To do so, mutagenic primer NM088 and reverse primers VH099 were used to generate megaprimer PCR. The resulting PCR product was isolated and used as a reverse primer in conjunction with the forward primer VH098 to generate the final mutated construct. Primers sequences are listed below:

```
VH098
                                (SEQ ID NO: 94)
5' GGT ATC TTT GGA TAA AAG GGC TAG CTC GGA GTG GGG
ACA G

VH099
                                (SEQ ID NO: 95)
5' GGA GAT CGA ATT CGG TAC CTA CAG CGG CGG GTT GG

NM088
                                (SEQ ID NO: 96)
5' CCC CGC TAC GAC CCT ACT TGT TCT CTG
```

The PcCel6A-S407P amplicon was digested with NheI and KpnI then ligated to the YEp352/PGK91-1/α$_{ss}$-NKE vector digested with NheI and KpnI. The ligation mix was transformed into chemically-competent *E. coli* DH5α cells, plasmid isolated, and sequenced to confirm sequence and cloning sites integrity. Resulting vector is called YEp352/PGK91-1-αss-NKE-PcCel6A-S407P (FIG. 5B). Introduction of the NheI site upstream the PcCel6A coding region changed the first two amino acids of the mature protein for an alanine and a serine respectively. Thus the parental glycosidase PcCel6A-S407P defined in SEQ ID NO: 5 is PcCel6A-Q1A-A2S-S407P.

Example 7: Construction of a Vector Expressing TrCel6A-S413P (SEQ ID NO: 4)

In order to facilitate cloning using NheI and KpnI restriction enzymes, the unique NheI site at position 1936 of the YEp352/PGK91-1 vector was blunted using the DNA Polymerase I large (Klenow) fragment to generate YEp352/PGK91-1 ΔNheI. The TrCel6A-S413P gene was amplified by PCR from the vector YEpFLAG ΔKpn10-S413P (U.S. Pat. No. 7,785,854) using primers 5'NheCel6A and 3'BglKpnCel6A. In parallel, the yeast alpha-factor leader sequence was amplified by PCR from the YEpFLAG-1 vector (Sigma) using primers (5'BglAlphaSS and 3'NheAlphaSS) to introduce a BglII at the 5' end and an NheI site at the 3' end of the amplicon.

Figure 6:
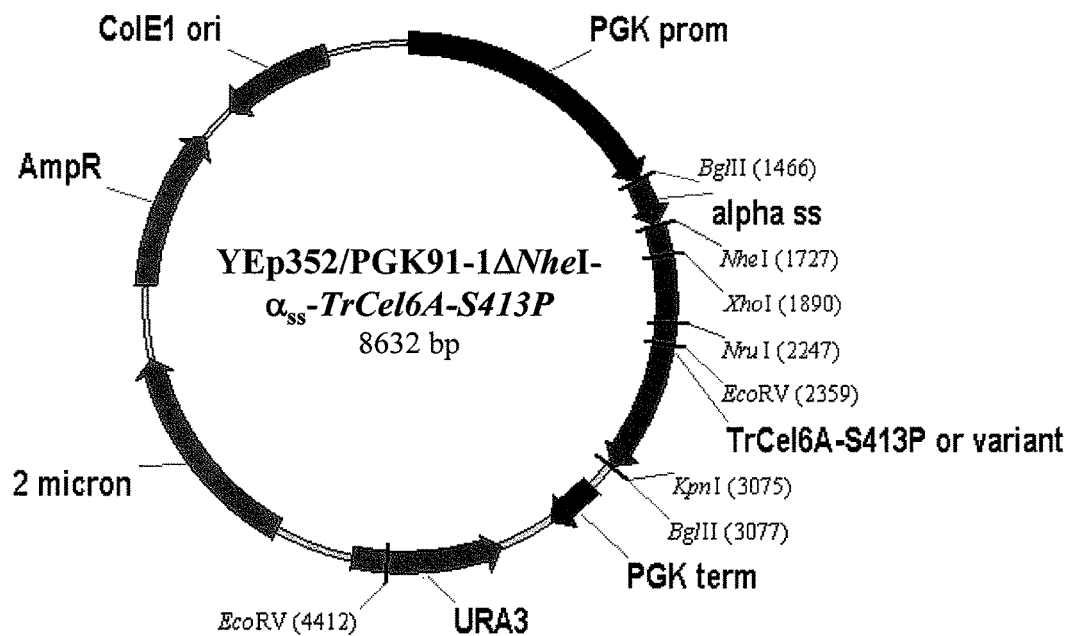
FIG. 6 depicts plasmid vector YEp352/PGK91-1ΔNheI-$\alpha_{ss}$-TrCel6A-S413P directing the expression and secretion of parental and modified TrCel6A from recombinant *Saccharomyces cerevisiae*.

The yeast alpha-factor leader sequence was isolated by BglII/NheI digestion and a three-piece ligation performed with the TrCel6A-S413P gene (isolated by NheI/BglII digestion) and the YEp352/PGK91-1 ΔNheI vector (isolated by BglII digestion). The resulting vector YEp352/PGK91-1 ΔNheI-α$_{ss}$-TrCel6A-S413P (FIG. 6) was transformed into yeast strain BY4742 using the procedure described by Gietz, R. D. and Woods, R. A. (2002). Primer sequences are listed below:

```
5'BglAlphaSS:
                                (SEQ ID NO: 103)
5'ACC AAA AGA TCT ATG AGA TTT CCT TCA ATT 3'NheAlphaSS:
                                (SEQ ID NO: 104)
5'TGA GCA GCT AGC CCT TTT ATC CAA AGA TAC 5'NheCel6A:
                                (SEQ ID NO: 105)
5'AAA AGG GCT AGC TGC TCA AGC GTC TGG GGC 3'BglKpnCel6A:
                                (SEQ ID NO: 106)
5'GAG CTC AGA TCT GGT ACC TTA CAG GAA CGA TGG GTT
```

Example 8: Generation of Error Prone-PCR Libraries

Random mutagenesis libraries were generated using the Mutazyme® II DNA polymerase contained in the GeneMorph® II Random Mutagenesis Kit (Stratagene®). To make a HiAvi2 library, a PCR was performed for 20 amplification cycles using 58 ng of YEp352/PGK91-1/α$_{ss}$NKE-HiAvi2 as template with primers YalphaN21 and 3'PGK-term. To make the PcCel6A-S407P library, a PCR was performed for 30 amplification cycles using 57 ng of YEp352/PGK91-1/α$_{ss}$ NKE-PcCel6A-S407P as template with primers YalphaN21 and 3'PGK-term. The YEp352/PGK91-1/α$_{ss}$ NKE vector was digested with NheI and KpnI and then purified. This vector fragment and each final amplicon were transformed simultaneously and cloned by in vivo recombination into yeast strain YDR483W BY4742 [14317] (Butler et al., 2003).

YalphaN21
(SEQ ID NO: 97)
5' AGC ACA AAT AAC GGG TTA TTG

3'PGK-term
(SEQ ID NO: 98)
5' GCA ACA CCT GGC AAT TCC TTA CC

Example 9: Expression and Isolation of Parental and Modified TrCel6A, HiAvi2, and PcCel6A Cellulases from Microplate Cultures This example describes the selection and expression of TrCel6A, HiAvi2 and PcCel6A and modified TrCel6A, HiAvi2 and PcCel6A cellulases from *Saccharomyces cerevisiae* for use in high-throughput screening assays.

*Saccharomyces cerevisiae* transformants were grown for 4 days at 30° C. on plates containing synthetic complete medium (SC: 2% agar w/v, 0.17% yeast nitrogen base w/v, 0.078%—Ura drop-out supplement w/v, 2% glucose w/v, 2% casamino acids w/v, 0.5% ammonium sulfate w/v, pH 5.5). Replica plates were prepared by transferring colonies to synthetic complete medium plates containing 0.12% Azo-barley-beta-glucan (Megazyme) and incubated at 30° C. overnight.

Colonies showing visible clearing halos after 6 hours of incubation at 50° C. were selected for liquid media pre-cultures by toothpick inoculation of 0.15 mL synthetic complete media (SC: 0.17% yeast nitrogen base w/v, 0.078%—Ura drop-out supplement w/v, 2% glucose w/v, 2% casamino acids w/v, 0.5% ammonium sulfate w/v) in 96-well microplates containing one glass bead. Pre-cultures were grown overnight (16-18 h) at 30° C. with orbital shaking to stationary phase. For expression culture inoculation, 25 µL of pre-culture was used to inoculate 1 mL of SC media in deep well microplates containing one glass bead. Expression cultures were grown for 3 days at 30° C. with orbital shaking and humidity control. Plates were centrifuged at 710×g for 5 minutes to pellet cells and the supernatant was aspirated for screening assays. To the remaining pre-culture, stocks were prepared by the addition of glycerol to a final concentration of 20% and stored at −80° C.

Example 10: High-Throughput Screening for Modified Glycosidase Enzymes Comprising Modified Family 1 CBMs a. Screening of TrCel6A-S413P Libraries This example describes the screening of modified TrCel6A glycosidases in order to identify those with resistance to inactivation by lignin in comparison to the parental TrCel6A-S413P glycosidase that had been cloned into *Saccharomyces cerevisiae*.

An aliquot (0.15 mL) of yeast supernatant was pre-incubated with lignin (1.6% w/v) in a 0.25 mL citrate buffered (50 mM; pH 5) reaction. An equivalent aliquot of supernatant from each modified glycosidase was also pre-incubated with BSA pre-treated lignin (1.6% w/v). Pre-incubation was performed for 5.5 hour at 50° C. with orbital shaking (NB Innova 44) in a 96-well microplate containing 1 glass bead per well. Each 96-well microplate contained six parental TrCel6A-S413P controls for comparison. Following pre-incubation, microplates were centrifuged for 5 min at 2800×g and the supernatant was aspirated for residual activity assays.

Figure 8:
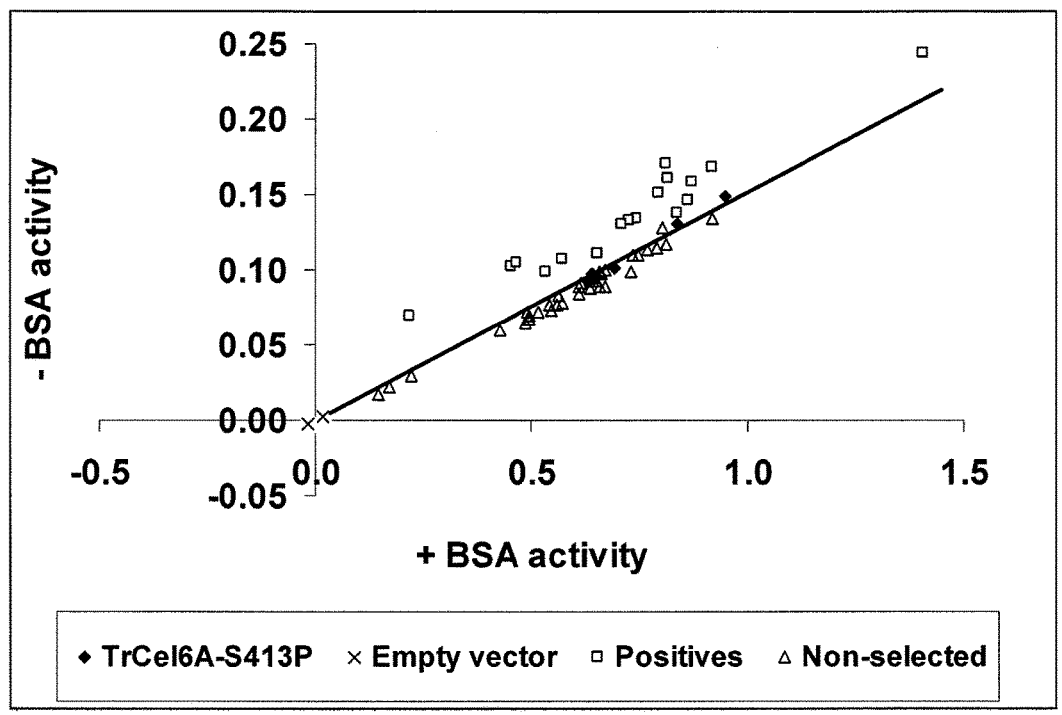
FIG. 8 shows a scatter plot of enzyme activity in the presence of BSA-treated lignin (+BSA activity) versus enzyme activity in the presence of untreated lignin (−BSA activity) for the high-throughput assay described in Example 10a. The data relate to the screening of filtrates from microplate cultures (Example 9) containing parental (TrCel6A-S413P) and modified TrCel6A cellulases or filtrates from empty vector transformants.

Supernatant (0.05 mL) was incubated with 0.5% beta-glucan in a 100 µL citrate buffered (50 mM; pH 5) reaction. Residual activity assays were performed in a PCR plate at 50° C. for 16 hours for samples pre-incubated with lignin and 3 hours for samples pre-incubated with BSA-treated lignin. A glucose standard curve was placed in the first column of the PCR plate ranging from 3 to 0.05 mg/mL. Following incubation, 0.08 mL of DNS reagent was added to all wells and the plates were boiled for 10 min. An aliquot (0.15 mL) was transferred to a microplate and the absorbance was measured at 560 nm. Residual enzyme activity was determined by converting $A_{560}$ values to reducing equivalents using the glucose standard curve and dividing by the appropriate incubation time (16 h or 3 h) to obtain mg/mL/h. An activity ratio was calculated for all modified TrCel6A glycosidases and the parental TrCel6A-S413P glycosidase controls by dividing the residual enzyme activity in the presence of untreated lignin by the residual enzyme activity in the presence of BSA-treated lignin. The activity ratio for each modified TrCel6A glycosidase was compared to the average of six parental TrCel6A-S413P glycosidase controls on a particular microplate and positives (those having increased ratios) were selected at the 95% confidence level using a t-test. All positive modified TrCel6A glycosidases were produced again in microculture and re-screened to reduce the number of false positives. A sample of the data from one screening plate is shown in FIG. 8.

| DNS reagent contains: | |
|---|---|
| Component | g/L |
| 3,5-Dinitrosalicylic acid (Acros) | 20 |
| Sodium hydroxide (Fisher) | 20 |
| Phenol (Sigma) | 4 |
| Sodium metabisulfate (Fisher) | 1 | b. Screening of HiAvi2 Gene Libraries

This example describes the screening of modified HiAvi2 glycosidases in order to identify those with resistance to inactivation by lignin in comparison to the parental HiAvi2 that had been cloned into *Saccharomyces cerevisiae*.

An aliquot (0.15 mL) of yeast supernatant was pre-incubated with lignin (0.4% w/v) in a 0.25 mL citrate buffered (50 mM; pH 5) reaction. An equivalent aliquot of supernatant from each modified cellulase was also pre-incubated with BSA pre-treated lignin (0.4% w/v). Pre-incubation was performed for 1 hour at 50° C. with orbital shaking (NB Innova 44) in a 96-well microplate containing 1 glass bead per well. Each 96-well microplate comprised six parental HiAvi2 controls for comparison. Following pre-incubation, microplates were centrifuged for 5 min at 2800×g and the supernatant was aspirated for residual activity assays.

Supernatant (0.05 mL) was incubated with 0.5% beta-glucan in a 100 µL citrate buffered (50 mM; pH 7) reaction. Residual activity assays were performed in a PCR plate at 65° C. for 16 hours for samples pre-incubated with lignin and 3 hours for samples pre-incubated with BSA-treated lignin. A glucose standard curve was placed in the first column of the PCR plate ranging from 3 to 0.05 mg/mL. Following incubation, 0.08 mL of DNS reagent was added to all wells and the plates were boiled for 10 min. An aliquot (0.15 mL) was transferred to a microplate and the absorbance was measured at 560 nm. Residual enzyme activity was determined by converting $A_{550}$ values to reducing equivalents using the glucose standard curve and dividing by the appropriate incubation time (16 h or 3 h) to obtain mg/mL/h. An activity ratio was calculated for all modified HiAvi2 glycosidases and the parental HiAvi2 glycosidase controls by dividing the residual enzyme activity in the presence of untreated lignin by the residual enzyme activity in the presence of BSA-treated lignin. The activity ratio for each modified HiAvi2 glycosidase was compared to the average of six parental HiAvi2 glycosidase controls on a particular microplate and positives (those having increased ratios) were selected at the 95% confidence level using a t-test. All positive modified HiAvi2 glycosidases were produced again in microculture and re-screened to reduce the number of false positives. A sample of the data from one screening plate is shown in FIG. 7A.

c. Screening of PcCel6A-S407P Gene Libraries

This example describes the screening of modified PcCel6A glycosidase in order to identify those with resistance to inactivation by lignin in comparison to the parental PcCel6A-S407P glycosidase that had been cloned into *Saccharomyces cerevisiae*.

An aliquot (0.15 mL) of yeast supernatant was pre-incubated with lignin (0.4% w/v) in a 0.25 mL citrate buffered (50 mM; pH 5) reaction. An equivalent aliquot of supernatant from each modified glycosidase was also pre-incubated with BSA pre-treated lignin (0.4% w/v). Pre-incubation was performed for 2 hour at 50° C. with orbital shaking (NB Innova 44) in a 96-well microplate containing 1 glass bead. Each 96-well microplate comprised six parental PcCel6A-S407P controls for comparison. Following pre-incubation, microplates were centrifuged for 5 min at 2800×g and the supernatant was aspirated for residual activity assays.

Supernatant (0.05 mL) was incubated with 0.5% beta-glucan in a 100 µL citrate buffered (50 mM; pH 5) reaction. Residual activity assays were performed in a PCR plate at 50° C. for 16 hours for samples pre-incubated with lignin and 3 hours for samples pre-incubated with BSA-treated lignin. A glucose standard curve was placed in the first column of the PCR plate ranging from 3 to 0.05 mg/mL. Following incubation, 0.08 mL of DNS reagent was added to all wells and the plates were boiled for 10 min. An aliquot (0.15 mL) was transferred to a microplate and the absorbance was measured at 560 nm. Residual enzyme activity was determined by converting $A_{560}$ values to reducing equivalents using the glucose standard curve and dividing by the appropriate incubation time (16 h or 3 h) to obtain mg/mL/h. An activity ratio was calculated for all modified PcCel6A glycosidases and the parental PcCel6A-S407P controls by dividing the residual enzyme activity in the presence of untreated lignin by the residual enzyme activity in the presence of BSA-treated lignin. The activity ratio for each modified PcCel6A glycosidase was compared to the average of six parental PcCel6A-S407P controls on a particular microplate and positives (those having increased ratios) were selected at the 95% confidence level using a t-test. All positive modified PcCel6A glycosidases were produced again in microculture and re-screened to reduce the number of false positives. A sample of the data from one screening plate is shown in FIG. 7B.

Example 11: Statistical Analysis of EP-PCR Libraries

Figure 10:
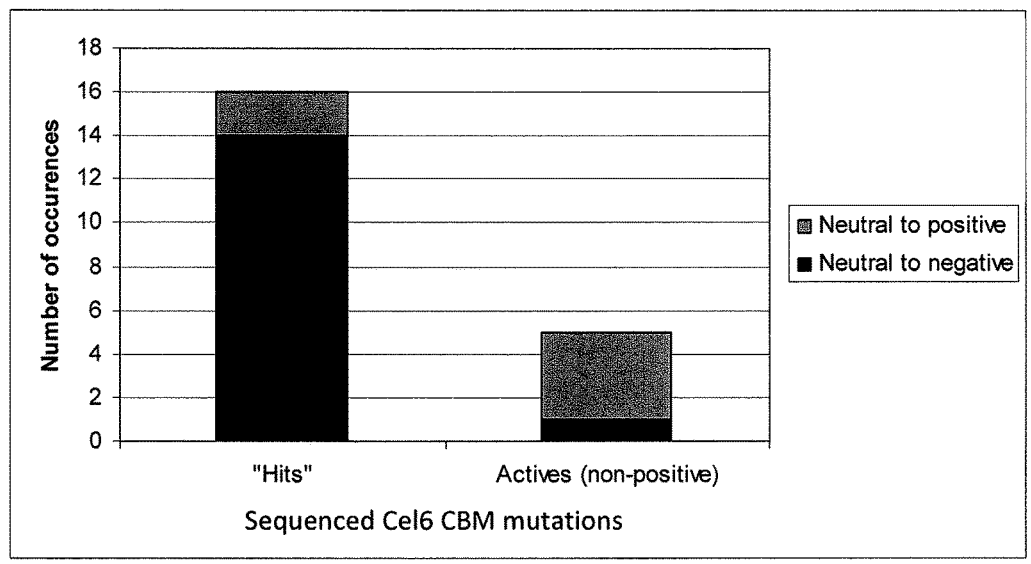
FIG. 10 depicts the distribution of amino acid substitutions within the CBM domains among two populations of modified glycosidases—i.e., lignin-resistant "hits" and non-selected, but active glycosidases—from the TrCel6A, HiAvi2 and PcCel6A-S407P error-prone PCR libraries. Amino acid changes were grouped as those that introduce positive charge (i.e., convert a neutral amino acid to a basic amino acid such as His, Lys or Arg) or those changes than introduce negative charge (i.e., convert a neutral amino acid to Glu or Asp).

Amino acid charge changes within the CBM, was compared between glycosidase variants having lignin resistance to those of a random population of active glycosidase variants. Several variants showing activity on beta-glucan following pre-incubation with BSA-treated lignin were randomly picked and sequenced from all three libraries (TrCel6A-S413P, HiAvi2 and PcCel6A-S407P). From this population of random active variants, five charge change mutations were found: 4 neutral amino acids were changed to positive amino acids and 1 neutral amino acid was changed to a negative amino acid. For the population of lignin resistant variants, regardless of parental glycosidase, there were 16 charge change mutations: 2 neutral amino acids were changed to positive amino acids and 14 neutral amino acids were changed to negative amino acids (FIG. 10). A significant difference (P=0.0035) between neutral-to-positive versus neutral-to-negative charge change was observed between the two populations using the following equation:

$$z = \left| \frac{\frac{x_1}{n_1} - \frac{x_2}{n_2}}{\sqrt{\hat{p}(1-\hat{p})\left(\frac{1}{n_1} + \frac{1}{n_2}\right)}} \right|$$

$$\hat{p} = \frac{x_1 + x_2}{n_1 + n_2}$$

These results support that the introduction of acidic amino acids on the surface of the CBM results in a modified Family 1 CBM with reduced binding to lignin.

Example 12: Construction of Modified TrCel6A Glycosidases

Using Yep352/PGK91-1-$\alpha_{ss}$-Cel6A-S413P as a template, additional mutations were introduced into the Family 1 CBM of TrCel6A-S413P (SEQ ID NO: 4) using a two-step PCR method involving megaprimer synthesis followed by megaprimer PCR (Table 5). The internal primers were modified to introduce the desired amino acid substitutions into the TrCel6A-S413P construct. The external plasmid primers (YalphaN21 and 3'PGK-term) were used to amplify the final product. Megaprimers and final products were purified using the Wizard® SV Gel and PCR Clean-Up System.

TABLE 5

| Generation of the modified TrCel6A enzymes by PCRα | | | | | |
|---|---|---|---|---|---|
| PCR | Step | Template | Primer 1 | Primer 2 | Amplicon |
| 1 | 1 | Yep352/PGK91-1-$\alpha_{ss}$-Cel6A(S413P) | YalphaN21 | DKX02 | PCR 1 Step 1 |
|   | 1 | Yep352/PGK91-1-$\alpha_{ss}$-Cel6A(S413P) | DKX01 | 3'PGK-term | PCR 1 Step 1 |

TABLE 5-continued

Generation of the modified TrCel6A enzymes by PCRα

| PCR | Step | Template | Primer 1 | Primer 2 | Amplicon |
|---|---|---|---|---|---|
|  | 2 | Both PCR 1 Step 1 megaprimers | YalphaN21 | 3'PGK-term | trcel6A-S413P-G17D |
| 2 | 1 | Yep352/PGK91-1-α$_{ss}$-Cel6A(S413P) | YalphaN21 | DK270 | PCR 2 Step 1 |
|  | 1 | Yep352/PGK91-1-α$_{ss}$-Cel6A(S413P) | DK269 | 3'PGK-term | PCR 2 Step 1 |
|  | 2 | Both PCR 2 Step 1 megaprimers | YalphaN21 | 3'PGK-term | trcel6A-S413P-Y29D |
| 3 | 1 | Yep352/PGK91-1-α$_{ss}$-Cel6A(S413P) | YalphaN21 | DK274 | PCR 3 Step 1 |
|  | 1 | Yep352/PGK91-1-α$_{ss}$-Cel6A(S413P) | DK273 | 3'PGK-term | PCR 3 Step 1 |
|  | 2 | Both PCR 3 Step 1 megaprimers | YalphaN21 | 3'PGK-term | Trcel6A-S413P-N31T |

The final PCR products were digested with NheI+KpnI and ligated into vector Yep352/PGK91-1-α$_{ss}$-Cel6A-S413P linearized with NheI+KpnI. The ligation mix was transformed into chemically-competent DH5α *E. coli* cells, plasmid extracted, and sequenced.

```
5'YalphaN21
                                      (SEQ ID NO: 97)
5'-AGCACAAATAACGGGTTATTG-3'

3'PGK-term
                                      (SEQ ID NO: 98)
5'-GCAACACCTGGCAATTCCTTACC-3'

5'DKX01
                                     (SEQ ID NO: 106)
5'-GAATTGGTCGGATCCGACTTGCTGTGCTTC-3'

3'DKX02
                                     (SEQ ID NO: 107)
5'-AGCAAGTCGGATCCGACCAATTCTGGCC-3'

5'DK269
                                     (SEQ ID NO: 108)
5'-GCACATGCGTCGACTCCAACGAC-3'

3'DK270
                                     (SEQ ID NO: 109)
5'-GTCGTTGGAGTCGACGCATGTGC-3'

5'DK273
                                     (SEQ ID NO: 110)
5'-CGTCTACTCCACCGACTATTACT-3'

3'DK274
                                     (SEQ ID NO: 111)
5'-AGTAATAGTCGGTGGAGTAGACG-3'
```

Example 13: Construction of Modified TrCel7A Glycosidases

Using pTrCel7A-pyr4-TV as a template, additional mutations were introduced into *T. reesei* Cel7A (SEQ ID NO: 124) using a two-step PCR method involving megaprimer synthesis followed by megaprimer PCR (Table 6). The internal primers were modified to introduce the desired amino acid substitutions into the TrCel7A construct. The external plasmid primers (FT016 and AC413) were used to amplify the final product. Megaprimers and final products were purified using the Wizard® SV Gel and PCR Clean-Up System.

TABLE 6

Generation of the modified TrCel7A enzymes by PCR

| PCR | Step | Template | Primer 1 | Primer 2 | Amplicon |
|---|---|---|---|---|---|
| 1 | 1 | pTrCel7A-pyr4-TV | FT016 | DK298 | PCR 1 Step 1 |
|  | 1 | pTrCel7A-pyr4-TV | DK297 | AC413 | PCR 1 Step 1 |
|  | 2 | Both PCR 1 Step 1 megaprimers | FT016 | AC413 | trcel7A-C469S |
| 2 | 1 | pTrCel7A-pyr4-TV | FT016 | DK300 | PCR 2 Step 1 |
|  | 1 | pTrCel7A-pyr4-TV | DK299 | AC413 | PCR 2 Step 1 |
|  | 2 | Both PCR 2 Step 1 megaprimers | FT016 | AC413 | trcel7A-G470C |
| 3 | 1 | pTrCel7A-pyr4-TV | FT016 | DK302 | PCR 3 Step 1 |
|  | 1 | pTrCel7A-pyr4-TV | DK301 | AC413 | PCR 3 Step 1 |
|  | 2 | Both PCR 3 Step 1 megaprimers | FT016 | AC413 | trcel7A-G471D |
| 4 | 1 | pTrCel7A-pyr4-TV | FT016 | DK316 | PCR 4 Step 1 |
|  | 1 | pTrCel7A-pyr4-TV | DK315 | AC413 | PCR 4 Step 1 |
|  | 2 | Both PCR 4 Step 1 megaprimers | FT016 | AC413 | trcel7A-C480Y |
| 5 | 1 | pTrCel7A-pyr4-TV | FT016 | DK346 | PCR 5 Step 1 |
|  | 1 | pTrCel7A-pyr4-TV | DK345 | AC413 | PCR 5 Step 1 |
|  | 2 | Both PCR 5 Step 1 megaprimers | FT016 | AC413 | trcel7A-C496Y |

The final PCR products were digested with MluI+KpnI and ligated into vector pTrCel7A-pyr4-TV linearized with MluI+KpnI. The ligation mix was transformed into chemically-competent DH5α *E. coli* cells, plasmid extracted, and sequenced.

```
5'FT016
                                     (SEQ ID NO: 112)
5'-GCCTGCACTCTCCAATCG-3'

3'AC413
                                     (SEQ ID NO: 113)
5'-GTTGCTCATTTGCGGTCTAC-3'

5'DK297
                                     (SEQ ID NO: 114)
5'-TACGGCCAGTCTGGCGGTATTGGCTACAG-3'

3'DK298
                                     (SEQ ID NO: 115)
5'-AATACCGCCAGACTGGCCGTAGTGAGAC-3'

5'DK299
                                     (SEQ ID NO: 116)
5'-GGCCAGTGCTGCGGTATTGGC-3'
```

-continued

3'DK300
(SEQ ID NO: 117)
5'-CAATACCGCAGCACTGGCCGT-3'

5'DK301
(SEQ ID NO: 118)
5'-AGTGCGGCGACATTGGCTACAGCGGCC-3'

3'DK302
(SEQ ID NO: 119)
5'-GTAGCCAATGTCGCCGCACTGGCCGT-3'

5'DK315
(SEQ ID NO: 120)
5'-CACGGTCTATGCCAGCGGCACAACTT-3'

3'DK316
(SEQ ID NO: 121)
5'-GCCGCTGGCATAGACCGTGGGGCCG-3'

5'DK345
(SEQ ID NO: 122)
5'-TACTACTCTCAGTACCTGTAAGGTACC-3'

3'DK346
(SEQ ID NO: 123)
5'-GGTACCTTACAGGTACTGAGAGTAGTA-3'

Example 14: Measuring Cellulase Recovery from Hydrolysis Residue

Cellulose hydrolysis experiments were done using steam exploded pretreated wheat straw, prepared as described in U.S. Pat. No. 4,461,648, and a cellulase mixture from a strain of *Trichoderma reesei* that over-expressed TrCel3A as described in U.S. Pat. No. 6,015,703. Samples of hydrolysis slurry were taken throughout the hydrolysis time-course and centrifuged to separate the solids from the supernatant. The glucose concentration in the supernatant was measured using a glucose oxidase-horseradish peroxidase coupled enzyme assay (Trinder et al., 1969). The concentration of Cel7A in the supernatant was measured by ELISA as described in U.S. Pat. No. 7,785,854. Glucose concentrations were converted to units of Fractional Cellulose Conversion and Cel7A protein or activity converted to units of fraction of initial Cel7A (Fractional Cel7A Recovery).

Immediately following the addition of enzyme to these substrates, only about 10% of the total Cel7A remained in the supernatant (FIG. 11). The concentration of Cel7A in the supernatant increased slowly as the fractional conversion increased from about 0 to about 0.60. As the conversion of BSA-WS increased above 0.60, the concentration of Cel7A in the supernatant increased gradually until 76% of the total Cel7A was recovered in the supernatant once cellulose conversion reached about 99%. The fractional concentration of Cel7A recovered in the supernatant from the hydrolysis of bWS increased markedly beginning at about 91% cellulose conversion, resulting in a total recovery of about 89% of the total Cel7A once cellulose conversion reached about 99%. By comparison the recovery of Cel7A from the hydrolysis of pretreated wheat straw was about 48% at the same level of cellulose conversion (99%). These experiments demonstrated that removal or blocking of in situ lignin markedly increases the recovery of cellulase, such as TrCel7A, from a hydrolysis reaction containing pre-treated lignocellulose.

Example 15: Expression and Purification of Modified Cel6A Glycosidases from Large Scale Cultures of *S. cerevisiae*

500 mL of sterile YPD medium (10 g/L yeast extract, 20 g/L peptone and 20 g/L glucose) was inoculated with 10 mL of an overnight culture of transformed *S. cerevisiae* grown from cells freshly picked from an agar plate. The 500 mL cultures were then incubated for 96 hours at 30° C. with orbital shaking.

After incubation, the broth from each culture was centrifuged for 10 minutes at 16,700×g and the pellet (containing yeast cells) discarded. The pH of the supernatant was adjusted to 5.0 and then allowed to cool to 4° C. for an hour. Subsequent to cooling, 625 g $(NH_4)_2SO_4$ was added to bring the yeast supernatant to 93% saturation. Precipitation was allowed to occur over a period of 2 hours at 4° C. with constant stirring. After centrifugation for 15 minutes at 16,700×g, the supernatant was discarded.

The pellet was resuspended with pipetting in 20 mL of 50 mM citrate, pH 5.0. Once the pellet was resuspended, 80 mL of 0.1 M sodium acetate, 200 mM glucose and 1 mM gluconic acid lactone, pH 5.0 was added. Samples were then incubated at 4° C. for 30 min with gentle stirring. Each sample was then centrifuged at 710×g for 3 minutes to pellet any insoluble material. The supernatant was removed carefully with a pipette to prevent disruption of the pellet and retained. The Cel6A cellulase in each sample was purified by APTC affinity chromatography as described by (Piyachomkwan et al., 1997). Purified Cel6A cellulases were buffer exchanged into 50 mM citrate, pH 5.0 and concentrated using a Centricon (Millipore) centrifugal concentrator with a 5 kDa NMWL polyethersulfone membrane. Protein concentrations were measured by the method of Bradford. Samples of the purified parental and modified Cel6A glycosidases were separated by SDS-PAGE and visualized by Coomassie Blue staining in order to confirm that each preparation was substantially pure and free of cored enzyme.

Example 16: Characterizing the Inactivation of Modified Cel6A Glycosidases Expressed from *S. cerevisiae* in the Presence of Lignin The testing of purified parental and modified TrCel6A and PcCel6A glycosidases was done in a manner similar to that described in Example 4. The protein and lignin masses used in each of these experiments were 0.08 mg and 28 mg, respectively. The total reaction volume in these experiments was 2 mL and samples were taken over the course of 24 h.

TrCel6A lignin inactivation profiles were modeled in a manner similar to that described in Example 4. The $K_L$ associated with each of the modified TrCel6A glycosidases was divided by the $K_L$ associated with the parental TrCel6A-S413P glycosidase in order to calculate a relative $K_L$. The relative $K_L$ values for modified TrCel6A glycosidases are presented in FIG. 17. The modified TrCel6A-S413P glycosidase variants containing modified Family 1 CBMs with a G17D, a N29D or a N31T substitution all show reduced binding to lignin (as evidenced by a 1.3- to 1.7-fold higher $K_L$ than the parental TrCel6A-S413P glycosidase).

For the purpose of analyzing the modified PcCel6A glycosidases, a model free approach was used to identify modified glycosidases that were less inactivated in the presence of lignin, relative to the parental PcCel6A-S407P glycosidase. The residual PcCel6A activity was measured only before the addition of lignin (t=0 h) and in the lignin slurry 24 h after the addition of enzyme (t=24 h). The PcCel6A activity measured in the lignin slurry after 24 h of incubation was divided by the enzyme activity measured at t=0 h in order to calculate a fractional residual activity for each enzyme. The fractional residual activity for each modified PcCel6A glycosidase was then divided by the fractional residual activity for the parental PcCel6A-S407P in order to calculate a relative residual activity at 24 h. The relative residual activities of the parental and four modified PcCel6A glycosidases are shown in FIG. 16. These assays were done with four independent replicate experiments for each parental or modified PcCel6A glycosidase. The error bars represent the standard errors of these experiments for each modified PcCel6A glycosidase. The relative residual activity of the modified glycosidases comprising mutations at the equivalents of positions 12, 14 and 24 of SEQ ID NO: 30 (PcCel6A-S407P-G10D, PcCel6A-S407P-G12D and PcCel6A-S407P-G22D) were markedly higher (1.9- to 2.9-fold higher) than that of the parental glycosidase PcCel6A-S407P glycosidase, indicating that the mutations in the Family 1 CBM of the modified glycosidases conferred greater resistance to lignin binding and/or lignin inactivation.

Example 17: Expression of Modified TrCel7A Glycosidases a. Host *Trichoderma reesei* Strain Construction A uridine auxotroph *Trichoderma reesei* strain P297J (P297Jaux4) was used for expression of modified TrCel6A and TrCel7A cellulases. This strain contains disruption of the cel7a, cel7b and cel6a genes and is deficient in production of TrCel7A, TrCel7B and TrCel6A cellulases as described in WO2010/0096931A1.

b. PEG Transformation of *Trichoderma reesei* Protoplasts $5 \times 10^6$ spores of P297Jaux4 were plated onto sterile cellophane on Potato Dextrose agar supplemented with 5 mM uridine and were incubated for 20 hours at 30° C. to facilitate spore germination and mycelial growth. Cellophane discs with mycelia were transferred to 10 mL of a protoplasting solution containing 7.5 g/L Driselase and 4 g/L beta-glucanase (InterSpex Products Inc., Cat. Nos. 0465-1 and 0439-2, respectively) in 50 mM potassium phosphate buffer, pH 6.5 containing 0.6 M ammonium sulfate (Buffer P). The mycelial mat was digested for 5 hours with shaking at 60 rpm. Protoplasts were separated from undigested mycelia by filtration though sterile No. 30 MIRACLOTH™ and collected into a sterile 50 mL round-bottom centrifuge tube and recovered by centrifugation at 1000-1500×g for 10 min at room temperature. Protoplasts were washed with 5 mL of Buffer P and centrifuged again at 1000-1500×g for 10 min at room temperature. Protoplasts were resuspended in 1 mL of STC buffer (1.2 M sorbitol, 10 mM $CaCl_2$, 10 mM Tris-HCL, pH 7.5). For transformation, 0.1 mL of resuspended protoplasts were combined with 10 μg of vector pTrCel7A-pyr4-TV DNA (or a similar vector encoding the modified TrCel7A glycosidases constructed as described in Example 13) and 25 μL of PEG solution (25% PEG 3350, 50 mM $CaCl_2$, 10 mM Tris-HCl, pH 7.5). After incubation in an ice water bath for 30 min, 1 mL of PEG solution was added and the mixture incubated for 5 min at room temperature. Transformation mix was diluted with 2 mL of STC buffer and the entire mix was added to 50 mL of molten MMSS agar media (see below) cooled to about 47° C., split in half, and poured over MMSS agar. Plates were incubated at 30° C. until colony growth was visible. Transformants were transferred to individual plates containing MM agar and allowed to sporulate. Spores were collected and plated at high dilution on MM agar to isolate homokaryon transformants, which were then plated onto PDA to allow for growth and sufficient sporulation to inoculate the screening cultures described below.

Minimal Medium (MM) Agar Contains:

| Component* | Per L |
|---|---|
| $KH_2PO_4$ | 10 g |
| $(NH_4)_2SO_4$ | 6 g |
| $Na_3Citrate \cdot 2H_2O$ | 3 g |
| $FeSO_4 \cdot 7H_2O$ | 5 mg |
| $MnSO_4 \cdot H_2O$ | 1.6 mg |
| $ZnSO_4 \cdot 7H_2O$ | 1.4 mg |
| $CaCl_2 \cdot 2H_2O$ | 2 mg |
| Agar | 20 g |
| 20% Glucose | 50 mL |
| 1M $MgSO4-7H_2O$. | 4 mL |
| | pH to 5.5 |

*MMSS agar contains the same components as MM agar plus 1.2M sorbitol, 6.6 g/L YNB (Yeast Nitrogen Base w/o Amino Acids from DIFCO Cat. No. 291940) and 1.92 g/L amino acids (-Ura DO Supplement from Sigma Cat. No. Y1501-20G).

c. Production of Modified Glycosidases in *Trichoderma reesei* Microcultures

Sets of five random independent transformants expressing each modified TrCel7A glycosidase were selected for pre-screening in 24-well microcultures. Individual colonies of *Trichoderma* were transferred to PDA plates for the propagation of each culture. Sporulation was necessary for the uniform inoculation micro-cultures which were used in testing the ability of the culture to produce cellulase. The culture media was composed of the following:

| Component | g/L |
|---|---|
| $(NH_4)_2SO_4$ | 12.7 |
| $KH_2PO_4$ | 8.00 |
| $MgSO_4 \cdot 7H_2O$ | 4.00 |
| $CaCl_2 \cdot 2H_2O$ | 1.02 |
| CSL | 5.00 |
| $CaCO_3$ | 20.00 |
| Carbon source** | 30-35 |
| Trace elements* | 2 mL/L |

*Trace elements solution contains 5 g/L $FeSO_4*7H_2O$; 1.6 g/L $MnSO_4*H_2O$; 1.4 g/L1 $ZnSO_4*7H_2O$.
**glucose, Solka floc, lactose, cellobiose, sophorose, corn syrup, or Avicel. The carbon source can be sterilized separately as an aqueous solution at pH 2 to 7 and added to the remaining media initially or though the course of the fermentation.

Individual transformants were grown in the above media in 1 mL cultures in 24-well micro-plates. The initial pH was 5.5 and the media sterilized by steam autoclave for 30 minutes at 121° C. prior to inoculation. For both native and transformed cells, spores were isolated from the PDA plates, suspended in water and $10^4$-$10^6$ spores per mL are used to inoculate each culture. The cultures were shaken at 250 rpm at a temperature of 30° C. for a period of 6 days. The biomass was separated from the filtrate containing the secreted protein by centrifugation at 12,000 rpm. The protein concentration was determined using the Bio-Rad Protein Assay (Cat. No. 500-0001).

The relative abundance (in weight % of total secreted protein) of TrCel7A in the microculture filtrates was determined by ELISA. Culture supernatants and purified component standards were diluted to 0.01-10 μg/mL in phosphate-buffered saline, pH 7.2 (PBS) and incubated overnight at 4° C. in microtitre plates (Costar EIA #9018). These plates were washed with PBS containing 0.1% Tween-20 (PBS/Tween) and then incubated in PBS containing 1% bovine serum albumin (PBS/BSA) for 1 h at room temperature. Blocked microtitre wells were washed with PBS/Tween. Rabbit polyclonal antisera specific for TrCel7A was diluted in PBS/BSA, added to separate microtitre plates and incubated for 2 h at room temperature. Plates were washed and incubated with a goat anti-rabbit antibody coupled to horseradish peroxidase (Sigma #A6154), diluted 1/2000 in PBS/

BSA, for 1 h at room temperature. After washing, tetramethylbenzidine was added to each plate and incubated for 30 min at room temperature. The absorbance at 360 nm was measured in each well and converted into protein concentration using a TrCel7A standard curve.

Example 18: Characterization of Modified TrCel7A Glycosidases

One transformant expressing each modified TrCel7A glycosidase and exhibiting the highest TrCel7A expression levels in microculture filtrates (as described in Example 17) were grown in 50 mL of microculture media in shake flasks for 6 days at 30° C. with shaking at 250 rpm. Supernatants were collected and the lignin inactivation of the modified TrCel7A glycosidases was assessed as described in Example 4. The relative lignin dissociation constants (relative $K_L$) of the modified TrCel7A glycosidases comprising mutations at the equivalents of positions 10, 11, 12, 14, 21 and 37 of SEQ ID NO: 30 (TrCel7A-C469S, TrCel7A-G470C, TrCel7A-G471D, TrCel7A-C480Y and TrCel7A-C496Y) were markedly higher (1.8- to 3.2-fold higher) than that of the parental glycosidase TrCel7A glycosidase, indicating that the mutations in the Family 1 CBM of the modified glycosidases conferred greater resistance to lignin binding and/or lignin inactivation.

REFERENCES

Altschul, S. F., Madden, T. L., Schäffer, A. A., Zhang, J., Zhang, Z., Miller, W. and Lipman, D. J. (1997) Gapped BLAST and PSI-BLAST: a new generation of protein database search programs. *Nucleic Acids Research*, 25: 3389-3402.

Altschul, S. F., Gish, W., Miller, W., Myers, E. W. and Lipman, D. J. (1990) Basic local alignment search tool. *Journal of Molecular Biology*, 215: 403-10.

Bae, K., Mallick, B. K and Elsik, C. G. (2008) Prediction of Protein Interdomain Linker Regions by a Nonstationary Hidden Markov Model. *Journal of the American Statistical Association*, 103(483): 1085-99.

Berlin, A., Gilkes, N., Kurabi, A., Bura, R., Tu, Maobing, Kilburn, D. and Saddler, J. (2005) Weak Lignin-Binding Enzymes. *Applied Biochemistry and Biotechnology*, Spring (121-124):163-170.

Bhikhabhai, R., et al. (1984) "Isolation of Cellulolytic Enzymes from *Trichoderma reesei* QM 9414", Journal of Applied Biochemistry, 6: 336-345.

Birkett C. R., et al. (1985) "Use of monoclonal antibodies to analyse the expression of a multi-tubulin family", FEBS Letters, 187(2): 211-218.

Bradford, M. M., et al. (1976) "A rapid and sensitive method for quantitation of microgram quantities of protein utilizing the principle of protein-dye binding", Analytical Biochemistry, 72: 248-254.

Boisset, C., Borsali, R., Schulein, M. and Henrissat, B. (1995) Dynamic light scattering study of a two-domain structure of *Humicola insolens* endoglucanase V. *FEBS Letters*, 376(1-2): 49-52.

Boraston, A. B., Bolam, D. N., Gilbert, H. J. and Davies, G. J. (2004). Carbohydrate-binding modules: fine tuning polysaccharide recognition. *Biochemical Journal*, 382: 769-81.

Butler, T. and Alcalde, M. (2003) In Methods in Molecular Biology, vol. 231: (F. H. Arnold and G. Georgiou, editors), Humana Press Inc. Totowa (New Jersey), pages 17-22.

Chernoglazov, V. M., Ermolova, O. V. and Klyosov, A. A. (1988) Adsorption of high-purity endo-1,4-beta-glucanases from *Trichoderma reesei* on components of lignocellulosic materials: Cellulose, lignin, and xylan, *Enzyme and Microbial Technology*, 10(8): 503-507.

Davies, G and Henrissat, B. (1995) Structures and mechanisms of glycosyl hydrolases. *Structure*. 3(9): 853-9.

Escoffier, G., Toussaint, B. and Vignon, M. R. (1991) Saccharification of steam-exploded poplarwood. *Biotechnology and Bioengineering*, 38(11): 1308-1317.

Fagerstam, L. G., Pettersson, G. and Engstrom, J. A. (1984) The primary structure of a 1,4-β-glucan cellobiohydrolase from the fungus *Trichoderma reesei* QM 9414. *FEBS Letters*, 167: 309-315.

Foreman, P. K., Brown, D., Dankmeyer, L., Dean, R., Diener, S., Dunn-Coleman, N. S., Goedegebuur, F., Houfek, T. D., England, G. J., Kelley, A. S., Meerman, H. J., Mitchell, T., Mitchinson, C., Olivares, H. A., Teunissen, P. J., Yao, J. and Ward, M. (2003) Transcriptional regulation of biomass-degrading enzymes in the filamentous fungus *Trichoderma reesei*, *Journal of Biological Chemistry*, 278(34): 31988-97.

Gietz, R. D. and Woods, R. A. (2002) Transformation of yeast by the LiAc/ss carrier DNA/PEG method. *In Methods in Enzymology*, 350: 87-96.

Gilkes, N. R., Henrissat, B., Kilburn, D. G., Miller, R. C. Jr. and Warren R. A. (1991) Domains in microbial beta-1,4-glycanases: sequence conservation, function, and enzyme families. *Microbiology Reviews*, 55(2): 303-315.

Hashimoto, H. (2006) Recent structural studies of carbohydrate-binding modules. *Cell. Mol. Life Sci.*, 63: 2954-2967.

Herner, M. L., Melnick, M. S., and Rabinovich, M. L. (1999) Enhancement of the affinity of cellobiohydrolases I and its catalytic domain to cellulose in the presence of the reaction product—cellobiose. *Biochemistry (Moscow)* 64 (9): 1012-1020.

Holtzapple, M. T., Jun, J., Ashok, G., Patibanadala, S. L and Dale, B. E. (1991) The ammonia freeze explosion (AFEX) process: A practical lignocellulosic pretreatment. *Applied Biochemistry and Biotechnology*, 28/29: 59-74.

Kaya, F., Heitmann, J. A. and Joyce, T. W. (2000) Influence of lignin and its degradation products on enzymatic hydrolysis of xylan. *Journal of Biotechnology*, 80(3): 241-247.

Kong, F., Engler, C. R. and Soltes, E. J. (1992) Effects of cell-wall acetate, xylan backbone, and lignin on enzymatic hydrolysis of aspen. *Applied Biochemistry and Biotechnology*, 34/35: 23-25.

Kraulis, J., Clore, G. M., Nilges, M., Jones, T. A., Pettersson, G., Knowles, J. and Gronenborn, A. M. (1989) Determination of the three-dimensional solution structure of the C-terminal domain of cellobiohydrolase I from *Trichoderma reesei*. A study using nuclear magnetic resonance and hybrid distance geometry-dynamical simulated annealing. *Biochemistry*, 28: 7241-7257.

Linder, M., Mattinen, M-L., Kontteli, M., Lindeberg, G., Ståhlberg, J., Drakenber, T., Reinikainen, T., Petterson, G., and Annila, A. (1995) Identification of functionally important amino acids in the cellulose-binding domain of *Trichoderma reesei* cellobiohydrolase I. *Protein Science*, 4: 1056-1064.

Linder, M., Nevanen, T., and Teeri, T. T. (1999) Design of a pH-dependent cellulose-binding domain. *FEBS Letters*, 447: 13-16.

Mattinen, M. L., Linder, M., Teleman, A. and Annila, A. (1997) Interaction between cellohexaose and cellulose binding domains from *Trichoderma reesei* cellulases. *FEBS Letters*, 407(3): 291-296.

Meunier-Goddik, L. and Penner, M. H. (1999) Enzyme-catalyzed saccharification of model celluloses in the presence of lignacious residues. *Journal of Agricultural and Food Chemistry*, 47(1): 346-351.

Mooney, C. A., Mansfield, S. D., Touhy, M. G. and Saddler, J. N. (1998) The effect of initial pore volume and lignin content on the enzymatic hydrolysis of softwoods. *Bioresource Technology*, 64: 113-119.

Needleman, S. B. and Wunsch, C. D. (1970) A general method applicable to the search for similarities in the amino acid sequence of two proteins. *Journal of Molecular Biology*, 48: 443-53.

Nidetzky B, Steiner W, Claeyssens M. (1994) Cellulose hydrolysis by the cellulases from *Trichoderma reesei*: adsorption of two cellobiohydrolases, two endocellulases and their core proteins on filter paper and their relation to hydrolysis. *Biochem. J.* 303: 817-823.

Palonen, H., Tjerneld, F., Zacchi, G. and Tenkanen, M. (2004) Adsorption of *Trichoderma reesei* CBH I and EG II and their catalytic domains on steam pretreated softwood and isolated lignin. *Journal of Biotechnology*, 107: 65-72.

Pearson, W. R. and Lipman, D. J. (1988) Improved tools for biological sequence comparison. *Proceedings of the National Academy of Sciences of the United States of America*, 85: 2444-8.

Piyachomkwan, K., Gable, K. P. and Penner, M. H. (1997) p-Aminophenyl 1-thio-β-D-cellobioside: Synthesis and application in affinity chromatography of exo-type cellulases. *Carbohydrate Research*, 303: 255-259.

Piyachomkwan, K., et al. (1998) "Aryl Thioglycoside-Based Affinity Purification of Exo-Acting Cellulases", *Analytical Biochemistry*, 255: 223-235.

Receveur, V., Czjzek, M., Schulein, M., Panine, P. and Henrissat, B. (2002) Dimension, Shape, and Conformational Flexibility of a Two Domain Fungal Cellulase in Solution Probed by Small Angle X-Ray Scattering. *Journal of Biological Chemistry*, 277(43): 40887-40892.

Reinikainen, T., Ruohonen, L., Nevanen, T., Laaksonen, L., Kraulis, P., Jones, T. A., Knowles, J. K. and Teeri, T. T. (1992) Investigation of the function of mutated cellulose-binding domains of *Trichoderma reesei* cellobiohydrolase I. *Proteins*, 14(4):475-482.

Saloheimo, M., Paloheimo, M., Hakola, S., Pere, J., Swanson, B., Nyyssonen, E., Bhatia, A., Ward, M. and Penttilä, M. (2002) Swollenin, a *Trichoderma reesei* protein with sequence similarity to the plant expansins, exhibits disruption activity on cellulosic materials. *European Journal of Biochemistry*, 269:4202-11.

Shen, H., Schmuck, M., Pilz, I., Gilkes, N. R., Kilburn, D. G., Miller, R. C. Jr. and Warren, A. J. (1991) Deletion of the Linker Connecting the Catalytic and Cellulose-Binding Domains of Endoglucanase A (CenA) of *Cellulomonas firmi* Alters Its Conformation and Catalytic Activity. *Journal of Biological Chemistry*, 266(17):11335-11340.

Smith, T. F. and Waterman, M. S. (1981) Comparison of biosequences. *Advances in Applied Mathematics*, 2:482-89.

Suyama, M. and Ohara, O. (2003) DomCut: prediction of inter-domain linker regions in amino acid sequences. *Bioinformatics*, 19(5):673-4, (2003)

Tormo, J., Lamed, R., Chirino, A. J., Morag, E., Bayer, E. A., Shoham, Y. and Steitz, T. A. (1996) Crystal structure of a bacterial family-III cellulose-binding domain: a general mechanism for attachment to cellulose. *EMBO Journal*, 15(21):5739-5751.

Trinder, P. (1969) Determination of glucose in blood using glucose oxidase with an alternative oxygen accepter. *Annals of Clinical Biochemistry*, 6:24-27.

Tu, M., Chandra, R. P. and Saddler, J. N. (2007) Evaluating the distribution of cellulases and the recycling of free cellulases during the hydrolysis of lignocellulosic substrates. *Biotechnology Progress*, 23(2):398-406.

Yang, B. and Wyman, C. E. (2006) BSA treatment to enhance enzymatic hydrolysis of cellulose in lignin containing substrates. *Biotechnology and Bioengineering*, 94(4):611-617.

The invention claimed is:

1. A modified Family 1 carbohydrate binding module (CBM) comprising one or more amino acid substitutions selected from the group consisting of:
   (a) substitution at position 10 to serine;
   (b) substitution of at position 14 to aspartic acid;
   (c) substitution at position 21 to tyrosine;
   (d) substitution at position 29 to aspartic acid;
   (e) substitution at position 31 to aspartic acid,
   (f) substitution at position 33 to asparagine; and
   (g) substitution at position 37 to tyrosine,
the position determined from alignment of the Family 1 CBM amino acid sequence with a *Trichoderma reesei* Cel6A carbohydrate binding module amino acid sequence as defined by amino acids 1 to 38 of SEQ ID NO: 1,
   wherein the modified Family 1 carbohydrate binding module binds to crystalline cellulose and exhibits reduced binding to lignin relative to the unmodified Family 1 CBM, and
   wherein the modified Family 1 carbohydrate binding module comprises an amino acid sequence that is 75% to 99.9% identical to amino acids 1 to 38 of SEQ ID NO:1.

2. The modified Family 1 carbohydrate binding module (CBM) of claim 1, wherein the amino acid sequence is 80% to 99.9% identical to amino acids 1 to 38 of SEQ ID NO:1.

3. The modified Family 1 carbohydrate binding module (CBM) of claim 1, wherein the amino acid sequence is 85% to 99.9% identical to amino acids 1 to 38 of SEQ ID NO:1.

4. The modified Family 1 carbohydrate binding module (CBM) of claim 1, wherein the amino acid sequence is 90% to 99.9% identical to amino acids 1 to 38 of SEQ ID NO:1.

5. The modified Family 1 carbohydrate binding module (CBM) of claim 1, wherein the amino acid sequence is 95% to 99.9% identical to amino acids 1 to 38 of SEQ ID NO:1.

6. The modified Family 1 carbohydrate binding module of claim 1, wherein
   the amino acid substitution at position 10 is from cysteine to serine,
   the amino acid substitution at position 14 is from asparagine to aspartic acid,
   the amino acid substitution at position 21 is from cysteine to tyrosine,
   the amino acid substitution at position 29 is from tyrosine to aspartic acid, the amino acid substitution at position 31 is from asparagine to aspartic acid, the amino acid substitution at position 33 is from tyrosine to asparagine, and the amino acid substitution at position 37 is from cysteine to tyrosine.

7. The modified Family 1 carbohydrate binding module of claim 1, wherein the modified Family 1 carbohydrate binding module confers reduced binding to lignin of a glycosidase enzyme comprising the modified Family 1 carbohydrate binding module and one or more catalytic domain joined to the modified Family 1 carbohydrate binding module by one or more linker peptide.

8. A modified glycosidase enzyme comprising one or more catalytic domain and one or more carbohydrate binding module,
wherein the one or more catalytic domain and one or more carbohydrate binding modules are functionally joined by one or more linker peptide, and
wherein at least one of the one or more carbohydrate binding module is the modified Family 1 carbohydrate binding module of claim 1, the modified glycosidase enzyme exhibiting an increase in hydrolyzing activity in the presence of lignin and/or a reduction in lignin binding relative to a parental glycosidase comprising a parental Family 1 carbohydrate binding module from which the modified carbohydrate binding module is derived, the same one or more catalytic domain and the same one or more carbohydrate binding module joined by the same one or more linker peptide.

9. The modified glycosidase enzyme of claim 8, wherein the one or more catalytic domain is selected from the group consisting of a cellulase catalytic domain, a hemicellulase catalytic domain, a beta-glucosidase catalytic domain, and an accessory component catalytic domain.

10. The modified glycosidase enzyme of claim 9,
wherein the cellulase catalytic domain is a member of Glycoside Hydrolase Family 5, 6, 7, 8, 9, 12, 44, 45, 48, 51, 61 or 74,
wherein the hemicellulase catalytic domain is a member of Glycoside Hydrolase Family 5, 8, 10, 11, 26, 43, 51, 54, 62 or 113,
wherein the beta-glucosidase catalytic domain is a member of Glycoside Hydrolase Family 1 or 3; and
wherein the accessory component catalytic domain is a swollenin, CIP or expansin catalytic domain.

11. The modified glycosidase enzyme of claim 10, comprising a Glycoside Hydrolase Family 6 or 7 cellulase catalytic domain.

12. The modified glycosidase enzyme of claim 11, wherein the cellulase catalytic domain comprises amino acids 83-447 of SEQ ID NO: 1 (*Trichoderma reesei* Cel6A), amino acids 1-436 of SEQ ID NO: 124 (*Trichoderma reesei* Cel7A), amino acids 97-460 of SEQ ID NO: 2 (*Humicola insolens* Avi2), or amino acids 81-440 of SEQ ID NO: 3 (*Phanerochaete chrysosporium* Cel6A).

13. The modified glycosidase enzyme of claim 11, wherein the cellulase catalytic domain is amino acids 83-447 of SEQ ID NO: 1 (*Trichoderma reesei* Cel6A) comprising one or more amino acid substitutions selected from the group consisting of Y103H, Y103K, Y103R, Y103A, Y103V, Y103L, Y103P, K129E L136V, L136I, S186K, S186T, S186Y, Q204K, G231D, A322D, Q363E, G365D, G365E, G365Q, G365S, R410A, R410F, R410L, R410Q, and R410S.

14. The modified glycosidase enzyme of claim 9, comprising a beta-glucosidase catalytic domain, wherein the beta-glucosidase catalytic domain is *Trichoderma reesei* Cel3A of SEQ ID NO: 100 comprising one or more amino acid substitutions selected from the group consisting of V43X, V66X, S72X, V101X, T235X, N248X, F260X, N369X, A386X, and I543X.

15. The modified glycosidase enzyme of claim 9, wherein the one or more catalytic domain is from a fungal glycosidase enzyme.

16. The modified glycosidase enzyme of claim 15, wherein the fungal glycosidase enzyme is from *Trichoderma* ssp., *Aspergillus* ssp., *Hypocrea* ssp., *Humicola* ssp., *Neurospora* ssp., *Orpinomyces* ssp., *Gibberella* ssp., *Emericella* ssp., *Chaetomium* ssp., *Chrysosporium* ssp., *Fusarium* ssp., *Penicillium* ssp., *Magnaporthe* ssp., or *Phanerochaete* ssp., *Trametes* ssp., *Lentinulaedodes, Gleophyllumtrabeiu, Ophiostomapiliferum, Corpinuscinereus, Geomycespannorum, Cryptococcus laurentii, Aureobasidiumpullulans, Amorphothecaresinae, Leucosporidiumscotti, Cunninghamellaelegans, Thermomyceslanuginosa, Myceliophthora thermophilum* or *Sporotrichum thermophile*.

17. The modified glycosidase enzyme of claim 16, wherein the fungal glycosidase is from *Trichoderma reesei*.

18. The modified glycosidase enzyme of claim 8, wherein the one or more linker peptide is a modified linker peptide from 6 to 60 amino acids in length and of which at least 50% of the amino acids are proline, serine or threonine,
wherein the modified linker peptide comprises one or more amino acid substitutions, insertions, or deletions that result in:
(a) a decrease in the calculated isoelectric point of the linker peptide;
(b) an increase in the ratio of threonine:serine in the linker peptide; or
(c) both (a) and (b), and
wherein relative to a parental linker peptide from which the modified linker peptide is derived, the modified linker peptide confers to the modified glycosidase an increase in hydrolyzing activity in the presence of lignin and/or a reduction in lignin binding relative to a parental glycosidase comprising the parental linker positioned between the same cellulase catalytic domain and carbohydrate binding module.

19. A process for hydrolyzing a cellulose or hemicellulose substrate to sugars comprising contacting the substrate with the modified glycosidase enzyme of claim 8 in the presence of lignin.

20. The process of claim 19, wherein the cellulose or hemicellulose substrate is a pretreated lignocellulosic substrate.

21. The process of claim 19, wherein the modified glycosidase enzyme exhibits improved recovery from the process relative to a parental glycosidase enzyme comprising the same one or more catalytic domain, one or more linker peptide and one or more carbohydrate binding module in which at least one of the one or more carbohydrate binding module is a parental Family 1 carbohydrate binding module from which the modified Family 1 carbohydrate binding module in the modified glycosidase is derived.

22. The process of claim 19, wherein the process is conducted as a continuous, semi-continuous or fed-batch process.

23. The process of claim 19, further comprising microbial fermentation of the sugars to alcohol or sugar alcohol.

* * * * *